(12) United States Patent
Chi et al.

(10) Patent No.: US 10,190,104 B2
(45) Date of Patent: Jan. 29, 2019

(54) ISOFORM OF ANAPLASTIC LYMPHOMA KINASE AND ITS USES

(71) Applicant: Memorial Sloan-Kettering Cancer Center, New York, NY (US)

(72) Inventors: Ping Chi, New York, NY (US); Thomas Wiesner, New York, NY (US); Yu Chen, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/288,531

(22) Filed: Oct. 7, 2016

(65) Prior Publication Data

US 2017/0022485 A1 Jan. 26, 2017

Related U.S. Application Data

(63) Continuation of application No. PCT/US2015/025289, filed on Apr. 10, 2015.

(60) Provisional application No. 61/978,106, filed on Apr. 10, 2014.

(51) Int. Cl.
| | |
|---|---|
| *C12N 9/12* | (2006.01) |
| *A61K 31/506* | (2006.01) |
| *A61K 31/5377* | (2006.01) |
| *A61K 31/545* | (2006.01) |
| *G01N 33/574* | (2006.01) |
| *A61K 31/4545* | (2006.01) |
| *C12Q 1/6886* | (2018.01) |

(52) U.S. Cl.
CPC ............ *C12N 9/12* (2013.01); *A61K 31/4545* (2013.01); *A61K 31/506* (2013.01); *A61K 31/5377* (2013.01); *A61K 31/545* (2013.01); *C12Q 1/6886* (2013.01); *C12Y 207/10* (2013.01); *G01N 33/57484* (2013.01); *C12Q 2600/106* (2013.01); *C12Q 2600/158* (2013.01); *G01N 2333/912* (2013.01); *G01N 2500/10* (2013.01); *G01N 2800/52* (2013.01)

(58) Field of Classification Search
CPC ............................ C12N 9/12; A61K 31/4545
See application file for complete search history.

(56) References Cited

U.S. PATENT DOCUMENTS

| 2009/0118216 A1 | 5/2009 | Chiarle et al. |
| 2012/0101108 A1 | 4/2012 | Haack et al. |
| 2012/0288872 A1 | 11/2012 | Rikova et al. |
| 2013/0244893 A1 | 9/2013 | Morris et al. |

FOREIGN PATENT DOCUMENTS

| WO | WO 2012/070730 A1 | 5/2012 | |
| WO | WO2013/059740 | * 4/2013 | ............... C12N 9/12 |
| WO | WO 2013/059740 A1 | 4/2013 | |

OTHER PUBLICATIONS

Weisner et al. (Nature. Oct. 15, 2015; 526(7573): 453-457. doi:10.1038/nature15258) (Year: 2015).*
An integrated encyclopedia of DNA elements in the human genome. The ENCODE Project Consortium. Nature 489:57-74 (2012).
Anders et al., "Detecting differential usage of exons from RNA-seq data," Genome Res 22:2008-2017 (2012).
Bennett et al., "A Line of Non-Tumorigenic Mouse Melanocytes, Syngeneic With the B16 Melanoma and Requiring a Tumor Promoter for Growth," Int. J Cancer 39:414-418 (1987).
Boeva et al., "Control-free calling of copy number alterations in deep-sequencing data using GC-content normalization," Bioinformatics 27(2):268-269 (2011).
Bresler et al., "Differential Inhibitor Sensitivity of Anaplastic Lymphoma Kinase Variants Found in Neuroblastoma," Sci Transl Med 3:108ra114 (2011).
Calo et al., Modification of Enhancer Chromatin: What, How, and Why? Mol Cell 49:825-837 (2013).
Carbon et al., "AmiGO: online access to ontology and annotation data," Bioinformatics 25(2):288-289 (2009).
Cazes et al., "Characterization of Rearrangements Involving the ALK Gene Reveals a Novel Truncated Form Associated with Tumor Aggressiveness in Neuroblastoma," Cancer Res 73(1):195-204 (2013).
Chen et al., "Oncogenic mutations of ALK kinase in neuroblastoma," Nature 455:971-974 (2008).
Chi et al., "ETV1 is a lineage survival factor that cooperates with KIT in gastrointestinal stromal tumours," Nature 467:849-853 (2010).
Cibulskis et al., "Sensitive detection of somatic point mutations in impure and heterogeneous cancer samples," Nat Biotechnol 31(3):213-219 (2013).
Comprehensive genomic characterization of squamous cell lung cancers. The Cancer Genome Atlas Network. Nature 489:519-525 (2012).
Comprehensive molecular characterization of human colon and rectal cancer. The Cancer Genome Atlas Network. Nature 487:330-337 (2012).
DePristo et al., "A framework for variation discovery and genotyping using next-generation DNA sequencing data," Nat Genet 43(5):491-498 (2011).
Geiss et al., "Direct multiplexed measurement of gene expression with color-coded probe pairs," Nat Biotechnol 26(3):317-325 (2008).
George et al., "Activating mutations in ALK provide a therapeutic target in neuroblastoma," Nature 455:975-978 (2008).
Grant et al., "FIMO: scanning for occurrences of a given motif," Bioinformatics 27(7):1017-1018 (2011).
Horn et al., "TERT Promoter Mutations in Familial and Sporadic Melanoma," Science 339:959-961 (2013).

(Continued)

*Primary Examiner* — Scott Long
(74) *Attorney, Agent, or Firm* — Foley & Lardner LLP

(57) ABSTRACT

The present invention relates to a Truncated isoform of Anaplastic Lymphoma Kinase ("TALK"). Expression of this isoform is associated with malignancy and with responsiveness to ALK inhibitors. Detection of the isoform may be used in diagnostic and therapeutic methods. Because it arises as a result of variant transcription rather than genetic rearrangement, its presence would be undetected by genomic testing.

7 Claims, 63 Drawing Sheets

Specification includes a Sequence Listing.

(56) References Cited

OTHER PUBLICATIONS

Huang et al., "Highly Recurrent TERT Promoter Mutations in Human Melanoma," Science 339:957-959 (2013).
Imielinski et al., "Mapping the Hallmarks of Lung Adenocarcinoma with Massively Parallel Sequencing," Cell 150:1107-1120 (2012).
International Search Report and Written Opinion dated Oct. 13, 2015 in International Application No. PCT/US2015/025289.
Janoueix-Lerosey et al., "Somatic and germline activating mutations of the ALK kinase receptor in neuroblastoma," Nature 455:967-970 (2008).
Karolchik et al., "The UCSC Table Browser data retrieval tool," Nucleic Acids Res 32:D493-D496 (2004).
Kouzarides, T., "Chromatin Modifications and Their Function," Cell 128:693-705 (2007).
Krueger et al., "Bismark: a flexible aligner and methylation caller for Bisulfite-Seq applications," Bioinformatics 27(11):1571-1572 (2011).
Krzywinski et al., "Circos: An information aesthetic for comparative genomics," Genome Res 19:1639-1645 (2009).
Lappalainen et al., "Transcriptome and genome sequencing uncovers functional variation in humans," Nature 501:506-511 (2013).
Lawrence et al., "Discovery and saturation analysis of cancer genes across 21 tumor types," Nature 505:495-501(2014).
Lawrence et al., "Mutational heterogeneity in cancer and the search for new cancer-associated genes," Nature 499:214-218 (2013).
Lemmon et al., "Cell Signaling by Receptor Tyrosine Kinases," Cell 141:1117-1134 (2010).
Li et al., "Fast and accurate short read alignment with Burrows-Wheeler transform," Bioinformatics 25(14):1754-1760 (2009).
Li et al., "The Sequence Alignment/Map format and SAMtools," Bioinformatics 25(16):2078-2079 (2009).
Lipson et al., "Identification of new ALK and RET gene fusions from colorectal and lung cancer biopsies," Nat Med 18(3):382-384 (2012).
Mathelier et al., "JASPAR 2014: an extensively expanded and updated open-access database of transcription factor binding profiles," Nucleic Acids Res 42:D142-D147 (2014).
McKenna et al., "The Genome Analysis Toolkit: A MapReduce framework for analyzing next-generation DNA sequencing data," Genome Research 20:1297-1303 (2010).
McLaren et al., "Deriving the consequences of genomic variants with the Ensembl API and SNP Effect Predictor," Bioinformatics 26(16):2069-2070 (2010).
Mitelman et al., "The impact of translocations and gene fusions on cancer causation," Nature Reviews. Cancer 7:233-245 (2007).
Montavon et al., "Wild-type ALK and activating ALK-R1275Q and ALK-F1174L mutations upregulate Myc and initiate tumor formation in murine neural crest progenitor cells," Oncotarget 5(12):4452-4466 (2014).
Moog-Lutz et al., "Activation and Inhibition of Anaplastic Lymphoma Kinase Receptor Tyrosine Kinase by Monoclonal Antibodies and Absence of Agonist Activity of Pleiotrophin," J Biol Chem 280(28):26039-26048 (2005).
Morris et al., "Fusion of a Kinase Gene, ALK, to a Nucleolar Protein Gene, NPM, in Non-Hodgkin's Lymphoma," Science 263:1281-1284 (1994).
Mosse et al., "Identification of ALK as a major familial neuroblastoma predisposition gene," Nature 455:930-935 (2008).
Northcott et al., "Enhancer hijacking activates GFI1 family oncogenes in medulloblastoma," Nature 511:428-434 (2014).
Okubo et al., "Aberrant activation of ALK kinase by a novel truncated form ALK protein in neuroblastoma," Oncogene 31:4667-4676 (2012).
Passoni et al., "Mutation-Independent Anaplastic Lymphoma Kinase Overexpression in Poor Prognosis Neuroblastoma Patients," Cancer Res 69(18):7338-7346 (2009).
Ponomarev et al., "A novel triple-modality reporter gene for whole-body fluorescent, bioluminescent, and nuclear noninvasive imaging," Eur J Nucl Med Mol Imaging 31:740-751 (2004).
Ram et al., "Combinatorial Patterning of Chromatin Regulators Uncovered by Genome-wide Location Analysis in Human Cells," Cell 147:1628-1639 (2011).
Rausch et al., "DELLY: structural variant discovery by integrated paired-end and split-read analysis," Bioinformatics 28:i333-i339 (2012).
Refaeli et al., "Interferon γ Is Required for Activation-induced Death of T Lymphocytes," J. Exp. Med. 196(7):999-1005 (2002).
Reis et al., "mRNA transcript quantification in archival samples using multiplexed, color-coded probes," BMC Biotechnol 11:46 (2011).
Robinson et al., "Integrative genomics viewer," Nat Biotechnol 29(1):24-26 (2011).
Sboner et al., "FusionSeq: a modular framework for finding gene fusions by analyzing paired-end RNA-sequencing data," Genome Biology 11:R104 (2010).
Schulte et al., "High ALK Receptor Tyrosine Kinase Expression Supersedes ALK Mutation as a Determining Factor of an Unfavorable Phenotype in Primary Neuroblastoma," Clin Cancer Res 17(15):5082-5092 (2011).
Soda et al., "Identification of the transforming EML4-ALK fusion gene in non-small-cell lung cancer," Nature 448:561-566 (2007).
The Genotype-Tissue Expression (GTEx) project. The GTEx Consortium. Nat Genet 45(6):580-585 (2013).
Trapnell et al., "TopHat: discovering splice junctions with RNA-Seq," Bioinformatics 25(9):1105-1111 (2009).
Vogelstein et al., "Cancer Genome Landscapes," Science 339:1546-1558 (2013).
Wang et al., "Combinatorial patterns of histone acetylations and methylations in the human genome," Nat Genet 40(7):897-903 (2008).
Wang et al., "CREST maps somatic structural variation in cancer genomes with base-pair resolution," Nat Methods 8(8):652-654 (2011).
Weinstein et al., "The Cancer Genome Atlas Pan-Cancer analysis project," Nat Genet 45(10):1113-1120 (2013).
Wiesner et al., "Kinase fusions are frequent in Spitz tumors and spitzoid melanomas," Nat Commun 5:3116 (2014).
Won et al., "Detecting Somatic Genetic Alterations in Tumor Specimens by Exon Capture and Massively Parallel Sequencing," J Vis Exp. 80:e50710 (2013).
Xie et al., "DNA hypomethylation within specific transposable element families associates with tissue-specific enhancer landscape," Nat Genet 45(7):836-841 (2013).
Zhang et al., "Model-based Analysis of ChIP-Seq (MACS)," Genome Biology 9:R137 (2008).
Figueiredo-Pontes et al., "Identification and characterization of ALK kinase splicing isoforms in non-small cell lung cancer", Journal of Thoratic Oncology, vol. 9, Feb. 1, 2014 (Feb. 1, 2014), pp. 248-253, XP055405883.
Hiroyuki Mano et al: "EML4-ALK Fusion in Lung", American Journal of Pathology., vol. 176, No. 3, Mar. 1, 2010 (Mar. 1, 2010), pp. 1552-1554, XP055406811, US ISSN:0002-9440, DOI: 10.2353/ajpath.2010.091057.

* cited by examiner

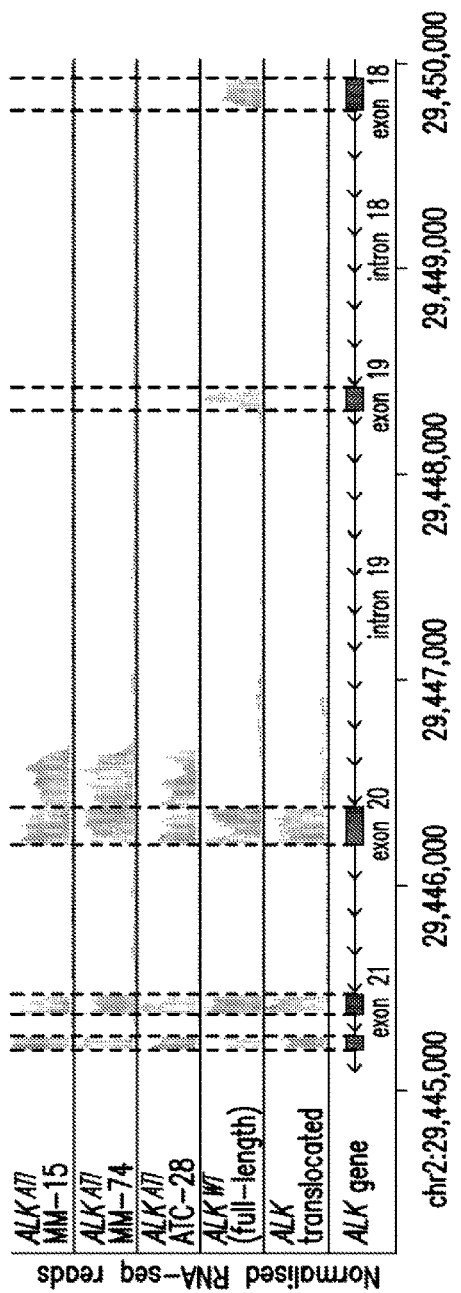
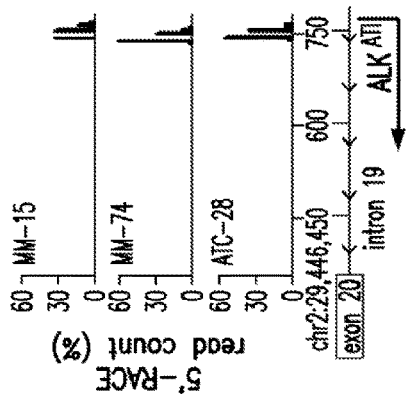
FIG. 1A
FIG. 1B

| ID | Name | Accession | TargRegion | Target Sequence |
|---|---|---|---|---|
| 1 | ALK_ex10-19_v1 | NM_004304.4 | 2844-2943 | GCCTGGACTGCTACCTCACCATTAGCGGAGAGGACAAGATCCTGCAGAATACAGC ACCAAATCAAGAAACCTGTTTGAGAGAACCCAAACAAGGAGCT |
| 2 | ALK_ex10-19_v2 | NM_004304.3 | 3496-3595 | TAACTCCTCGGTTCTAGGCTAAACGCCAATTCCGGAGCCCAGGTGGTCGGAGG TGGCTGGAATGATAACACTTCCTTGCTCTGGGCCGGAAAATCTTTG |
| 3 | ALK_in19-UTR_v1 | ALK_001.1 | 261-360 | TTTATTAGTATTTCTAAGTATGATGGAAAGGTTCAGAGCTCAGGGGAGGATATGGA GATCCAGGGAGGCTTCCTGTGAGGAAGTGGCCTGTAGTGCTTC |
| 4 | ALK_in19-UTR_v2 | ALK_002.1 | 10-109 | CTTCAAGGGCCCAGGCTGCCAGGCCATGTTGCAGCTGACCACCCACCTGCAGTGT ACCGCCGGAAGCACCAGGAGCTGCAAGCCATGCAGATGGAGCTGCA |
| 5 | ALK_ex20-29_v1 | NM_004304.4 | 4846-4945 | AGAGGCCTTCATGGAAGGAATATTCACTTCTAAAACAGACACATGGTCTTTGGAG TGCTGTCTATGGGAAATCTTTTCTCTTGGATATATGCCATACCCC |
| 6 | ALK_ex20-29_v2 | NM_004304.4 | 5825-5924 | CACACTCACTCTCTCTTCCTTGGGATCCCTAAGACCGTGGAGGAGAGAGGCAAT GGCTCCTTCACAAACCAGAGACCAAATGTCACGTTTGTTTGTG |
| 7 | ACTB | NM_001101.2 | 1011-1110 | TGCAGAAGGAGATCACTGCCCTGGCAGCACCCAGCACAATGAAGATCAAGATCATTGC TCCTCCTGAGGCCAAGTACTCCGTGTGGATCGGCGGCTCCATCCT |
| 8 | RPL27 | NM_000988.3 | 24-123 | GGGCGGGTGTTGCCCTGGCTGGACGCTACTCCGGACGAAGCTCAAAACCTGGGAAGGTGGT GCTGTCCTGGCTGGACGCTACTCCGGACGAAGCTGTCATCGTG |
| 9 | RPS13 | NM_001017.2 | 332-431 | GCATCTTGAGAGAACAAGAAAGGATAAGGATGCTAAATTCCGTCTGATTCTAATAG AGAGCCGGATTCACCGTTTGGCTCGATATTATAAGACCAAGCGA |
| 10 | RPS20 | NM_001023.2 | 187-286 | TCGAATCACCCTAACAAGCCGCAAGCTAAAATCCTTGGAAAAGGTGTGTGCTGAC TTGATAAGAGGGCCAAAAGAAAAGAATCTCAAAGTGAAAGGACCA |

FIG. 1H

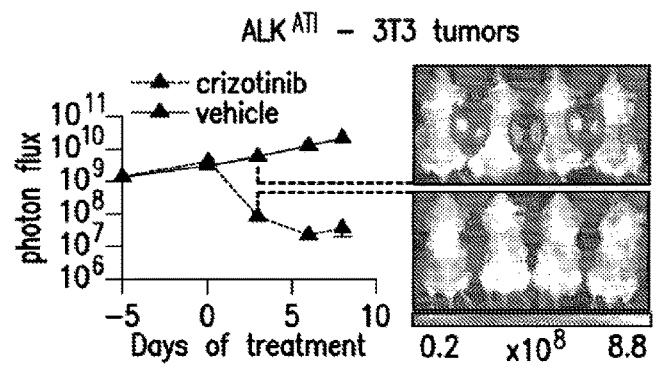
FIG. 4E
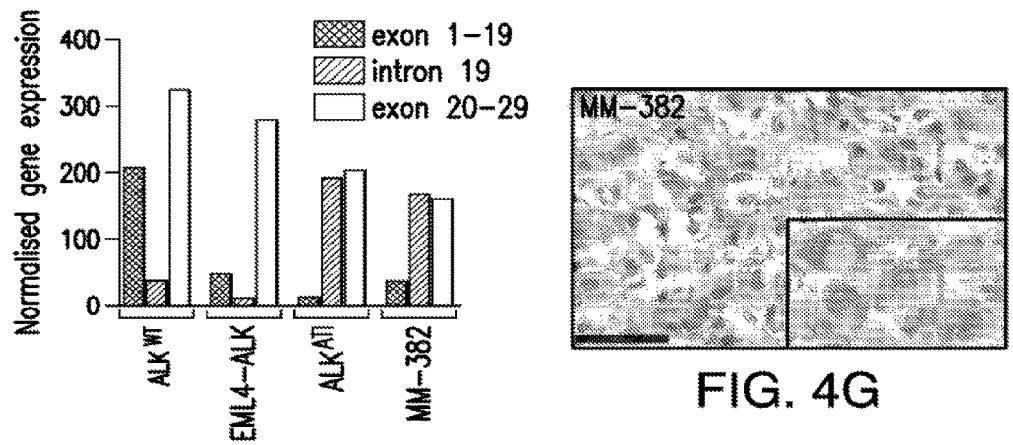
FIG. 4F
FIG. 4G
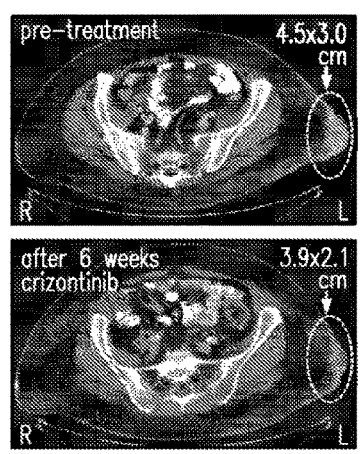
FIG. 4H

| Transciptional initiation site | MM-15 in % | MM-74 in % | ATC-28 in % | Transciptional initiation site | MM-15 in % | MM-74 in % | ATC-28 in % |
|---|---|---|---|---|---|---|---|
| 29,446,768 | 0.05 | 0.01 | 0.01 | 29,446,755 | 2.39 | 0.63 | 0.83 |
| 29,446,767 | 1.98 | 0.47 | 0.23 | 29,446,754 | 0.38 | 0.21 | 0.24 |
| 29,446,766 | 7.05 | 1.05 | 1.02 | 29,446,753 | 0.24 | 0.15 | 0.12 |
| 29,446,765 | 11.99 | 1.35 | 3.27 | 29,446,752 | 0.13 | 0.03 | 0.04 |
| 29,446,764 | 0.33 | 0.05 | 0.08 | 29,446,751 | 0.13 | 0.09 | 0.09 |
| 29,446,763 | 0.43 | 0.11 | 0.19 | 29,446,750 | 0.04 | 0.03 | 0.02 |
| 29,446,762 | 0.39 | 0.25 | 0.32 | 29,446,749 | 0.03 | 0.04 | 0.02 |
| 29,446,761 | 4.58 | 6.25 | 3.87 | 29,446,748 | 0.03 | 0.02 | 0.02 |
| 29,446,760 | 0.07 | 0.03 | 0.03 | 29,446,747 | 0.04 | 0.01 | 0.04 |
| 29,446,759 | 0.07 | 0.04 | 0.04 | 29,446,746 | 0.04 | 0.01 | 0.01 |
| 29,446,758 | 0.12 | 0.11 | 0.07 | 29,446,745 | 0.12 | 0.11 | 0.09 |
| 29,446,757 | 1.56 | 0.57 | 0.15 | 29,446,744 | 32.07 | 59.48 | 53.12 |
| 29,446,756 | 31.22 | 27.12 | 34.01 | 29,446,743 | 0.33 | 0.28 | 0.27 |

FIG. 6B

```
CAGCCTTCCC TGGCTCCCTC CCGATTTCCT CTCATGGCCA TTTCTTCTAA TAAAATCTGC AGACCATATT GGGTCTAATC CCATCTCCAG TCTGCTTCTT       100
CGAGGAACCA GACTAACATG ACTCTGCCCT ATATAATACA AATAATTATT TTCCATATAT CTGATTTTTA GCTTTGCATT TACTTTAAAT CATGCTTCAA       200
TTAAAGACAC ACCTTCTTTA ATGATTTTAT TAGTATTTCT AAGTATGATG AGGCCTCAGGG GAAAGGTTCA GAGCTCAGGG GAGGATATGG AGATCCAAGGG AGGCTTCCTG       300
TAGGCAGTGG CCTGTGTAGT GCTTCAAGGG CCAGGCTGCC AGCAAGCTGC GCAGCTGACC ACCCACCTGC AGTGTACCGC CGGAAGCACC AGGAGCTGCA       400
ACCCATGCAG ATGGAGCTGC AGACCCTGA GTACACGCTC AGCAAGCTCC GCACCTGCAC CATCATGCAC GACTACACTG CCAACTACTG CTTTGCTGGC       500
AAGACCTCCT CCATCAGTGA CCTGAAGGAG GTGCGCGGGA AAAAGATCAC CCTCATTCGG GGTCTGGGCC ATGGGCCTT TGGGAGGTG TATGAAGGCC       600
AGGTGTCCGG AATGCCCAAC GACCCAAGCC CCCTCCAAGT GGCTGTGAAG ACGGTGCGTC AAGTGTCGTC TGAACAGGAC GAACTGGATT TCCTCATGGA       700
AGCCCTGATC ATCAGCAAAT TCAACCACGA GAACATTGTT CGGTCCATTG GGGTGAGCCT GGGTGAGGCT GCAATCCCTG CCCCGGTTGA TCCTGCTGGA GCTCATGCCC       800
GGGGAGAGCC TCAAGTCCTT CCTCCGAGAG ACGGGCCCTC GCCGAGCCA CCGACACATT GCTCCAGAGA ACTACTCCAC GTGCCCATGC TGGACCTGCT GACCTGGCCT CGGGACATTG       900
CCTGTGGCTG TCAGTATTTG GAGGAAAACC ACTTCATCCA CCGAGACCC AGCTACTATA GAAAGGGAGG CTGTGCCATG GACCTTGTTT GACCTTGTCA GCCCTGGAA CAGTGCCAA       1000
GATTGGAGAC TTCGGGATGC CCCAGACAT CTACAGACCC AGTCACATGG CCTTCGATGT GATCTGGAGT GCTGCTATGG GAAATCTTTT CTCTGGATA TATGCCATAC CCCAGAGCC       1100
TTCATGGAAG GAATATTCAC TTCTAAAACA CACACATGGT CCTTGGAGT GCTGCTATGG CCCAAGAACC TGTGCTATGG ATAATGACTG AGTGCTGGCA       1200
CCAACCAGGA AGTGTCACCA TTTGTCACCA GTGGAGGCCG GATGGAGCCCG TGGACTTTTTG AGACGACCCG AATACTGCAC CCAGGACCCG GTTCCTCCTC TCAACAGGCA AAACGGGAGG       1300
ACATCAGGCT GAAGACAGCC CCAACTTTGC CATCATTTTG GAGAGGATTG GAGAGGATTC GCCCAAGGA GTGCCTGTGA GTTCCTCCTC TCAACAGGCA AAACGGGAGG       1400
TATGCTCCAA TTGTGGAAGA GGAAGAGAAA GTGCCTGTGA GCCCAAGGA GTTCCTCCTC AAGGCTGCAA AGAAACCCAC AGAAACCCAC AGTGCAGAG ATCTCTGTTC GAGTCCCTAC       1500
ACGAGCCAG CCCAGCTGCC CCACAGCTC TGCCCACTGC TATGGCATTC GGAGTTGCAC AAGGCTCCAC AAGGTCCACG GAGGTTGCAC AGAAGCAGGG GATCCAGAA CAAGCCACC       1600
AGGGGCCGGC GTGAAGCGGG GACAGACA GACAGACA GACAGACA GACAGACA CGAGTTGCAG GATCCAGAA GACAGACA GACAGACA GATCCAGAA CAAGCCACC       1700
AGCTGTGCCA ACCCACCTA CGGCTGGGTCG TTTACAGAGA AACCCACCAA AAGAATAAT CCTATAGCAA AGAAGCAGGG ACACGACAGG GGTAACCTGG       1800
GGCTGGAGGG AAGCTGTACT GTCCACCTA AGCTTGCAAC TGGGACACTT CCCGGCCCT CACTGCTTCT AGAGCCCTCT TGCCTGACTG CCAATATGAA       1900
CGAGGTAGCT CTGTGCAGG TACGTCACTT CCCTGTCACTT CCCTGTCACTT AATGTCAATT ACGGCTACCA GGAACAGGGC TGGCCTTAG AAGCGGTAC TGCCCTGA       2000
GCTGGTCATT ACGAGGATAC CATTCTGAAA AGGAAGAATA GCATCAACCA ACCAGAGACC GCCTGGGCGG TGAGCTGGGT CGCACACTA TGCCAACCTA CTTCCTTCC TTGGATCCC       2100
TAAGACCGTG GAGGAGAGAG AGGCAATGGC TCCTTCACAA TCCTTCACAA TCCTTCACAA TCCTTCACAA MATGTCACG TTTTGTTTTG CGCACACTGA TGCCAACCTA CCACCAAAAA       2200
AGCTGTATTT TGAAAATGCT TAGAAAGCT TTTTATCGA GGTTCATCCT ATTCTTCCTT AAGAAGAAAA TATCATAAAA ATGAGTAGATA AATACAAGC       2300
CCAGATGTGG TTGCATAAGC TTTTATGCA TGTTTGTTGT ATGCTTCCTT ATGCTTCCTT CAAATTGTCTGCT GTGCTCTGCT TCAATGTAGT CAGAATTAGC       2400
TCCTCTATG TTTCATATTG GGGCTGCAG ATGTTTCCTT GCCTGTCGTGA TGTGACATG AGCCATTTGA GGGAGAGGG AACGGAAATA AAGGAGTAT       2500
TGTAATGAC TAA [SEQ ID NO: 11]                                                                                                           2513
```

FIG. 6D

MQNELQSPEY KLSKLRTSTI MTDYNPNYCF AGKTSSISDL KEVPRKNITL IRGLGHGAFG EVYEGQVSGM PNDPSPLQVA VKTLPEVCSE QDELDFLMEA 100
LIISKFNHQN IVRCIGVSLQ SLPRETLLEL MAGGDLKSFL RETRPRPSQP SSLAMLDLLH VARDIACGCQ YLEENHFIHR DIAARNCLLT CPGPGRVAKI 200
GDFGMARDIY RASYYRKGGC AMLPVKWMPP EAFMEGIFTS KTDIWSFGVL LWEIFSLGYM PYPSKSNQEV LEFVTSGGRM DPPKNCPGPV YRIMTQCWQH 300
QPEDRPNFAI ILERIEYCTQ DPDVINTALP IEYGPLVEEE EKVPVRPKDP EGVPPLLVSQ QAKREEERSP AAPPPLPTTS SGKAAKKPTA AEISVRVPRG 400
PAVEGGHVNM AFSQSNPPSE LHKVHGSRNK PTSLWNPTYG SWFTEKPTKK NNPIAKKEPH DRGNLGLEGS CTVPPNVATG RLPGASLLLE PSSLTANMKE 500
VPLFRLRHFP CGNVNYGYQQ QGLPLEAIATA PGAGHYEDTI LKSKNSMNQP GP* [SEQ ID NO: 12] 552

FIG. 6E

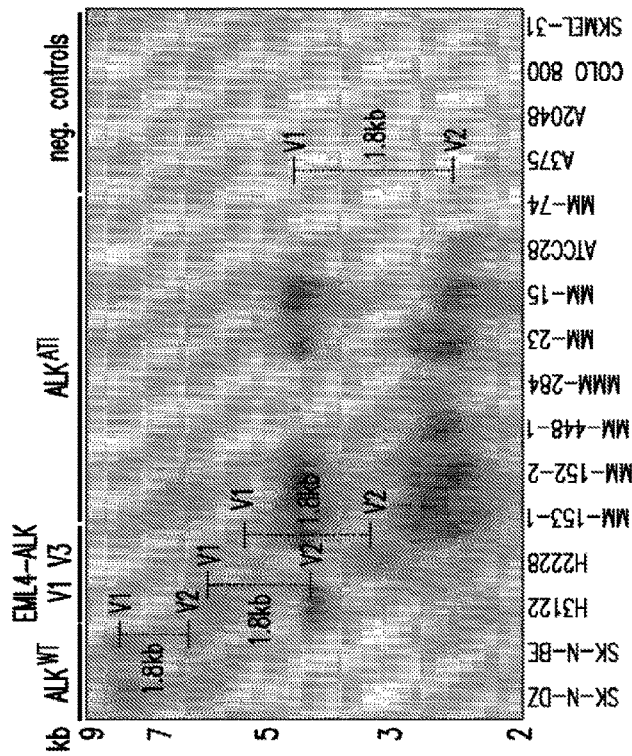

FIG. 6F

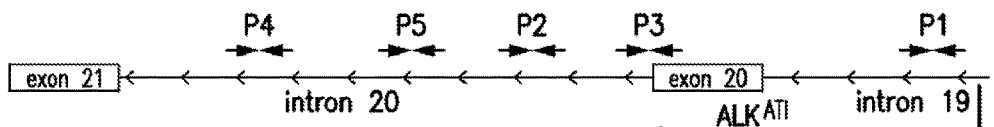
FIG. 7A
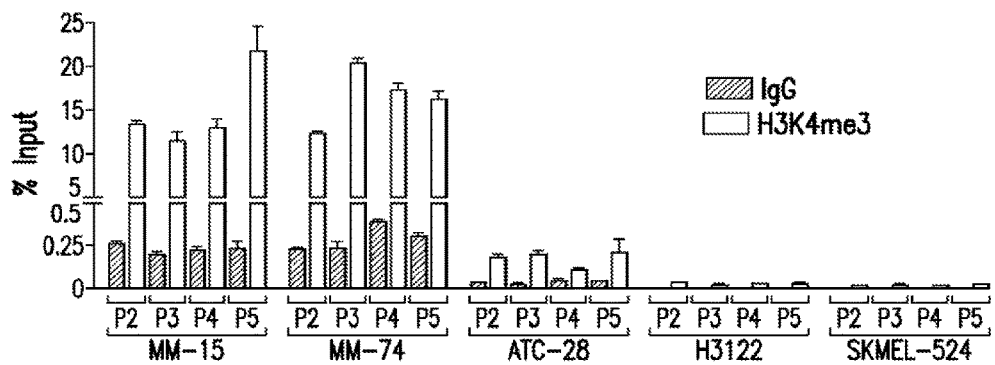
FIG. 7B
FIG. 7C
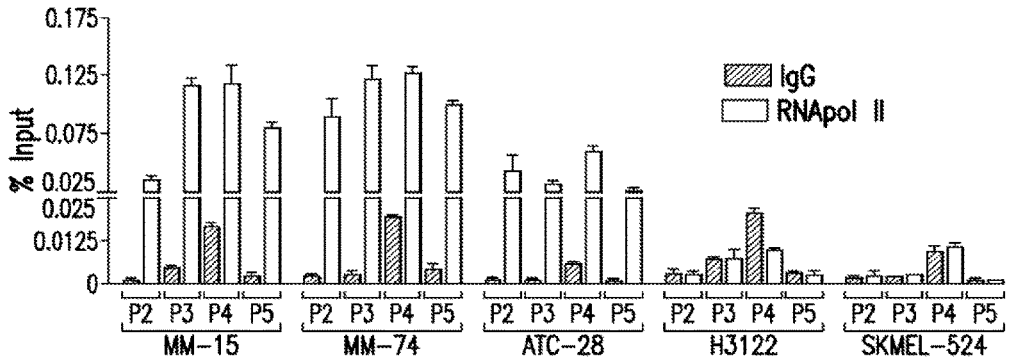
FIG. 7D

| Type | ALK$^{ATI}$ | Total # of cases | % |
|---|---|---|---|
| Skin cutaneous melanoma (SKCM) | 38 | 334 | 11.34 |
| Lung adenocarcinoma (LUAD) | 3 | 470 | 0.64 |
| Lung squamous cell carcinoma (LUSC) | 1 | 482 | 0.20 |
| Kidney renal clear cell carcinoma (KIRC) | 2 | 480 | 0.42 |
| Breast invasive carcinoma (BRCA) | 1 | 988 | 0.10 |
| Thyroid carcinoma (THCA) | 0 | 482 | 0.00 |
| Glioblastoma multiforme (GBM) | 0 | 153 | 0.00 |
| Brain lower grade glioma (LGG) | 0 | 271 | 0.00 |
| Bladder urothelial carcinoma (BLCA) | 0 | 182 | 0.00 |
| Prostate adenocarcinoma (PRAD) | 0 | 195 | 0.00 |
| Uterine corpus endometrial carcinoma (UCEC) | 0 | 118 | 0.00 |
| Kidney chromophobe (KICH) | 0 | 66 | 0.00 |
| Colorectal adenocarcinoma (COADREAD) | 0 | 316 | 0.00 |
| Ovarian carcinoma (OV) | 0 | 261 | 0.00 |
| Head and neck squamous cell carcinoma (HNSC) | 0 | 303 | 0.00 |

FIG. 8A

| # | Start Position | End Position | MM-15 | MM-74 | ATC-28 | Reference Allele | Tumor Allele | Frequency | Localization |
|---|---|---|---|---|---|---|---|---|---|
| 1 | 29,420,634 | 29,420,634 | | | X | T | - | 0.37 | Intron |
| 2 | 29,460,522 | 29,460,522 | X | | | G | A | 0.43 | Intron |
| 3 | 29,470,032 | 29,470,032 | | X | | T | - | 0.39 | Intron |
| 4 | 29,492,095 | 29,492,095 | | | X | G | A | 0.26 | Intron |
| 5 | 29,499,955 | 29,499,955 | | | X | C | T | 0.45 | Intron |
| 6 | 29,519,637 | 29,519,637 | | | X | G | A | 0.44 | Intron |
| 7 | 29,537,765 | 29,537,765 | | | X | C | A | 0.74 | Intron |
| 8 | 29,566,924 | 29,566,924 | X | | | C | T | 0.57 | Intron |
| 9 | 29,567,833 | 29,567,833 | | | X | G | A | 0.46 | Intron |
| 10 | 29,587,837 | 29,587,837 | | X | | G | C | 0.47 | Intron |
| 11 | 29,604,104 | 29,604,104 | | | X | G | A | 0.45 | Intron |
| 12 | 29,624,468 | 29,624,468 | X | | | G | A | 0.56 | Intron |
| 13 | 29,642,007 | 29,642,007 | | | X | G | A | 0.69 | Intron |
| 14 | 29,661,584 | 29,661,584 | X | | | C | T | 0.12 | Intron |
| 15 | 29,677,601 | 29,677,601 | X | | | T | G | 0.55 | Intron |
| 16 | 29,679,303 | 29,679,303 | X | | | T | C | 0.58 | Intron |
| 17 | 29,684,682 | 29,684,682 | X | | | G | A | 0.41 | Intron |
| 18 | 29,690,777 | 29,690,778 | X | | | AT | - | 0.33 | Intron |
| 19 | 29,709,870 | 29,709,870 | X | | | T | C | 0.41 | Intron |
| 20 | 29,726,177 | 29,726,177 | X | | | T | G | 0.57 | Intron |
| 21 | 29,750,006 | 29,750,006 | | | X | T | C | 0.38 | Intron |
| 22 | 29,758,564 | 29,758,564 | | | | C | T | 0.44 | Intron |
| 23 | 29,761,096 | 29,761,096 | X | | | G | T | 0.42 | Intron |
| 24 | 29,764,306 | 29,764,306 | | | X | A | T | 0.28 | Intron |
| 25 | 29,770,527 | 29,770,527 | | | X | C | T | 0.26 | Intron |
| 26 | 29,804,173 | 29,804,173 | | | X | G | A | 0.74 | Intron |

| # | Start | End | | | | B1 | B2 | Val | Region |
|---|---|---|---|---|---|---|---|---|---|
| 27 | 29,819,803 | 29,819,803 | x |   |   |   | A | 0.39 | Intron |
| 28 | 29,857,339 | 29,857,340 | x |   |   | , | A | 0.45 | Intron |
| 29 | 29,863,910 | 29,863,910 |   |   |   | A | C | 0.49 | Intron |
| 30 | 29,867,114 | 29,867,114 | x |   |   | C | T | 0.1 | Intron |
| 31 | 29,874,965 | 29,874,965 |   | x |   | T | G | 0.42 | Intron |
| 32 | 29,878,627 | 29,878,627 |   |   |   | C | C | 0.41 | Intron |
| 33 | 29,879,612 | 29,879,612 |   | x |   | T | , | 0.42 | Intron |
| 34 | 29,879,617 | 29,879,617 |   | x x |   | G | G | 0.46 | Intron |
| 35 | 29,885,468 | 29,885,468 |   |   |   | T | A | 0.27 | Intron |
| 36 | 29,887,819 | 29,887,819 | x |   | x | G | C | 0.41 | Intron |
| 37 | 29,891,658 | 29,891,658 |   |   |   | T | C | 0.22 | Intron |
| 38 | 29,897,910 | 29,897,910 |   |   | x x | T | C | 0.59 | Intron |
| 39 | 29,915,442 | 29,915,442 |   | x |   | G | A | 0.51 | Intron |
| 40 | 29,953,528 | 29,953,528 |   |   |   | T | C | 0.71 | Intron |
| 41 | 29,961,164 | 29,961,164 |   |   |   | T | C | 0.27 | Intron |
| 42 | 29,972,014 | 29,972,014 | x x |   | x x x | C | C | 0.46 | Intron |
| 43 | 29,978,898 | 29,978,898 |   |   |   | G | T | 0.42 | Intron |
| 44 | 29,985,171 | 29,985,171 |   |   |   | C | A | 0.41 | Intron |
| 45 | 29,994,457 | 29,994,457 |   | x |   | G | T | 0.5 | Intron |
| 46 | 30,004,526 | 30,004,527 |   |   | x | TG | A | 0.61 | Intron |
| 47 | 30,033,145 | 30,033,145 |   | x x x |   | G | , | 0.48 | Intron |
| 48 | 30,044,269 | 30,044,269 |   | x x x |   | C | A | 0.42 | Intron |
| 49 | 30,044,579 | 30,044,579 |   | x |   | T | T | 0.47 | Intron |
| 50 | 30,070,597 | 30,070,597 | x |   |   | T | G | 0.61 | Intron |
| 51 | 30,075,004 | 30,075,004 |   |   | x | G | C | 0.4 | Intron |
| 52 | 30,096,355 | 30,096,355 | x |   |   | C | A | 0.46 | Intron |
| 53 | 30,100,743 | 30,100,743 |   |   |   | T | T | 0.54 | Intron |
| 54 | 30,102,577 | 30,102,577 | x |   |   | G | G | 0.47 | Intron |
| 55 | 30,112,153 | 30,112,153 | x |   |   | C | A | 0.41 | Intron |
| 56 | 30,146,896 | 30,146,896 |   |   |   | T | C | 0.41 | 5'Flank |

| Transcription Factor | Motif Start Position from Chr2:29,445,000 | Motif Stop Position from Chr2:29,445,000 | Score | p-value | q-value | Matched_Sequence |
|---|---|---|---|---|---|---|
| AR | 1339 | 1325 | 11.948 | 4.47E-05 | 0.18 | GAGTACAAGCTGAGC |
| Bach1::Mafk | 1653 | 1639 | 10.8694 | 1.86E-05 | 0.073 | AACATGACTCTGCCC |
| Bach1::Mafk | 1653 | 1639 | 10.8694 | 1.86E-05 | 0.073 | AACATGACTCTGCCC |
| Bach1::Mafk | 521 | 535 | 8.6477 | 4.32E-05 | 0.085 | ATAATGAGGCAGCTG |
| Bach1::Mafk | 521 | 535 | 8.6477 | 4.32E-05 | 0.085 | ATAATGAGGCAGCTG |
| BHLHE40 | 1800 | 1810 | 11.3822 | 7.93E-05 | 0.325 | CCCACGTGAAC |
| BRCA1 | 110 | 116 | 9.01131 | 6.51E-05 | 0.258 | ACAACAC |
| CTCF | 1250 | 1232 | 13.6407 | 7.73E-06 | 0.031 | TGACCTGAAGGAGGTGCCG |
| CTCF | 91 | 73 | 9.20027 | 6.33E-05 | 0.127 | TCTCCAGTAGGAGACTCCC |
| Ddit3::Cebpa | 1988 | 1999 | 12.5036 | 2.87E-05 | 0.12 | CAGTGCAATCAC |
| Ddit3::Cebpa | 1988 | 1999 | 12.5036 | 2.87E-05 | 0.12 | CAGTGCAATCAC |
| Ddit3::Cebpa | 1988 | 1999 | 12.5036 | 2.87E-05 | 0.12 | CAGTGCAATCAC |
| Ddit3::Cebpa | 629 | 640 | 11.3202 | 6.55E-05 | 0.137 | CTATGCAATCTC |
| Ddit3::Cebpa | 629 | 640 | 11.3202 | 6.55E-05 | 0.137 | CTATGCAATCTC |
| Ddit3::Cebpa | 629 | 640 | 11.3202 | 6.55E-05 | 0.137 | CTATGCAATCTC |
| E2F3 | 1825 | 1811 | 15.6755 | 3.89E-06 | 0.0142 | TTCCCTCCCTCCCTC |
| E2F3 | 1821 | 1807 | 14.0027 | 1.14E-05 | 0.0208 | CTCCCTCCCTCGTTC |
| E2F3 | 933 | 919 | 12.1626 | 2.84E-05 | 0.0344 | TTCCCTCCAGGGGAG |
| E2F3 | 1817 | 1803 | 10.9916 | 4.48E-05 | 0.0408 | CTCCCTCGTTCACGT |
| E2F3 | 1754 | 1740 | 10.3225 | 5.62E-05 | 0.0409 | CTCCCTCCCCATTTC |
| E2F6 | 1817 | 1827 | 15.5096 | 3.49E-06 | 0.0105 | GGGAGGGAAGG |
| E2F6 | 1813 | 1823 | 15.1708 | 5.28E-06 | 0.0105 | GGGAGGGAGGG |
| E2F6 | 925 | 935 | 13.6464 | 1.82E-05 | 0.0208 | TGGAGGGAAGG |
| E2F6 | 1746 | 1756 | 13.477 | 2.08E-05 | 0.0208 | GGGAGGGAGCC |

FIG. 11H

| | | | | | |
|---|---|---|---|---|---|
| E2F6 | 1809 | 1819 | 11.9525 | 5.00E-05 | 0.0399 | ACGAGGGAGGG |
| EBF1 | 931 | 921 | 13.3621 | 2.20E-05 | 0.081 | CCCTCCAGGGG |
| EBF1 | 1495 | 1505 | 11.7176 | 5.46E-05 | 0.081 | CTCCCCTGAGC |
| EBF1 | 816 | 806 | 11.512 | 6.07E-05 | 0.081 | CTCCCCAAGGA |
| EBF1 | 1739 | 1729 | 10.4842 | 9.12E-05 | 0.0913 | CTCTCATGGGC |
| EGR1 | 312 | 299 | 15.5788 | 4.20E-06 | 0.0169 | CCTCCTCCTCTCC |
| EGR1 | 315 | 302 | 13.097 | 1.97E-05 | 0.0396 | CAGCCTCCTCTCC |
| EGR1 | 801 | 788 | 11.1879 | 5.35E-05 | 0.0717 | GAACCTCCCCGGG |
| EGR1 | 297 | 284 | 10.2334 | 8.31E-05 | 0.0728 | CACCCTCCCTTCT |
| EGR1 | 411 | 398 | 10.0425 | 9.05E-05 | 0.0728 | CCCAAGCCCCTGC |
| EGR2 | 312 | 298 | 10.2839 | 7.97E-05 | 0.315 | CCTCCTCCTCTCC |
| EHF | 873 | 866 | 14.3145 | 2.41E-05 | 0.0972 | CCTTCCTC |
| ELK1 | 1391 | 1382 | 12.6123 | 1.09E-05 | 0.0454 | CCGCCGGAAG |
| ELK4 | 1379 | 1389 | 14.1514 | 1.08E-05 | 0.0433 | GTGCTTCCGGC |
| Erg | 1736 | 1746 | 13.8707 | 1.48E-05 | 0.0606 | AGAGGAAATGG |
| Erg | 1736 | 1746 | 13.8707 | 1.48E-05 | 0.0606 | AGAGGAAATGG |
| Erg | 1736 | 1746 | 13.8707 | 1.48E-05 | 0.0606 | AGAGGAAATGG |
| Erg | 1736 | 1746 | 13.8707 | 1.48E-05 | 0.0606 | AGAGGAAATGG |
| Erg | 865 | 875 | 11.9167 | 5.42E-05 | 0.1 | AGAGGAAGGCG |
| Erg | 1467 | 1477 | 11.3306 | 7.32E-05 | 0.1 | ACAGGAAGCCT |
| Erg | 865 | 875 | 11.9167 | 5.42E-05 | 0.1 | AGAGGAAGGCG |
| Erg | 1467 | 1477 | 11.3306 | 7.32E-05 | 0.1 | ACAGGAAGCCT |
| Erg | 865 | 875 | 11.9167 | 5.42E-05 | 0.1 | AGAGGAAGGCG |
| Erg | 1467 | 1477 | 11.3306 | 7.32E-05 | 0.1 | ACAGGAAGCCT |
| Erg | 865 | 875 | 11.9167 | 5.42E-05 | 0.1 | AGAGGAAGGCG |
| Erg | 1467 | 1477 | 11.3306 | 7.32E-05 | 0.1 | ACAGGAAGCCT |
| ESR1 | 1421 | 1440 | 11.205 | 4.17E-05 | 0.119 | ATGGCCTGGCAGCCTGGCCC |

FIG. 11H (Continued)

| | | | | | |
|---|---|---|---|---|---|
| ESR1 | 449 | 468 | 10.5073 | 6.31E-05 | 0.119 | CCCCAAAGGGGCCATGGCCC |
| ESR1 | 1780 | 1761 | 9.80968 | 9.43E-05 | 0.119 | CTGCTGGTTCACCCAGCCTT |
| ESR2 | 183 | 197 | 10.5306 | 6.49E-05 | 0.265 | GGGTGAGGGTGTCTC |
| ESRRA | 350 | 360 | 13.5237 | 1.38E-05 | 0.0552 | CCAAGGGCAGG |
| Esrrb | 347 | 358 | 12.2027 | 3.32E-05 | 0.132 | AAGCCAAGGGCA |
| Ets1 | 1747 | 1733 | 14.2216 | 8.55E-06 | 0.0347 | CCCATTTCCTCTCAT |
| Ets1 | 876 | 862 | 11.7651 | 4.44E-05 | 0.0861 | GCGCCTTCCTCTGTC |
| Ets1 | 1487 | 1501 | 11.11 | 6.37E-05 | 0.0861 | TCCATATCCTCCCCT |
| FLI1 | 1736 | 1746 | 12.5362 | 3.03E-05 | 0.104 | AGAGGAAATGG |
| FLI1 | 1389 | 1379 | 11.6687 | 5.18E-05 | 0.104 | GCCGGAAGCAC |
| FLI1 | 1467 | 1477 | 10.9747 | 7.76E-05 | 0.104 | ACAGGAAGCCT |
| Foxd3 | 707 | 718 | 13.6322 | 1.31E-05 | 0.0525 | AAATGTTTATTC |
| Foxd3 | 1048 | 1037 | 12.8787 | 2.51E-05 | 0.0525 | GTATGTTGGCTT |
| FOXH1 | 2013 | 2003 | 11.2367 | 7.28E-05 | 0.304 | TCAAATCGACT |
| Foxq1 | 707 | 717 | 14.3755 | 8.64E-06 | 0.0361 | AAATGTTTATT |
| Foxq1 | 1025 | 1015 | 12.1488 | 4.63E-05 | 0.0967 | CATAGTTTATG |
| GABPA | 1388 | 1378 | 14.2072 | 1.10E-05 | 0.0431 | CCGGAAGCACC |
| GATA2 | 1159 | 1146 | 12.6573 | 3.33E-05 | 0.139 | TGAATGTTATCACA |
| Gfi1 | 1992 | 2001 | 11.6665 | 3.64E-05 | 0.152 | GCAATCACAG |
| HNF4G | 916 | 902 | 12.5633 | 2.18E-05 | 0.0881 | GGGGAGCAAAGGGCC |
| HNF4G | 1515 | 1501 | 11.0704 | 5.34E-05 | 0.108 | AAGGTTCAGAGAGCTCA |
| HSF1 | 68 | 54 | 13.1771 | 1.48E-05 | 0.0577 | ATTCTAGACACTTCT |
| INSM1 | 396 | 407 | 12.5085 | 2.34E-05 | 0.0938 | TTGCAGGGGGCT |
| Klf4 | 292 | 301 | 12.5704 | 2.59E-05 | 0.1 | AGGGTGGGGA |
| KLF5 | 301 | 292 | 14.1793 | 1.36E-05 | 0.0522 | TCCCCACCCT |
| KLF5 | 1754 | 1745 | 11.1006 | 7.53E-05 | 0.0522 | CTCCCTCCCC |
| KLF5 | 306 | 297 | 10.9081 | 8.33E-05 | 0.0522 | CCTCCTCCCC |

FIG. 11H (Continued)

| | | | | | |
|---|---|---|---|---|---|
| KLF5 | 904 | 895 | 10.9081 | 8.33E-05 | 0.0522 | GCCCCTCCTC |
| KLF5 | 191 | 182 | 10.5233 | 9.29E-05 | 0.0522 | CCCTCACCCC |
| KLF5 | 1821 | 1812 | 10.5233 | 9.29E-05 | 0.0522 | CTCCCTCCCT |
| KLF5 | 1825 | 1816 | 10.5233 | 9.29E-05 | 0.0522 | TTCCCTCCCT |
| Meis1 | 868 | 854 | 12.0071 | 4.41E-05 | 0.131 | CTCTGTCACTCACTG |
| Meis1 | 824 | 810 | 11.3328 | 6.42E-05 | 0.131 | ATCTGTCTCCCCA |
| Myb | 536 | 527 | 10.9878 | 7.98E-05 | 0.33 | CCAGCTGCCT |
| MYCN | 1800 | 1807 | 12.8822 | 3.18E-05 | 0.124 | CCCACGTG |
| NFATC2 | 1619 | 1613 | 12.1547 | 7.93E-05 | 0.33 | TTTTCCA |
| NFE2::MAF | 1650 | 1636 | 11.9662 | 1.81E-05 | 0.0754 | ATGACTCTGCCCTAT |
| Nfe2l2 | 1654 | 1640 | 12.005 | 2.53E-05 | 0.105 | TAACATGACTCTGCC |
| Nfe2l2 | 1765 | 1779 | 9.60768 | 7.83E-05 | 0.163 | CTGGGTGAACCAGCA |
| NFKB1 | 779 | 789 | 11.7116 | 4.50E-05 | 0.182 | TGGCTTTTCCC |
| NHLH1 | 527 | 538 | 11.731 | 3.33E-05 | 0.0565 | AGGCAGCTGGGG |
| NHLH1 | 884 | 873 | 11.3939 | 3.88E-05 | 0.0565 | GAGCAACTGCGC |
| NHLH1 | 2027 | 2016 | 11.1691 | 4.31E-05 | 0.0565 | TCCCAGCTGCAC |
| Nkx2-5 | 147 | 157 | 12.7707 | 3.59E-05 | 0.146 | AAGCTCTCCAG |
| Nkx2-5 | 1564 | 1570 | 9.93746 | 9.66E-05 | 0.405 | TTAATTG |
| NKX3-1 | 1522 | 1528 | 12.2428 | 9.66E-05 | 0.405 | ATACTTA |
| NR1H2::RXRA | 1515 | 1499 | 0.20754 | 1.66E-05 | 0.0692 | AAGGTTCAGAGCTCAGG |
| NR2C2 | 164 | 178 | 15.4648 | 3.28E-06 | 0.013 | TGGGGCAGAGGGGA |
| NR2F1 | 1501 | 1514 | 10.4372 | 5.44E-05 | 0.224 | TGAGCTCTGAACCT |
| Nr5a2 | 346 | 360 | 11.4456 | 4.03E-05 | 0.163 | CAAGCCAAGGGCAGG |
| Nr5a2 | 1058 | 1072 | 9.49644 | 9.70E-05 | 0.196 | AATGTCAAGGCTTGT |
| Pax6 | 1579 | 1566 | 12.0533 | 2.99E-05 | 0.0995 | ATCATGCTTCAATT |
| Pax6 | 1568 | 1581 | 11.2937 | 4.77E-05 | 0.0995 | TTGAAGCATGATTT |
| PLAG1 | 1081 | 1094 | 13.5435 | 3.77E-06 | 0.0143 | GAGGGCTAGGGGTG |

FIG. 11H (Continued)

| | | | | | |
|---|---|---|---|---|---|
| PLAG1 | 165 | 178 | 10.155 | 1.37E-05 | 0.0239 | GGGGGCAGAGGGGA |
| PLAG1 | 1875 | 1888 | 9.2837 | 1.89E-05 | 0.0239 | AAGGCCCTAAGGGG |
| PLAG1 | 164 | 177 | 4.83031 | 8.41E-05 | 0.0796 | TGGGGGCAGAGGGG |
| PPARG::RXRA | 164 | 178 | 14.69 | 3.84E-06 | 0.0152 | TGGGGGCAGAGGGGA |
| PPARG::RXRA | 164 | 178 | 14.69 | 3.84E-06 | 0.0152 | TGGGGGCAGAGGGGA |
| PPARG::RXRA | 916 | 902 | 13.1479 | 1.33E-05 | 0.0227 | GGGGAGCAAAGGGCC |
| PPARG::RXRA | 85 | 99 | 12.8052 | 1.72E-05 | 0.0227 | CTGGAGAAAAGGGGA |
| PPARG::RXRA | 916 | 902 | 13.1479 | 1.33E-05 | 0.0227 | GGGGAGCAAAGGGCC |
| PPARG::RXRA | 85 | 99 | 12.8052 | 1.72E-05 | 0.0227 | CTGGAGAAAAGGGGA |
| REL | 416 | 425 | 12.7526 | 2.27E-05 | 0.095 | TGGGCATTCC |
| RELA | 242 | 233 | 11.0708 | 5.10E-05 | 0.125 | CTGGATTTCC |
| RELA | 416 | 425 | 10.2963 | 6.12E-05 | 0.125 | TGGGCATTCC |
| RFX5 | 1857 | 1843 | 12.8927 | 2.23E-05 | 0.089 | CTCCATGGCACCCAG |
| RREB1 | 190 | 171 | 4.46988 | 5.78E-05 | 0.152 | CCTCACCCCAACTCCCTCT |
| RREB1 | 193 | 174 | 3.48298 | 7.81E-05 | 0.152 | CACCCTCACCCAACTCCCC |
| RUNX1 | 197 | 207 | 13.6666 | 8.73E-06 | 0.0176 | CTCTGTGGCTT |
| RUNX1 | 2076 | 2066 | 13.6637 | 8.73E-06 | 0.0176 | CTCTGTGGCTT |
| RUNX1 | 1119 | 1129 | 11.3637 | 6.81E-05 | 0.0916 | TTTTGTGGCTA |
| RUNX2 | 194 | 208 | 13.094 | 2.25E-05 | 0.0918 | TCTCTCTGTGGCTTT |
| RUNX2 | 2079 | 2065 | 11.2266 | 6.84E-05 | 0.101 | CAACTCTGTGGCTTG |
| RUNX2 | 1116 | 1130 | 11.0709 | 7.41E-05 | 0.101 | GCCTTTTGTGGCTAG |
| Rxra | 350 | 360 | 11.1142 | 7.78E-05 | 0.19 | CCAAGGGCAGG |
| Rxra | 1443 | 1433 | 10.7563 | 9.48E-05 | 0.19 | CAAGGGCCAGG |
| RXRA::VDR | 1022 | 1008 | 11.7512 | 8.50E-06 | 0.0355 | AGTTTATGGAGTTTA |
| SMAD2::SMAD3::SMAD4 | 822 | 810 | 11.2364 | 5.20E-05 | 0.108 | CTGTCTCTCCCCA |

FIG. 11H (Continued)

| | | | | | |
|---|---|---|---|---|---|
| SMAD2::SMAD3::SMAD4 | 1758 | 1746 | 11.0832 | 5.66E-05 | 0.108 | CTGGCTCCCTCCC |
| SMAD2::SMAD3::SMAD4 | 822 | 810 | 11.2364 | 5.20E-05 | 0.108 | CTGTCTCTCCCCA |
| SMAD2::SMAD3::SMAD4 | 1758 | 1746 | 11.0832 | 5.66E-05 | 0.108 | CTGGCTCCCTCCC |
| SMAD2::SMAD3::SMAD4 | 822 | 810 | 11.2364 | 5.20E-05 | 0.108 | CTGTCTCTCCCCA |
| SMAD2::SMAD3::SMAD4 | 1758 | 1746 | 11.0832 | 5.66E-05 | 0.108 | CTGGCTCCCTCCC |
| Sox17 | 705 | 697 | 11.9846 | 4.55E-05 | 0.191 | ACCATTGTC |
| Sox2 | 704 | 697 | 13.0228 | 6.51E-05 | 0.272 | CCATTGTC |
| SP2 | 587 | 573 | 14.5465 | 6.55E-06 | 0.0145 | CCCCGCCTCTCGTG |
| SP2 | 312 | 298 | 13.735 | 1.12E-05 | 0.0145 | CCTCCTCCTCCTCCC |
| SP2 | 904 | 890 | 13.735 | 1.12E-05 | 0.0145 | GCCCCTCCTCTGAGC |
| SP2 | 301 | 287 | 12.9236 | 1.84E-05 | 0.0179 | TCCCCACCCTCCCCT |
| SP2 | 1825 | 1811 | 12.4367 | 2.42E-05 | 0.0189 | TTCCTCCTCCTCGTC |
| SP2 | 309 | 295 | 11.7876 | 3.43E-05 | 0.0223 | CCTCCTCCTCCCCAC |
| SP2 | 1821 | 1807 | 10.6515 | 5.99E-05 | 0.0333 | CTCCCTCCCTCGTTC |
| SP2 | 1754 | 1740 | 10.327 | 6.94E-05 | 0.0334 | CTCCCTCCCCATTTC |
| SP2 | 306 | 292 | 10.0024 | 8.01E-05 | 0.0334 | CCTCCTCCCCACCCT |
| SP2 | 297 | 283 | 9.84008 | 8.59E-05 | 0.0334 | CACCCTCCCCTTCTC |
| Sp1 | 1732 | 1746 | 12.0562 | 3.40E-05 | 0.135 | CATGAGAGGAAATGG |
| Spi1 | 861 | 875 | 10.7681 | 6.97E-05 | 0.138 | TGACAGAGGAGGCG |
| SPIB | 865 | 871 | 11.288 | 6.51E-05 | 0.136 | AGAGGAA |
| SPIB | 1736 | 1742 | 11.288 | 6.51E-05 | 0.136 | AGAGGAA |
| SREBF1 | 324 | 315 | 11.2408 | 7.58E-05 | 0.3 | CTCAGCTCAC |
| SRF | 1690 | 1707 | 9.62959 | 8.57E-05 | 0.357 | TTAGACCCAATATGGTCT |

FIG. 11H (Continued)

| | | | | | |
|---|---|---|---|---|---|
| Stat5a::Stat5b | 1926 | 1936 | 11.5378 | 7.54E-05 | 0.204 | ACTCCCAGGAA |
| Stat5a::Stat5b | 1533 | 1523 | 10.9522 | 9.89E-05 | 0.204 | ATTTCTAAGTA |
| Stat5a::Stat5b | 1926 | 1936 | 11.5378 | 7.54E-05 | 0.204 | ACTCCCAGGAA |
| Stat5a::Stat5b | 1533 | 1523 | 10.9522 | 9.89E-05 | 0.204 | ATTTCTAAGTA |
| Stat5a::Stat5b | 1926 | 1936 | 11.5378 | 7.54E-05 | 0.204 | ACTCCCAGGAA |
| Stat5a::Stat5b | 1533 | 1523 | 10.9522 | 9.89E-05 | 0.204 | ATTTCTAAGTA |
| TAL1::GATA1 | 1154 | 1137 | 15.2089 | 4.32E-06 | 0.018 | GTTATCACAGCACCGCAG |
| TAL1::GATA1 | 633 | 650 | 9.8736 | 9.93E-05 | 0.207 | GCAATCTCGGGCTTCCAG |
| Tcfl2 | 528 | 538 | 14.8249 | 1.10E-05 | 0.0434 | GGCAGCTGGGG |
| Tcf3 | 2026 | 2016 | 16.394 | 1.17E-06 | 0.00455 | CCCAGCTGCAC |
| Tcf3 | 537 | 527 | 15.8065 | 3.64E-06 | 0.006 | CCCAGCTGCCT |
| Tcf3 | 1406 | 1396 | 15.4148 | 4.63E-06 | 0.006 | CCCACCTGCAG |
| Tcf3 | 427 | 437 | 11.302 | 8.89E-05 | 0.0691 | GACACCTGGCC |
| Tcf3 | 1409 | 1419 | 11.302 | 8.89E-05 | 0.0691 | GTCAGCTGCAA |
| TEAD1 | 875 | 864 | 8.21141 | 9.73E-05 | 0.402 | CGCCTTCCTCTG |
| TFAP2A | 799 | 785 | 11.5594 | 4.54E-05 | 0.17 | ACCTCCCCGGGAA |
| TFAP2A | 1107 | 1093 | 10.3116 | 8.93E-05 | 0.17 | CCCTCCCTATGGGCA |
| TFAP2C | 799 | 785 | 12.3611 | 3.43E-05 | 0.0663 | ACCTCCCCGGGAA |
| TFAP2C | 934 | 920 | 12.3611 | 3.43E-05 | 0.0663 | CTTCCCTCCAGGGGA |
| THAP1 | 283 | 275 | 10.2961 | 5.25E-05 | 0.162 | CTGCCCAGA |
| THAP1 | 172 | 164 | 9.90304 | 7.89E-05 | 0.162 | CTGCCCCCA |
| TLX1::NFIC | 2066 | 2053 | 8.9703 | 2.09E-05 | 0.0825 | TGGCAGTTCTCCAA |
| TLX1::NFIC | 2090 | 2077 | 5.9266 | 6.13E-05 | 0.121 | TGGCTCTTCTCCAA |
| TP53 | 1072 | 1058 | 8.41515 | 8.75E-05 | 0.365 | ACAAGCCTTGACATT |
| USF1 | 436 | 426 | 10.3469 | 9.56E-05 | 0.399 | GCCAGGTGTCC |
| YY1 | 616 | 627 | 11.4769 | 4.22E-05 | 0.125 | CAACATGGCTTT |
| YY1 | 1417 | 1428 | 10.7443 | 5.97E-05 | 0.125 | CAACATGGCCTG |

FIG. 11H (Continued)

| | | | | | |
|---|---|---|---|---|---|
| ZEB1 | 653 | 661 | 12.939 | 3.41E-05 | 0.0974 | CTTCACCTG |
| ZEB1 | 1407 | 1399 | 12.4199 | 4.84E-05 | 0.0974 | ACCCACCTG |
| znf143 | 1774 | 1755 | 14.312 | 6.38E-06 | 0.0248 | GTTCACCCAGCCTTCCCTGG |
| znf143 | 304 | 285 | 10.8665 | 3.08E-05 | 0.0566 | TCCTCCCCACCCTCCCCTTC |
| znf143 | 1852 | 1833 | 9.98301 | 4.38E-05 | 0.0566 | TGGCACCCAGGGTGCTTCCA |
| znf143 | 908 | 927 | 8.74616 | 7.03E-05 | 0.0623 | TTGCTCCCTGCTCCCCTGG |
| znf143 | 1765 | 1746 | 8.39278 | 8.03E-05 | 0.0623 | GCCTTCCCTGGCTCCCTCC |
| ZNF263 | 287 | 307 | 22.9123 | 6.75E-09 | 2.70E-05 | AGGGGAGGGGTGGGGAGGAGGA |
| ZNF263 | 299 | 319 | 19.6374 | 1.25E-07 | 0.00025 | GGAGGGAGGAGGAGGCTGTGAG |
| ZNF263 | 290 | 310 | 18.0963 | 4.13E-07 | 0.000551 | GGAGGGTGGGGAGGAGGAGGA |
| ZNF263 | 282 | 302 | 17.3258 | 7.24E-07 | 0.00058 | AGAGAAGGGGAGGGTGGGGAG |
| ZNF263 | 1811 | 1831 | 17.3258 | 7.24E-07 | 0.00058 | GAGGGAGGAGGAGGAAGGTTGG |
| ZNF263 | 291 | 311 | 14.0509 | 6.31E-06 | 0.00421 | GAGGGTGGGGAGGAGGAGGAG |
| ZNF263 | 1744 | 1764 | 13.473 | 8.94E-06 | 0.00511 | TGGGGAGGGAGCCAGGAAGG |
| ZNF263 | 293 | 313 | 13.0877 | 1.12E-05 | 0.00558 | GGGTGGGGAGGAGGGAGGAGGC |
| ZNF263 | 1815 | 1835 | 12.8951 | 1.25E-05 | 0.00558 | GAGGGAGGGAAGGGGTGGGTGG |
| ZNF263 | 166 | 186 | 12.1245 | 1.94E-05 | 0.00707 | GGGGCAGAGGGGAGTGCAGTGT |
| ZNF263 | 1185 | 1165 | 12.1245 | 1.94E-05 | 0.00707 | GAGGGAAGGTTGGGTGGAAGC |
| ZNF263 | 1819 | 1839 | 11.7392 | 2.40E-05 | 0.00801 | GGGGCAGGGGAGCAAGGGGG |
| ZNF263 | 165 | 185 | 11.5466 | 2.67E-05 | 0.00821 | GGAGCAGGGAGCAAGGGCC |
| ZNF263 | 922 | 902 | 11.1613 | 3.28E-05 | 0.00909 | AGAAGGGGGTGGGGAGGA |
| ZNF263 | 284 | 304 | 10.9687 | 3.63E-05 | 0.00909 | AAAGGAAGAACAAGAGGAGA |
| ZNF263 | 481 | 501 | 10.9687 | 3.63E-05 | 0.00909 | GAGGGAAGGGGAGCCAGGTAG |
| ZNF263 | 927 | 947 | 10.7761 | 4.02E-05 | 0.00947 | GAAGAGGTGCCGCGGAAAAA |
| ZNF263 | 1244 | 1224 | 10.1981 | 5.41E-05 | 0.012 | CGTGAACGAGGGAGGGAGGGA |
| ZNF263 | 1804 | 1824 | 10.0055 | 5.97E-05 | 0.0126 | TGGGCAGAGAAGGGGAGGGTG |
| ZNF263 | 277 | 297 | 9.81286 | 6.58E-05 | 0.0132 | |

FIG. 11H (Continued)

| ZNF263 | 285 | 305 | 9.62022 | 7.24E-05 | 0.0138 | GAAGGGGAGGGTGGGAGGAG |
| ZNF263 | 281 | 301 | 9.23494 | 8.74E-05 | 0.0152 | CAGAGAAGGGGAGGGTGGGGA |
| ZNF263 | 302 | 322 | 9.23494 | 8.74E-05 | 0.0152 | GGAGGAGGAGGCTGTGAGCTG |
| ZNF263 | 928 | 948 | 9.0423 | 9.60E-05 | 0.0154 | AGGGAAGGGGAGCCAGGTAGA |
| ZNF263 | 1736 | 1756 | 9.0423 | 9.60E-05 | 0.0154 | AGAGGAAATGGGGAGGGAGCC |

FIG. 11H (Continued)

ISOFORM OF ANAPLASTIC LYMPHOMA KINASE AND ITS USES

CROSS-REFERENCE TO RELATED APPLICATIONS

This application is a continuation of PCT International Patent Application No. PCT/US2015/025289, filed on Apr. 10, 2015, which claims the benefit of U.S. Provisional Patent Application Ser. No. 61/978,106 filed Apr. 10, 2014, the contents of each of which are hereby incorporated by reference in their entirety herein, and to each of which priority is claimed.

GRANT INFORMATION

This invention was made with government support under grant number CA174499 awarded by the National Institutes of Health. The government has certain rights in the invention.

SEQUENCE LISTING

The specification further incorporates by reference the Sequence Listing submitted herewith via EFS on Oct. 7, 2016. Pursuant to 37 C.F.R. § 1.52(e)(5), the Sequence Listing text file, identified as 072734.0241USSEQ.txt, is 78,868 bytes and was created on Oct. 7, 2016. The Sequence Listing, electronically filed herewith, does not extend beyond the scope of the specification and thus does not contain new matter.

INTRODUCTION

The present invention relates to a Truncated isoform of Anaplastic Lymphoma Kinase ("TALK"). Expression of this isoform is associated with malignancy and with responsiveness to ALK inhibitors. Detection of the isoform may be used in diagnostic and therapeutic methods. Because it arises as a result of variant transcription rather than genetic rearrangement, its presence would be undetected by genomic testing.

BACKGROUND OF THE INVENTION

Comprehensive characterization of genetic aberrations underlying human cancer is essential for improving tumor diagnostics, identifying therapeutic targets, developing rational combination therapies and optimizing clinical trial designs[3]. Large scale sequencing studies, such as The Cancer Genome Atlas (TCGA) project, continue to reveal an increasingly detailed picture of the genetic aberrations in many cancer types, but focus largely on characterizing genetic aberrations in the coding regions of DNA[2-5]. However, in a significant proportion of tumors, the number of detectable genetic aberrations in driver oncogenes is too low to explain malignant transformation[6]. This is exemplified by a recent study, in which ~15% of lung adenocarcinoma lacked gene mutations affecting any of the hallmarks of cancer[7,8]. These observations suggest that mechanisms other than genetic aberrations may be involved in malignant transformation.

SUMMARY OF THE INVENTION

The present invention relates to a truncated isoform of anaplastic lymphoma kinase, also referred to as "TALK" herein, and its use in diagnosis and treatment of cancer patients. It is based, at least in part, on the discovery of a novel oncogenic TALK, termed "ALK$^{ATI}$", that arose as a result of the establishment of a de novo alternative transcriptional initiation (ATI) site in ALK intron 19 independent of genetic aberrations at the ALK locus. The ALK$^{ATI}$ transcript encodes three proteins with a molecular weight of 61.1, 60.8 and 58.7 kDa consisting primarily of the intracellular tyrosine kinase domain. ALK$^{ATI}$ was found to stimulate multiple oncogenic signaling pathways, drive growth factor-independent cell proliferation in vitro, and promote tumourigenesis in vivo. ALK inhibitors were found to suppress the kinase activity of ALK$^{ATI}$, suggesting that patients with ALK$^{ATI}$-expressing tumors may benefit from ALK inhibitors. Expression of ALK$^{ATI}$ was found in more than 10% (~11%) of melanomas and sporadically in other cancer types, but not in normal tissues. Detection of TALK, e.g., ALK$^{ATI}$ in a cell of a subject may be used to diagnose a cancer in the subject and may be used to determine whether treatment of the subject with an ALK inhibitor would be more likely to confer therapeutic benefit. It is an advantage of the invention that a subject expressing TALK who would appear normal by genomic testing may be identified by detecting TALK transcription, mRNA or protein.

The present invention provides an isolated nucleic acid molecule comprising exons 20-29 and a portion but not all of intron 19 of an Anaplastic Lymphoma Kinase (ALK) gene, where the nucleic acid molecule does not comprise exons 1-19 of the ALK gene, either individually or in any combination. In certain embodiments, the ALK gene is a human ALK gene. In one non-limiting embodiment, the portion of intron 19 of the ALK gene is about 400 bp in length located upstream of exon 20 of the ALK gene. In certain embodiments, the nucleic acid molecule is about 2300-2600 bp in length, such as about 2500 bp in length, e.g., about 2513 bp in length. In one non-limiting embodiment, the nucleic acid molecule is a messenger RNA (mRNA) transcript. In certain embodiments, the isolated nucleic acid molecule comprises the nucleotide sequence set forth in SEQ ID NO: 11 or a sequence that is at least about 95% homologous thereto.

The present invention also provides an isolated nucleic acid molecule consisting essentially of exons 20-29 and a portion but not all of intron 19 of an Anaplastic Lymphoma Kinase (ALK) gene, wherein the nucleic acid molecule does not comprise exons 1-19 of the ALK gene, either individually or in any combination. In certain embodiments, the isolated nucleic acid molecule consists essentially of the nucleotide sequence set forth in SEQ ID NO: 11 or a sequence that is at least about 95% homologous thereto.

The present invention further provides an isolated complementary DNA (cDNA) molecule comprising exons 20-29 of an Anaplastic Lymphoma Kinase (ALK) gene, wherein the cDNA molecule does not comprise exons 1-19 of the ALK gene, either individually or in any combination. In certain embodiments, the ALK gene is a human ALK gene. In certain embodiments, the isolated cDNA molecule comprises nucleic acids 405-2063 of the nucleotide sequence set forth in SEQ ID NO: 11 or a sequence that is at least about 95% homologous thereto. In certain embodiments, the isolated cDNA molecule comprises nucleic acids 411-2063 of the nucleotide sequence set forth in SEQ ID NO: 11 or a sequence that is at least about 95% homologous thereto. In certain embodiments, the isolated cDNA molecule comprises nucleic acids 465-2063 of the nucleotide sequence set forth in SEQ ID NO: 11 or a sequence that is at least about 95% homologous thereto.

Additionally, the present invention provides an isolated complementary DNA (cDNA) molecule consisting essentially of exons 20-29 of an Anaplastic Lymphoma Kinase (ALK) gene, wherein the cDNA molecule does not comprise exons 1-19 of the ALK gene, either individually or in any combination. Also provided is an isolated cDNA molecule consisting essentially of nucleic acids 405-2063 of the nucleotide sequence set forth in SEQ ID NO: 11 or a sequence that is at least about 95% homologous thereto, wherein the cDNA molecule does not comprise exons 1-19 of the ALK gene, either individually or in any combination. The present invention further provides an isolated cDNA molecule consisting essentially of nucleic acids 411-2063 of the nucleotide sequence set forth in SEQ ID NO: 11 or a sequence that is at least about 95% homologous thereto, wherein the cDNA molecule does not comprise exons 1-19 of the ALK gene, either individually or in any combination. The present invention further provides an isolated cDNA molecule consisting essentially of nucleic acids 465-2063 of the nucleotide sequence set forth in SEQ ID NO: 11 or a sequence that is at least about 95% homologous thereto, wherein the cDNA molecule does not comprise exons 1-19 of the ALK gene, either individually or in any combination.

The present invention provides an isolated nucleic acid molecule comprising a nucleotide sequence encoding the amino acid sequence set forth in SEQ ID NO: 12 or a sequence that is at least about 95% homologous thereto; an isolated nucleic acid molecule comprising a nucleotide sequence encoding amino acids 3 to 552 of the amino acid sequence set forth in SEQ ID NO: 12 or a sequence that is at least about 95% homologous thereto; or an isolated nucleic acid molecule comprising a nucleotide sequence encoding amino acids 21 to 552 of the amino acid sequence set forth in SEQ ID NO: 12 or a sequence that is at least about 95% homologous thereto.

The present invention also provides a vector comprising the above-described isolated nucleic acid molecule, or the above-described isolated cDNA molecule. The invention provides a host cell comprising such vector. Furthermore, the invention provides an isolated polypeptide encoded by the above-descried nucleic acid molecule, or an isolated polypeptide encoded by the above-described cDNA molecule.

The present invention further provides an isolated polypeptide comprising the amino acid sequence set forth in SEQ ID NO: 12 or a sequence that is at least about 95% homologous thereto, where the polypeptide does not comprise the amino acid sequence set forth in SEQ ID NO; 3. Also provided is an isolated polypeptide comprising amino acids 3 to 552 of the amino acid sequence set forth in SEQ ID NO: 12 or a sequence that is at least about 95% homologous thereto, where the polypeptide does not comprise the amino acid sequence set forth in SEQ ID NO; 3. The present invention further provides an isolated polypeptide comprising amino acids 21 to 552 of the amino acid sequence set forth in SEQ ID NO: 12 or a sequence that is at least about 95% homologous thereto, where the polypeptide does not comprise the amino acid sequence set forth in SEQ ID NO; 3.

Additionally, the present invention provides an isolated polypeptide comprising the amino acid sequence set forth in SEQ ID NO: 12 or a sequence that is at least about 95% homologous thereto, where the polypeptide does not comprise the amino acid sequence set forth in SEQ ID NO; 4. Also provided is an isolated polypeptide comprising amino acids 3 to 552 of the amino acid sequence set forth in SEQ ID NO: 12 or a sequence that is at least about 95% homologous thereto, where the polypeptide does not comprise the amino acid sequence set forth in SEQ ID NO; 4. The present invention further provides an isolated polypeptide comprising amino acids 21 to 552 of the amino acid sequence set forth in SEQ ID NO: 12 or a sequence that is at least about 95% homologous thereto, where the polypeptide does not comprise the amino acid sequence set forth in SEQ ID NO; 4.

The invention also provides an antibody that binds to any of the above-described polypeptides, wherein the antibody does not bind to a wild type ALK. In certain embodiments, the wild type ALK is a wild type human ALK, e.g., one comprising the amino acid sequence set forth in SEQ ID NO: 1.

The present invention also provides a method of diagnosing a cell as a cancer cell comprising detecting the presence of a Truncated isoform of Anaplastic Lymphoma Kinase (TALK) in the cell, where the presence of the TALK indicates that the cell is a cancer cell. In certain embodiments, the method comprises determining the presence of a detectable TALK mRNA transcript, a detectable TALK cDNA molecule corresponding thereto, a detectable TALK polypeptide encoded thereby, and/or a detectable alternative transcriptional initiation (ATI) site in intron 19 of an ALK gene in the cell.

The present invention provides a method of determining whether an anti-cancer effect is likely to be produced in a cancer by an ALK inhibitor, comprising determining whether one or more cell of the cancer contains a detectable TALK, wherein the presence of a detectable TALK in the cell indicates that an ALK inhibitor would have an anti-cancer effect on the cancer. In certain embodiments, the method comprises determining the presence of a detectable TALK mRNA transcript, a detectable TALK cDNA molecule corresponding thereto, a detectable TALK polypeptide encoded thereby, and/or a detectable ATI site in intron 19 of an ALK gene in the cell.

The present invention further provides a method of treating a subject having a cancer comprising: (a) determining whether a subject is likely to obtain therapeutic benefit from an ALK inhibitor, comprising determining whether one or more cancer cell of the subject contains a detectable TALK, wherein the presence of a detectable TALK in the cancer cell of the subject indicates that the subject is likely to benefit from an ALK inhibitor; and (b) treating the subject who is likely to benefit from an ALK inhibitor with a therapeutic amount of an ALK inhibitor. In certain embodiments, the method comprises treating the subject with an alternative therapy other than an ALK inhibitor if no detectable TALK is present in the cancer cell of the subject. In certain embodiments, the method further comprises obtaining a sample of one or more cancer cell of the subject before treating the subject with an ALK inhibitor. In certain embodiments, the subject who is likely to benefit from an ALK inhibitor receives an ALK inhibitor and one or more additional cancer treatment selected from the group consisting of one or more BRAF inhibitor, one or more MEK inhibitor, one or more immunologic inhibitor, one or more CDK4 inhibitor, one or more CDK6 inhibitor, one or more alklyating agent, one or more topoisomerase inhibitor, one or more anti-metabolite, one or more anti-microtubule agent, one or more cytotoxic antibiotic, radiation therapy, chemotherapy, and combinations thereof. In certain embodiments, the immunologic inhibitor is selected from the group consisting an anti-PD-1 antibody, an anti-CTLA-4 antibody, an anti-PD-L1 antibody. In one non-limiting embodiment, the subject who is likely to benefit from an ALK inhibitor receives an ALK inhibitor, an anti-CTLA-4 antibody, and an anti-PD-1 antibody. In one non-limiting embodiment, the subject further receives radiation and chemotherapy. In certain embodiments, the method comprises determining the presence of a detectable TALK mRNA transcript, a detectable TALK cDNA molecule, a detectable TALK polypeptide encoded thereby, and/or a detectable ATI site in intron 19 of an ALK gene in the cell.

The present invention also provides a kit for determining whether an anti-cancer effect is likely to be produced in a cancer by an ALK inhibitor, comprising a means for determining the presence of a detectable TALK in one or more cell of the cancer. In certain embodiments, the kit comprises means for determining the level of a TALK mRNA transcript, a TALK cDNA molecule corresponding thereto, and/or a TALK polypeptide encoded thereby. In certain embodiments, the means for determining the level of a TALK mRNA transcript is selected from the group consisting of probe hybridization, polymerase chain reaction (PCR), Northern blot, sequencing, microarray, and combinations thereof. In certain embodiments, the kit comprises a nucleic acid probe that hybridizes with the TALK mRNA transcript to determine the level of the TALK mRNA transcript. In certain embodiments, the probe hybridization is a probe-based NanoString nCounter assay. In certain embodiments, the kit comprises a color coded probe pair that hybridizes with the TALK mRNA transcript to determine the level of the TALK mRNA transcript. In certain embodiments, the PCR is selected from the group consisting of reverse transcription polymerase chain reaction (RT-PCR), quantitative reverse transcriptase PCR, real-time PCR, quantitative real-time PCR, and combinations thereof. In certain embodiments, the kit comprises a pair of nucleic acid primers that hybridizes with the TALK mRNA to determine the level of the TALK mRNA transcript. In certain embodiments, the means for determining the level of a TALK cDNA molecule is PCR. In certain embodiments, the kit comprises a pair of nucleic acid primers that hybridize with the TALK cDNA molecule to determine the level of the TALK cDNA molecule. In certain embodiments, the means for determining the level of a TALK polypeptide is selected from the group consisting of antibody binding, immunohistochemistry, Western blot, a functional assay, enzyme linked immunosorbent assay (ELISA), radioimmunoassays (RIA), enzyme immunoassays (EIA), mass spectrometry, a 1-D or 2-D gel-based analysis system, immunoprecipitation, and combinations thereof. In certain embodiments, the kit comprises an antibody or a fragment thereof that specifically binds to the TALK polypeptide. In one non-limiting embodiment, the functional assays is a kinase assay.

In certain embodiments, the kit comprises means for determining the presence of an ATI site in intron 19 of an ALK gene in one or more cell of the cancer. In certain embodiments, the means for determining the presence of an ATI site in intron 19 of an ALK gene is selected from the group consisting of Northern blot, Chromatin immunoprecipitation (ChIP)-seq, ChIP-qPCR, Rapid Amplification of cDNA Ends (RACE)-PCR, and combinations thereof.

The present invention provides a means for determining the presence of a detectable TALK for use in a method of determining whether an anti-cancer effect is likely to be produced in a cancer by an ALK inhibitor, the method characterized by determining whether one or more cell of the cancer contains a detectable TALK, where the presence of a detectable TALK in the cell indicates that an ALK inhibitor would have an anti-cancer effect on the cancer. In certain embodiments, the means is for determining the level of a TALK mRNA transcript in one or more cell of the cancer. In certain embodiments, the means is selected from the group consisting of probe hybridization, polymerase chain reaction (PCR), Northern blot, sequencing, microarray, and combinations thereof. In one non-limiting embodiment, the probe hybridization is a probe-based NanoString nCounter assay. In certain embodiments, the PCR is selected from the group consisting of reverse transcription polymerase chain reaction (RT-PCR), quantitative reverse transcriptase PCR, real-time PCR, quantitative real-time PCR, and combinations thereof. In certain embodiments, the means is for determining the level of a TALK cDNA molecule in one or more cell of the cancer. In one non-limiting embodiment, the means is PCR. In certain embodiments, the means is for determining the level of a TALK polypeptide in one or more cell of the cancer. In certain embodiments, the means is selected from the group consisting of antibody binding, immunohistochemistry, Western blot, a functional assay, enzyme linked immunosorbent assay (ELISA), radioimmunoassays (RIA), enzyme immunoassays (EIA), mass spectrometry, a 1-D or 2-D gel-based analysis system, immunoprecipitation, and combinations thereof. In one non-limiting embodiment, the functional assays is a kinase assay. In certain embodiments, the means is for determining the presence of an ATI site in intron 19 of an ALK gene in one or more cell of the cancer. In certain embodiments, the means is selected from the group consisting of Northern blot, Chromatin immunoprecipitation (ChIP)-seq, ChIP-qPCR, Rapid Amplification of cDNA Ends (RACE)-PCR, and combinations thereof.

The present invention further provides an ALK inhibitor for use in treating a subject having cancer, wherein the ALK inhibitor is more likely to produce an anti-cancer effect if one or more cancer cell of the subject contains a detectable TALK.

In certain embodiments, the cancer is selected from the group consisting of melanoma, thyroid carcinoma, lung adenocarcinoma, lung squamous cell carcinoma, renal clear cell carcinoma, and breast cancer. In one non-limiting embodiment, the cancer is melanoma. In one non-limiting embodiment, the cancer is anaplastic thyroid carcinoma.

In certain embodiments, the ALK inhibitor is selected from the group consisting of crizotinib, ceritinib, NVP-TAE684, alectinib; AP26113, ASP-3026, CEP-37440, NMS-E628, PF-06463922, TSR-011, RXDX-101, and X-396. In one non-limiting embodiment, the ALK inhibitor is crizotinib.

In certain embodiments, the TALK mRNA transcript is the above-described nucleic acid molecule. In certain embodiments, the TALK cDNA molecule is the above-described cDNA molecule. In certain embodiments, the TALK polypeptide is the above-described polypeptide.

BRIEF DESCRIPTION OF THE FIGURES

FIGS. 1A-1H. Alternative transcriptional initiation (ATI) results in a novel ALK transcript. 1A, Distribution of RNA-seq reads of ALK variant transcripts: $ALK^{ATI}$ RNAseq reads aligned to both ALK intron 19 and exons 20-29; full-length $ALK^{WT}$ RNA-seq reads aligned to all ALK exons, but not to the introns; translocated ALK RNA-seq reads aligned only to ALK exons 20-29. 1B, Mapping of the ATI sites of ALKALI by 5'-RACE and next-generation sequencing. More than 95% of the ALKATI transcripts start within a 25 base-pair region in ALK intron 19 (hg19 ch2:29,446,768-29,446,744; blue shaded area). 1C, ChIP-seq profile of H3K4me3 at the ATI site of an $ALK^{ATI}$- expressing tumor (MM-15), a melanoma cell line (SKMEL-524) without ALK$^{ATI}$ expression, and a lung cancer cell line (H3122) with a EML4-ALK fusion. The shape of the peak shows a slow taper towards the gene body characteristic of active promoters. 1D, ChIP-qPCR validation of H3K4me3 binding at the ATI site. Mean± SEM, n=3. 1E, ChIP-qPCR of RNA-pol II binding at the ATI site. Mean±SEM, n=3. 1F, Quantitative mRNA profiling of different ALK variants using Nanostring nCounter. Two ALK$^{WT}$-expressing neuroblastoma cell lines (SK-N-BE2, SK-N-DZ), two lung cancer cell lines (H3122, H2228) with EML4-ALK translocations, nine ALKATI expressing tumors: 8 melanomas (MM) and 1 anaplastic thyroid carcinoma (ATC). 1G, Similar SNV frequencies in DNA-seq, RNA-seq and ChIP-seq (H3K4me3) data indicate that ALK$^{ATI}$ is bi-allelically expressed and that both ALK alleles are decorated with H3K4me3. 1H, Table showing the probe set used for the Nanostring nCounter Assay to quantify the mRNA levels of ALK$^{ATI}$, ALK$^{WT}$, and translocated ALK.

FIGS. 2A-2F. The ALKATI transcript encodes three shortened ALK proteins containing mainly the ALK kinase domain. 2A, Illustration of ALK protein isoforms. ALK, wildtype (ALK$^{WT}$) consists of a signaling peptide from amino acid (aa) position 1-18, an extracellular segment with two MAM domains (meprin, A-5 protein, and receptor protein-tyrosine phosphatase mu) and one glycine rich region (Gly), a transmembrane segment, a juxtamembrane segment, and an intracellular segment with the tyrosine kinase domain (kinase, aa 1116-1392). Activating ALK mutations occur usually in the kinase domain, such as ALK$^{F1174L}$. The EML4-ALK fusion protein and ALK$^{ATI}$ contain the entire kinase domain and parts of the juxtamembrane segment. The translation of ALK$^{ATI}$ initiates at one of three in-frame start codons (ATGs) as indicated. 2B, Immunoblots of total-(t-) and phosphorylated-(p-) ALK in two ALK$^{WT}$-expressing neuroblastoma cell lines (SK-N-DZ, SK-N-BE2), two lung cancer cell lines (H3122, H2228) expressing different variants of EML4-ALK fusion, three tumor samples expressing ALK$^{ATI}$ (MM-15, MM-74, ATC-28) and a negative control melanoma cell line (SKMEL-28). 2C, Immunoblots of 293T cells transduced with ALK$^{ATI}$, in which the three predicted start codons were mutated from ATG to AAG, individually or in combination as indicated. 2D, Co-immunoprecipitation (IP) and immunoblots (IB) of the indicated epitopes in 293T cells with exogenous expression of V5-tagged ALK$^{ATI}$ (V5-ALK$^{ATI}$) or HA-tagged ALKATI (HA-ALK$^{ATI}$), or both, demonstrating that ALK$^{ATI}$ proteins self-interact. 2E, ALK immunofluorescence in NIH-3T3 cells expressing the indicated ALK isoforms. Scale bar, 25 μm. 2F, HE (haematoxylin-eosin) stain and ALK immunohistochemistry in ALK$^{ATI}$-expressing human tumor samples. Scale bar, 50 μm.

Figure 3A:
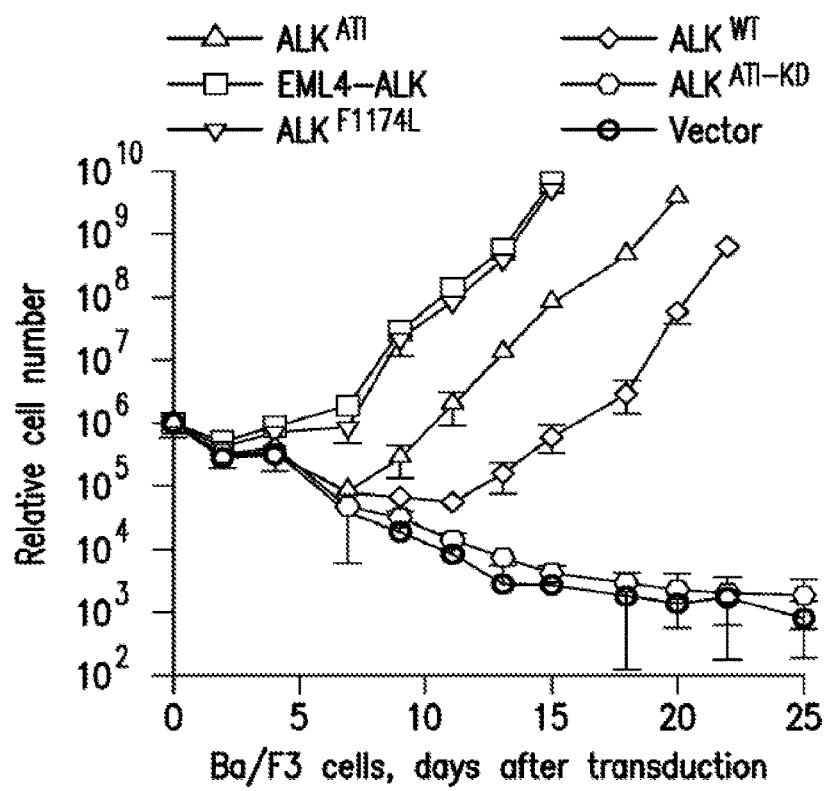
Figure 3B:
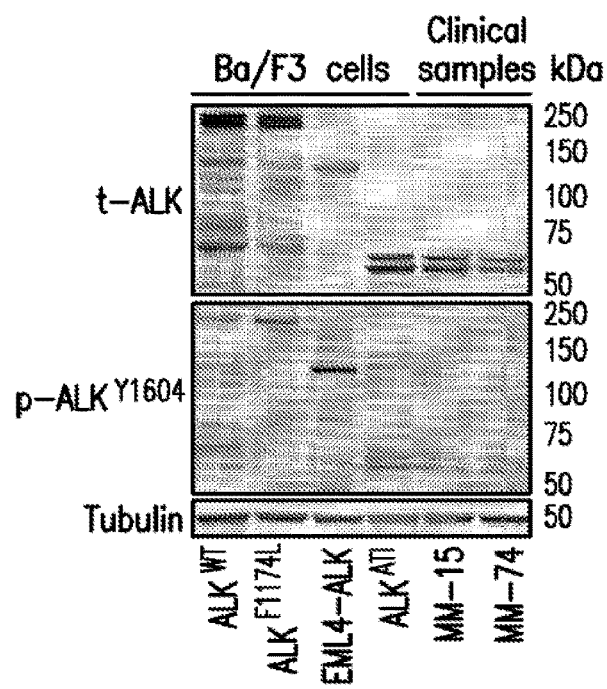
Figure 3C:
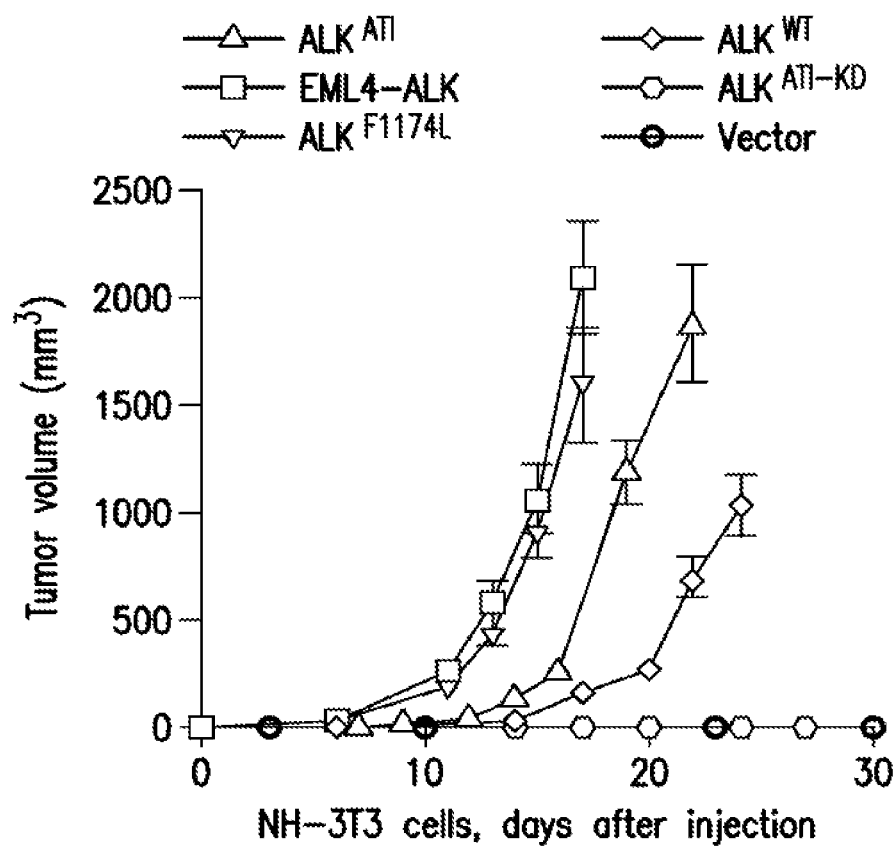

FIGS. 3A-3C. ALKATI promotes growth factor-independent proliferation in vitro and tumourigenesis in vivo. 3A, Growth curves of Ba/F3 cells stably expressing the indicated ALK isoforms in the absence of interleukin 3 (IL-3). Mean±SEM, n=4. 3B, Immunoblots to determine the ALK levels in Ba/F3 cells. Cells were previously transformed by the expression of different ALK isoforms and selected for growth in the absence of IL-3. All ALK variants were phosphorylated when expressed at levels required for IL-3-independent growth. 3C, Growth curves of tumor grafts of NIH-3T3 cells stably expressing the indicated ALK isoforms. ALK$^{F1174L}$, EML4-ALK, and overexpression and amplification of ALK$^{WT}$ are well-established oncogenic drivers in various tumors. Mean±SEM, n=8.

FIGS. 4A-4H. ALK$^{ATI}$-expression confers sensitivity to ALK inhibitors in vitro and in vivo. 4A, Dose-response curves for the ALK inhibitor crizotinib in Ba/F3 cells expressing the indicated ALK isoforms in the presence or absence of IL-3. Mean±SEM, n=3. 4B, Representative immunoblots of Ba/F3 cells expressing ALK$^{ATI}$ and treated with increasing concentrations of crizotinib for 2 hours. 4C, Normalised tumor volume over time in SCID mice implanted with NIH-3T3 cells expressing the indicated ALK isoforms and treated with either vehicle or crizotinib (100 mg/kg/day). Mean±SEM, n=8. 4D, Haematoxylineosin (HE) staining and immunohistochemistry (IHC) of explanted ALK$^{ATI}$-expressing tumors 48 hours after first crizotinib treatment. Scale bar, 50 μm. 4E, Normalised bioluminescence of luciferase-labelled NIH-3T3 grafted tumors expressing ALKATI over time in SCID mice treated with either vehicle or crizotinib (100 mg/kg/day). Mean±SEM, n=4. 4F, RE staining and ALK-IHC (insert) of the melanoma metastasis from patient 1 (MM-382). 4G, Quantitative mRNA profiling of ALK$^{ATI}$ using Nanostring nCounter. Controls expressing ALK$^{WT}$, EML4-ALK or ALK$^{ATI}$ compared to the melanoma metastasis of patient MM-382. Scale bar, 50 μm. 4H, Computed tomography (CT) images of a representative subcutaneous melanoma metastasis on the left hip of patient 1 (MM-382) before and after crizotinib treatment, respectively.

Figure 5A:
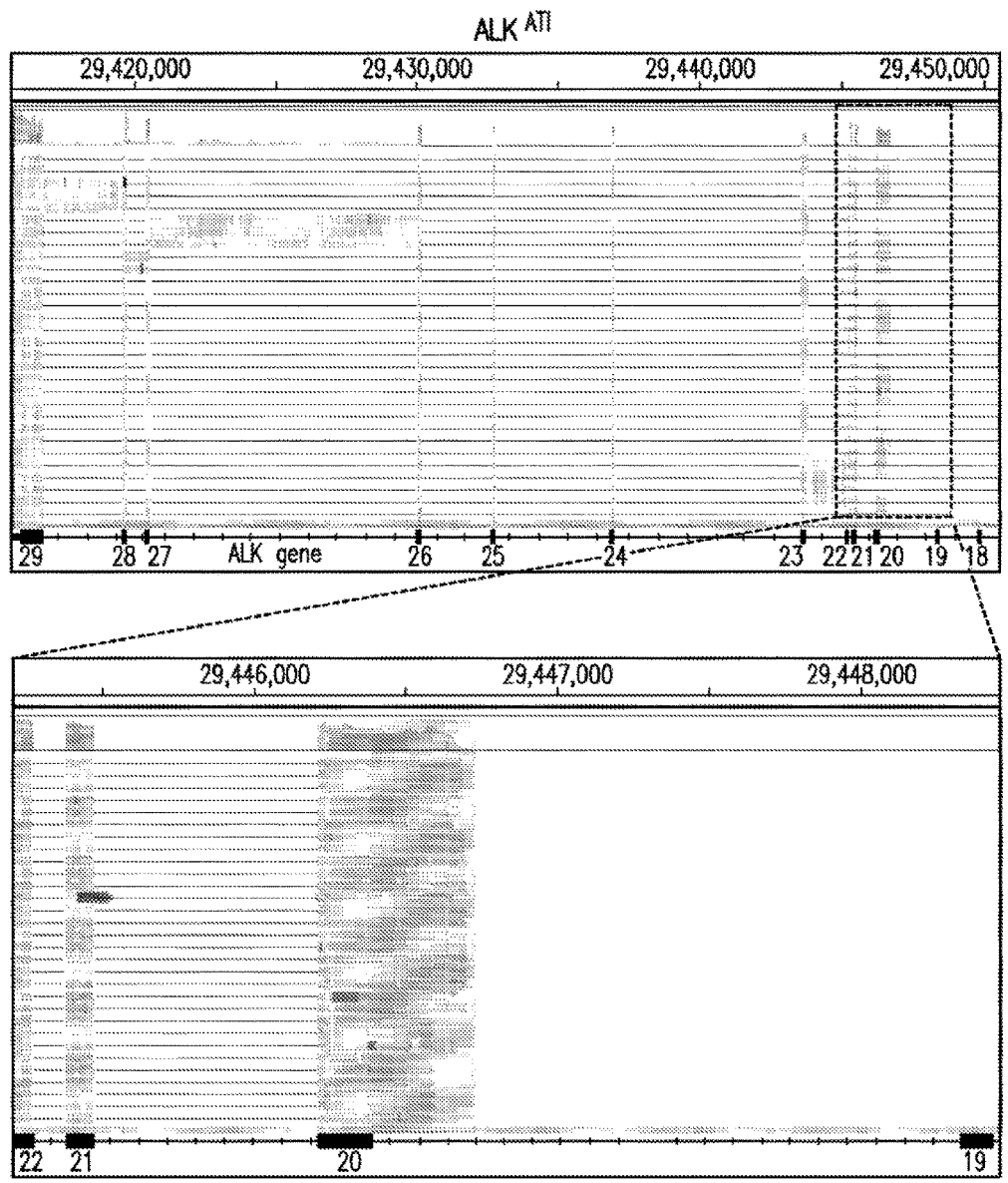
Figure 5B:
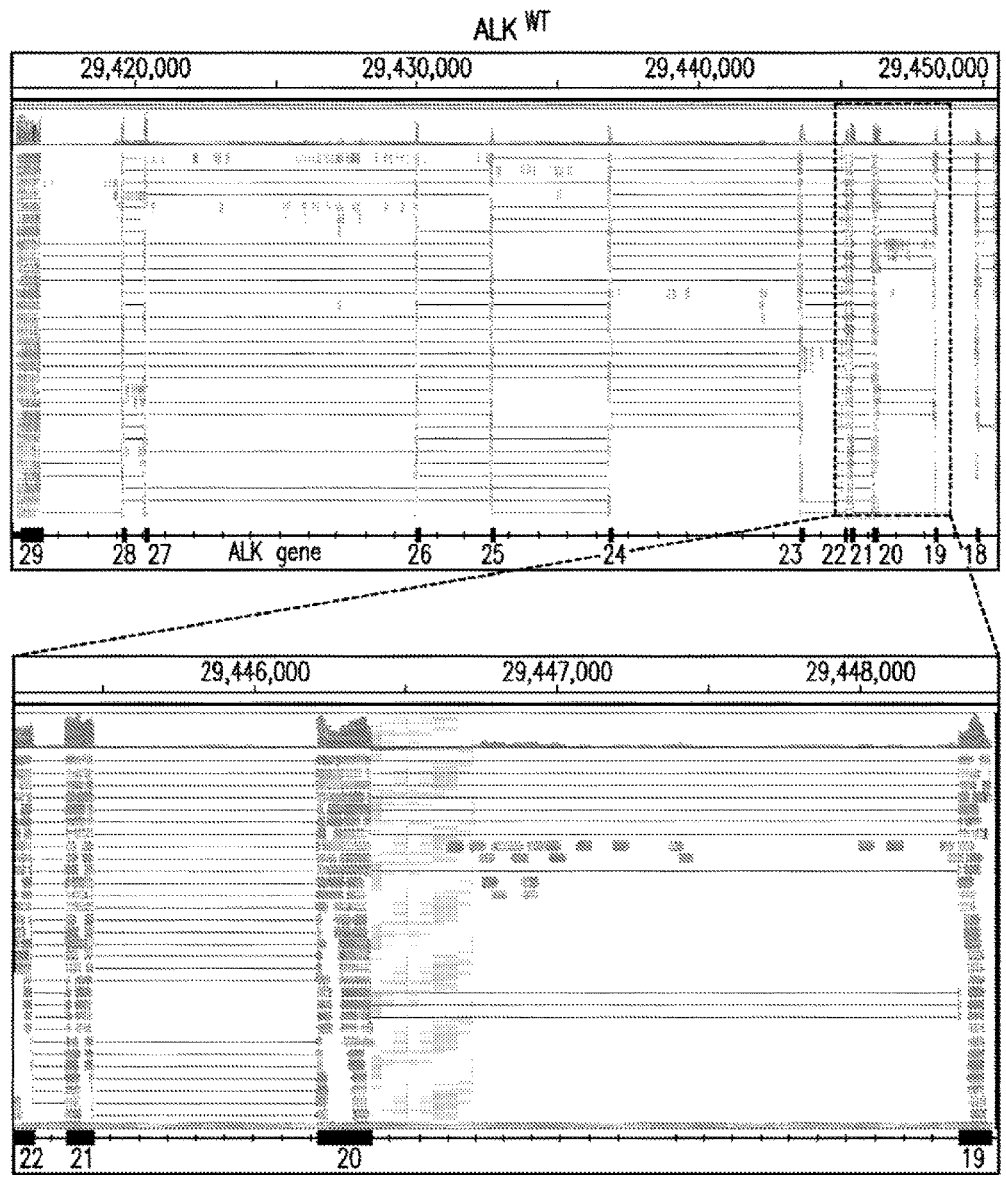
Figure 5C:
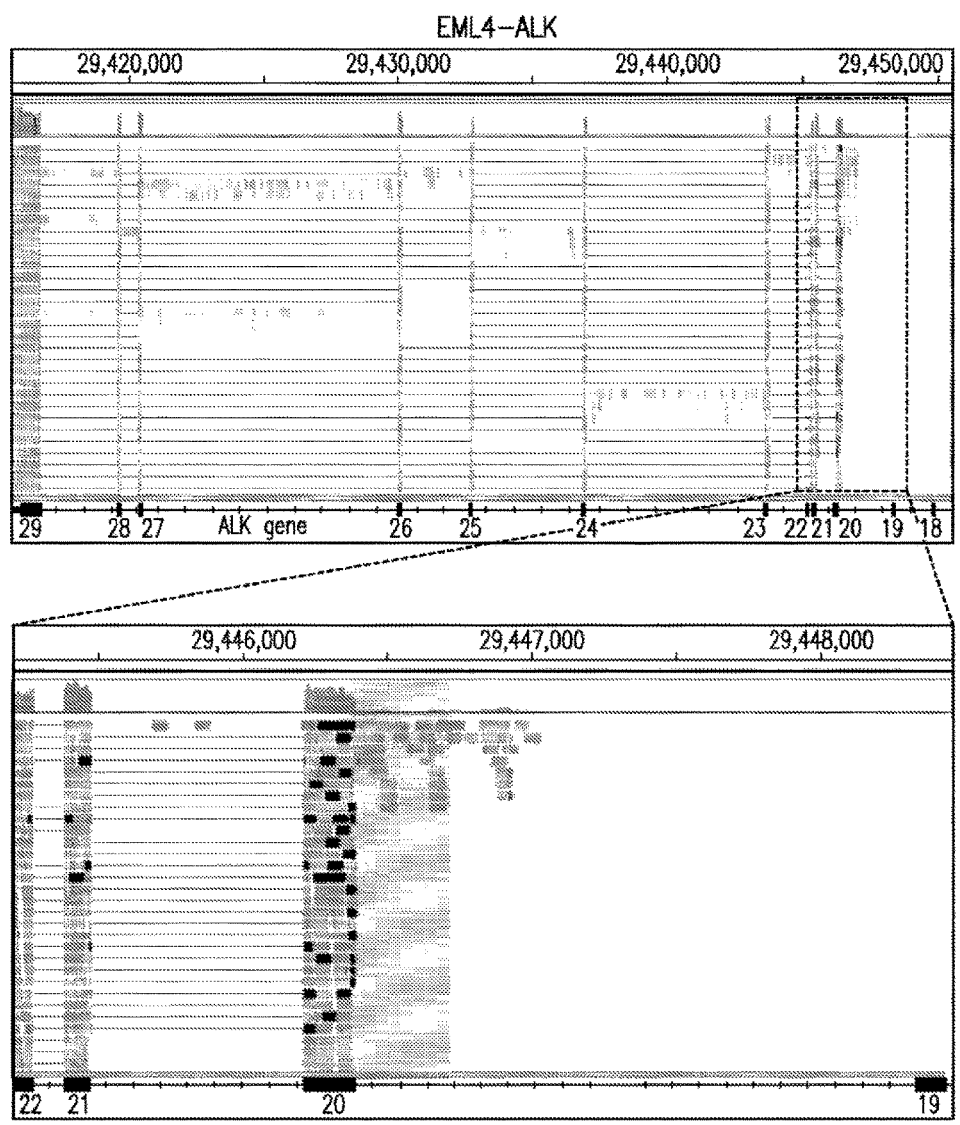

FIGS. 5A-5C. Comparison of the RNA seq profiles of various ALK transcript. RNA-seq data are displayed in the Integrative Genomics Viewer (IGV). The grey bars/arrows indicate the sequencing reads. The blue lines connect sequencing reads that are aligned over the splice site of joining exons. 5A, The ALK$^{ATI}$ transcript shows expression of ALK exons 20-29 and of approx. 400 bps in intron 19 (blue shaded area). No expression of exon 1-19 or intronic areas, other than in intron 19, is observed. The detailed view illustrates that the sequencing reads align continuously between exon 20 and intron 19 indicating uninterrupted transcription. The 5'-UTR of ALK$^{ATI}$ (intron 19) and exon 20-29 are expressed at comparable levels. 5B, The full-length ALK$^{WT}$ transcript shows expression of all ALK exons and only very little expression of the introns. The detailed view displays that the sequencing reads align sharply to the exons, but not to the intron 19 region, which is present in ALK$^{ATI}$ (blue shaded area). 5C, The ALK fusion transcript of a non-small cell lung cancer with an EML4-ALK translocation shows expression of ALK exons 20-29, and little expression of exons 1-19 and all introns. The detailed view illustrates that the transcription starts mainly at exon 20 due to the preserved splice site. Only few reads are aligned to the intron 19 region (blue shaded area). The green-labelled reads highlight chimeric read pairs indicating the EML4-ALK translocation.

FIGS. 6A-6G. Identification of the novel ALK$^{ATI}$ transcript. 6A, IGV view of the 5'-RACE-cDNA fragments obtained by massively parallel sequencing. The vast majority of sequencing reads (grey arrows) start within the main ATI site of 25 base pairs (hg19 chr2:29,446,744-768). 6B, Percentage of reads starting at the ATI site in ALK$^{ATI}$-expressing tumor samples. 6C, Sanger sequencing of the cloned 5'-RACE-cDNA fragments confirm the continuous transcription starting in ALK intron 19 and extending to exons 20-21. 6D, The ALK$^{ATI}$ transcript consists of approximately 400 bp upstream of exon 20 and of ALK exons 20-29. The transcriptional initiation site was defined as the first base pair at which more than 5% of the transcripts were initiated (chr2:29,446,766). Other major transcriptional initiation sites are marked in red, the 5'- and 3'-UTRs in dark blue, the coding DNA sequence (CDS) in black and in box, and the first and last base of each exon in light blue. The translation is initiated at 3 start codons (ATGs; bold and underlined): 1st ATG: hg19 chr2:29,446,360-2, 2nd ATG (+7-9), and 3rd ATG (+61-3). 6E, The amino acid sequence of ALK$^{ATI}$. The translation is initiated at one of 3 start codons. The corresponding 3 methionines (bold and underlined) result in 3 different proteins, 61.08 kDa (552 amino acids), 60.82 kDa (550 amino acids) and 58.71 kDa (532 amino acids). The kinase domain is highlighted in red letters. The lysine in the ATP binding domain in ALK$^{WT}$ is marked bold and underlined, and was mutated to methionine (p.K1150M) in the kinase-dead ALKATI-KD. 6F, Northern blot of full-length ALK$^{WT}$ (neuroblastoma cell lines), EML4-ALK (lung cancer cell lines; variant 1 and 3), ALK$^{ATI}$ from human melanomas, and negative controls (melanoma cell lines). Except for the negative controls, each lane shows two bands; the lower V2 band matches the shorter canonical (RefSeq) ALK transcript ending at ~chr2: 29,415,640; the upper V1 band corresponds to a transcript with a 1.8 kb longer 3' UTR ending at ~chr2:29,413,840. Two ALK$^{ATI}$ expressing tumors, MM-284 and MM-74, show only weak signals because less than 1 µg RNA were available; for all other samples 5-10 µg RNA were used. 6G, RNA-seq Sashimi plot illustrating the shorter V2 and the longer V1 ALK transcripts by the sharp drop of sequencing reads in the 3' UTR at chr2:29,415,640 for V2 and at chr2:29,413,840 for V1.

Figure 1C:
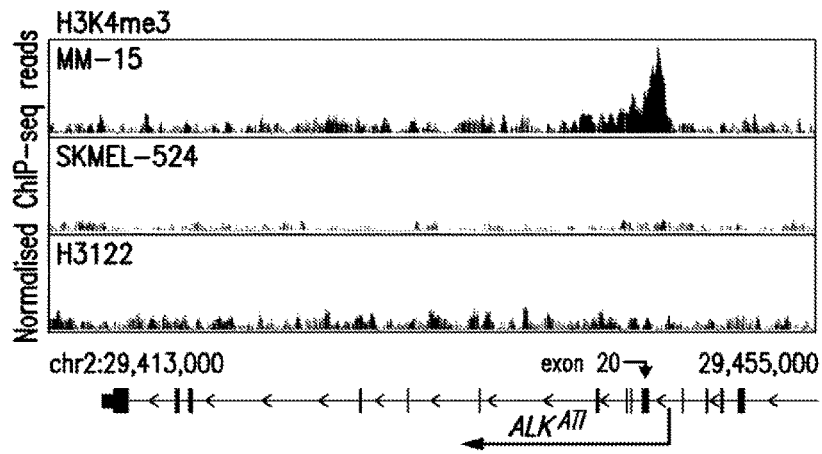
Figure 1D:
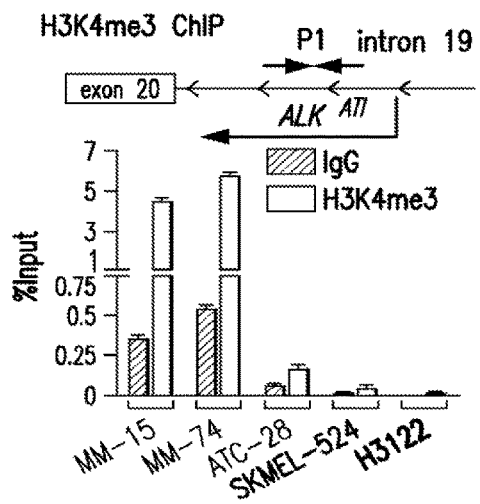
Figure 1E:
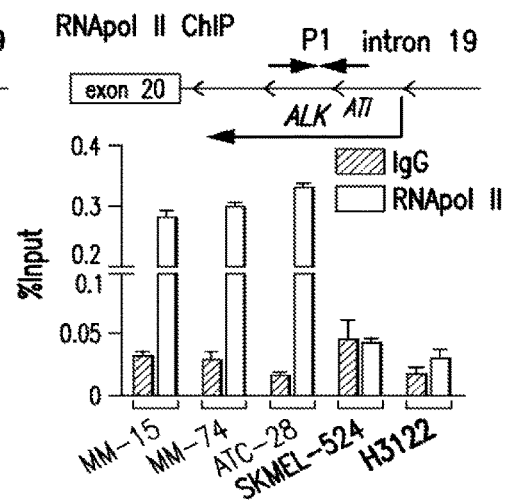

FIGS. 7A-7D. RNApol II and H3K4me3 are enriched at the ATI site of ALK$^{ATI}$-expressing tumor samples. 7A, Primer sequences used for ChIP-qPCR. 7B, Schematics of the ChIP-qPCR primer binding sites at the ALK$^{ATI}$ locus. 7C and 7D, ChIP-qPCR of (C) H3K4me3 and (D) RNApol II at the ATI site demonstrating enrichment of both marks in the ALK$^{ATI}$-expressing human tumor samples, but not in the negative controls, including a lung cancer cell line with EML4-ALK translocation (H3122), and a melanoma cell line (SKMEL-524). Results for primer pair 1 (P1) are shown in FIGS. 1D-1E. Mean±SEM, n=3.

FIGS. 8A-8E. ALK$^{ATI}$-expressing tumors in the TCGA dataset. 8A, The frequency of ALK$^{ATI}$-expressing tumors in more than 5,000 tumor samples from 15 different cancer types in the TCGA RNA-seq dataset. 8B-8E, IGV views of the ALK locus of representative ALK$^{ATI}$-expressing tumor types in the TCGA dataset including B, melanoma; C, lung adenocarcinoma; D, breast invasive carcinoma; E, clear cell renal cell carcinoma. The absence of chimeric sequencing read pairs indicates no translocations in these cases.

FIGS. 9A-9D ALK$^{ATI}$ is transcribed from a genomically intact ALK locus. 9A, Interphase FISH with ALK flanking probes demonstrates juxtaposed green and orange signals indicating no ALK rearrangement in MM-15. Scale bar, 10 µm. 9B, Interphase FISH shows no ALK rearrangement, but 3 green/orange fusion signals in the majority of cell nuclei indicating a trisomy 2 in MM-74. Scale bar, 10 µm. 9C, the top panel shows the genome-wide array CGH profile of MM-15 with numerous chromosomal gains and losses across the entire genome, which are characteristic of metastatic melanoma. The chromosomes are aligned along the x-axis. The blue line illustrates the relative copy number (log 2 ratio) and the blue bars highlight copy number gains and losses. The middle panel illustrates the relative copy number (blue line) across chromosome 2. Distal to the ALK locus, a loss on the p-arm of chromosome 2 is indicated. The lower panel illustrates the relative copy number across the ALK gene. The red and green squares represent the log 2 ratio of individual aCGH probes (green: positive log 2 ratio; red: negative log 2 ratio). No disruption or selective gains or losses are found at the ALK locus. 9D, The genome-wide array CGH profile of MM-74 shows numerous chromosomal gains and losses across the entire genome in the top panel. The middle panel displays a relative copy number gain of the entire chromosome 2, which is in line with the trisomy of chromosome 2 as indicated by FISH. The lower panel also displays trisomy of chromosome 2 and shows no focal gains and losses at the ALK locus.

FIGS. 10A-10D. Targeted sequencing and whole-genome sequencing reveals no recurrent genomic aberrations at the ALK locus. 10A, Data from ultra-deep sequencing of the entire ALK locus are displayed in IGV. The genomic region around intron 19 reveals several single nucleotide variations (SNVs). However, the vast majority of SNVs at the ALK locus are also found in the general population as they are detected in the pool of normal DNA, which was used as the control (pooled normal, bottom panel). Numerous SNVs are also documented in The Single Nucleotide Polymorphism database (db SNP—www.ncbi.nlm.nih.gov/SNP/). No genomic aberrations were found at the transcriptional initiation site of ALK$^{ATI}$. 10B and 10C, Circos plots of the whole-genome sequencing data of (B) MM-15 and (C) ATC-28 illustrating numerous SNV and structural aberrations. 10D, Single nucleotide polymorphisms and small indels at the ALK locus detected by ultra-deep sequencing.

FIGS. 11A-11H. Local chromatin context at the alternative transcription initiation (ATI) site. 11A, UCSC Genome Browser view at the ATI site. The RepeatMasker track shows transposable elements at the ATI region, including a long-terminal repeat (LTR) in intron 19 (LTR16B2) and a long-interspaced element (LINE) in intron 18. The ENCODE tracks reveal a DNase I hypersensitivity cluster and H3K4me1 enrichment, but no H3K27ac enrichment. 11B, The methylation status of the ALK locus was assessed by custom capture of the entire ALK footprint, followed by bisulfite treatment and next-generation sequencing. Bisulfite sequencing results of H3122 and MM-15 are displayed in the CG-bisulfite mode of IGV. The red color denotes "C" (Cytosine) corresponding to methylated cytosine, which is preserved during the bisulfite reaction. The blue color denotes "T" (thymine) corresponding to un-methylated cytosine, which is converted to uracil in the bisulfite reaction, and subsequently amplified to thymine during PCR. 11C, Methylation level at CpGs in ALK$^{ATI}$-expressing tumor samples (MM-15 and ATC-28) and non-ALK$^{ATI}$-expressing control cells (H3122, a lung cancer cell line with EML4-ALK expression and SKMEL-28, a melanoma cell line without ALK$^{ATI}$ expression) at the indicated genomic loci. Black lines mark the LTR16B2 (LTR), red lines mark the LINE. 11D, Comparison of the methylation status of CpGs adjacent to the ATI site in ALK$^{ATI}$-expressing tumor samples (MM-15 and ATC-28) and non-ALK$^{ATI}$-expressing control cells (H3122 and SKMEL-28). The regions flanking LTR16B2 have significantly lower CpG methylation levels in ALK$^{ATI}$-expressing samples than controls; red dots indicate a statistically significant difference (p<0.05) between ALK$^{ATI}$-expressing and non-expressing samples. Black dots indicate no statistically significant difference. 11E, ChIP-seq profile of H3K27ac at the ALK$^{ATI}$ locus. The 17 blue profiles were retrieved from ENCODE, the 5 red profiles are original data from the inventors' lab. Only the three melanoma samples (MM-15, SKMEL-28, SKMEL-524; bottom), but not the 19 non-melanoma cell lines, show H3K27ac enrichment at the ATI site. 11F, ChIP-qPCR validation for the H3K27ac enrichment at the ATI site in 6 melanoma cell lines. Mean±SEM, n=3. 11G, Luciferase reporter assay of LTR16B2 in melanoma cell lines (red) and lung cancer cell lines expressing EML4-ALK (green). In contrast to the lung cancer cell lines with no luciferase activity, melanoma cell lines show low to moderate luciferase activity. 11H, Transcription factor motif analysis of the proximal cis-regulatory region (hg19 chr2: 29,445,000 to 29,447,100).

FIGS. 12A-12I. $ALK^{ATI}$ is active in vitro, shows nuclear and cytoplasmic localization by immunohistochemistry, and induces tumourigenesis. 12A, In vitro kinase assay. The indicated ALK variants were stably expressed in NIH-3T3 cells, immune-precipitated, and assayed for tyrosine kinase activity. After the enzymatic reaction, the immune-precipitated material was used for immunoblots to assess the amount of ALK protein used in the kinase assay. Mean±SEM, n=4. 12B, Human tumor (MM-15) expressing ALKATI shows cytoplasmic and nuclear localization of ALK by immunohistochemistry. Melanocytic tumor expressing a TPM3-ALK translocation showed cytoplasmic localization of the ALK fusion protein without any nuclear staining by immunohistochemistry. Fibroblasts, epithelial cells and reactive lymphocytes serve as internal negative controls. Scale bars, 100 μm. 12C, Flow cytometry analysis for green-fluorescent-protein (GFP) co-expressed with the indicated ALK isoforms. Cells were cultured in IL-3 supplemented medium until day 0 (blue curve) and the number of GFP-positive was assessed. 14 days after IL-3 withdrawal, the number of GFP-positive, ALK-expressing cells was assessed again (red curve). 12D, Immunoblots of explanted NIH-3T3 tumor grafts expressing various ALK isoforms. $ALK^{ATI}$ was expressed at similar protein levels as in two $ALK^{ATI}$-expressing human tumor samples. 12E, Growth curves of tumor grafts of melan-a cells stably expressing the indicated ALK isoforms. Mean±SEM, n=8. 12F, Immunoblots of explanted melan-a tumor grafts expressing various ALK isoforms in comparison to $ALK^{ATI}$-expressing human tumor samples. 12G, Flow cytometry analysis of the GFP signal in NIH-3T3 cells stably expressing low ($ALK^{ATI}$-low) or high levels of $ALK^{ATI}$ ($ALK^{ATI}$-high) prior to grafting into SCID mice. 12H, Immunoblot of t-ALK in $ALK^{ATI}$-low and $ALK^{ATI}$-high cells, confirming differential expression of ATI. 12I Growth curves of tumor grafts of $ALK^{ATI}$-low and $ALK^{ATI}$-high cells.

Figure 4A:
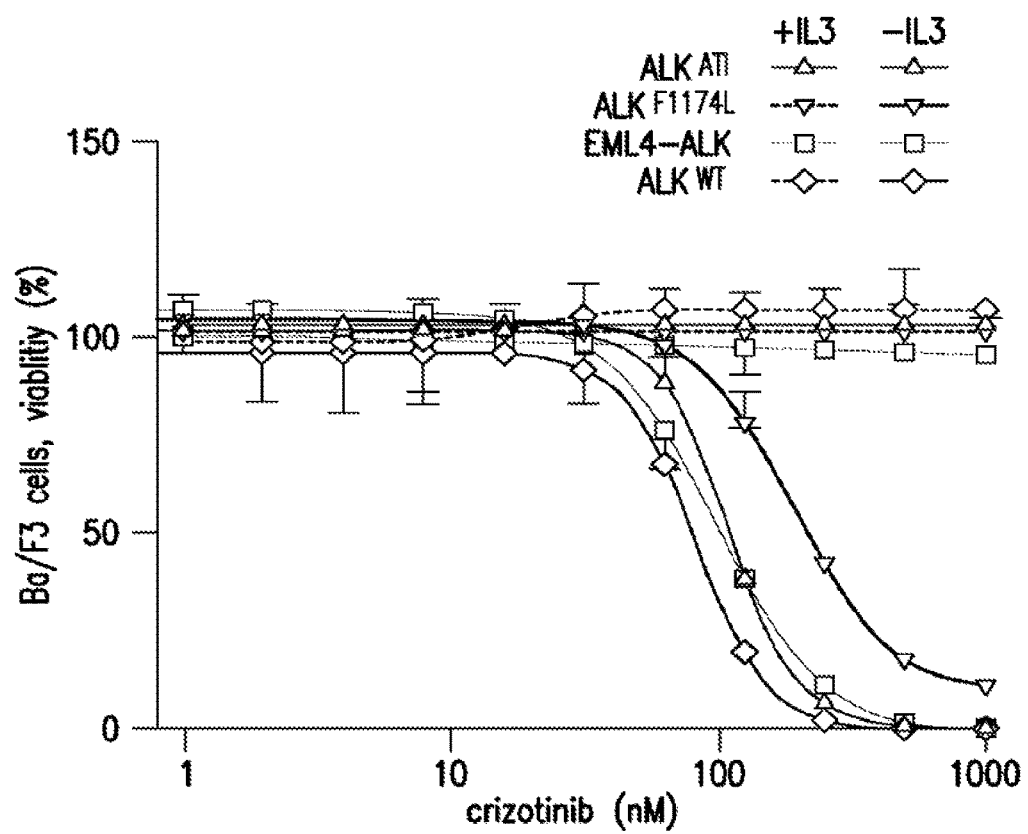
Figure 4B:
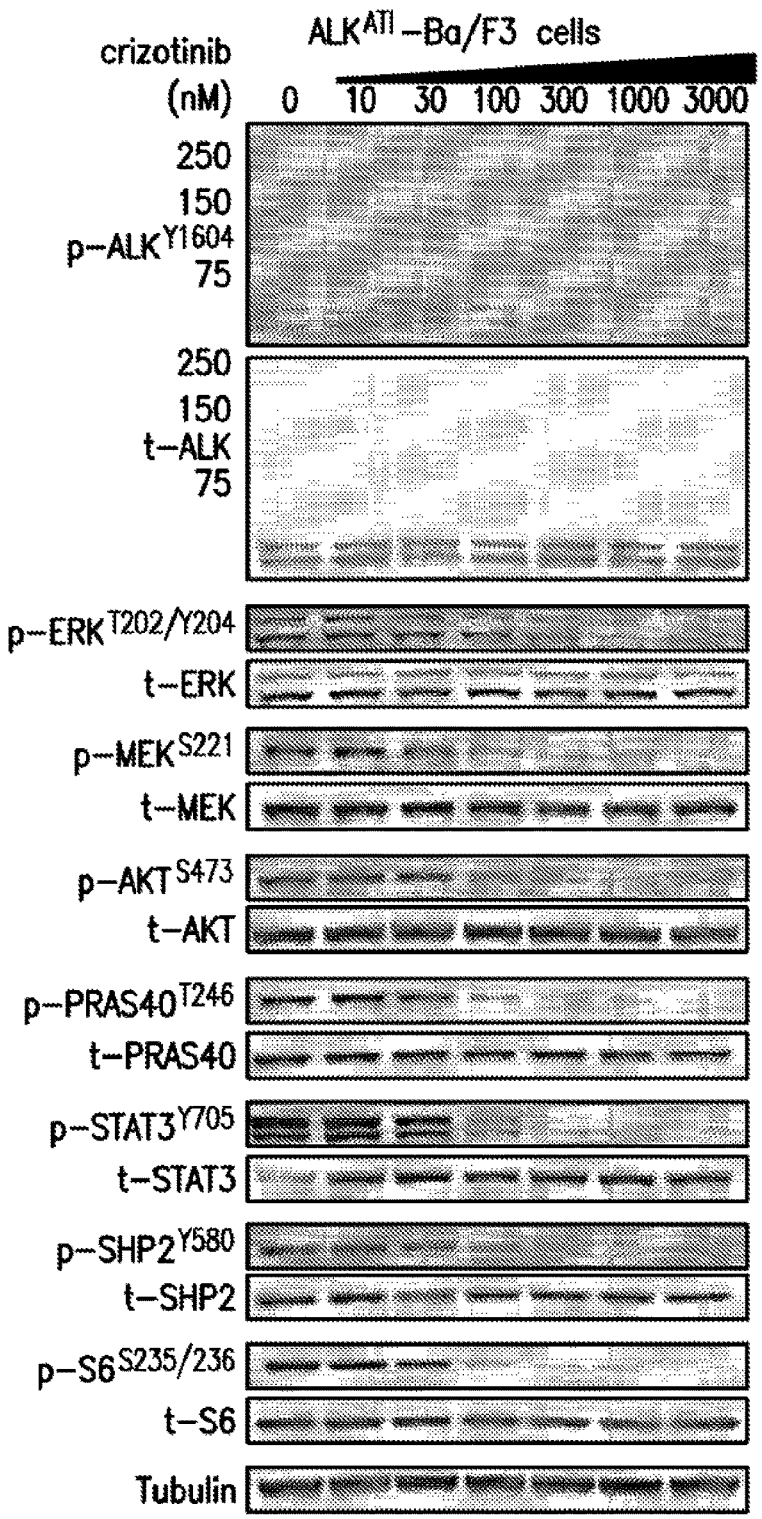
Figure 4C:
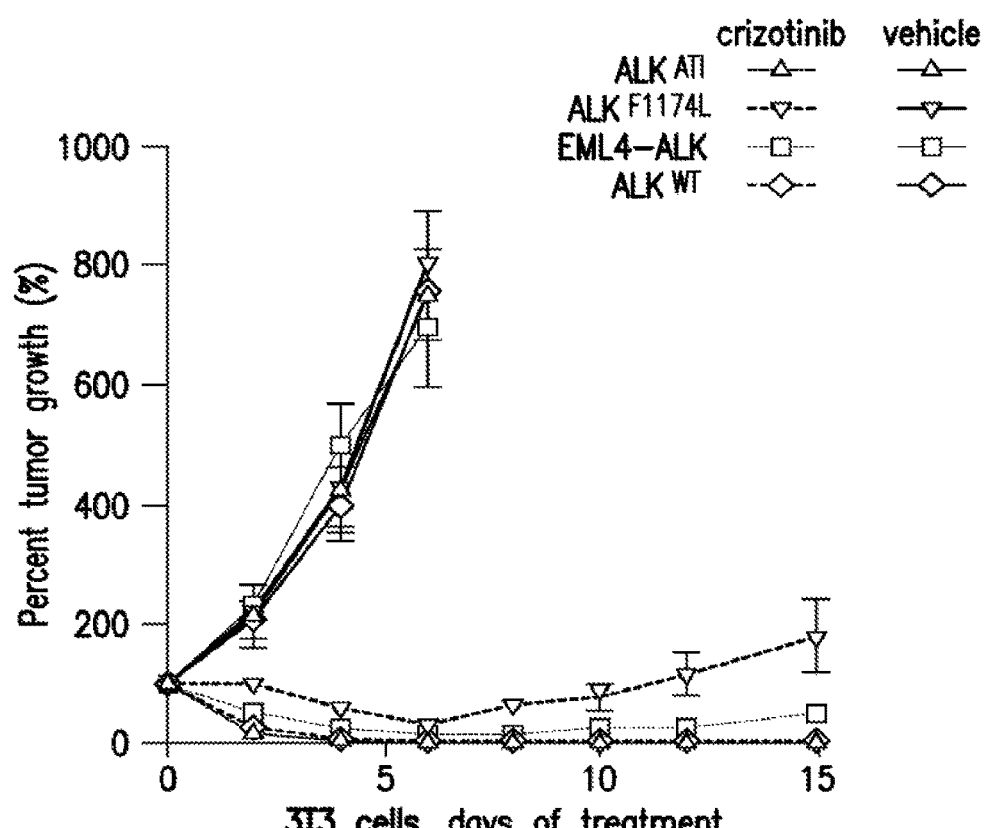

FIGS. 13A-13E. Concentration dependent ALK inhibition in $ALK^{ATI}$, $ALK^{WT}$-, $ALK^{F1174L}$-, and EML4-ALK-expressing Ba/F3 cells. 13A and 13B, Cell viability assay of Ba/F3 cells, either in the presence or absence of IL-3 (1 ng/ml), expressing the indicated ALK isoforms and treated with the indicated doses of ALK inhibitors (A) ceritinib and (B) TAE-684. Cell viability was measured after 72 hours of drug treatment. Mean±SEM, n=4. 13C-13E, Representative immunoblots of Ba/F3 cells stably expressing (C) $ALK^{WT}$, (D) $ALK^{F1174L}$, or (E) EML4-ALK and treated with increasing concentrations of crizotinib for 2 hours. Immunoblots for $ALK^{ATI}$ are shown in FIG. 4B.

Figure 4D:
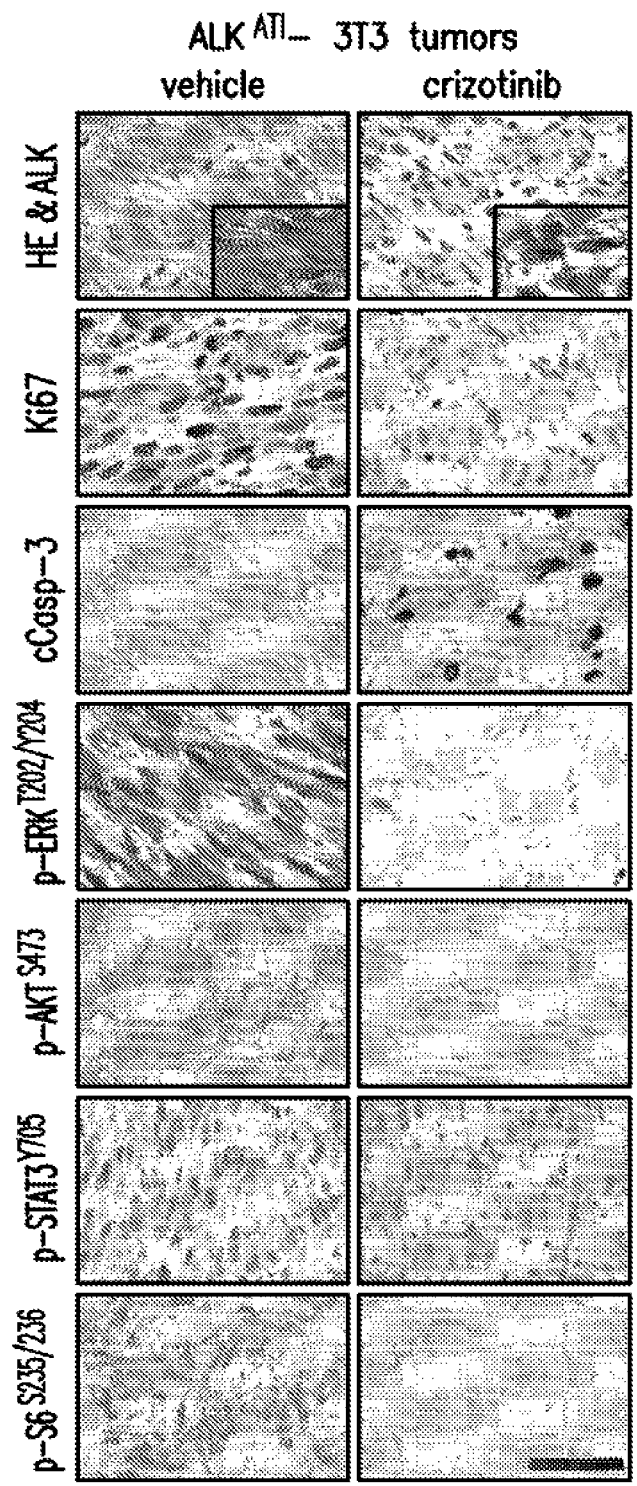

FIGS. 14A-14F. Expression of $ALK^{WT}$, $ALK^{F1174L}$, and EML4-ALK confers sensitivity to the ALK inhibitor, crizotinib, in vivo. 14A-14C, Bioluminescence of luciferase-labelled NIH-3T3 grafted tumors expressing (A) $ALK^{WT}$, (B) $ALK^{F1174L}$, or (C) EML4-ALK over time in SCID mice treated with either vehicle or crizotinib (100 mg/kg/day). Data for $ALK^{ATI}$-expressing tumors are shown in FIG. 4E. 14D-14F, Haematoxylin-eosin staining (HE) and immunohistochemistry of explanted tumors expressing (D) $ALK^{WT}$, (E) $ALK^{F1174L}$, or (F) EML4-ALK 48 hours after first crizotinib treatment. Data from $ALK^{ATI}$-expressing tumors are shown in FIG. 4D. Scale bar, 50 μm.

DETAILED DESCRIPTION OF THE INVENTION

For clarity and not by way of limitation, the detailed description of the invention is divided into the following subsections:
(i) Definitions
(ii) TALKs;
(iii) Detection of TALKs;
(iv) Diagnostic methods;
(v) Methods of treatment; and
(vi) Kits.

Definitions

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv), fusion polypeptides, humanized antibodies derived from a non-human antibody, and unconventional antibodies.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, e.g., a recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a cancer), or otherwise reduce the pathological consequences of the disease (e.g., a cancer). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "subject" refers to any animal (e.g., a mammal), including, but not limited to, humans, non-human primates, rodents, and the like (e.g., which is to be the recipient of a particular treatment, or from whom cells are harvested).

As used herein, the term "an anti-cancer effect" means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, a reduction in tumor metastasis and/or an increase in the proportion of senescent cancer cells.

TALKs

The human anaplastic lymphoma kinase (ALK) gene is located at chr 2p23, contains 29 exons, and encodes a 1,620 amino acid, 220 kDa classical insulin superfamily tyrosine kinase. The mature human ALK protein undergoes post-translational N-linked glycosylation and consists of an extracellular ligand-binding domain, a transmembrane domain, and a single intracellular tyrosine kinase domain.

The term "TALK" may be used to refer to the truncated isoforms of ALK referred to herein and the mRNA and corresponding cDNA molecule encoding them.

In certain non-limiting embodiments, the present invention provides for an ALK isoform comprising exons 20-29 but lacking the transmembrane domain and/or extracellular domain. The TALK arises as a result of the establishment of a de novo alternative transcriptional initiation ("ATI") site rather than a genomic rearrangement or a genomic aberration at the ALK locus. Thus, the TALK is termed as ALK$^{ATI}$.

In certain non-limiting embodiments, the ALK isoform is not comprised in fusion with a portion of another native protein, for example arising from a translocation event, for example, where the 3' portion of ALK is fused to a portion of the ATIC, C2orf44, CARS, CLTC, EML4, FN1, KIF5B, KLC1, MSN, NPM1, PPFIBP1, RANBP2, SEC31A, SQSTM1, STRN, TFG, TPM3, TPM4, or VCL protein (see the COMIC database, http://cancer.sanger.ac.uk/cancergenome/projects/cosmic/)

In certain non-limiting embodiments, the present invention provides for an ALK isoform encoded by a mRNA transcript comprising exons 20-29 and a portion but not all of intron 19, but not exons comprised in the transmembrane domain and/or extracellular domain of ALK. In certain non-limiting embodiments, the present invention provides for an ALK isoform encoded by a mRNA transcript comprising exons 20-29 and a portion but not all of intron 19, but not exons 1-19, of the ALK gene, either individually or in any combination. In certain non-limiting embodiments, the present invention provides for a nucleic acid molecule comprising the transcript. In certain non-limiting embodiments, the size of the transcript is about 2300-2600 bases, or about 2500 bases, or about 2513 bases. Certain non-limiting embodiments of the transcript comprise about 400 bases of intron 19 upstream of exon 20. Certain non-limiting embodiments of the invention provide for a cDNA molecule corresponding to said mRNA transcript. Said cDNA molecule may optionally be operably linked to a promoter and/or incorporated into a nucleic acid vector. Said promoter may be positioned directly before the coding sequence. In certain non-limiting embodiments, the promoter is a heterologous promoter (that is to say, not the ALK promoter). In certain non-limiting embodiments, said mRNA transcript or cDNA molecule lacks nucleic acid sequence encoding at least a 10 or 20 amino acid long fragment of a protein other than ALK.

In certain non-limiting embodiments, the ALK is human ALK.

In certain non-limiting embodiments, the corresponding human ALK gene has a sequence as provided by NCBI Reference Sequence: NG_009445.1 Accession No. NG_009445 or an allelic variant thereof.

In certain non-limiting embodiments, the human ALK protein has the amino acid sequence provided by NCBI Reference Sequence: NP_004295.2 Accession No. NP_004295 (provided below) or an allelic variant thereof.

[SEQ ID NO: 1]

```
  1   mgaigllwll plllstaavg sgmgtgqrag spaagpplqp replsysrlq rkslavdfvv 61   pslfrvyard lllppsssel kagrpeargs laldcapllr llgpapgvsw tagspapaea 121   rtlsrvlkgg svrklrrakq lvlelgeeai legcvgppge aavgllqfnl selfswwirq 181   gegrlrirlm pekkasevgr egrlsaaira sqprllfqif gtghsslesp tnmpspspdy 241   ftwnitwimk dsfpflshrs ryglecsfdf pceleysppl hdlrnqswsw rripseeasq 301   mdlldgpgae rskemprgsf lllntsadsk htilspwmrs ssehctlays vhrhlqpsgr
```

-continued

```
 361  yiaqllphne aareilllmpt pgkhgwtvlq grigrpdnpf rvaleyissg nrslsavdff
 421  alkncsegts pgskmalqss ftcwngtvlq lgqacdfhqd caggedesqm crklpvgfyc
 481  nfedgfcgwt qgtlsphtpq wqvrtlkdar fqdhqdhall lsttdvpase satvtsatfp
 541  apiksspcel rmswlirgvl rgnvslvlve nktgkeqgrm vwhvaayegl slwqwmvlpl
 601  ldvsdrfwlq mvawwgqgsr aivafdnisi sldcyltisg edkilqntap ksrnlfernp
 661  nkelkpgens prqtpifdpt vhwlfttcga sgphgptqaq cnnayqnsnl svevgsegpl
 721  kgiqiwkvpa tdtysisgyg aaggkggknt mmrshgvsvl gifnlekddm lyilvgqqge
 781  dacpstngli qkvcigennv ieeeirvnrs vhewagggggg gggatyvfkm kdgvpvplii
 841  aaggggrayg aktdtfhper lennssvlgl ngnsgaaggg ggwndntsll wagkslgega
 901  tgghscpqam kkwgwetrgg fggggggcss gggggggyigg naasnndpem dgedgvsfis
 961  plgilytpal kvmeghgevn ikhylncshc evdechmdpe shkvicfcdh gtvlaedgvs
1021  civsptpeph lplslilsvv tsalvaalvl afsgimivyr rkhgelqamq melgspeykl
1081  sklrtstimt dynpnycfag ktssisdlke vprknitlir glghgafgev yegqvsgmpn
1141  dpsplqvavk tlpevcseqd eldflmeali iskfnhqniv rcigvslqsl prfillelma
1201  ggdlksflre trprpsqpss lamldllhva rdiacgcqyl eenhfihrdi aarnclltcp
1261  gpgrvakigd fgmardiyra syyrkggcam lpvkwmppea fmegiftskt dtwsfgvllw
1321  eifslgympy psksnqevle fvtsggrmdp pkncpgpvyr imtqcwqhqp edrpnfaiil
1381  erieyctqdp dvintalpie ygplveeeek vpvrpkdpeg vppllvsqqa kreeerspaa
1441  ppplpttssg kaakkptaae isvrvprgpa vegghvnmaf sqsnppselh kvhgsrnkpt
1501  slwnptygsw ftekptkknn piakkephdr gnlglegsct vppnvatgrl pgaslllleps
```

In certain non-limiting embodiments, the untruncated or wild type human ALK mRNA has the nucleotide sequence provided by NCBI Reference Sequence: NM_004304.4 Accession No. NM_004304 (provided below) or an allelic variant thereof.

```
                                                            [SEQ ID NO: 2]
  1  agctgcaagt ggcgggcgcc caggcagatg cgatccagcg gctctggggg cggcagcggt
 61  ggtagcagct ggtacctccc gccgcctctg ttcggagggt cgcggggcac cgaggtgctt
121  tccggccgcc ctctggtcgg ccacccaaag ccgcgggcgc tgatgatggg tgaggagggg
181  gcggcaagat tcgggcgcc cctgccctga acgccctcag ctgctgccgc cggggccgct
241  ccagtgcctg cgaactctga ggagccgagg cgccggtgag agcaaggacg ctgcaaactt
301  gcgcagcgcg ggggctggga ttcacgccca gaagttcagc aggcagacag tccgaagcct
361  tcccgcagcg gagagatagc ttgagggtgc gcaagacggc agcctccgcc ctcggttccc
421  gcccagaccg ggcagaagag cttggaggag ccaaaaggaa cgcaaaaggc ggccaggaca
481  gcgtgcagca gctgggagcc gccgttctca gccttaaaag ttgcagagat tggaggctgc
541  cccgagaggg gacagacccc agctccgact gcggggggca ggagaggacg gtacccaact
601  gccacctccc ttcaaccata gtagttcctc tgtaccgagc gcagcgagct acagacgggg
661  gcgcggcact cggcgcggag agcgggaggc tcaaggtccc agccagtgag cccagtgtgc
721  ttgagtgtct ctggactcgc ccctgagctt ccaggtctgt ttcatttaga ctcctgctcg
781  cctccgtgca gttgggggaa agcaagagac ttgcgcgcac gcacagtcct ctggagatca
841  ggtggaagga gccgctgggt accaaggact gttcagagcc tcttcccatc tcggggagag
```

-continued

```
 901 cgaagggtga ggctgggccc ggagagcagt gtaaacggcc tcctccggcg ggatgggagc
 961 catcgggctc ctgtggctcc tgccgctgct gctttccacg gcagctgtgg gctccgggat
1021 ggggaccggc cagcgcgcgg gctcccccagc tgcggggccg ccgctgcagc cccgggagcc
1081 actcagctac tcgcgcctgc agaggaagag tctggcagtt gacttcgtgg tgccctcgct
1141 cttccgtgtc tacgcccggg acctactgct gccaccatcc tcctcggagc tgaaggctgg
1201 caggcccgag cccgcggct cgctagctct ggactgcgcc ccgctgctca ggttgctggg
1261 gccggcgccg ggggtctcct ggaccgccgg ttcaccagcc ccggcagagg cccggacgct
1321 gtccaggtg ctgaagggcg gctccgtgcg caagctccgg cgtgccaagc agttggtgct
1381 ggagctgggc gaggaggcga tcttggaggg ttgcgtcggg ccccccgggg aggcggctgt
1441 ggggctgctc cagttcaatc tcagcgagct gttcagttgg tggattcgcc aaggcgaagg
1501 gcgactgagg atccgcctga tgcccgagaa gaaggcgtcg gaagtgggca gagagggaag
1561 gctgtccgcg gcaattcgcg cctcccagcc ccgccttctc ttccagatct tcgggactgg
1621 tcatagctcc ttggaatcac caacaaacat gccttctcct tctcctgatt attttacatg
1681 gaatctcacc tggataatga aagactcctt cccttcctg tctcatcgca gccgatatgg
1741 tctggagtgc agctttgact tcccctgtga gctggagtat tcccctccac tgcatgacct
1801 caggaaccag agctggtcct ggcgccgcat cccctccgag gaggcctccc agatggactt
1861 gctggatggg cctggggcag agcgttctaa ggagatgccc agaggctcct ttctccttct
1921 caacacctca gctgactcca agcacaccat cctgagtccg tggatgagga gcagcagtga
1981 gcactgcaca ctggccgtct cggtgcacag gcacctgcag ccctctggaa ggtacattgc
2041 ccagctgctg ccccacaacg aggctgcaag agagatcctc ctgatgccca ctccagggaa
2101 gcatggttgg acagtgctcc agggaagaat cgggcgtcca gacaacccat ttcgagtggc
2161 cctggaatac atctccagtg gaaaccgcag cttgtctgca gtggacttct ttgccctgaa
2221 gaactgcagt gaaggaacat ccccaggctc caagatggcc ctgcagagct ccttcacttg
2281 ttggaatggg acagtcctcc agcttgggca ggcctgtgac ttccaccagg actgtgccca
2341 gggagaagat gagagccaga tgtgccggaa actgcctgtg gttttttact gcaactttga
2401 agatggcttc tgtggctgga cccaaggcac actgtcaccc cacactcctc aatggcaggt
2461 caggacccta aaggatgccc ggttccagga ccaccaagac catgctctat tgctcagtac
2521 cactgatgtc cccgcttctg aaaagtgctac agtgaccagt gctacgtttc ctgcaccgat
2581 caagagctct ccatgtgagc tccgaatgtc ctggctcatt cgtggagtct tgaggggaaa
2641 cgtgtccttg gtgctagtgg agaacaaaac cgggaaggag caaggcagga tggtctggca
2701 tgtcgccgcc tatgaaggct tgagcctgtg gcagtggatg tgttgcctc tcctcgatgt
2761 gtctgacagg ttctggctgc agatggtcgc atggtgggga caaggatcca gagccatcgt
2821 ggcttttgac aatatctcca tcagcctgga ctgctacctc accattagcg gagaggacaa
2881 gatcctgcag aatacagcac ccaaatcaag aaacctgttt gagagaaacc caaacaagga
2941 gctgaaaccc ggggaaaatt caccaagaca gaccccccatc tttgacccta cagttcattg
3001 gctgttcacc acatgtgggg ccagcgggcc ccatggcccc acccaggcac agtgcaacaa
3061 cgcctaccag aactccaacc tgagcgtgga ggtggggagc gagggccccc tgaaaggcat
3121 ccagatctgg aaggtgccag ccaccgacac ctacagcatc tcgggctacg gagctgctgg
3181 cgggaaaggc gggaagaaca ccatgatgcg gtcccacggc gtgtctgtgc tgggcatctt
3241 caacctggag aaggatgaca tgctgtacat cctggttggg cagcagggag aggacgcctg
3301 ccccagtaca aaccagttaa tccagaaagt ctgcattgga gagaacaatg tgatagaaga
```

-continued

```
3361  agaaatccgt gtgaacagaa gcgtgcatga gtgggcagga ggcggaggag gagggggtgg
3421  agccacctac gtatttaaga tgaaggatgg agtgccggtg cccctgatca ttgcagccgg
3481  aggtggtggc agggcctacg gggccaagac agacacgttc cacccagaga gactggagaa
3541  taactcctcg gttctagggc taaacggcaa ttccggagcc gcaggtggtg gaggtggctg
3601  gaatgataac acttccttgc tctgggccgg aaaatctttg caggagggtg ccaccggagg
3661  acattcctgc ccccaggcca tgaagaagtg ggggtgggag acaagagggg gtttcggagg
3721  gggtggaggg gggtgctcct caggtggagg aggcggagga tatataggcg gcaatgcagc
3781  ctcaaacaat gaccccgaaa tggatgggga agatgggggtt tccttcatca gtccactggg
3841  catcctgtac accccagctt taaaagtgat ggaaggccac ggggaagtga atattaagca
3901  ttatctaaac tgcagtcact gtgaggtaga cgaatgtcac atggaccctg aaagccacaa
3961  ggtcatctgc ttctgtgacc acgggacggt gctggctgag gatggcgtct cctgcattgt
4021  gtcacccacc ccggagccac acctgccact ctcgctgatc ctctctgtgg tgacctctgc
4081  cctcgtggcc gccctggtcc tggctttctc cggcatcatg attgtgtacc gccggaagca
4141  ccaggagctg caagccatgc agatggagct gcagagccct gagtacaagc tgagcaagct
4201  ccgcacctcg accatcatga ccgactacaa ccccaactac tgctttgctg gcaagacctc
4261  ctccatcagt gacctgaagg aggtgccgcg gaaaaacatc accctcattc ggggtctggg
4321  ccatggcgcc tttgggaggg tgtatgaagg ccaggtgtcc ggaatgccca acgacccaag
4381  cccctgcaa gtggctgtga agacgctgcc tgaagtgtgc tctgaacagg acgaactgga
4441  tttcctcatg gaagccctga tcatcagcaa attcaaccac cagaacattg ttcgctgcat
4501  tggggtgagc ctgcaatccc tgccccggtt catcctgctg gagctcatgg cggggggaga
4561  cctcaagtcc ttcctccgag agacccgccc tcgcccgagc cagccctcct ccctggccat
4621  gctggacctt ctgcacgtgg ctcgggacat tgcctgtggc tgtcagtatt tggaggaaaa
4681  ccacttcatc caccgagaca ttgctgccag aaactgcctc ttgacctgtc caggccctgg
4741  aagagtggcc aagattggag acttcgggat ggcccgagac atctacaggg cgagctacta
4801  tagaaaggga ggctgtgcca tgctgccagt taagtggatg cccccagagg ccttcatgga
4861  aggaatattc acttctaaaa cagacacatg gtcctttgga gtgctgctat gggaaatctt
4921  ttctcttgga tatatgccat accccagcaa aagcaaccag gaagttctgg agtttgtcac
4981  cagtggaggc cggatggacc cacccaagaa ctgccctggg cctgtatacc ggataatgac
5041  tcagtgctgg caacatcagc ctgaagacag gcccaacttt gccatcattt tggagaggat
5101  tgaatactgc acccaggacc cggatgtaat caacaccgct tgccgataga aatatggtcc
5161  acttgtgaa gaggaagaga aagtgcctgt gaggcccaag gaccctgagg gggttcctcc
5221  tctcctggtc tctcaacagg caaaacggga ggaggagcgc agcccagctg ccccaccacc
5281  tctgcctacc acctcctctg gcaaggctgc aaagaaaccc acagctgcag agatctctgt
5341  tcgagtccct agagggccgg ccgtggaagg gggacacgtg aatatggcat tctctcagtc
5401  caaccctcct tcggagttgc acaaggtcca cggatccaga aacaagccca ccagcttgtg
5461  gaacccaacg tacggctcct ggtttacaga gaaacccacc aaaaagaata tcctatagc
5521  aaagaaggag ccacacgaca ggggtaacct ggggctggag ggaagctgta ctgtcccacc
5581  taacgttgca actgggagac ttccgggggc ctcactgctc ctagagccct cttcgctgac
5641  tgccaatatg aaggaggtac ctctgttcag gctacgtcac ttcccttgtg ggaatgtcaa
5701  ttacggctac cagcaacagg gcttgcccttt agaagccgct actgcccctg gagctggtca
```

```
5761  ttacgaggat accattctga aaagcaagaa tagcatgaac cagcctgggc cctgagctcg 5821  gtcgcacact cacttctctt ccttgggatc cctaagaccg tggaggagag agaggcaatg 5881  gctccttcac aaaccagaga ccaaatgtca cgttttgttt tgtgccaacc tattttgaag 5941  taccaccaaa aaagctgtat tttgaaaatg ctttagaaag gttttgagca tgggttcatc 6001  ctattctttc gaaagaagaa aatatcataa aaatgagtga taaatacaag gcccagatgt 6061  ggttgcataa ggttttatg catgtttgtt gtatacttcc ttatgcttct ttcaaattgt 6121  gtgtgctctg cttcaatgta gtcagaatta gctgcttcta tgtttcatag ttggggtcat 6181  agatgtttcc ttgccttgtt gatgtggaca tgagccattt gaggggagag ggaacggaaa 6241  taaaggagtt atttgtaatg actaaaa
```

In certain non-limiting embodiments, the present invention provides for an isolated nucleic acid molecule comprising the nucleic acid sequence set forth in SEQ ID NO: 11 as shown in FIG. 6D, or a sequence that is at least 80%, at least 85%, at least 90%, or at least 95% homologous thereto, including sequences that are not identical to SEQ ID NO:11, but lacking sequence encoding exons 1-19 of ALK, either individually or in any combination.

In certain non-limiting embodiments, the nucleic acid molecule comprises a nucleotide sequence encoding the amino acid sequence set forth in SEQ ID NO: 12 as shown in FIG. 6E, or a sequence that is at least 80%, at least 85%, at least 90%, or at least 95% homologous thereto, including sequences that are not identical to SEQ ID NO: 12. In certain non-limiting embodiments, the nucleic acid molecule comprises a nucleotide sequence encoding an amino acid sequence that comprises at least one (e.g., no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, or no more than 20) amino acid variation relative to SEQ ID NO: 12, where the resulting sequence is not found in a naturally occurring protein, e.g., a wild-type protein.

In certain non-limiting embodiments, the nucleic acid molecule comprises a nucleotide sequence encoding amino acids 3-552 of SEQ ID NO: 12 or a sequence that is at least 80%, at least 85%, at least 90%, or at least 95% homologous thereto, including sequences that are not identical to amino acids 3-552 of SEQ ID NO:12. In certain non-limiting embodiments, the nucleic acid molecule comprises a nucleotide sequence encoding an amino acid sequence that comprises at least one (e.g., no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, or no more than 20) amino acid variation relative to amino acids 3-552 of SEQ ID NO: 12, where the resulting sequence is not found in a naturally occurring protein, e.g., a wild-type protein.

In certain non-limiting embodiments, the nucleic acid molecule comprises a nucleotide sequence encoding amino acids 21-552 of SEQ ID NO: 12 or a sequence that is at least 80%, at least 85%, at least 90%, or at least 95% homologous thereto, including sequences that are not identical to amino acids 21-552 of SEQ ID NO:12. In certain non-limiting embodiments, the nucleic acid molecule comprises a nucleotide sequence encoding an amino acid sequence that comprises at least one (e.g., no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, or no more than 20) amino acid variation relative to amino acids 21-552 of SEQ ID NO: 12, where the resulting sequence is not found in a naturally occurring protein, e.g., a wild-type protein.

In certain non-limiting embodiments, the amino acid sequence has altered glycosylation patterns compared to a naturally occurring protein, including but not limited to, an amino acid sequence produced in non-human cells, e.g., yeast cells, insect cells, CHO cells, etc.

In certain non-limiting embodiments, the present invention provides for an isolated nucleic acid molecule, which is a cDNA molecule, comprises nucleic acids 405-2063 of the nucleic acid sequence set forth in SEQ ID NO: 11 as shown in FIG. 6D or a sequence that is at least 80%, at least 85%, at least 90%, or at least 95% homologous thereto, including sequences that are not identical to nucleic acids 405-2063 of SEQ ID NO:11.

In certain non-limiting embodiments, the present invention provides for an isolated nucleic acid molecule, which is a cDNA molecule, comprises nucleic acids 411-2063 of the nucleic acid sequence set forth in SEQ ID NO: 11 as shown in FIG. 6D or a sequence that is at least 80%, at least 85%, at least 90%, or at least 95% homologous thereto, including sequences that are not identical to nucleic acids 411-2063 of SEQ ID NO:11.

In certain non-limiting embodiments, the present invention provides for an isolated nucleic acid molecule, which is a cDNA molecule, comprises nucleic acids 465-2063 of the nucleic acid sequence set forth in SEQ ID NO: 11 as shown in FIG. 6D or a sequence that is at least 80%, at least 85%, at least 90%, or at least 95% homologous thereto, including sequences that are not identical to nucleic acids 465-2063 of SEQ ID NO:11.

In certain non-limiting embodiments, said nucleic acid molecule is operably linked to a promoter, which may be a heterologous promoter. In certain non-limiting embodiments, the nucleic acid molecule comprises a cDNA molecule. In certain non-limiting embodiments, the isolated nucleic acid molecule is comprised in a vector which may, for example, be an expression vector or a virus.

In certain non-limiting embodiments, the present invention provides for a host cell comprising a vector that comprises the nucleic acid molecules described herein.

Sequence homology or sequence identity may be measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between e-3 and e-100 indicating a closely related sequence.

In certain non-limiting embodiments, the present invention provides for an isolated polypeptide encoded by any of the nucleic acid molecules described herein, including cDNA molecules.

In certain non-limiting embodiments, the present invention provides for an isolated polypeptide comprising the amino acid sequence set forth in SEQ ID NO: 12 as shown in FIG. 6E, but lacking the amino acid sequence set forth in SEQ ID NO: 3 (provided below) or a sequence that is at least 80%, at least 85%, at least 90%, or at least about 95% homologous thereto, including sequences that are not identical to SEQ ID NO:12.

[SEQ ID NO: 3]
MGAIGLLWLLPLLLSTAAVGSGMGTGQRAGSPAAGPPLQPREPL

SYSRLQRKSLAVDEVVPSLERVYARDLLLPPSSSELKAGRPEAR

GSLALDCAPLLRLLGPAPGVSWTAGSPAPAEARTLSRVLKGGSV

RKLRRAKQLVLELGEEAILEGCVGPPGEAAVGLLQFNLSELFSW

WIRQGEGRLRIRLMPEKKASEVGREGRLSAAIRASQPRLLFQIF

GTGHSSLESPTNMPSPSPDYFTWNLTWIMKDSFPFLSHRSRYGL

ECSFDFPCELEYSPPLHDLRNQSWSWRRIPSEEASQMDLLDGPG

AERSKEMPRGSFLLLNTSADSKHTILSPWMRSSSEHCTLAVSVH

RHLQPSGRYIAQLLPHNEAAREILLMPTPGKHGWTVLQGRIGRP

DNPFRVALEYISSGNRSLSAVDFFALKNCSEGTSPGSKMALQSS

FTCWNGTVLQLGQACDFHQDCAQGEDESQMCRKLPVGFYCNFED

GFCGWTQGTLSPHTPQWQVRTLKDARFQDHQDHALLLSTTDVPA

SESATVTSATFPAPIKSSPCELRMSWLIRGVLRGNVSLVLVENK

TGKEQGRMVWHVAAYEGLSLWQWMVLPLLDVSDREWLQMVAWWG

QGSRAIVAFDNISISLDCYLTISGEDKILQNTAPKSRNLFERNP

NKELKPGENSPRQTPIFDPTVHWLFTTCGASGPHGPTQAQCNNA

YQNSNLSVEVGSEGPLKGIQIWKVPATDTYSISGYGAAGGKGGK

NTMMRSHGVSVLGIFNLEKDDMLYILVGQQGEDACPSTNQLIQK

VCIGENNVIEEEIRVNRSVHEWAGGGGGGGGATYVFKMKDGVPV

PLIIAAGGGGRAYGAKTDTFHPERLENNSSVLGLNGNSGAAGGG

GGWNDNTSLLWAGKSLQEGATGGHSCPQAMKKWGWETRGGFGGG

GGGCSSGGGGGYIGGNAASNNDPEMDGEDGVSFISPLGILYTP

ALKVMEGHGEVNIKHYLNCSHCEVDECHMDPESHKVICFCDHGT

VLAEDGVSCIVSPTPEPHLPLSLILSVVTSALVAALVLAFSGIM

IVYRRKHQELQA

In certain non-limiting embodiments, the present invention provides for an isolated polypeptide comprising the amino acid sequence set forth in SEQ ID NO: 12 as shown in FIG. 6E, but lacking the amino acid sequence set forth in SEQ ID NO: 4 (provided below) or a sequence that is at least 80%, at least 85%, at least 90%, or at least about 95% homologous thereto, including sequences that are not identical to SEQ ID NO:12.

[SEQ ID NO: 4]
MGAIGLLWLLPLLLSTAAVGSGMGTGQRAGSPAAGPPLQPREPL

SYSRLQRKSLAVDFVVPSLFRVYARDLLLPPSSSELKAGRPEAR

GSLALDCAPLLRLLGPAPGVSWTAGSPAPAEARTLSRVLKGGSV

RKLRRAKQLVLELGEEAILEGCVGPPGEAAVGLLQFNLSELFSW

WIRQGEGRLRIRLMPEKKASEVGREGRLSAAIRASQPRLLFQIF

GTGHSSLESPTNMPSPSPDYFTWNLTWIMKDSFPFLSHRSRYGL

ECSFDFPCELEYSPPLHDLRNQSWSWRRIPSEEASQMDLLDGPG

AERSKEMPRGSFLLLNTSADSKHTILSPWMRSSSEHCTLAVSVH

RHLQPSGRYIAQLLPHNEAAREILLMPTPGKHGWTVLQGRIGRP

DNPFRVALEYISSGNRSLSAVDFFALKNCSEGTSPGSKMALQSS

FTCWNGTVLQLGQACDFHQDCAQGEDESQMCRKLPVGFYCNFED

GFCGWTQGTLSPHTPQWQVRTLKDARFQDHQDHALLLSTTDVPA

SESATVTSATFPAPIKSSPCELRMSWLIRGVLRGNVSLVLVENK

TGKEQGRMVWHVAAYEGLSLWQWMVLPLLDVSDRFWLQMVAWWG

QGSRAIVAFDNISISLDCYLTISGEDKILQNTAPKSRNLFERNP

NKELKPGENSPRQTPIFDPTVHWLFTTCGASGPHGPTQAQCNNA

YQNSNLSVEVGSEGPLKGIQIWKVPATDTYSISGYGAAGGKGGK

NTMMRSHGVSVLGIFNLEKDDMLYILVGQQGEDACPSTNQLIQK

VCIGENNVIEEEIRVNRSVHEWAGGGGGGGGATYVFKMKDGVPV

PLIIAAGGGGRAYGAKTDTFHPERLENNSSVLGLNGNSGAAGGG

GGWNDNTSLLWAGKSLQEGATGGHSCPQAMKKWGWETRGGFGGG

GGGCSSGGGGGYIGGNAASNNDPEMDGEDGVSFISPLGILYTP

ALKVMEGHGEVNIKHYLNCSHCEVDECHMDPESHKVICFCDHGT

VLAEDGVSCIVSPTPEPHLPLSLILSVVTSA

In certain non-limiting embodiments, the polypeptide comprises amino acids 3 to 552 of SEQ ID NO: 12. In certain non-limiting embodiments, the polypeptide comprises amino acids 21 to 552 of SEQ ID NO: 12.

In certain non-limiting embodiments, the isolated polypeptide comprises an amino acid sequence that comprises at least one (e.g., no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, or no more than 20) amino acid variation relative to SEQ ID NO: 12, where the resulting sequence is not found in a naturally occurring protein, e.g., a wild-type protein. In certain embodiments, the amino acid sequence comprises at least one amino acid variation relative to SEQ ID NO: 12 but lacks the amino acid sequence set forth in SEQ ID NO: 3. In certain embodiments, the amino acid sequence comprises at least one amino acid variation relative to SEQ ID NO: 12 but lacks the amino acid sequence set forth in SEQ ID NO: 4.

In certain non-limiting embodiments, the amino acid sequence has altered glycosylation patterns compared to a naturally occurring protein, including but not limited to, an amino acid sequence produced in non-human cells, e.g., yeast cells, insect cells, CHO cells, etc.

Amino acid variations or modifications may include amino acid substitutions, additions and/or deletions. Variations or modifications may be introduced by standard techniques known in the art, such as site-directed mutagenesis and PCR-mediated mutagenesis. In certain embodiments, the at least one amino acid variation comprises at least one amino acid conservative modification. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine.

In certain non-limiting embodiments, the polypeptide comprises amino acids 3 to 552 of SEQ ID NO: 12. In certain non-limiting embodiments, the polypeptide comprises amino acids 21 to 552 of SEQ ID NO: 12.

In certain non-limiting embodiments, the present invention provides for an isolated polypeptide comprising the amino acid sequence set forth in residues 1-552 of SEQ ID NO: 12 as shown in FIG. 6E. The polypeptide has an estimated molecular weight of about 61 kDa (e.g., 61.08 kDa).

In certain non-limiting embodiments, the present invention provides for an isolated polypeptide comprising the amino acid sequence set forth in residues 3-552 of SEQ ID NO: 12 as shown in FIG. 6E. The polypeptide has an estimated molecular weight of about 61 kDa (e.g., 60.82 kDa).

In certain non-limiting embodiments, the present invention provides for an isolated polypeptide comprising the amino acid sequence set forth in residues 21-552 of SEQ ID NO: 12 as shown in FIG. 6E. The polypeptide has an estimated molecular weight of about 59 kDa (e.g., 58.71 kDa).

In certain non-limiting embodiments, the polypeptide has an estimated molecular weight of between 58-64, e.g., about 61 kDa, or about 59 kDa.

In certain non-limiting embodiments, the polypeptide is linked to a heterologous peptide tag of between about 2-20 amino acids, or between about 3-15 amino acids.

In certain non-limiting embodiments, the polypeptide is detectably labeled.

In certain non-limiting embodiments, the polypeptide contains at least one conservative amino acid substitution relative to the wild-type sequence.

In certain non-limiting embodiments, the present invention provides for an antibody that binds to one of the above-described polypeptides, but that does not bind to a wild-type ALK polyeptide, e.g., one comprising the amino acid sequence set forth in SEQ ID NO: 1.

Detection of TALKs

Detection of TALKs may be performed by any method known in the art. A TALK may be detected in the form of a mRNA transcript, a corresponding cDNA molecule, its encoded polypeptide, or an ATI site in intron 19 of ALK. In one non-limiting embodiment, the TALK is ALK$^{ATI}$.

In certain non-limiting embodiments, a mRNA transcript encoding a TALK may be detected by a method comprising probe hybridization (e.g., probe-based NanoString nCounter assay), amplification, reverse transcription, polymerase chain reaction (PCR, e.g., reverse transcription polymerase chain reaction (RT-PCR), quantitative reverse transcriptase PCR, real-time PCR, quantitative real-time PCR), Northern blot, sequencing, microarray, or a combination thereof.

In certain non-limiting embodiments, a TALK polypeptide may be detected by a method comprising antibody binding, immunohistochemistry, Western blot, functional (e.g., kinase) assay, enzyme linked immunosorbent assays (ELISAs), radioimmunoassays (RIA), enzyme immunoassays (EIA), mass spectrometry, 1-D or 2-D gel-based analysis systems (e.g., Polyacrylamide gel electrophoresis (PAGE)), immunoprecipitation, or a combination thereof.

In certain non-limiting embodiments, a TALK cDNA molecule may be detected by PCR.

In certain non-limiting embodiments, an ATI site in intron 19 of an ALK gene imay be detected by a method comprising Northern blot, Chromatin immunoprecipitation (ChIP)-seq, ChIP-qPCR, Rapid Amplification of cDNA Ends (RACE)-PCR, or a combination thereof.

A detection method may be practiced in a cell or tissue or cell lysate collected from a subject. The cell may be collected as a sample, for example a sample of a tumor or neoplasm or other lesion. The sample may be a peripheral blood sample or other fluid sample (e.g., pleural effusion).

In one particular non-limiting embodiment of the invention, the transcriptional start site and 5"-end of a TALK transcript, for example the ALK$^{ATI}$ transcript, may be ascertained using the 5'-RACE technique. For example, a tobacco-acid-pyrophosphatase 5'-RACE technique may be performed according to the manufactures protocol (Exact-START Eukaryotic mRNA RACE Kit, #ES80910, Epicentre) using the following primers: 5'-TCATACACATAC-GATTTAGGTGACACTATAGAGCGGCCGCCTGCAGG-AAA-3' [SEQ ID NO: 5]; reverse 5'-CAGGTCACTGATG-GAGGAGGTCTTGCCAGCAAAGCA-3' [SEQ ID NO: 6]. The 5'-RACE products may then be sequenced, for example using an Illumina MiSeq System with a 150 bp paired-end protocol according to the manufactures protocol. Alternatively, the following reverse primers may be used: forward primer 5'-CTAATACGACTCACTATAGGGC-3' [SEQ ID NO: 7], reverse primer 5'-ACACCTGGCCTTCATACAC-CTCC-3' [SEQ ID NO: 8].

In another particular non-limiting embodiment of the invention, a cDNA molecule of a TALK (e.g., the ALK$^{ATI}$) transcript may be amplified using the ALK specific primers 5'-CACCATCCCATCTCCAGTCTGCTTC-3' [SEQ ID NO: 9] and 5'-AGAGAAGTGAGTGTGCGACC-3' [SEQ ID NO: 10].

In other particular non-limiting embodiments of the invention, the presence of a TALK may be detected using an ALK-specific antibody as well as a technique that demonstrates a molecular weight lower than wild-type protein, such as but not limited to polyacrylamide gel electrophoresis and Western blot. Non-limiting examples of antibodies that may be used include Anti-α-Tubulin antibody (#T9026-.5ML), Anti-V5 (#MA1-81617), and anti-HA3F10 (#12158167001), Phospho-ALK (Tyr1278/1282/1283) Rabbit mAb (#3983), Phospho-ALK (Tyr1604) Rabbit mAb (#3341), ALK (D5F3) Rabbit mAb (#3633), Phospho-Akt (Ser473) (#4060), Akt (#4685), Phospho-Stat3 (Tyr705) (#9145), Stat3 (#4904), Phospho-S6 (Ser235/236) (#4858), S6 (#2217), Phospho-p44/42 MAPK (Erk1/2) (Thr202/Tyr204) (#4370), p44/42 MAPK (Erk1/2) (#4695), Phospho-MEK1/2 (Ser221) (#2338), MEK1/2 (#9122).

In certain non-limiting embodiments, a TALK may be detected via the presence of an ATI site in intron 19 of ALK, for example using ChIP-seq and ChIP-qPCR. The chromatin marks 'trimethylated histone H3 lysine 4 (H3K4me3)' and 'RNApol-II' are well characterized to enrich at poised and actively transcribed ATI site.[17-19]

In certain non-limiting embodiments, a NanoString nCounter assay with probe sets in ALK exons 1-19, exons 20-29 and intron 19 may be used (see, for FIG. 1H and its legend) to distinguish wild-type ALK (ALK$^{WT}$), translocated ALK and ALK$^{ATI}$ transcripts. NanoString nCounter assay is based on digital detection and direct molecular barcoding of target molecules through the use of a color coded probe pair. The probe pair consists of a Reporter Probe, which carries the signal on its 5' end, and a Capture Probe which carries a biotin on the 3' end.[51]

In certain non-limiting embodiments, a TALK may be detected via its cellular localization, in that TALK has a greater presence in the nucleus relative to wild-type ALK. Such studies may be performed, for example, using immunohistochemistry and primary or secondary fluorescent antibody probes.

Diagnostic Methods

The present invention provides for a method of diagnosing a cell as a cancer cell comprising detecting the presence of a TALK in a cell, where the presence of a TALK indicates that the cell is a cancer cell. The cell may be in a sample collected from a subject. In certain non-limiting embodiments, a sample includes, but is not limited to, a clinical sample, cells in culture, cell supernatants, cell lysates, serum, blood plasma, biological fluid (e.g., lymphatic fluid) and tissue samples. The source of the sample may be solid tissue (e.g., from a fresh, frozen, and/or preserved organ, tissue sample, biopsy or aspirate), blood or any blood constituents, bodily fluids (such as, e.g., urine, lymph, cerebral spinal fluid, amniotic fluid, peritoneal fluid or interstitial fluid), or cells from the individual, including circulating tumor cells.

In certain non-limiting embodiments, where a TALK is found in a cell, the cell or another cell from the same subject (for example one or more additional cells from the same sample) may be tested for other markers indicative of a diagnosis of cancer, as are known in the art.

Non-limiting examples of cancers which may be indicated by the presence of a TALK include melanoma, thyroid carcinoma (e.g., anaplastic thyroid carcinoma), lung adenocarcinoma, lung squamous cell carcinoma, renal clear cell carcinoma, and breast cancer. In one particular non-limiting embodiment, the cancer is melanoma.

In certain non-limiting embodiments, the present invention provides a method of determining whether an anticancer effect is likely to be produced in a cancer by an ALK inhibitor, comprising determining whether one or more cell of the cancer contains a detectable TALK, wherein the presence of a detectable TALK in the cell indicates that an ALK inhibitor would have an anticancer effect on the cancer.

In certain non-limiting embodiments, the present invention provides for a method of determining the likelihood that a subject having a cancer may obtain therapeutic benefit from therapy with an ALK inhibitor, comprising determining whether a cancer cell of the subject contains a detectable TALK, where the presence of a detectable TALK indicates that the subject is more likely to benefit from ALK inhibitor therapy than a subject who lacks TALK or an activating genetic mutation of ALK.

In certain embodiments, the presence of a detectable TALK comprises the presence of a detectable TALK mRNA transcript, a detectable TALK cDNA molecule corresponding thereto, a detectable TALK polypeptide encoded thereby, and/or a detectable ATI site in intron 19 of an ALK gene in the cell.

In certain non-limiting embodiments, a cancer cell of a subject may have a wild-type (or normal) ALK locus and yet express a TALK, and therefore would not be identified as having an activated ALK by genomic testing.

Methods of Treatment

In certain non-limiting embodiments, the invention provides for a method of treating a subject suffering from a cancer, comprising (i) determining the likelihood that the subject would obtain therapeutic benefit from therapy with an ALK inhibitor, comprising determining whether a cancer cell of the subject contains a detectable TALK, where the presence of a detectable TALK indicates that the subject is more likely to benefit from ALK inhibitor therapy than a subject who lacks TALK or an activating genetic mutation of ALK; (ii) where the subject is determined to be more likely to benefit from ALK inhibitor therapy, treating the subject with an ALK inhibitor, and (iii) where the subject is determined to not be more likely to benefit from ALK inhibitor therapy, treating the subject with an alternative therapy which is not an ALK inhibitor but which may be surgical treatment, radiation therapy, or chemotherapy.

Non-limiting examples of cancers which may be treated by the above method include melanoma, thyroid carcinoma (e.g., anaplastic thyroid carcinoma), lung adenocarcinoma, lung squamous cell carcinoma, renal clear cell carcinoma, thyroid cancer, and breast cancer. In one particular non-limiting embodiment, the cancer is melanoma.

Non-limiting examples of ALK inhibitors which may be used in the above method include crizotinib ("Xalkori®"; (Pfizer); ceritinib (Zykadia®, also known as "LDK-378; Novartis), NVP-TAE684 (Novartis), alectinib (Chugai); AP26113 (Ariad); ASP-3026 (Astellas); CEP-37440 (Teva); NMS-E628 (Nerviano); PF-06463922 (Pfizer); TSR-011 (Tesoro); RXDX-101 (Ignyta Inc.), and X-396 (Xcovery). In one particular non-limiting embodiment, the ALK inhibitor is crizotinib.

Subjects treated according to the invention with one or more ALK inhibitor may further be treated with one or more additional cancer treatment, including but not limited to, one or more BRAF inhibitor, one or more MEK inhibitor, one or more immunologic inhibitor (e.g., an anti-CTLA-4 antibody, an anti-PD1 antibody, an anti-PD-L1 antibody), one or more CDK4 inhibitor, one or more CDK6 inhibitor, one or more alklyating agent, one or more topoisomerase inhibitor, one or more anti-metabolite, one or more anti-microtubule agent, one or more cytotoxic antibiotic, radiation therapy, chemotherapy, or a combination thereof. In one particular non-limiting embodiment, the subject receives a combination of an anti-CTLA-4 antibody and an PD-1 antibody in addition to an ALK inhibitor. In one non-limiting embodiment, the subject has been treated with a combination of an anti-CTLA-4 antibody and an anti-PD-1 antibody prior to the treatment with an ALK inhibitor. In certain embodiments, the subject further receives radiation and/or chemotherapy.

Kits

In certain non-limiting embodiments, the present invention provides for a kit comprising a means for detecting a TALK as described above, optionally together with written disclosure of one or more method set forth above, and optionally together with a positive control molecule such as a TALK protein and/or nucleic acid.

In certain embodiments, the kit comprises means for determining the level of a TALK mRNA transcript, a TALK cDNA molecule corresponding thereto, and/or a TALK polypeptide encoded thereby. The means for determining the level of a TALK mRNA transcript may be probe hybridization (e.g., probe-based NanoString nCounter assay), polymerase chain reaction (PCR, e.g., RT-PCR, quantitative reverse transcriptase PCR, real-time PCR, or quantitative real-time PCR), Northern blot, sequencing, microarray, or a combination thereof.

In certain embodiments, the means for determining the level of a TALK cDNA molecule may be PCR.

In certain embodiments, the means for determining the level of a TALK polypeptide may be antibody binding, immunohistochemistry, Western blot, a functional (e.g., kinase) assay, enzyme linked immunosorbent assays (ELISAs), radioimmunoassays (MA), enzyme immunoassays (EIA), mass spectrometry, 1-D or 2-D gel-based analysis systems (e.g., Polyacrylamide gel electrophoresis (PAGE)), immunoprecipitation, or a combination thereof.

In certain embodiments, the kit comprises means for determining the presence of an ATI site in intron 19 of an ALK gene in one or more cell of the cancer, which may be Northern blot, Chromatin immunoprecipitation (ChIP)-seq, ChIP-qPCR, Rapid Amplification of cDNA Ends (RACE)-PCR, or a combination thereof.

The present invention further provides for a means for determining the presence of a detectable TALK for use in a method of determining whether an anti-cancer effect is likely to be produced in a cancer by an ALK inhibitor, the method characterized by determining whether one or more cell of the cancer contains a detectable TALK, where the presence of a detectable TALK in the cell indicates that an ALK inhibitor would have an anti-cancer effect on the cancer.

Such a kit may therefore comprise one or more nucleic acid probe (e.g., that hybridizes with a TALK mRNA transcript (including a color coded probe pair used in a NanoString nCounter assay), or that hybridizes with a TALK cDNA molecule), primer, and/or primer pair (e.g., that hybridizes with a TALK mRNA transcript or a TALK cDNA molecule), and/or one or more antibody, antibody fragment, or single chain antibody (e.g., that binds specifically to a TALK polypeptide), any of which are optionally directly labeled with a chemical, fluorescent, enzymatic or radioactive marker. Alternatively, detection may be achieved via a secondary probe, enzyme, substrate, ligand, antibody, antibody fragment, single chain antibody, etc., using techniques known in the art.

In a specific non-limiting embodiment, the kit comprises the primer pair: 5'-TCATACACATACGATTTAGGT-GACACTATAGAGCGGCCGCCTGCAGGAAA-3' [SEQ ID NO: 5]; reverse 5'-CAGGTCACTGATGGAGGAG-GTCTTGCCAGCAAAGCA-3' [SEQ ID NO: 6], for example, but not by way of limitation, for use in a 5'-RACE technique.

In a specific non-limiting embodiment, the kit comprises the primer pair: forward primer 5'-CTAATACGACTCAC-TATAGGGC-3' [SEQ ID NO: 7], reverse primer 5'-ACAC-CTGGCCTTCATACACCTCC-3' [SEQ ID NO: 8], for example, but not by way of limitation, for use in a 5'-RACE technique.

In a specific non-limiting embodiment, the kit comprises the primer pair: 5'-CACCATCCCATCTCCAGTCT-GCTTC-3' [SEQ ID NO: 9] and 5'-AGAGAAGTGAGTGT-GCGACC-3' [SEQ ID NO: 10].

In a specific, non-limiting embodiment, the kit comprises an antibody or a fragment thereof that binds to ALK in a region comprised in exons 20-29 and optionally an antibody or a fragment thereof that binds to ALK in a region comprised in exons 1-19.

In a specific, non-limiting embodiment, the kit comprises means to identify an ATI site in intron 19 of ALK.

In a specific non-limiting embodiment, the kit comprises means to detect nuclear localization of TALK, for example a nucleic acid or antibody probe and a second nucleic acid or antibody probe that specifically binds to a binding partner in the nucleus or a chemical means of identifying or staining the nucleus.

EXAMPLE: ALTERNATIVE TRANSCRIPTIONAL INITIATION LEADS TO EXPRESSION OF A NOVEL AND METHODS

Materials and Methods

Human Tumor Samples.

The study was approved by the Institutional Review Boards/Ethics Committees of Memorial Sloan-Kettering Cancer Center, New York, and was conducted according to the Declaration of Helsinki. Representative parts of excised tumors were snap frozen in liquid nitrogen or fixed in 4% neutral buffered formalin, embedded in paraffin, processed using routine histologic methods and stained with hematoxylin-eosin. Specimens with insufficient tissue amount or severely degraded nucleic acids were excluded.

RNA Sequencing.

Total RNA was extracted from fresh-frozen tissue sections (17 metastatic melanoma and 6 thyroid carcinoma) using Qiagen's RNeasy Mini Kit (#74104, Qiagen). The isolated RNA was processed using the TruSeq RNA sample Prep kit (#15026495, Illumina) according to the manufactures protocol. Briefly, the RNA was poly-a selected, reverse transcribed and the obtained cDNA underwent an end-repair process, A-tailing, ligation of the indexes & adapters, and PCR enrichment. The created libraries were sequenced on an Illumina HiSeq-2500 platform with 50, 75 or 100 bp paired-end reads to obtain on average 40 to 100 million reads per sample. Sequencing data were mapped to the human reference genome (hg19) using Bowtie or BWA and analyzed using publicly available software packages: SAMtools[26], Tophat[27], FusionSeq[28], GATK[29], Picard (http://picard.sourceforge.net) and IGV[30].

Screening for Aberrantly Expressed Kinases.

For initial screening of RNA-seq data, candidate receptor tyrosine kinase genes (RTK) were defined by Gene Ontology annotation GO:0004714 as found in AmiGO[31]. DEX-Seq[9] was used to calculate exon level counts using RTK Ensembl Gene IDs. For each gene in each sample, the ratio of reads in the first half of the gene to the second half was calculated. ALK was identified as the top hit.

Analysis of Public Datasets.

RNA-seq data was downloaded from the Broad Institute GTEx Genotype-Tissue Expression Portal (http://www-.broadinstitute.org/gtex/) 2013_09_23 run using exon_quantification data from illuminahiseq_rnaseqv2_unc_udu. $ALK^{ATI}$ candidates were identified as samples with an ALK expression level of RSEM ≥100, ≥500 total reads across all ALK exons, and ≥10× greater average expression (by exon-level RPKM) in exons 20-29 compared to exons 1-19. To confirm $ALK^{ATI}$ expression, candidates were manually examined in IGV[30]. ENCODE ChIP-seq data for H3K27ac, mapped to hg19 and converted to bigwig track format, was downloaded from http://genome.ucsc.edu/ENCODE/dataMatrix/encodeChipMatrixHuman.html.

Promoter/Motif Analysis.

The proximal cis-regulatory region, chr2:29,445,000-29,447,100, was scanned for transcription factor motifs using FIMO[48] with default parameters against the known vertebrate transcription factor motifs in the JASPAR database[52].

5'-Rapid Amplification of cDNA Ends (5'-RACE).

Two independent 5'-RACE techniques were used to map the ATI site and the 5'-end of the $ALK^{ATI}$ transcript. A tobacco-acid-pyrophosphatase 5'-RACE technique according to the manufacture's protocol (ExactSTART Eukaryotic mRNA RACE Kit, #ES80910, Epicentre) using the following primers: 5'-TCATACACATACGATTTAGGTGACAC-TATAGAGCGGCCGCCTGCAGGAAA-3' [SEQ ID NO: 5]; reverse 5'-CAGGTCACTGATGGAGGAGGTCTTGC-CAGCAAAGCA-3' [SEQ ID NO: 6]. The 5'-RACE products were sequenced on an Illumina MiSeq System with a 150 bp paired-end protocol according to the manufacture's protocol. The sequencing reads were mapped to the human reference genome (hg19) using BWA, analyzed using Tophat[27] and visualized using IGV[30]. The continuous transcription starting in ALK intron 19 was confirmed with an independent oligonucleotide-based 5'-RACE kit (SMARTer™ RACE cDNA Amplification Kit, #634923, Clontech) according to the manufacture's protocol using the following reverse primers: forward primer 5'-CTAATAC-GACTCACTATAGGGC-3' [SEQ ID NO: 7], reverse primer 5'-ACACCTGGCCTTCATACACCTCC-3' [SEQ ID NO: 8]. The RACE cDNA products were cloned into plasmids (Zero Blunt® TOPO® PCR Cloning Kit, #K2800-20, Invitrogen) and were analyzed with Sanger sequencing using standard procedures. Two lung cancer cell lines (H3122, H2228) with EML4-ALK translocations were used as controls, and as expected, both controls showed the EML4 gene next to ALK exon 20.

Chromatin immunoprecipitation (ChIP)-seq and ChIP-qPCR. Chromatin was isolated from human tumor tissue and cell lines. Fresh-frozen human tumor tissue (MM-15, MM-74, ATC-28) was sectioned with a microtome and cross-linked in 1% paraformaldehyde for 15 min. The cross-linked tissue samples were quenched in 125 mM Glycine for 10 min, washed in PBS, re-suspended in lysis buffer, and dounced in a Tenbroeck-style tissue grinder and conicated.[32] Chromatin isolation from the cell-lines H3122 and SKMEL-524 cells and immunoprecipitation was performed as previously described[32]. Solubilized chromatin from human tumors and cell lines was immune-precipitated with antibodies against H3K4me3 (#39159, Active Motif), H3K27ac (#Ab4729, Abcam), and RNA-pol II (#39097, Active Motif).

ChIP-seq was performed on an Illumina HiSeq2500 with 51-bp single reads. Reads were aligned to the human genome hg19 using the Bowtie alignment software within the Illumina Analysis Pipeline. Duplicate reads were eliminated for subsequent analysis. Peak calling was performed using MACS 1.4 comparing immune-precipitated chromatin with input chromatin.[33] ChIP-qPCR was performed on a ViiA™ 7 Real Time PCR System (Life Technologies) using Power SYBR Master Mix (#4367659, Life Technology). ChIP-qPCR primers were designed using primer blast (http://www.ncbi.nlm.nih.gov/tools/primer-blast) and are described in FIGS. 7A and 7B.

Ultra-deep targeted sequencing of the entire ALK locus. Targeted sequencing of the entire ALK locus was performed using custom hybridization capture probes tiling hg19 chr2: 29400000-30300000 (RocheNimbleGen's SeqCap EZ). This region encompassed the entire genomic footprint of ALK as well as ~150 kb of upstream sequence. After the genomic DNA was fragmented (E220, Covaris), barcoded sequence libraries (New England Biolabs, Kapa Biosystems) were prepared, and hybridization capture on barcoded pools was performed using custom probes (Nimblegen SeqCap). 250 ng of genomic DNA was used for library construction from 7 separate samples: 2 melanoma tumors (MM-15, MM-74), 1 anaplastic thyroid carcinoma (ATC-28), 2 lung cancer cell lines (H3122, H2228) with EML4-ALK translocations, 1 melanoma (SKMEL-28) and 1 control pool of 10 "normal" blood samples. Libraries were pooled at equimolar concentrations (100 ng per library) and used in the capture reaction as previously described.[34] To prevent off-target hybridization, we spiked in a pool of blocker oligonucleotides complementary to the full sequences of all barcoded adaptors. The captured libraries were sequenced on an Illumina HiSeq 2500 to generate 75-bp paired-end reads. Sequence data were de-multiplexed using CASAVA, and aligned to the reference human genome (hg19) using BWA.[35]

Local realignment and quality score recalibration were performed using the Genome Analysis Toolkit (GATK) according to GATK best practices.[36] A mean unique target sequence coverage of 1778× per sample (range: 1293x-2188x) was achieved. Sequence data were analyzed to identify single nucleotide variants, small insertions/deletions (indels), and structural rearrangements. Single nucleotide variants were called using muTect[37] and were compared to the negative control pool (pooled "normal" blood samples). Variants were retained if the variant allele frequency in the tumor was >5 times than in the negative control and the frequency in the negative control was <0.02. Validated SNPs in the dbSNP database were filtered out. Indels were called using the SomaticIndelDetector tool in GATK[36] and were retained if the tumor harbored >3 supporting reads and the frequency in the negative control was <0.02. DELLY was used to search for structural rearrangements.[38]

Bisulfite Sequencing of the Entire ALK Locus.

Custom capture of the entire ALK locus was performed using custom hybridisation capture probes tiling the entire genomic footprint of ALK (900kb, chr2:29400000-30300000) followed by bisulfite sequencing. After fragmentation (E220, Covaris) of 3 µg genomic DNA of each sample (MM-15, ATC-28, H3122 and SKMEL-28), libraries were prepared with the KAPA Hyper Prep Kit (#KR0961, Kapa Biosystems) without PCR amplification to preserve the methylation status. 1 µg of each barcoded library was pooled at equimolar concentrations and captured according to the manufacturer's protocol (Roche/NimbleGen's SeqCap EZ). After washing the Dynabeads M-270 (#65306, Life Technologies), the non-biotinylated tumor/cell line DNA was dissociated from the biotinylated capture beads with 0.5M NaOH. The single stranded eluted DNA was used for bisulfite conversion using the EZ DNA Methylation-Gold™ Kit (#D5005, Zymo Research) according to the manufacturer's protocol, except for the 98° C. denaturation step. After bisulfite conversion, the KAPA HiFi Uracil PCR polymerase (#KK280, Kapa Biosystems) was used to amplify the library, the reaction with Agencourt AMPure XP beads (A63881, Beckman Coulter) was purified, and the library was sequenced on an Illumina MiSeq with a 150 bp paired-end protocol according to the manufacturer's instructions. Sequence data were aligned to hg19 and analyzed using BISMARK[53]. The methylation level at CpG sites was compared across all samples; no methylation was detected in the CHG and CHH contexts. Methylation was first computed as the number of methylated CpG reads vs. the number of total reads covering each CpG site (sites with <10 reads were excluded). A sliding window was used to determine the mean methylation level for every 250 bp region (with at least three CpGs) near the ALK promoter region (chr2:29,444,000-29,452,000). Differential methylation was evaluated using a Mann-Whitney test.

Whole-Genome Sequencing.

Whole-genome sequencing was performed at the New York Genome Center (New York). Briefly, genomic DNA libraries were prepared from MM-15 and ATC-28 (no matched normal DNA was available) using the Illumina PCR-free kit. Libraries were sequenced on a HiSeq 2500 using Illumina's 100 bp paired-end whole-genome sequencing protocol. Sequence reads were mapped using BWA[35] and processed using GATK[36]. Genome-wide analyses of mutations (HaplotypeCaller[36]), copy number alterations (FREEC)[54], and structural variations (CREST)[55] were performed. Mutations were annotated with the Ensembl Variant Effect Predictor[56] and filtered to 13 remove common polymorphisms. Non-synonymous mutations along with copy number alterations and structural variations were visualised using Circos[57].

Array CGH.

Genomic DNA samples were labeled using a Bioprime Array CGH Genomic Labeling Kit (#18095-011, Life Technologies) according to the manufacturer's instructions. Briefly, 1 μg tumor DNA and reference DNA (#G1471, Promega) were differentially labeled with dCTP-Cy5 (#45-001-291, GE Healthcare), and dCTP-Cy3 (#45-001-290, GE Healthcare). Genome-wide analysis of DNA copy number changes was conducted using an oligonucleotide SurePrint G3 Human CGH Microarray (#G4447A, Agilent) containing 1 million probes according to the manufacturer's protocol. Slides were scanned using Agilent's microarray scanner G2505B and analyzed using Agilent Genomic Workbench.

Interphase Fluorescence In Situ Hybridization (FISH).

A commercially available ALK break-apart probe (#06N38-020, Abbott) was used according to the manufacturer's protocol. The probes were hybridized on 5 μm-thick tissue sections. The number and localization of the hybridization signals was assessed in a minimum of 100 interphase nuclei with well-delineated contours. At least 10% of neoplastic cells had to show a split signal to report an ALK rearrangement.

Northern Blot.

Total RNA was extracted from fresh-frozen tissue or cell lines using Qiagen's RNeasy Mini Kit (#74104, Qiagen). Up to 10 μg RNA was used for running formaldehyde-based Northern analysis according to the manufacturer's protocol using the RNA Ambion NorthernMax® Kit (#AM1940, Ambion). After hybridisation with a 32P labelled probe, consisting of ALK exon 20-29, the membrane was washed and visualised.

NanoString.

Details of the nCounter Analysis System (NanoString Technologies) were reported previously.[39] In brief, two sequence-specific probes were constructed for ALK exons 1-19, intron 19, and exons 20-29, respectively. Four control genes (RPS13, RPL27, RPS20, ACTB) were used for normalization. The probes were complementary to a 100 base pair region of the target mRNA and are listed in FIG. 1H. 100 ng of total RNA from each sample was hybridized, the raw data were normalized to the standard curve generated via the nCounter system, and the average value of the two probes in each target region (exons 1-19, intron 19, exons 20-29) were printed in bar charts using GraphPad Prism software 6.0.

Cell Lines.

NIH-3T3 mouse embryonic fibroblast cells were obtained from the 'American Type Culture Collection' (#CRL-1658, ATCC) and were maintained in DMEM. The Interleukin 3 (IL-3) dependent murine pro B cell line, Ba/F3, was obtained from 'The Deutsche Sammlung von Mikroorganismen und Zellkulturen' (#ACC-300, DSMZ) and was cultured in RPMI supplemented with Interleukin 3 (1 ng ml; #403-ML-010, R&D Systems). Melan-a cells were provided by Dr. Dorothy Bennett (St. George's Hospital, University of London, London, UK)[40] and were maintained in RPMI supplemented with 200 nM of 12-O-tetradecanoylphorbol-13-acetate (TPA; #4174, Cell Signaling). For retrovirus production, 293T cells (#631507, Clontech) were purchased and cultured in DMEM. All cell culture media contained 10% FBS, L-glutamine (2 mM), penicillin (100 U ml-1), and streptomycin (100 μg ml-1). All cells were cultured at 37° C. in 5% $CO_2$.

Plasmids.

To investigate the functional roles and the activation of oncogenic signaling pathways, $ALK^{ATI}$, EML4-ALK and $ALK^{F1174L}$ expression constructs were generated. For the $ALK^{ATI}$ vector, RNA from MM-15 was reverse-transcribed with anchored oligo(dT) primers into cDNA (#04379012001, Roche), PCR amplified with ALK specific primers 5'-CACCATCCCATCTCCAGTCTGCTTC-3' [SEQ ID NO: 9] and 5'-AGAGAAGTGAGTGTGCGACC-3' [SEQ ID NO: 10], and the PCR product was cloned into a pENTR vector (#K2400-20, Life Technologies). The full-length ALK plasmid (HsCD00079531) was purchased from the DF/HCC DNA Resource Core (http://plasmid.med.harvard.edu), and EML4-ALKv1 was synthesized at GeneArt (Life Technologies). Site-directed mutagenesis was performed using QuikChange (#200523, Agilent): For kinase-dead $ALK^{ATI}$ ($ALK^{ATI\text{-}KD}$), the lysine in the ATP-binding site of the kinase domain was mutated to methionine (p.K1150M) in $ALK^{ATI}$, and for $ALK^{F1174L}$, a p.F1174L mutation was introduced into $ALK^{WT}$. Plasmids were subcloned into a pMIG-w vector[41] (#12282, www.addgene.org), resulting in MSCV-$ALK^{variant}$-IRES-GFP constructs, which were confirmed by digestion and sequencing. An empty pMIG-w vector with green-fluorescent-protein (GFP) was used as control for all ALK expression experiments. To confirm the start codons, the three start codons were mutated from ATG to AAG. For co-immuno-precipitation, $ALK^{ATI}$ was cloned into pcDNA3.1/nV5-Dest (#12290-010, Life Technologies) and MSCV N-HA FLAG-Dest (#41033, Addgene). For bioluminescence imaging, a triple modality retroviral reporter plasmid (red fluorescent protein (RFP)—thymidine kinase—luciferase)[42] was used.

Stable Gene Expression.

Retrovirus were produced in 293T cells by standard methods using ecotropic or amphotropic packaging vector and XtremeGene 9 (#06365809001, Roche). We harvested the virus-containing supernatant were harvested for 48, 64, 64 h and 72 hours after transfection. The supernatant was pooled, filtered through a 0.45 μm PVDF membrane, and used for transduction in the presence of polybrene (8 μg ml-1). Transduced stably expressing eGFP+ or RFP+ cells were sorted with a FACSAria II (BD Biosciences).

Co-Immunoprecipitation.

V5-ALK$^{ATI}$ and HA-ALK$^{ATI}$ was transiently transfected into 293T cells and after 24 hours, cells were lysed in 10 mM Tris HCl pH 7.5, 1% Triton X-100, 150 mM NaCl, 1 mM EDTA, 1 mM DTT, 1 mM PMSF, proteinase/phosphatase inhibitors. After incubation and centrifugation, 100 μl supernatant was used as input, and 300 μl for immunoprecipitation using the following antibodies: 2 μg of anti-V5 antibody (#MA1-81617, Thermo Scientific), 10 μl of EZview Red Anti-HA Affinity Gel (#E6779-1ML, Sigma), 2 μg of anti-mouse IgG (#sc-2025, Santa Cruz). 20 μl of Protein A/G UltraLink Resin (#53133, Thermo Scientific) were used for immunoprecipitation. The immune-precipitated material was eluted in 4× SDS loading buffer for immunoblotting.

In Vitro Kinase Assay.

Stably transduced NIH-3T3 cells were grown in a 15 cm dish, washed in PBS, and lysed in 20 mM Tris pH 8.0, 1% NP-40, 125 mM NaCl, 2.5 mM MgCl2, 1 mM EDTA with proteinase/phosphatase inhibitor. Lysates were incubated on ice, centrifuged, pre-cleared with 25 μl Protein A/G Ultra-Link Resin (#53133, Thermo Scientific) for 30 min at 4° C. under rotation, and immunoprecipitated with 10 μl ALK (D5F3) XP® Rabbit mAb (#3633) and 25 μl Protein A/G UltraLink Resin. After rotation for 120 min at 4° C., the immunoprecipitated material was washed and used according to the instructions of Universal Tyrosine Kinase Assay Kit (#MK410, Clontech). After the enzymatic reaction, the immunoprecipitated material was mixed with 4× SDS loading buffer for immunoblotting.

Immunohistochemistry.

Immunohistochemistry was performed on archival FFPE tumor specimens using a standard multimer/DAB detection protocol on a Discovery Ultra system (Roche/Ventana Medical Systems) with appropriate negative and positive controls. The following antibodies were purchased from Cell Signaling and were diluted in Signal Stain Antibody Diluent (#8112, Cell Signaling) as indicated: ALK (D5F3) XP® Rabbit mAb (#3633) 1:250, Phospho-Akt (Ser473) (D9E) Rabbit mAb (#4060) 1:50, Phospho-Stat3 (Tyr705) (D3A7) Rabbit mAb (#9145) 1:400, Phospho-S6 Ribosomal Protein (Ser235/236) (D57.2.2E) Rabbit mAb (#4858) 1:400, Phospho-p44/42 MAPK (Erk1/2) (Thr202/Tyr204) (D13. 14.4E) Rabbit mAb (#4370) 1:400, cleaved Caspase-3 (Asp175) Antibody (#9661) 1:400. The Anti-Ki67 antibody was purchased from Abcam (#ab15580) and was diluted 1:600.

Immunofluorescence.

Stably transduced NIH-3T3 cells were grown on coverslips, fixed in 4% formaldehyde, washed in PBS for 15 min at room temperature, washed in PBS for 10 min, and incubated in blocking solution (5% goat serum, 0.1% Triton X-100 in PBS) for 1 hour at room temperature. After aspirating blocking solution, cells were incubated with an ALK (D5F3) Rabbit mAb (#3633, Cell Signaling Technology) diluted 1:1000 in blocking buffer overnight at 4° C. After washing the cells 3× with 0.05% Tween 20 and PBS, cells were incubate with a secondary antibody (#A-11012, Life Technologies) diluted 1:500 in blocking buffer for 2 hours at room temperature. After washing in PBS, slides were mounted with Prolong® Gold Antifade Reagent with DAPI (#8961, Cell Signaling Technology) and imaged with a Leica TCS SP5 II confocal microscope.

Immunoblot.

Cell lysates were prepared in RIPA buffer (#9806, Cell Signaling) supplemented with Halt protease and phosphatase inhibitor cocktail (#78440, Thermo Scientific). Equal amounts of protein, as measured by BCA protein assay (#23225, Thermo Scientific), were resolved in NuPAGE® Novex® 4-12% Bis-Tris Protein Gels (#NP0321BOX, Life Technologies) and transferred electrophoretically onto a Nitrocellulose 0.45 μm membrane (#162-0115, BioRad). Membranes were blocked for 1 hour at room temperature in 50% Odyssey Blocking Buffer in PBS (#927-40000, LI-COR) and were incubated overnight at 4° C. with the primary antibodies diluted at 1:1000 in 50% Odyssey Blocking Buffer in PBS plus 0.1% Tween 20. Following primary antibodies were used: Anti-a-Tubulin antibody (#T9026-.5ML, Sigma-Aldrich), Anti-V5 (#MA1-81617, Thermo Scientific), and anti-HA3F10 (#12158167001, Roche); Cell Signaling Technology: Phospho-ALK (Tyr1604) Rabbit mAb (#3341), ALK (D5F3) Rabbit mAb (#3633), Phospho-Akt (5er473) (D9E) Rabbit mAb (#4060), Akt (pan) (11E7) Rabbit mAb (#4685), Phospho-Stat3 (Tyr705) (D3A7) Rabbit mAb (#9145), Stat3 (79D7) Rabbit mAb (#4904), Phospho-S6 Ribosomal Protein (5er235/236) (D57.2.2E) Rabbit mAb (#4858), S6 Ribosomal Protein (5G10) Rabbit mAb (#2217), Phospho-p44/42 MAPK (Erk1/2) (Thr202/Tyr204) (D13.14.4E) Rabbit mAb (#4370), p44/42 MAPK (Erk1/2) (137F5) Rabbit mAb (#4695), Phospho-MEK1/2 (5er221) (166F8) Rabbit mAb (#2338), MEK1/2 Antibody (#9122). After 4 washes of 5 minutes in PBST, membranes were incubated with secondary antibodies (IRDye 800CW Goat anti-Rabbit #926-32211, 1:20,000, LI-COR; IRDye 680RD Goat anti-Mouse #926-68070, 1:20,000, LI-COR) in 50% Odyssey Blocking Buffer in PBS plus 0,1% Tween 20 for 45 minutes at room temperature. After another 4 washes in PBS-T and a final wash with PBS, membranes were scanned with a LI-COR Odyssey CLx scanner and adjusted using LI-COR Image Studio.

Luciferase Reporter Assay.

The long terminal repeat in ALK intron 19 at the ATI site (LTR16B2, chr2:29,446,649-29,447,062; 414 bp) was amplified using genomic DNA from patient MM-15 and 5'-GTCCTCATGGCTCAGCTTGT-3' and 5'-AGCACTA-CACAGGCCACTTC-3' primers. The PCR product (chr2: 29,446,444-29,447,174; 731 bp) was cloned into pGL4.14-firefly luciferase vector (#E6691, Promega). To determine the promoter activity of LTR16B2, $10^5$ cells were transfected with 500m pGL4.14-LTR16B2 or vector alone; as internal control, 200 μg pRL-TK *Renilla* luciferase reporter vector (#E2241, Promega) was co-transfected. Luciferase activity was measured using Dual-Glo Luciferase Assay System (#E2920, Promega) 48 hours after transfection. Promoter activity was calculated by normalising firefly luciferase activity to the control *Renilla* luciferase activity and compared between pGL4.14-LTR16B2 and vector alone.

Flow Cytometry and Fluorescence-Activated Cell Sorting (FACS).

Flow cytometry analysis for in vitro transformation assays with Ba/F3 cells was performed on a LSRFortessa (BD Biosciences). GFP- or RFP-positive cells were sorted using a FITC (blue laser) or PE (yellow laser) channel, respectively, on a FACSAria II configured with 5 lasers (BD Biosciences).

In Vitro Transformation and Drug Treatment Assays.

Ba/F3 cells were stably transduced with MSCV-ALK$^{variant}$-IRES-GFP constructs with a multiplicity of infection (MOI) of ~0.26. Based on the MOI calculations, ~78% of cells were uninfected, ~20% of cells were infected with one virus particle, and ~2% of cells were infected by more than one viral particle. Stably transduced Ba/F3 cells were cultured in RPMI medium supplemented with IL-3 (1 ng ml-1) and the transduction rate of 20% was validated using flow cytometry for GFP, that was co-expressed with the ALK variants. For the cell proliferation assay, transduced Ba/F3 cells were transferred into IL-3 depleted RPMI medium and cell growth was quantified every 2-4 days with a luminescence assay (#G7571, Promega). For cell viability assays (ALK inhibitor)-dose response curve, 2000 Ba/F3 cells were plated in quadruplicates in wells of 96-well plates with increasing concentrations of the ALK inhibitors crizotinib (#C-7900, LC laboratories), TAE684 (#CT-TAE684, ChemieTek), or ceritinib (#CT-LDK378, ChemieTek) as indicated. All drugs were suspended in DMSO. The cell viability was assessed after 72 hours by a luminescence assay CellTiter-Glo (#G7571, Promega). Results were normalized to growth of cells in a medium containing an equivalent volume of DMSO. The inhibition curve was determined with GraphPad Prism 6.0 software using the 'log(inhibitor) vs. response variable slope' non-linear regression model. For western blot analysis, 10 million Ba/F3 cells were harvested after 2 hours treatment with crizotinib, washed in ice-cold PBS and lysed in RIPA buffer (#9806, Cell Signaling).

In Vivo Tumourigenicity and Drug Treatment Assays.

All animal experiments were performed in accordance with a protocol approved by MSKCC Institutional Animal Care and Use Committee. $10^6$ cells stably transfected NIH-3T3 or melan-a cells were re-suspended in 50 µl of 1:1 mix of PBS and Matrigel (#356237, BD Biosciences) and the cells were subcutaneously injected into the flanks of 6-8 weeks old female CB17-SCID mice (#CB17SC-F, Taconic). For tumor growth assays, 4 mice were injected with each cell line and 8 tumors were assessed. Tumor sizes were measured with calipers every 2 to 7 days for a period of up to 100 days. For in vivo drug sensitivity studies, 8 mice were injected with the stably transduced NIH-3T3 cells expressing a luciferase reporter construct and the indicated plasmids. When the tumors reached an average size of 200-250 mm$^3$, mice were randomized in a vehicle and or treat group. Mice were orally gavaged once a day with crizotinib (100 mg/kg/d) or vehicle. 8 tumors were measured with calipers every 2 to 3 days and growth curves were visualized with Prism GraphPad 6.0. In parallel, tumor growth was monitored by bioluminescence imaging of anesthetized mice by retro-orbitally injecting d-luciferin (150 mg per kg body weight) and imaging with the IVIS Spectrum Xenogen machine (Caliper Life Sciences). After euthanizing the mice, tumors were explanted either lysed in RIPA buffer (#9806, Cell Signaling Technology), or fixed overnight in 4% paraformaldehyde, washed, embedded in paraffin, and sectioned for hematoxylin-and-eosin (RE) staining or immunohistochemistry.

Statistics.

All statistical comparisons between two groups were performed by GraphPad Prism software 6.0 using a two-tailed unpaired t test.

Results and Discussion

To identify novel mechanisms of oncogene activation, transcriptome analyses (RNA-seq) of metastatic melanoma and thyroid carcinoma were performed. An algorithm[9] was used to investigate the differential expression of exons in receptor tyrosine kinases (RTKs). The analysis was focused on transcripts with a high expression of the kinase domain. A novel ALK transcript in two melanoma (MM-15, MM-74) and in one anaplastic thyroid carcinoma (ATC-28) was identified. The novel transcript contained the ALK exons 20-29 preceded by ~400 base pairs of intron 19, but not exons 1-19 (FIGS. 1A and 5A). This expression pattern was distinct from ALK wild-type (ALT$^{WT}$) and ALK translocations. The ALT$^{WT}$ shows expression of all exons, but no expression of introns (FIGS. 1A, 5B), and is commonly found in neuroblastoma in association with activating mutations.[10-13] ALK translocations are observed in various cancer types, including lymphoma, sarcoma, and lung cancer and typically occur in intron 19.[14-16] Due to preserved splice sites, ALK translocations usually encompass ALK exons 20-29 with little intronic expression (FIGS. 1A and 5C). ALKWT overexpression[10,58-60] and amplification[10,60], activating ALK mutations[10,11-13], and ALK translocations[15,16] are well-established oncogenic drivers in various cancer types, including melanocytic tumors[62].

To evaluate if the novel ALK transcript arises from alternative transcriptional initiation (ATI), a 5'-rapid amplification of cDNA ends (5'-RACE) was performed. The ATI site was mapped to a 25-bp region in intron 19 and the presence of the novel transcript was confirmed and termed as ALK$^{ATI}$ by Northern blot (FIGS. 1B and 6A-6G). ChIPseq and ChIP-qPCR showed that only ALK$^{ATI}$-expressing tumors, but not the controls, had significant enrichment of the chromatin marks trimethylated histone H3 lysine 4 (H3K4me3) and RNA polymerase II at the ATI site, which are characteristic for active promoters[17,18] (FIGS. 1C-1E and 7A-7D). Taken together, these data suggest that ALK$^{ATI}$ originates from a newly established bona fide ATI site associated with characteristic chromatin alterations.

To determine the prevalence of ALK$^{ATI}$ expression, more than 5000 samples from 15 different cancer types in the TCGA RNA-seq dataset were screened. ALK$^{ATI}$ was expressed in ~11% of melanoma (38 of 334 tumors) and sporadically in other cancer types, including lung adenocarcinoma, lung squamous cell carcinoma, clear cell renal cell carcinoma, and breast carcinoma (FIGS. 8A-8E). No ALK$^{ATI}$ expression was found in more than 1600 samples from 43 different normal tissues in the Genotype-Tissue Expression (GTEx) RNA-seq dataset[1], indicating that ALK$^{ATI}$ is primarily expressed in cancers, particularly melanoma.

Figure 1F:
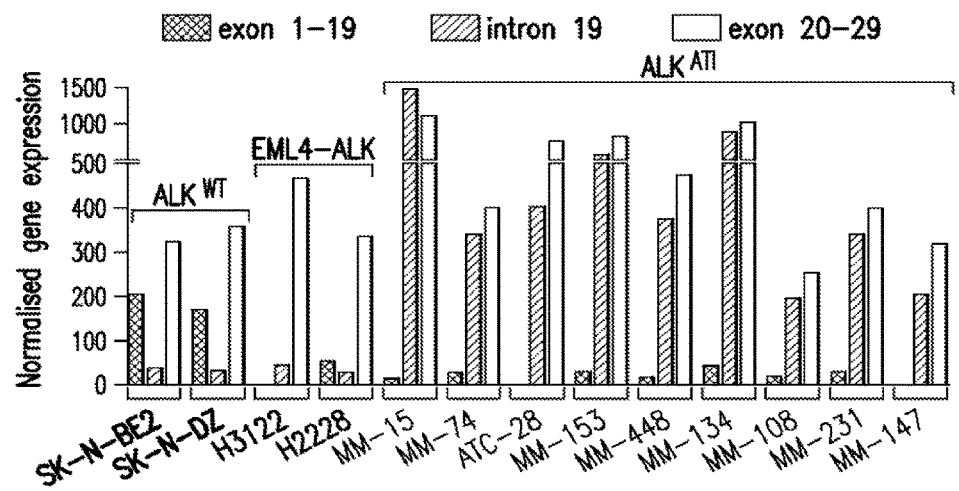

To accurately quantify ALK$^{ATI}$ expression in clinical specimens, a NanoString nCounter assay with probe sets in ALK exons 1-19, intron 19, and exons 20-29 was developed[51] (FIG. 1H). This assay was able to distinguish ALK$^{ATI}$, ALK$^{WT}$ and translocated ALK and identified additional ALK$^{ATI}$-expressing tumors derived from both fresh-frozen and formalin-fixed, paraffin-embedded (FFPE) clinical specimens (FIG. 1F).

Figure 1G:
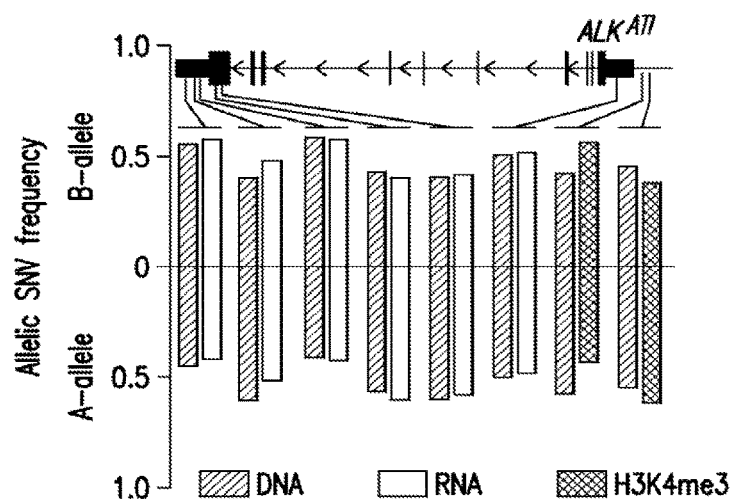
Figure 9A:
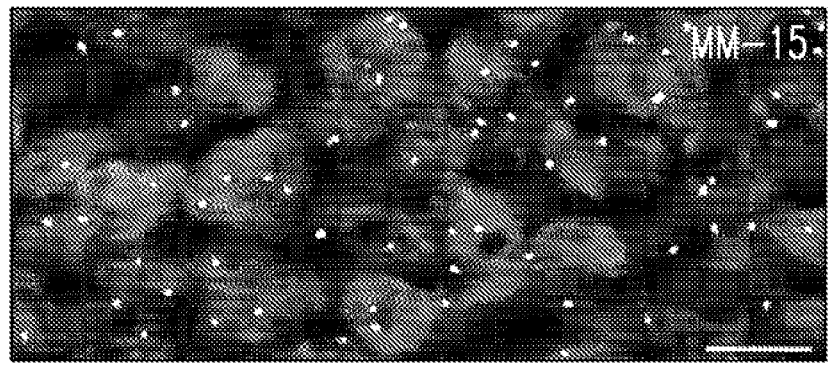
Figure 9B:
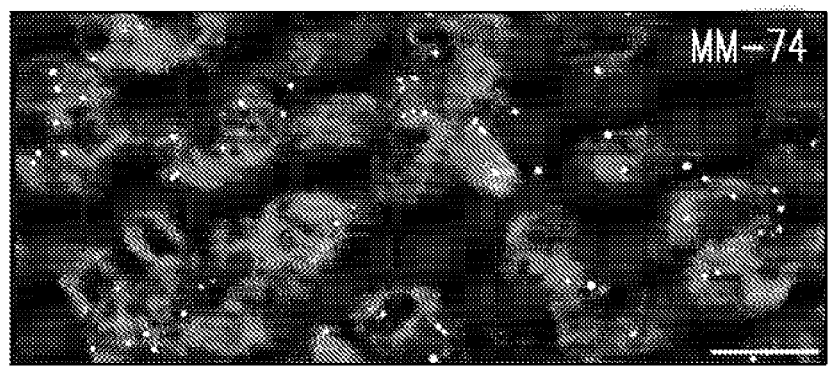
Figure 9C:
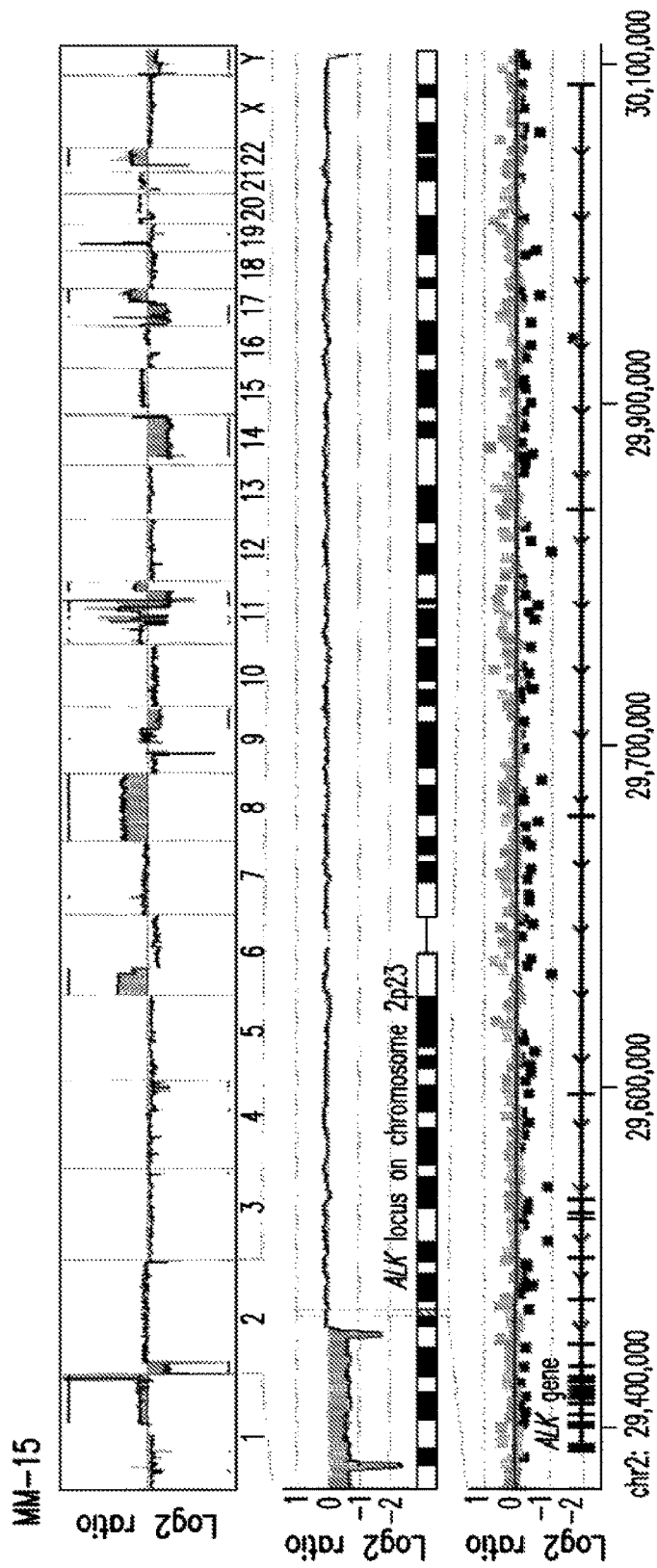
Figure 9D:
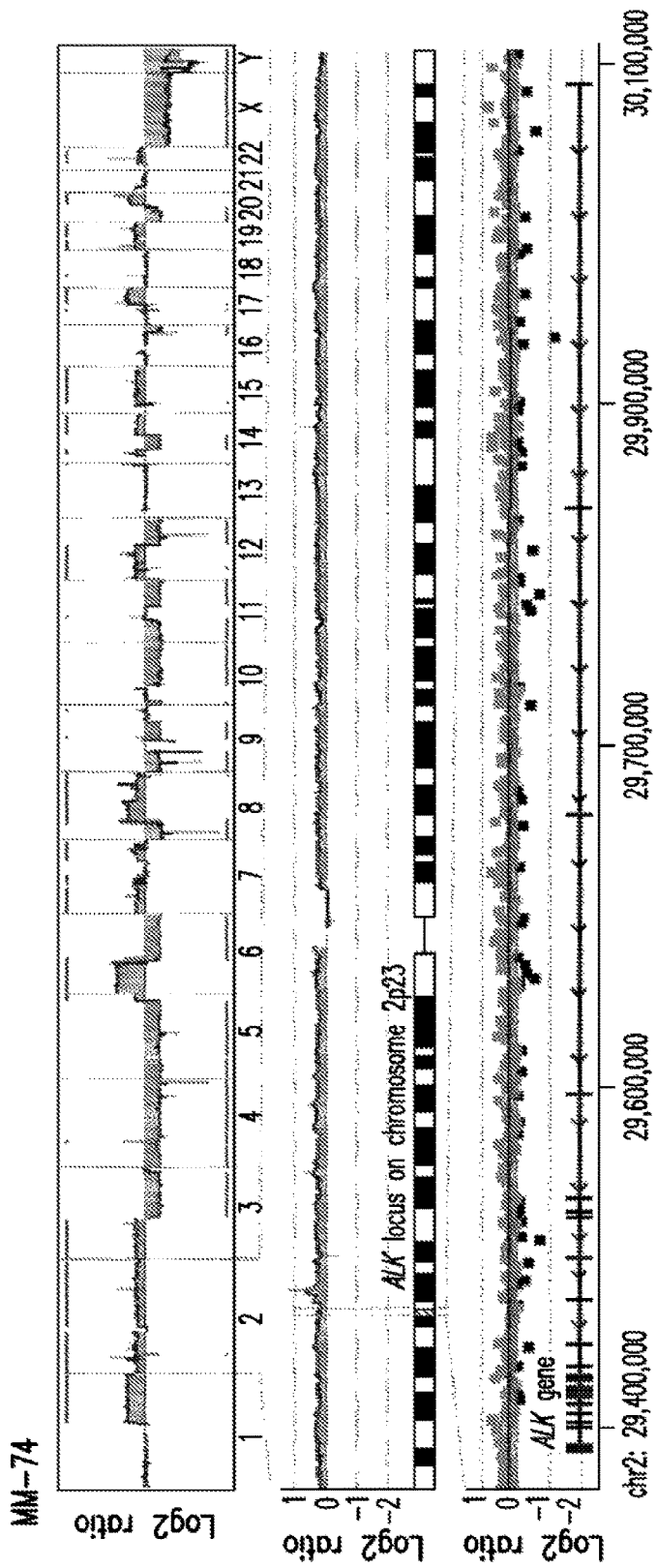
Figure 10A:
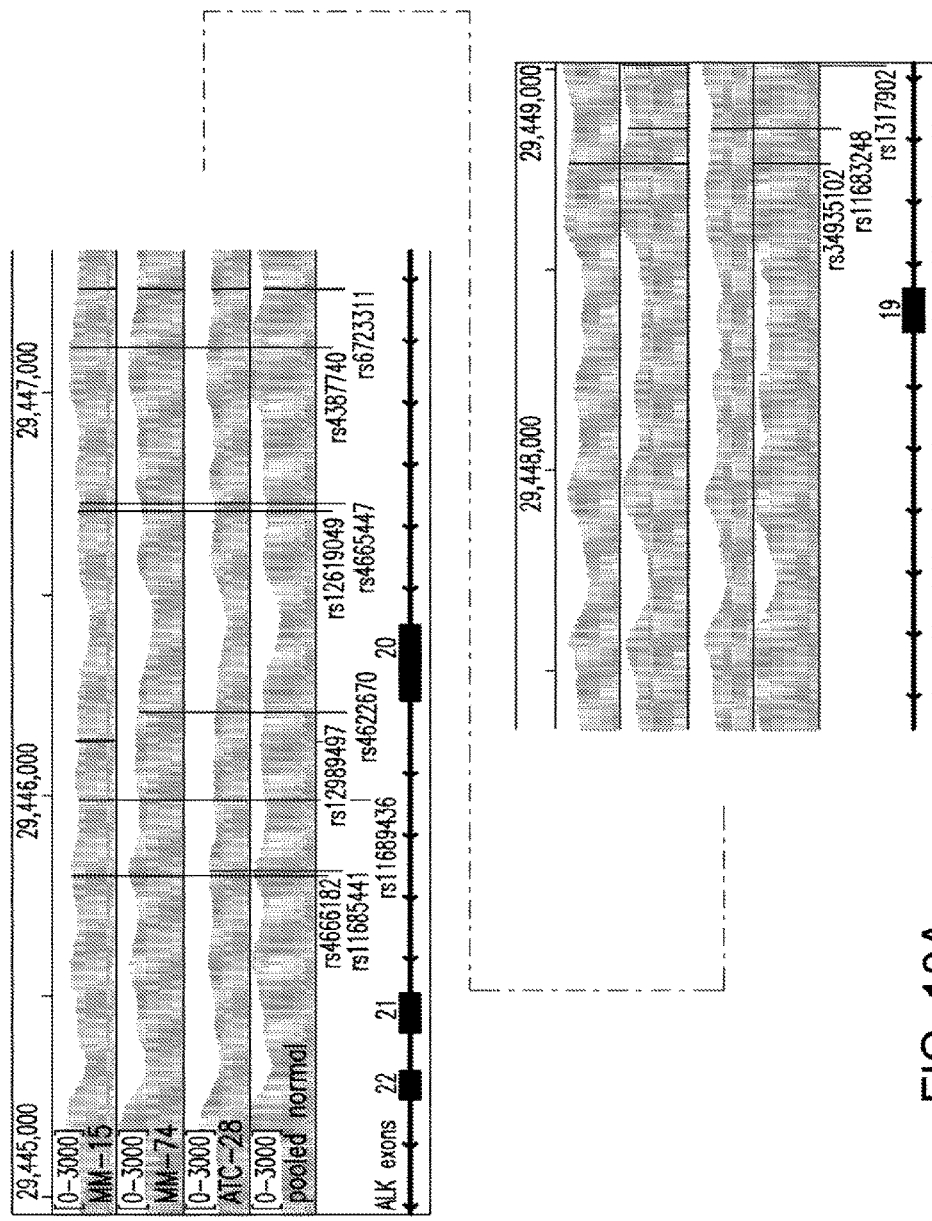
Figure 10B:
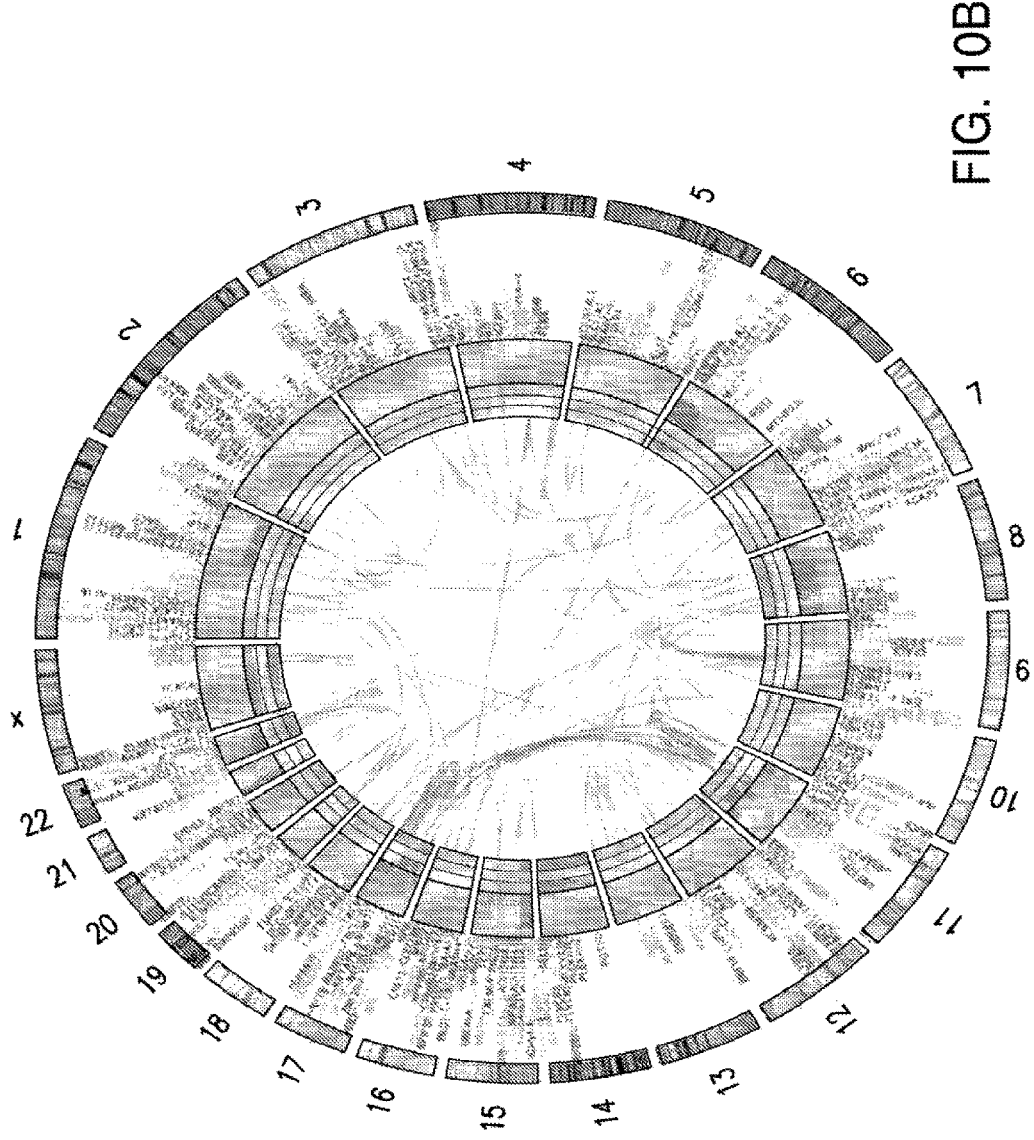
Figure 10C:
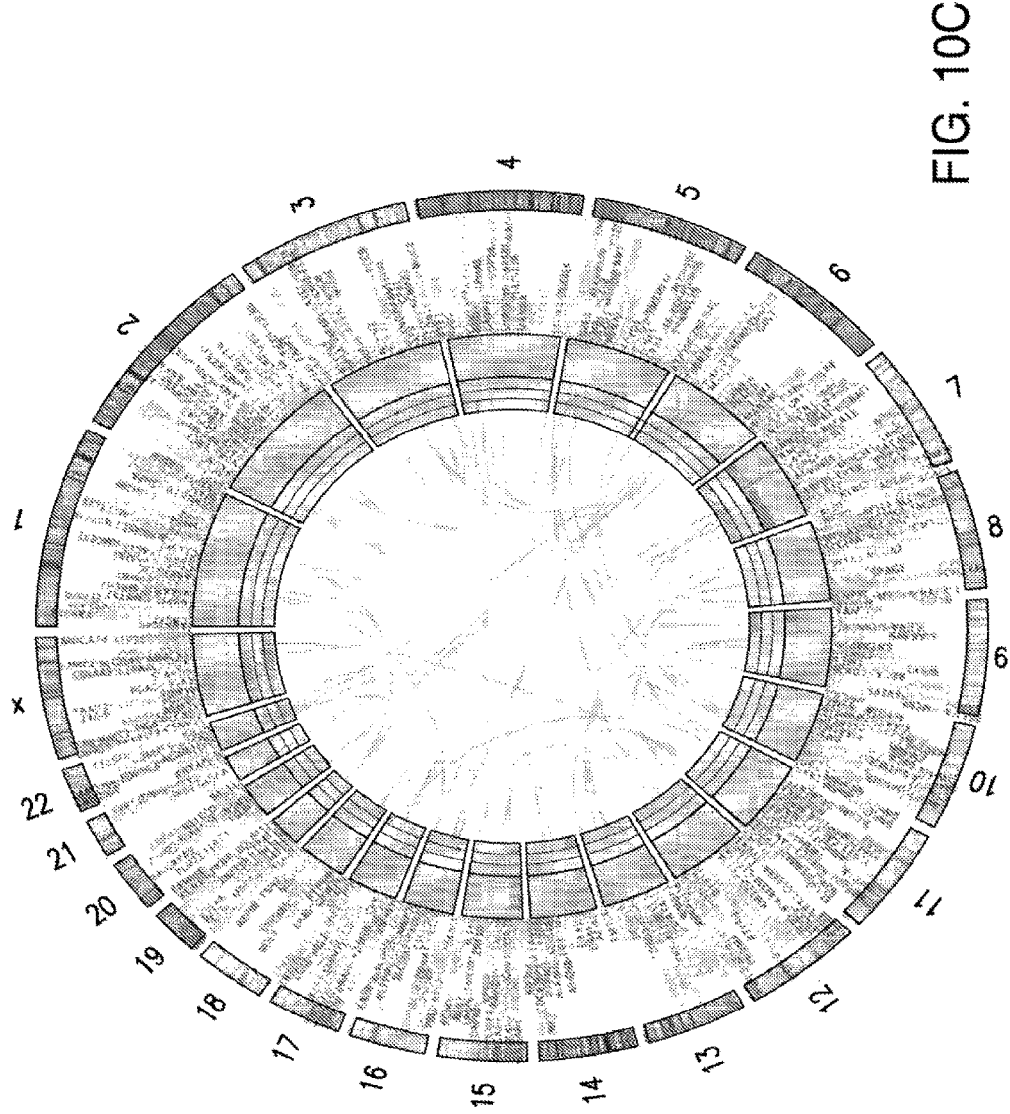

To determine whether somatic genomic aberrations at the ALK locus contribute to the establishment of the de novo ATI site, comprehensive genetic analyses including interphase fluorescence in situ hybridisation (FISH), genome-wide array-CGH, whole-genome sequencing, and ultra-deep sequencing of the entire ALK locus were performed, results of which are shown in FIGS. 9A-9D and 10A-10F. For example, since transcriptional activation may arise due to genomic rearrangements,[20] interphase FISH was performed using probes recognizing the 5' and 3' ends of ALK locus, but found no ALK rearrangements (FIGS. 9A and 9B). To examine the ALK locus for previously described small deletions[21,22] and tandem duplications,[16] genomewide array-CGH was used, but no genetic alterations was discovered (FIGS. 9C and 9D). Finally, to investigate whether ALK$^{ATI}$ could arise through genetic alterations that create a de novo ATI site similar to the recently described TERT promoter mutations in melanoma[23,24], ultra-deep targeted sequencing of the entire ALK locus was performed. No recurrent single nucleotide variations (SNVs), insertions, or deletions were identified in the ALK exons and introns (FIGS. 10A-10D). In summary, no genomic aberrations that could account for the de novo expression of ALK$^{ATI}$ were found. Reasoning that local genomic aberrations are usually cis-acting and only affect the expression of the effected allele,[25,43] the SNVs in the DNA-, RNA- and ChIP-sequencing data were analyzed. Compared to genomic DNA, similar allelic SNV frequencies in the RNA- and ChIP-sequencing data were found, which indicates that both ALK alleles are actively transcribed and decorated with H3K4me3 (FIG. 1G). The bi-allelic ALK$^{ATI}$ expression indicates that the transcriptional activation of ALK$^{ATI}$ is independent of genetic aberrations. However, aberrations affecting trans-acting elements, such as transcription factors or chromatin modifiers, may contribute to ALK$^{ATI}$ expression.

Figure 11A:
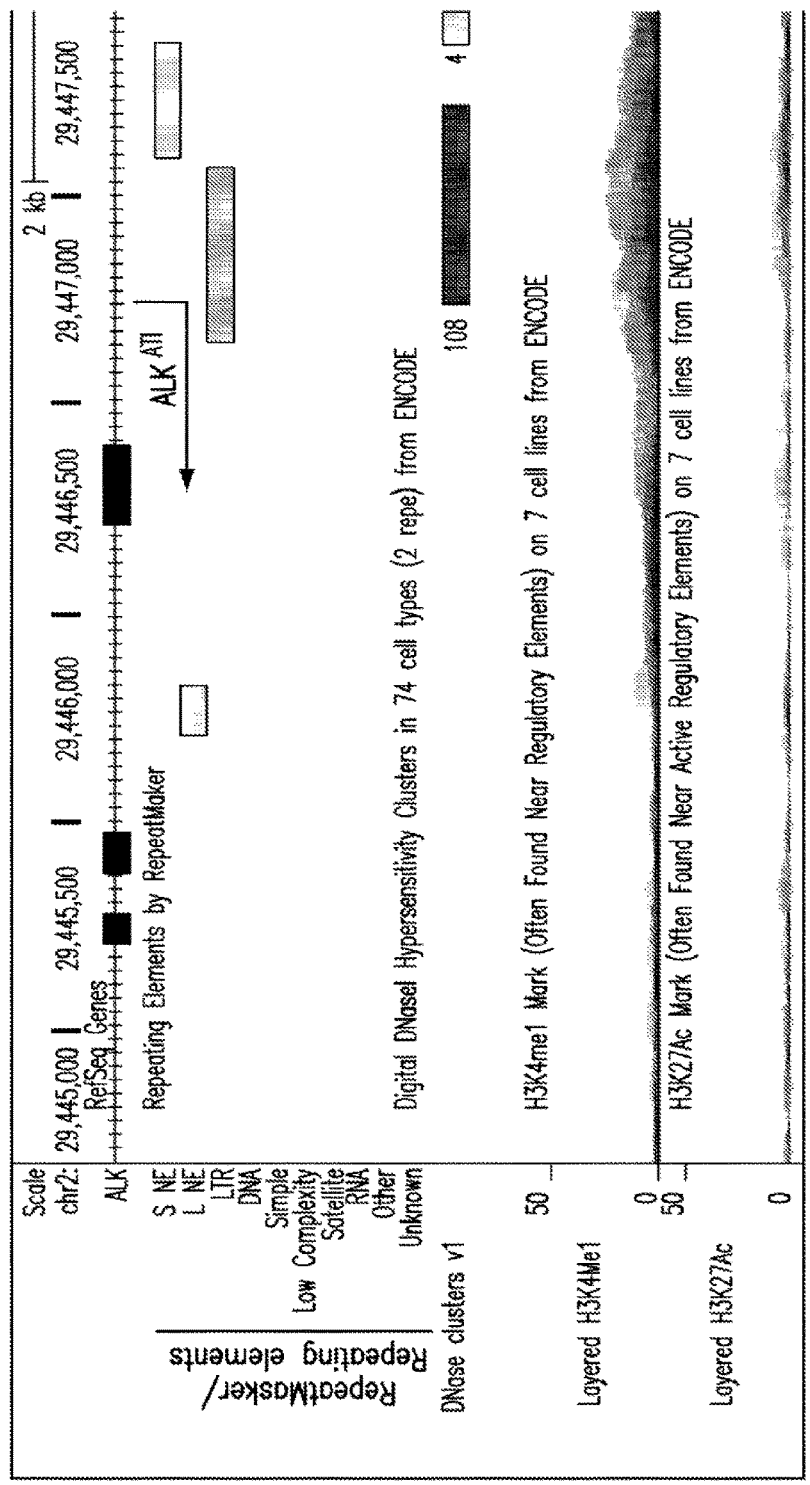
Figure 11A:
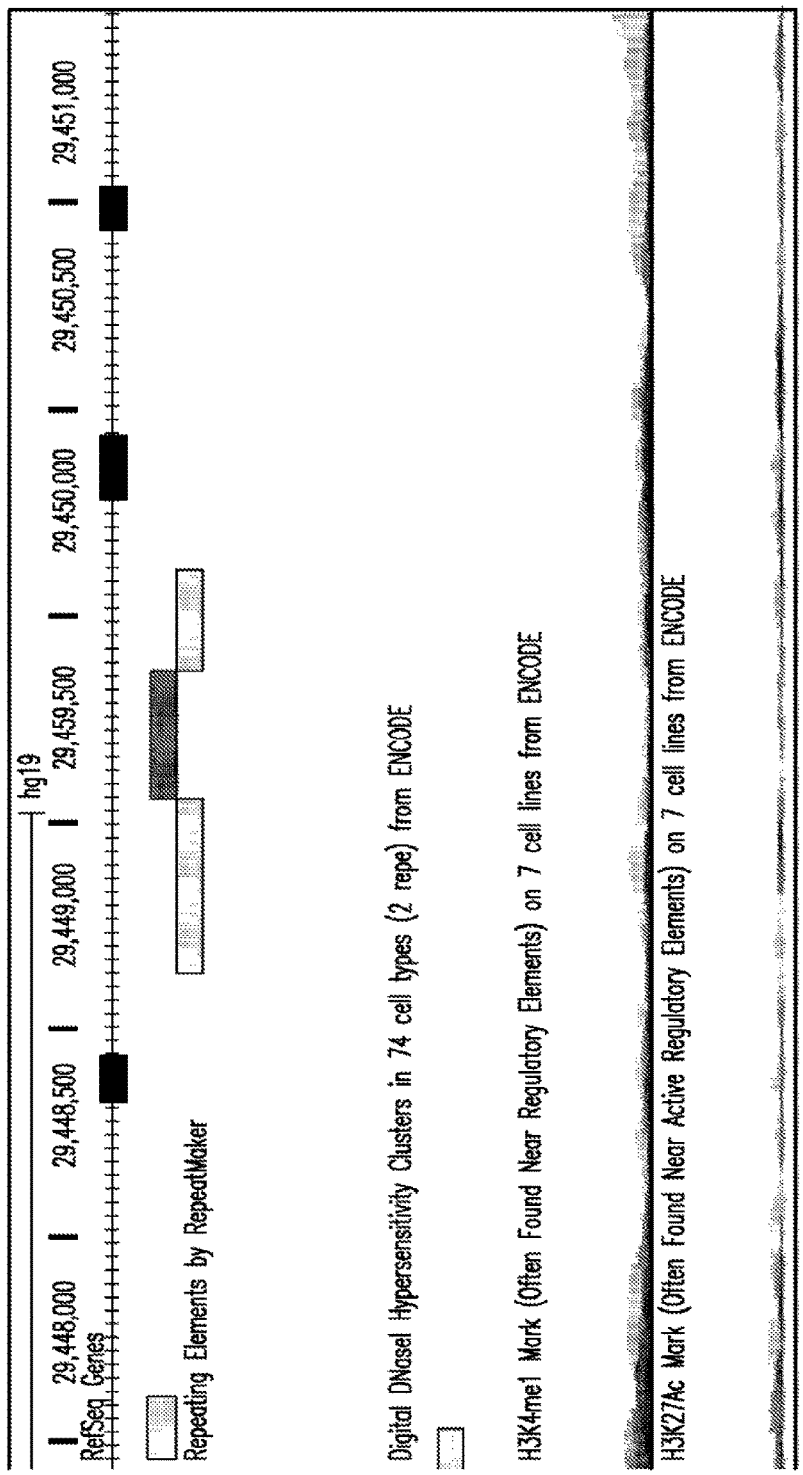
Figure 11B:
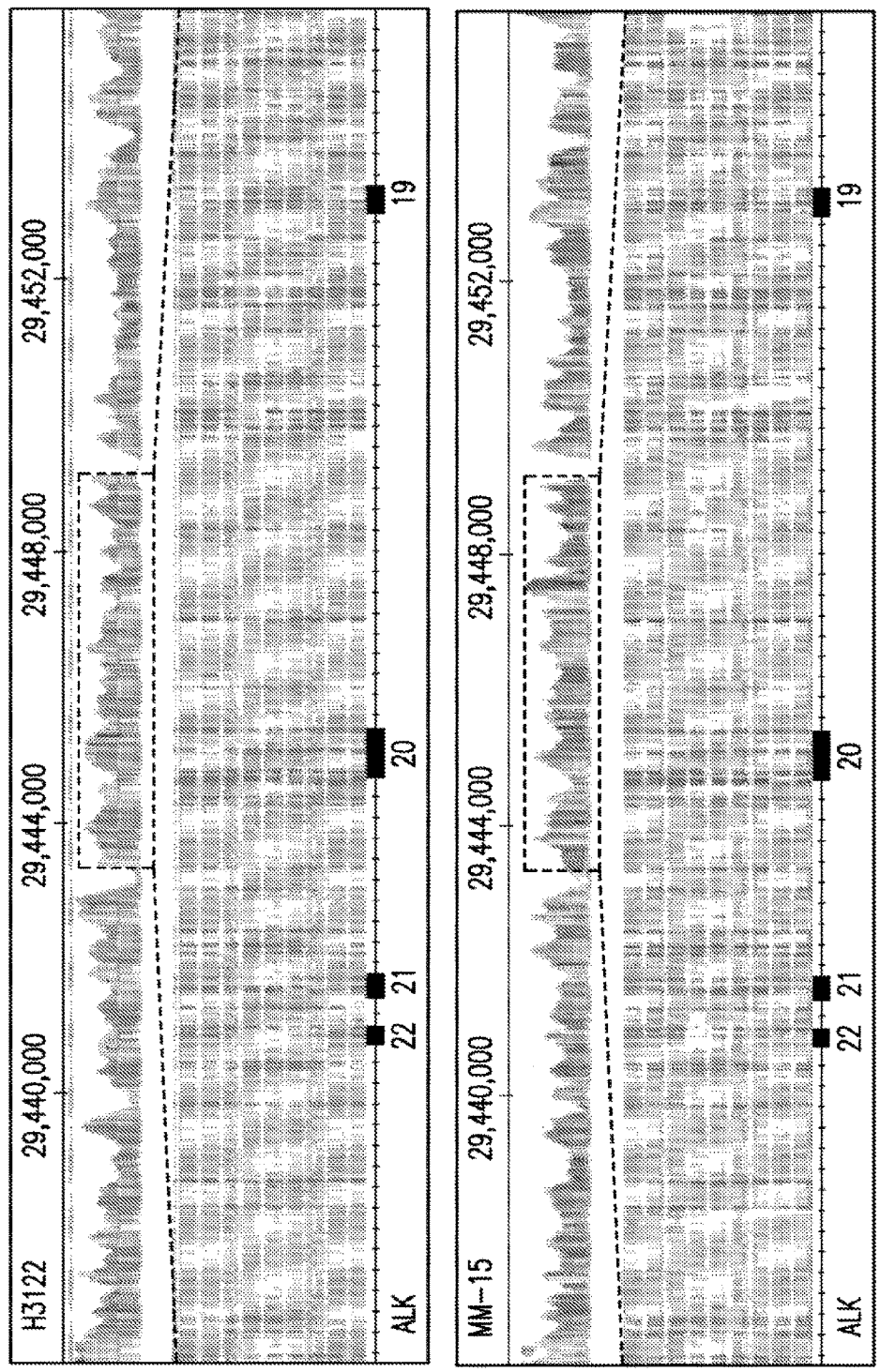
Figure 11C:
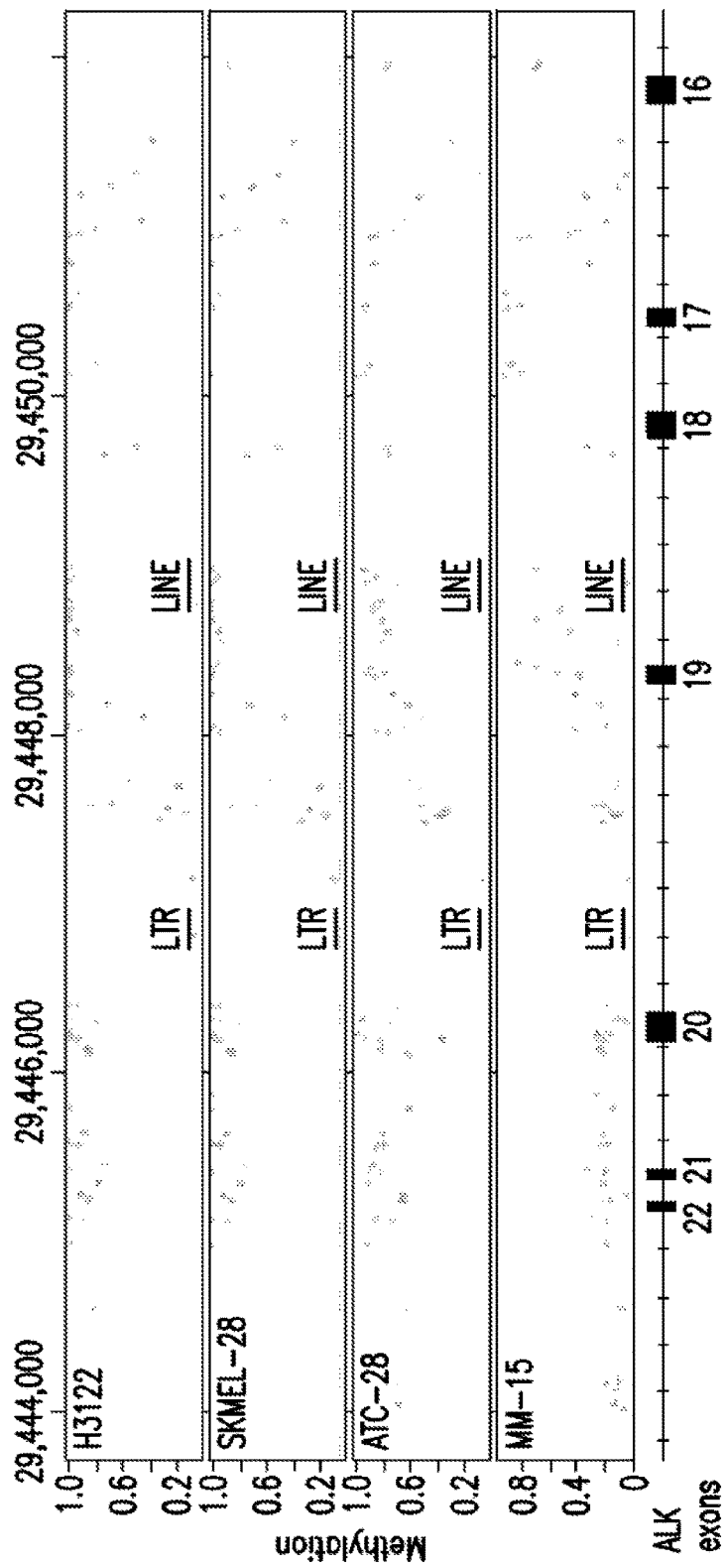
Figure 11D:
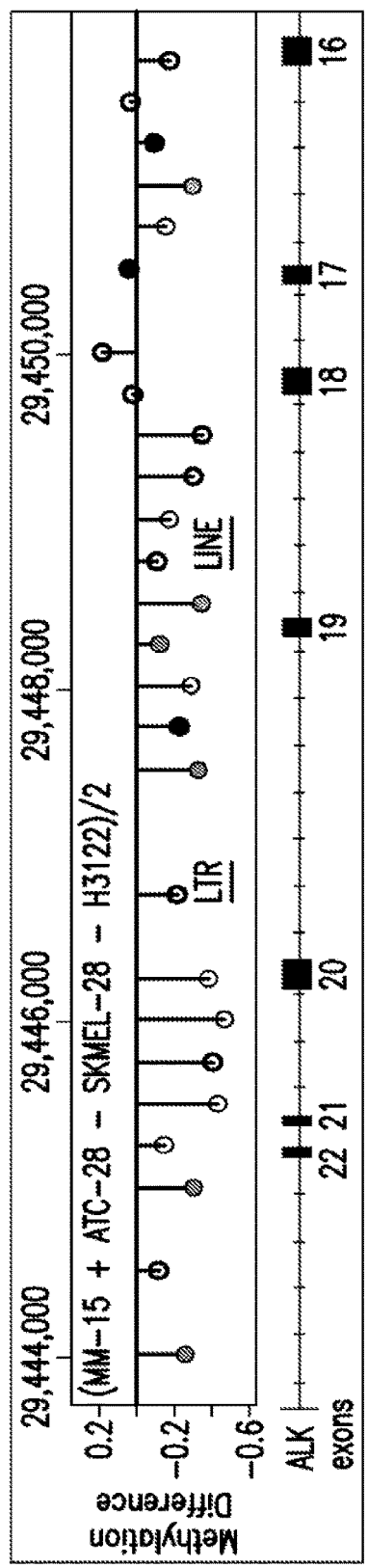
Figure 11E:
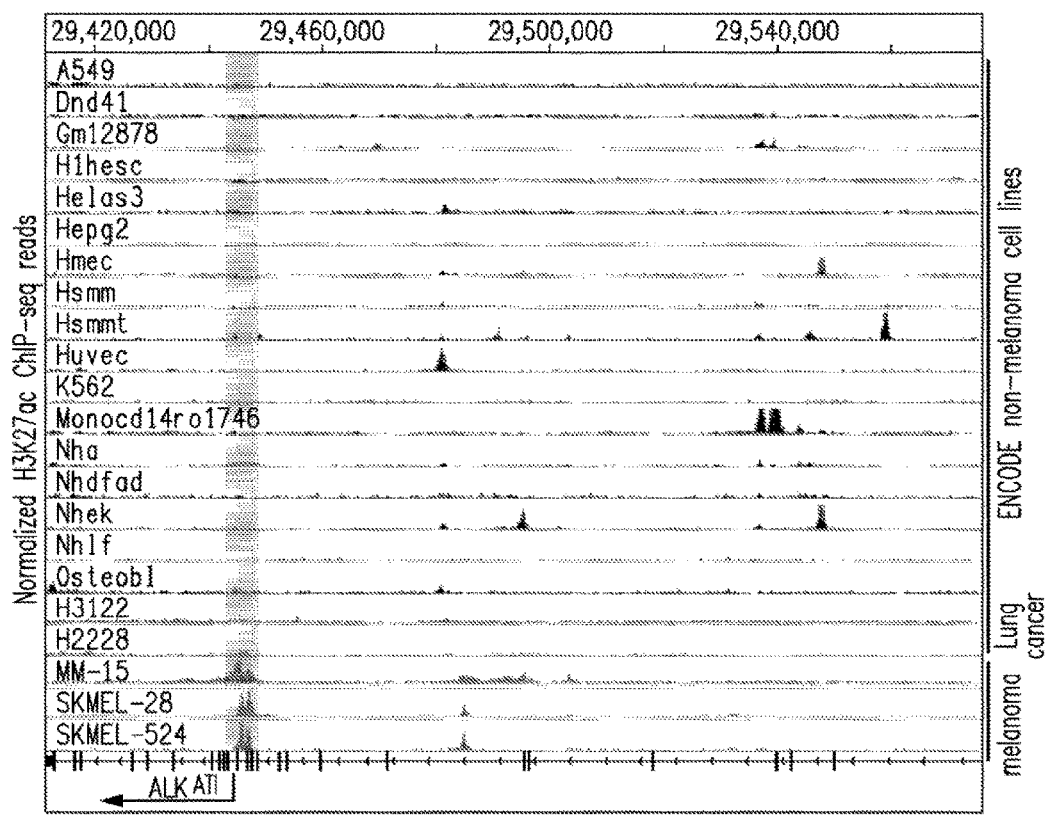
Figure 11F:
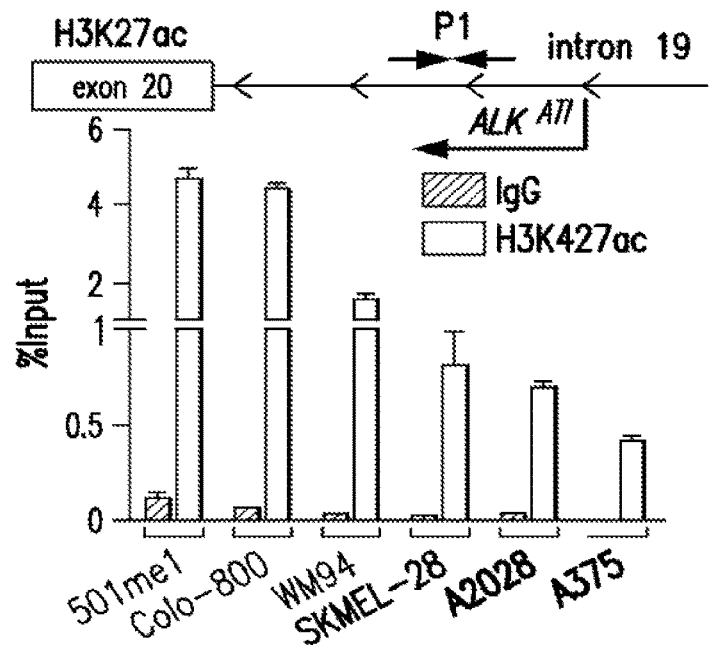
Figure 11G:
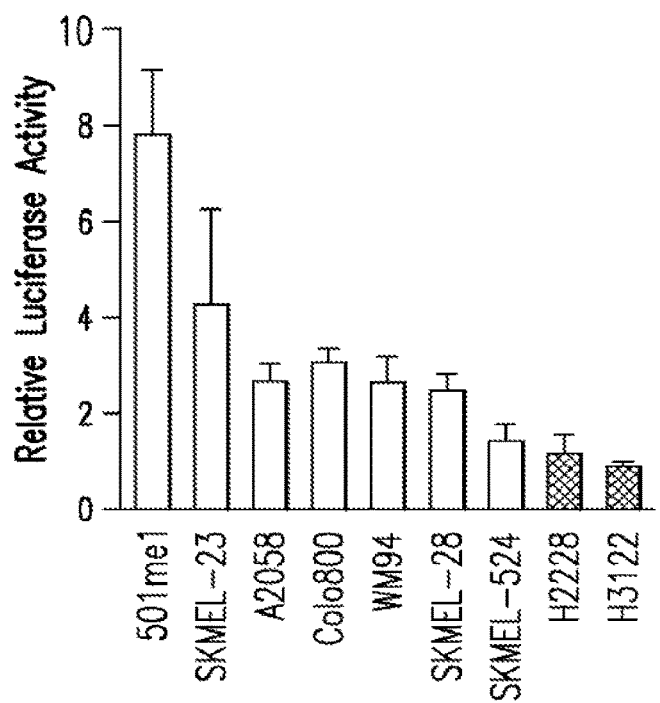

The ALK ATI region contains transposable elements, including a long-terminal repeat (LTR) in intron 19 and a long-interspaced element (LINE) in intron 18, both of which can regulate transcription[44,45] (FIG. 11A). To evaluate if CpG methylation of these elements might contribute to ALK$^{ATI}$ expression, bisulfite sequencing of the entire ALK locus was performed. Compared to the controls, the ALK$^{ATI}$-expressing samples showed lower CpG methylation in regions flanking the ATI site, including the LINE (FIG. 11B-D). The LTR contained only few CpGs with low methylation levels in all samples. The ENCODE data[46] revealed a DNase I hypersensitivity cluster and H3K4me1 enrichment at the ATI region. Independent of ALK$^{ATI}$ expression, H3K27ac enrichment (a histone mark characteristic of active promoters and enhancers[47]) was found in all analyzed melanoma samples, but not in the control lung cancer cell lines or in the 17 non-melanoma cell lines in ENCODE (FIGS. 11E and 11F). By integrating ChIP, DNase I hypersensitivity, and 5'-RACE data, the proximal cis-regulatory region was defined as chr2:29,445,000-29,447,100 and the potential transcription factor binding motifs were bioinformatically determined.[48] (FIG. 11H). To test if the LTR could function as a promoter, a luciferase reporter assay was used, and it was found that, in contrast to lung cancer cell lines, melanoma cell lines showed low but consistent luciferase activity (FIG. 11G). Taken together, these data suggest that the H3K27ac mark at the ATI site might prime melanomas for ALK$^{ATI}$ expression, which is consistent with the higher frequency of ALK$^{ATI}$ in melanomas compared to other cancer types. However, these data also indicate that full activation of ALK$^{ATI}$ expression requires additional trans-activating factors.

Figure 2A:
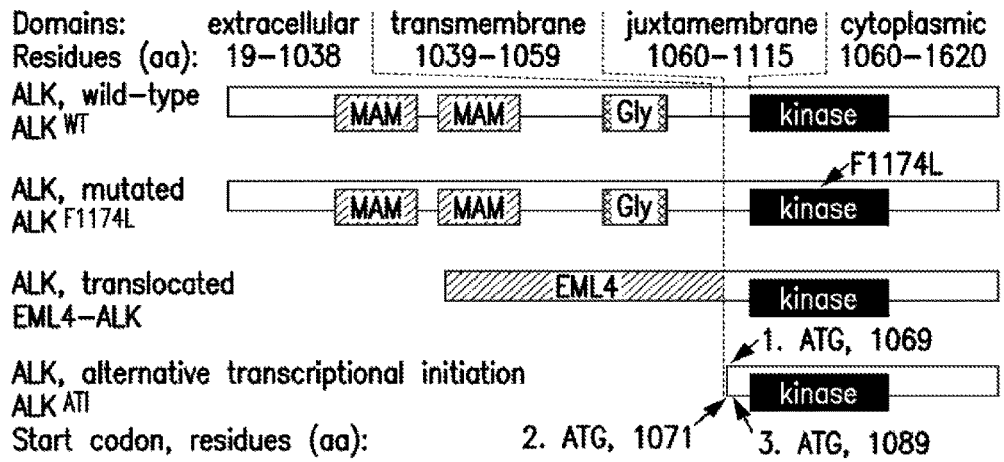
Figure 6A:
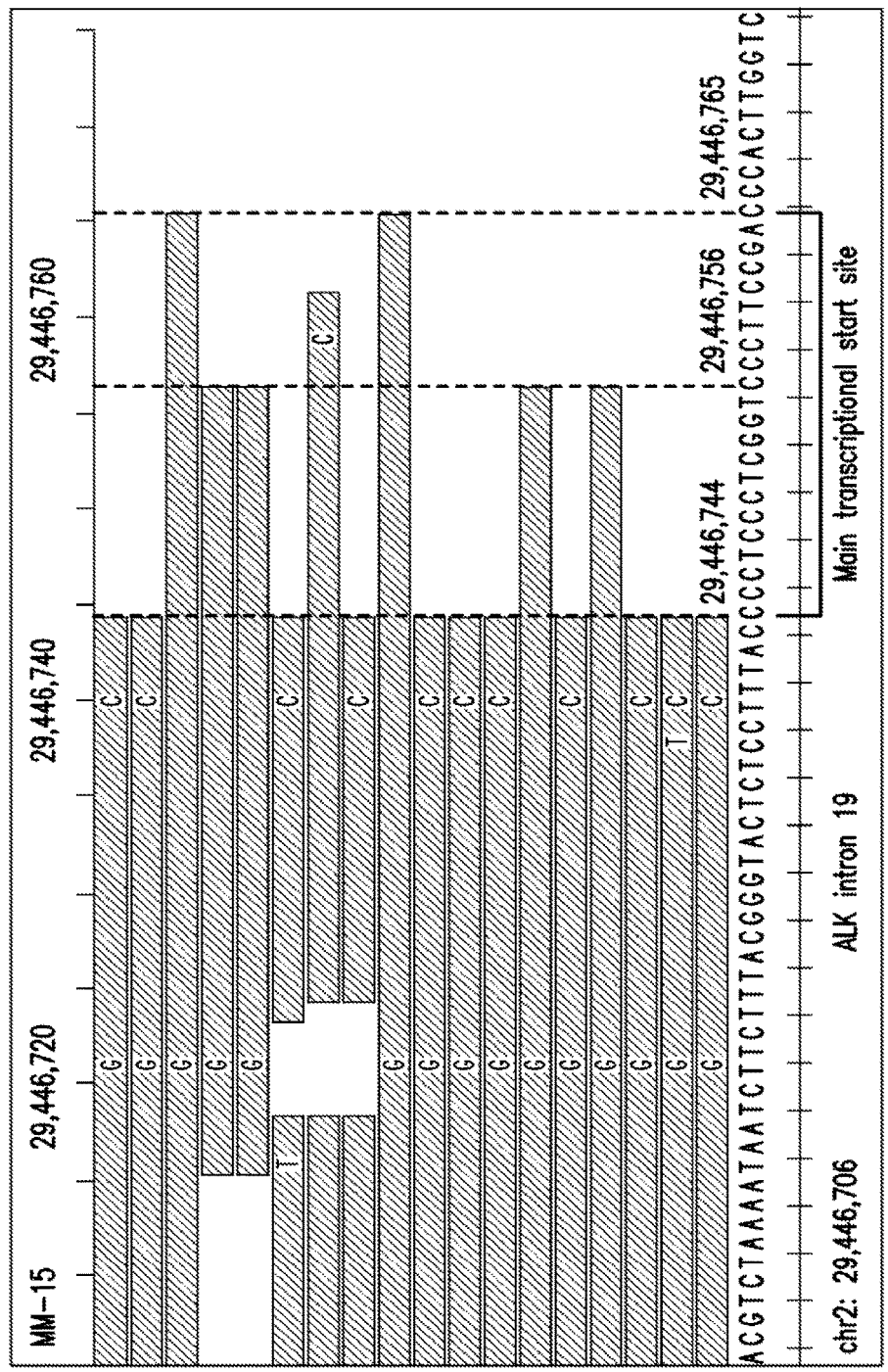
Figure 6C:
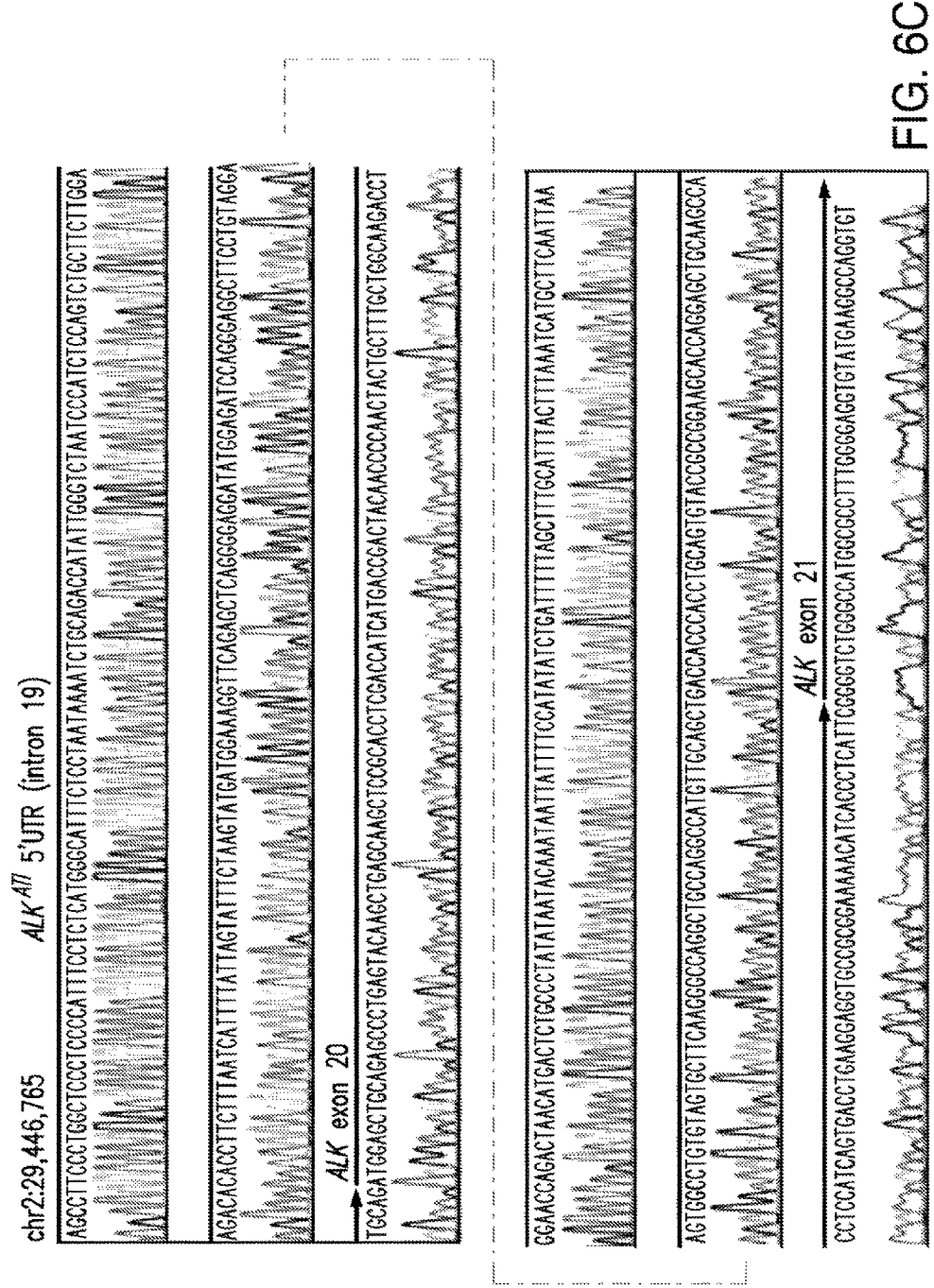
Figure 6G:
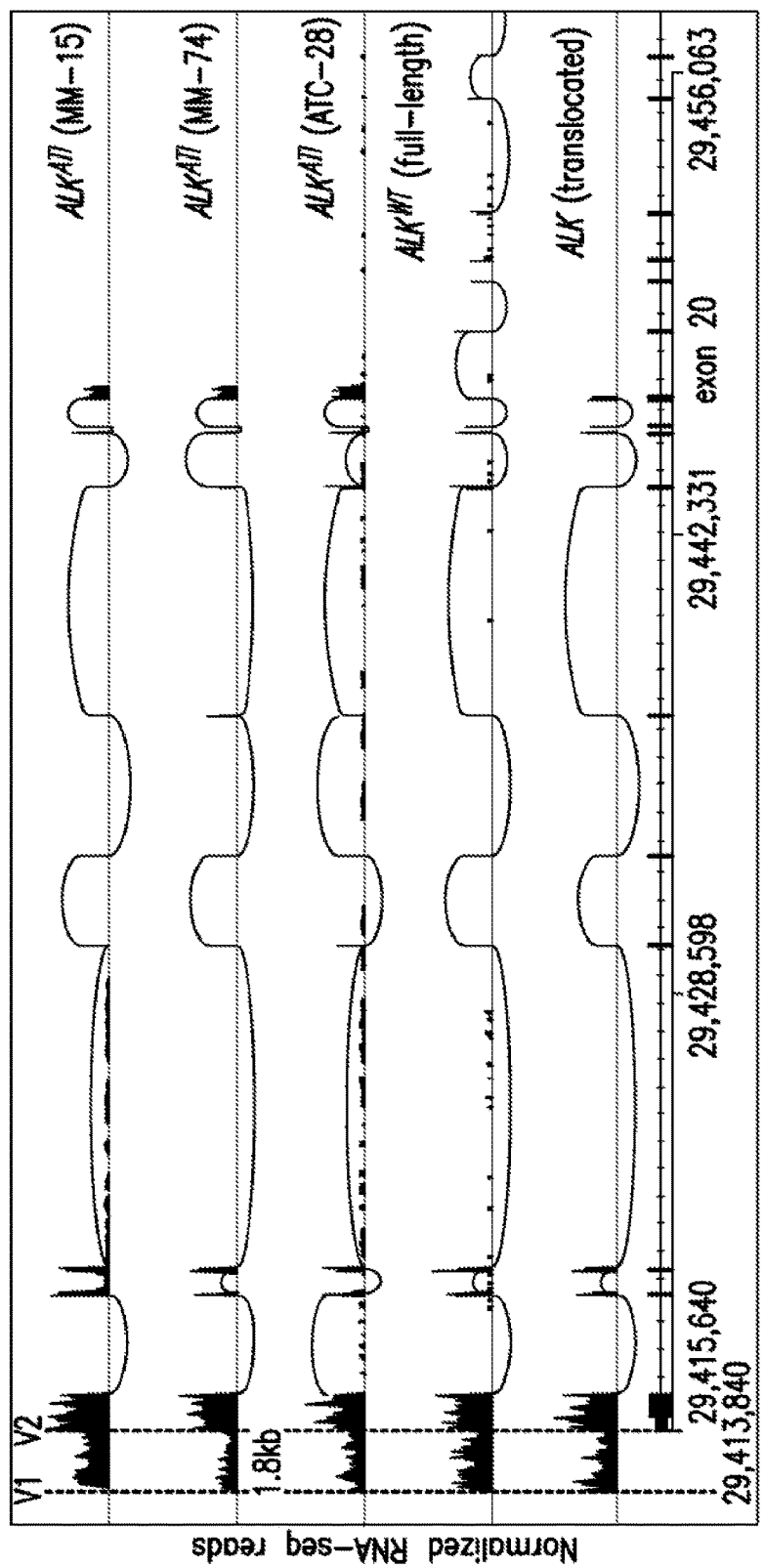
Figure 8B:
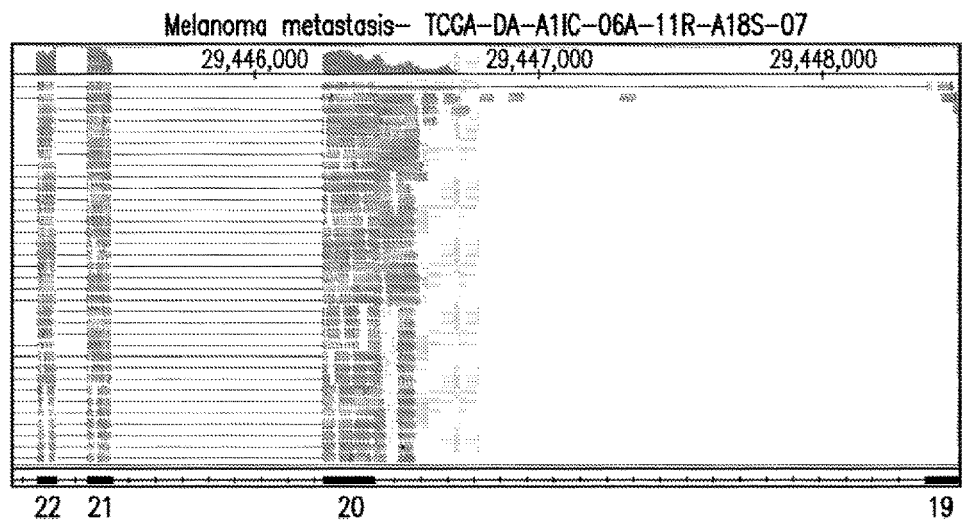
Figure 8C:
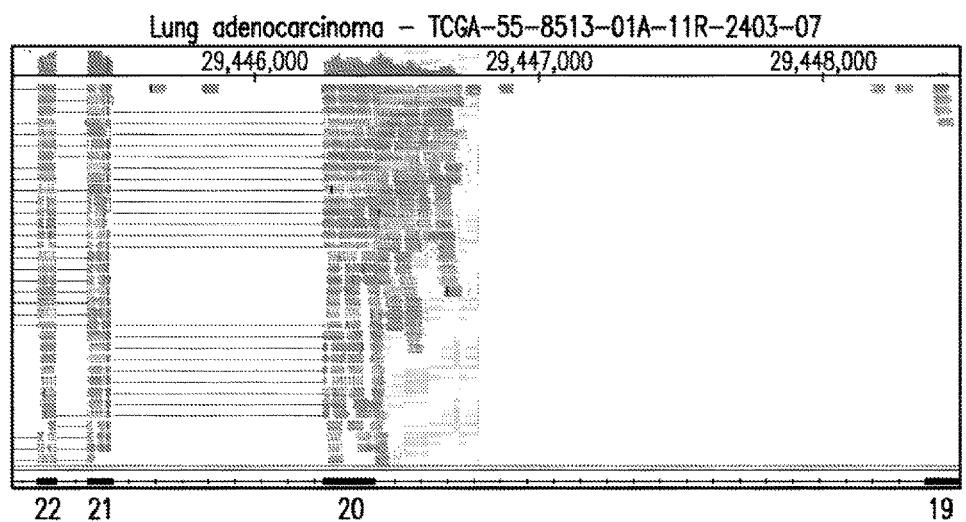
Figure 8D:
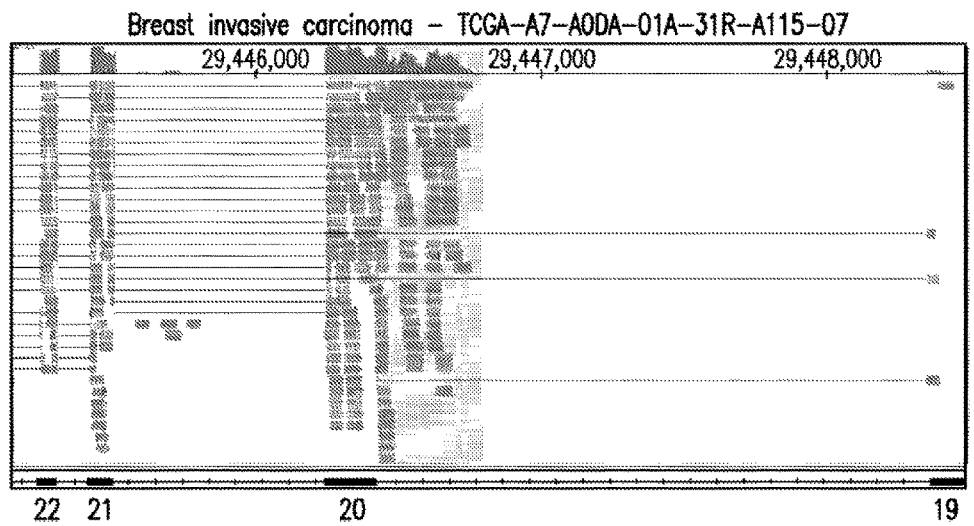
Figure 8E:
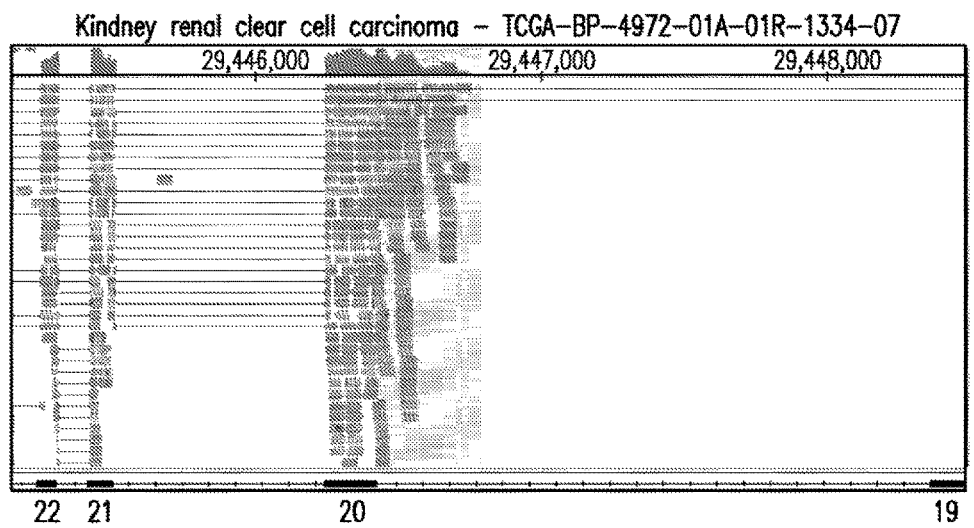

5'-RACE (5'-rapid amplification of cDNA ends) coupled with next-generation sequencing was used to determine the ALK$^{ATI}$ transcript. The ATI site was mapped to a 25 base pairs (bps) region in intron 19, approximately 400 bp upstream of ALK exon 20 (FIGS. 1B and 6A-C). The novel ALK transcript has a size of approximately 2500 bps (FIG. 7A). The ALK$^{ATI}$ transcript has three predicted in-frame start codons (ATGs) resulting in proteins with molecular weights (MW) of 61.1 kDa (552 amino acids), 60.8 kDa (550 amino acids) and 58.7 kDa (532 amino acids) (FIGS. 6D and 6E). All three proteins maintain the intracellular tyrosine kinase domain, but lack the extracellular and transmembrane domains of ALK$^{WT}$ (FIG. 2A).

Figure 2B:
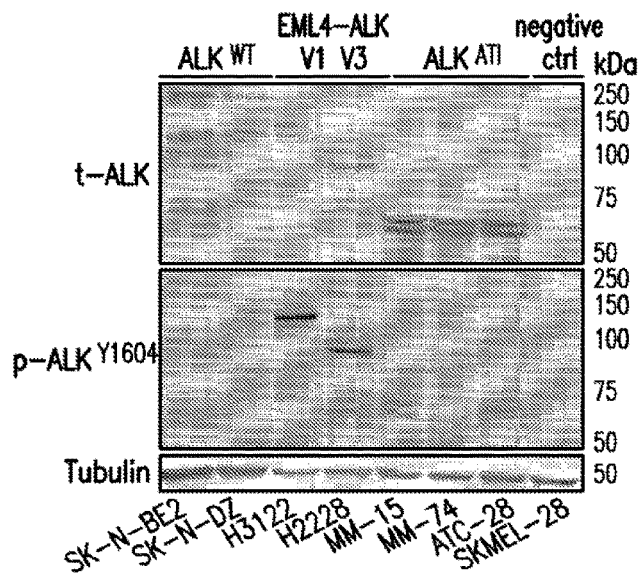
Figure 2C:
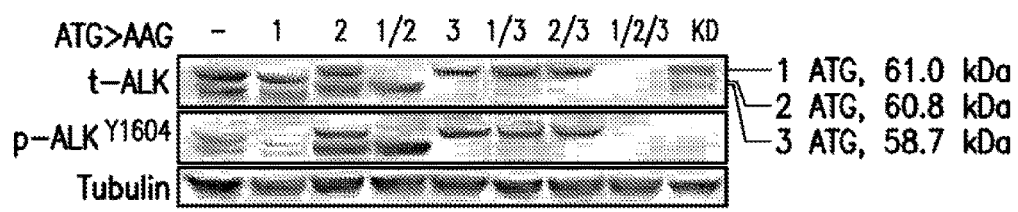

Immunoblots of two ALK-expressing neuroblastoma cell lines and two EML4-ALK variant-expressing lung cancer cell lines showed proteins at the expected MW of ~220 kDa for ALK$^{WT}$ (and a smaller cleavage product lacking part of the extracellular region[49]) and of ~120 kDa and ~90 kDa for two EML4-ALK variants. ATKATI-expressing tumors revealed a double band at ~60 kDa, suggesting that ALKATI is translated from more than one start codon (FIG. 2B). To experimentally confirm the predicted start codons, the three start codons were mutated individually or in combination and expressed them in 293T cells. Immunoblots revealed that each of the mutant ALK$^{ATI}$ lost the corresponding protein band, indicating that all three start codons in ALK$^{ATI}$ are functional and give rise to three distinct proteins (FIG. 2C).

Figure 2D:
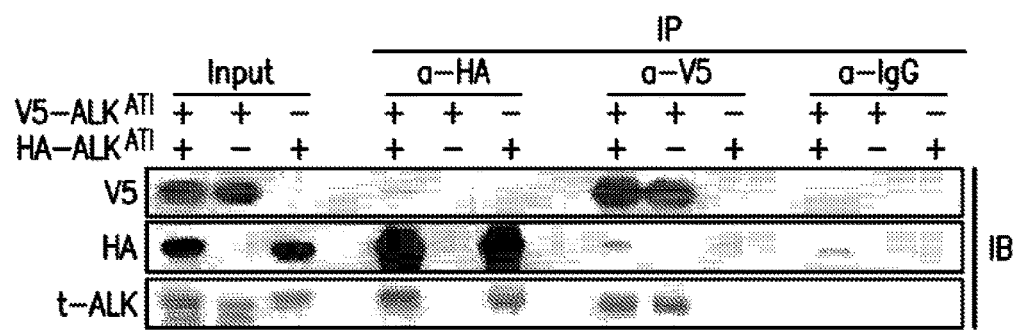
Figure 2E:
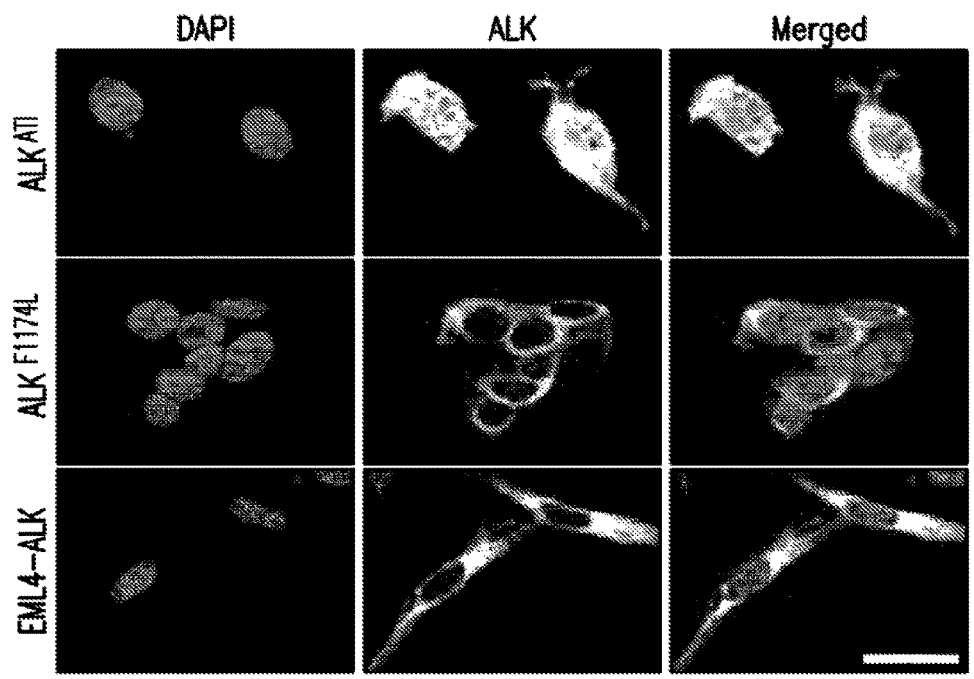
Figure 2F:
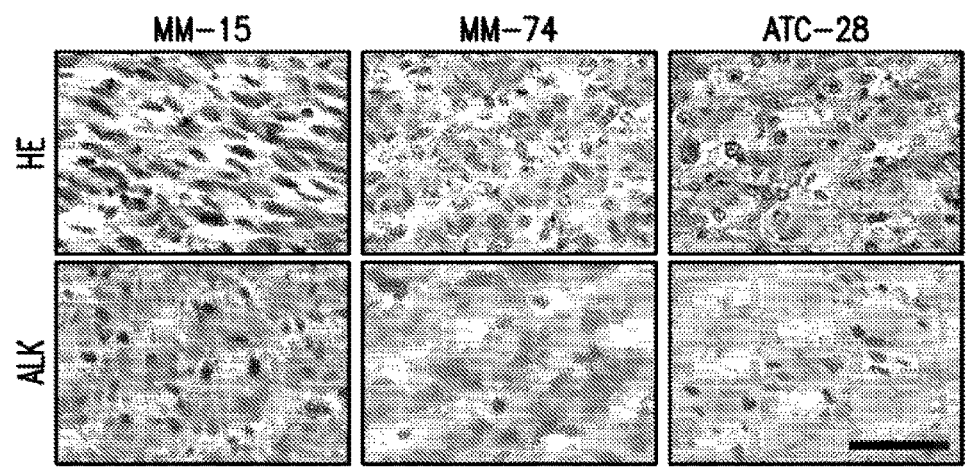
Figure 12A:
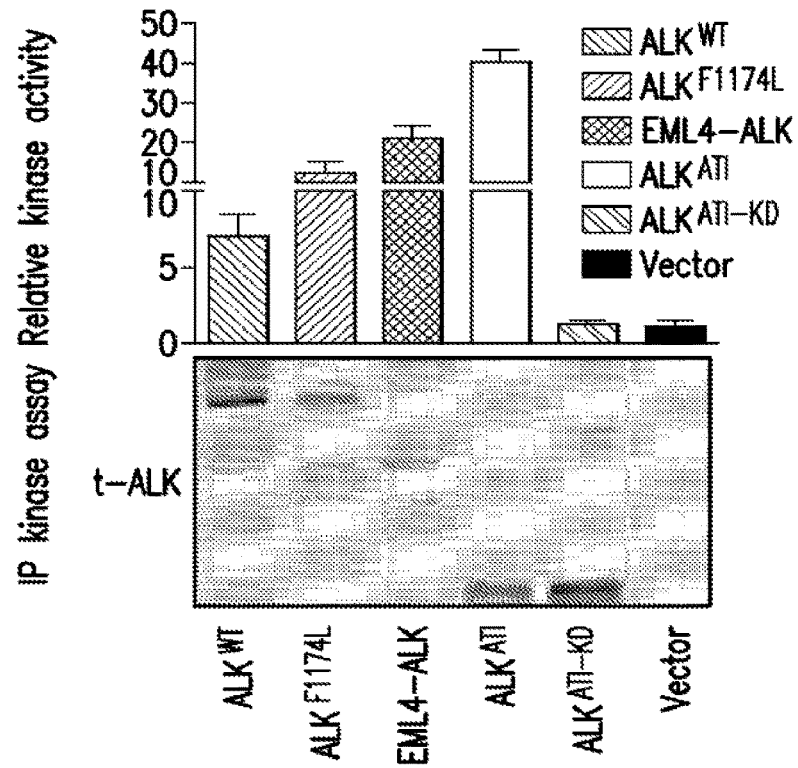
Figure 12B:
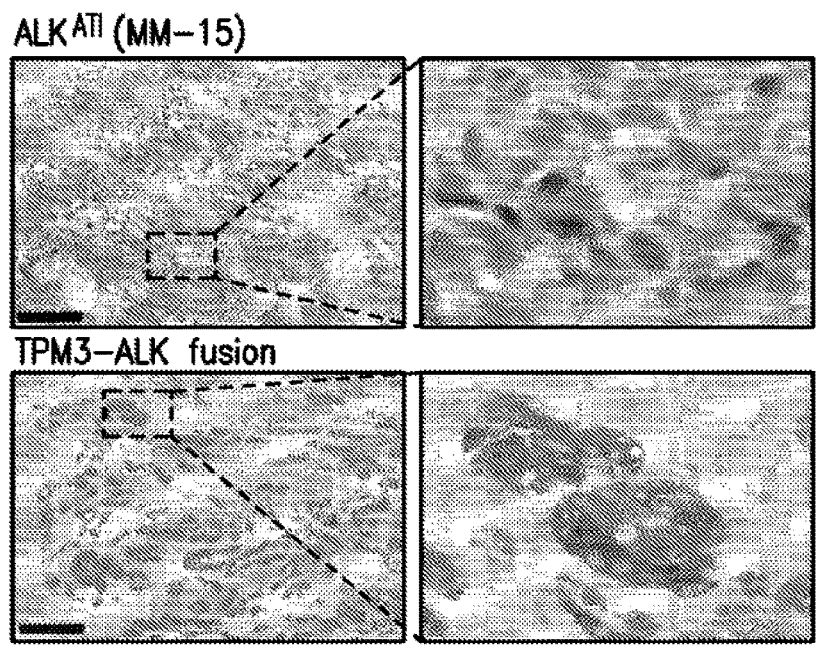

The ALK$^{ATI}$ proteins were phosphorylated in tumors with endogenous ALK$^{ATI}$ expression and in cells with exogenous ALK$^{ATI}$ expression (FIGS. 2B and 2C) indicating that ALK$^{ATI}$ is active. This was confirmed by an in vitro kinase assay (FIG. 12A). A kinase-dead-ALK$^{ATI}$ (ALK$^{ATI-KD}$), in which a lysine in the ATP-binding site of the kinase domain was replaced by a methionine[15], was not phosphorylated or active. Reasoning that ALK$^{ATI}$ may auto-activate by forming homodimers as do other RTKs[50], the ability of self-interaction was tested using co-immunoprecipitation with V5- or HAtagged ALK$^{ATI}$ proteins. The V5-ALK$^{ATI}$ readily co-immunoprecipitated with the HA-ALK$^{ATI}$ and vice versa, indicating that ALK$^{ATI}$ self-interacts resulting in autophosphorylation and kinase activation (FIG. 2D). Using immunofluorescence, ALK$^{ATI}$ was detected in both the nucleus and the cytoplasm, whereas ALK$^{KF1174L}$ and EML4-ALK were found in the cytoplasm or the cell membrane (FIG. 2E). ALK immunohistochemistry in clinical samples confirmed the nuclear and cytoplasmic localization of ALK$^{ATI}$, suggesting that nuclear ALK staining in immunohistochemistry could serve as a clinical biomarker to identify patients with ALK$^{ATI}$-expressing tumors (FIGS. 2F and 12B).

Figure 12C:
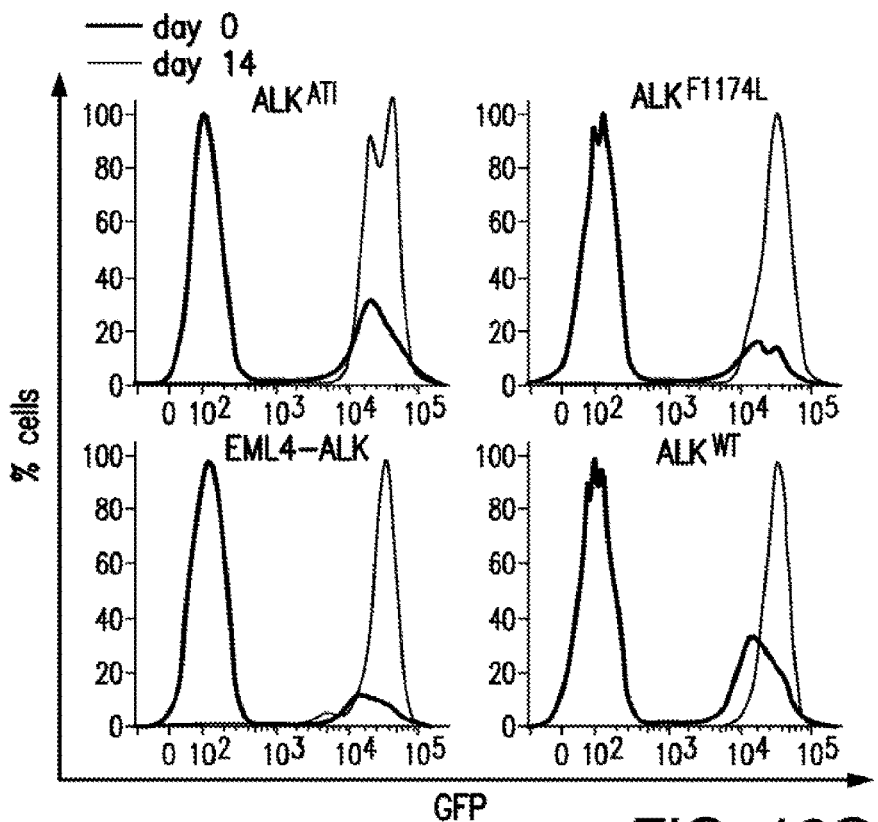
Figure 12D:
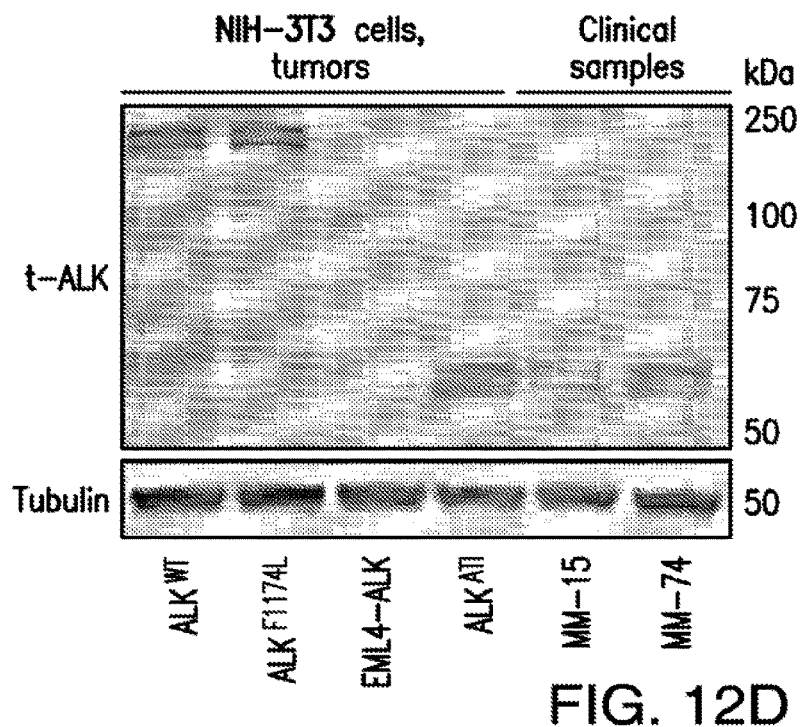
Figure 12E:
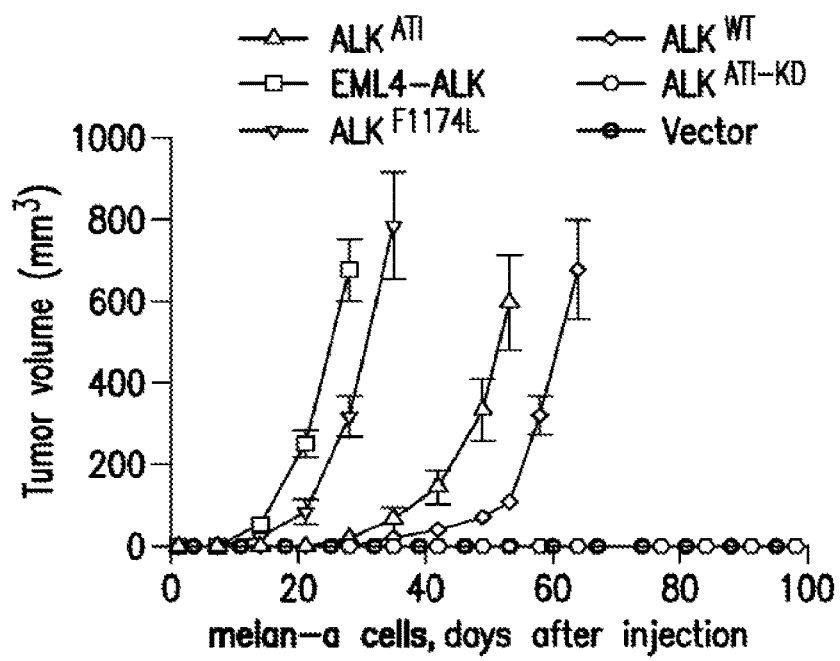
Figure 12F:
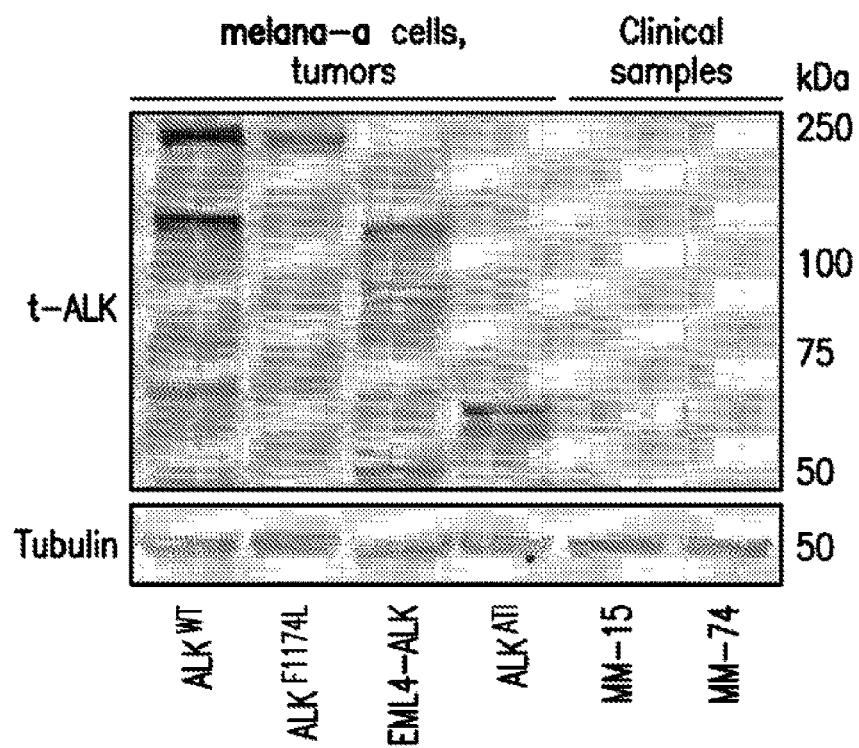

Based on the analysis of the GTEx RNA-seq dataset, ALK$^{ATI}$ is not expressed in normal tissues. To establish the functional consequences of ALK$^{ATI}$ expression, Ba/F3, NIH-3T3, and melan-a cells were stably transduced with ALK$^{ATI}$, negative controls (ALK$^{ATI}$, empty vector), and positive controls (the oncogenic ALK variants ALK$^{F1174L}$, EML4-ALK, and ALK$^{WT}$, which was previously shown to be sufficient to drive oncogenesis at high endogenous expression levels[6,12,58-61]). In Ba/F3 cells, ALK$^{ATI}$ expression led to IL-3-independent cell growth, as did the positive controls, but not the negative controls (FIG. 3A). In ALK-transformed Ba/F3 cells growing in media without IL-3, it was confirmed that ALK$^{ATI}$ was expressed at a similar level compared to human tumors and that all ALK isoforms were phosphorylated and therefore active (FIG. 3B). The ALK dependency of IL-3-independent growth was reflected in the selection of Ba/F3 cells expressing greenfluorescent-protein (GFP), which was co-expressed from the ALK expression vectors (FIG. 12C). Consistent with the in vitro data, ALK$^{ATI}$-expressing NIH-3T3 and melan-a cells efficiently induced tumor growth in SCID mice (FIGS. 3C and 12D-12F).

Figure 12G:
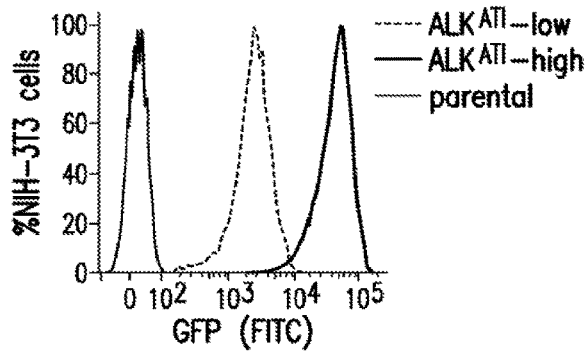
Figure 12H:
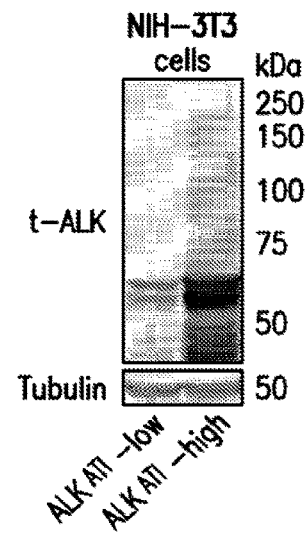
Figure 12I:
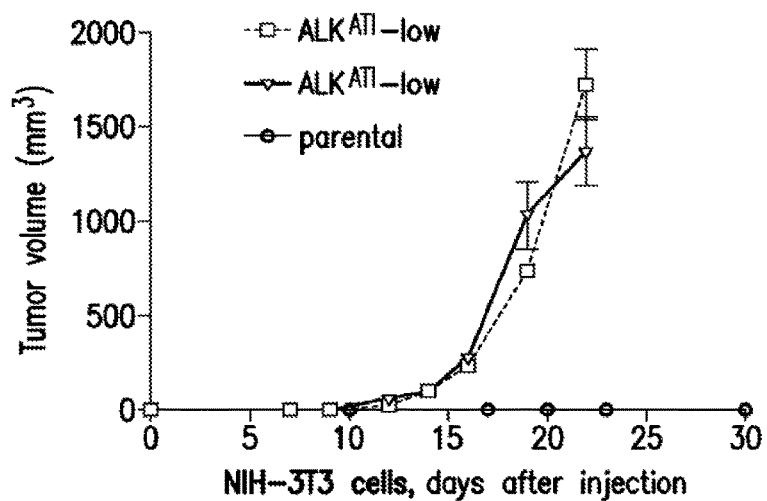

In summary, all of the ALK-variant expressing cells (ALK$^{ATI}$, ALK$^{F1174L}$, EML4-ALK, ALK$^{WT}$) were able to establish growth factor-independent proliferation and tumorigenesis, with similar growth rates once the tumors were established. Importantly, the observed oncogenic capacity of ALK$^{WT}$ is consistent with previous reports that high endogenous expression or amplification of ALK$^{WT}$ drives oncogenesis and confers sensitivity to ALK inhibitors in neuroblastomas[10,12,58-61]. To further explore the pathogenic role of ALK$^{ATI}$ expression levels, NIH-3T3 cells were stably transduced with either a low or high titre of ALK$^{ATI}$ resulting in cells expressing ALK$^{ATI}$ at either low or at high levels. It was found that a further increase in ALK$^{ATI}$ expression levels did not accelerate tumor graft formation and tumor growth indicating that ALKATI can drive tumourigenesis once a threshold of expression is reached (FIGS. 12G-12I).

Figure 13A:
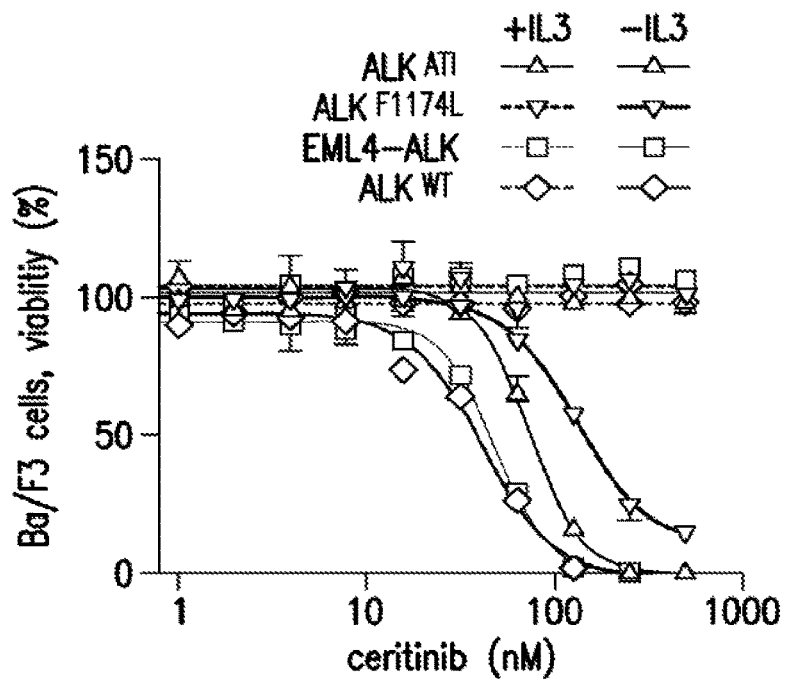
Figure 13B:
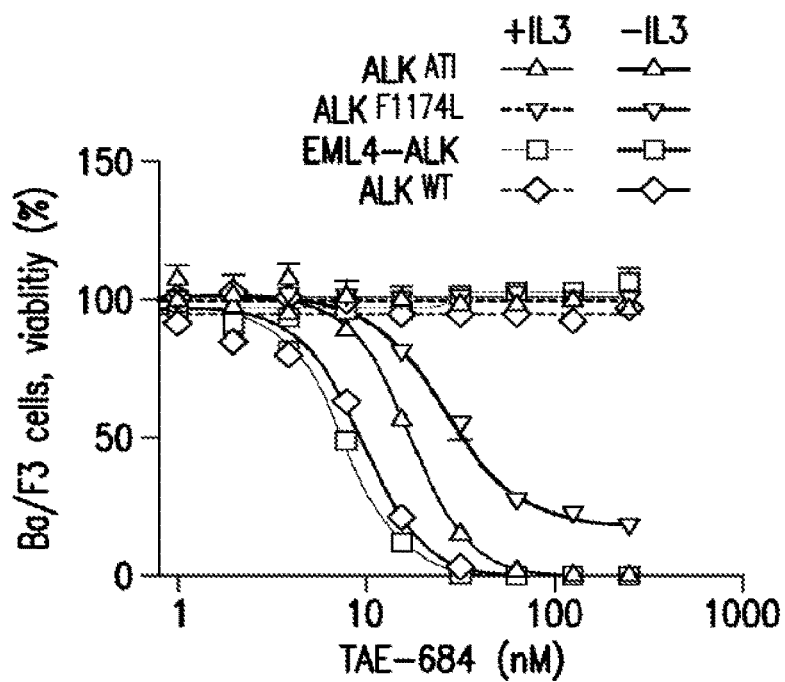
Figure 13C:
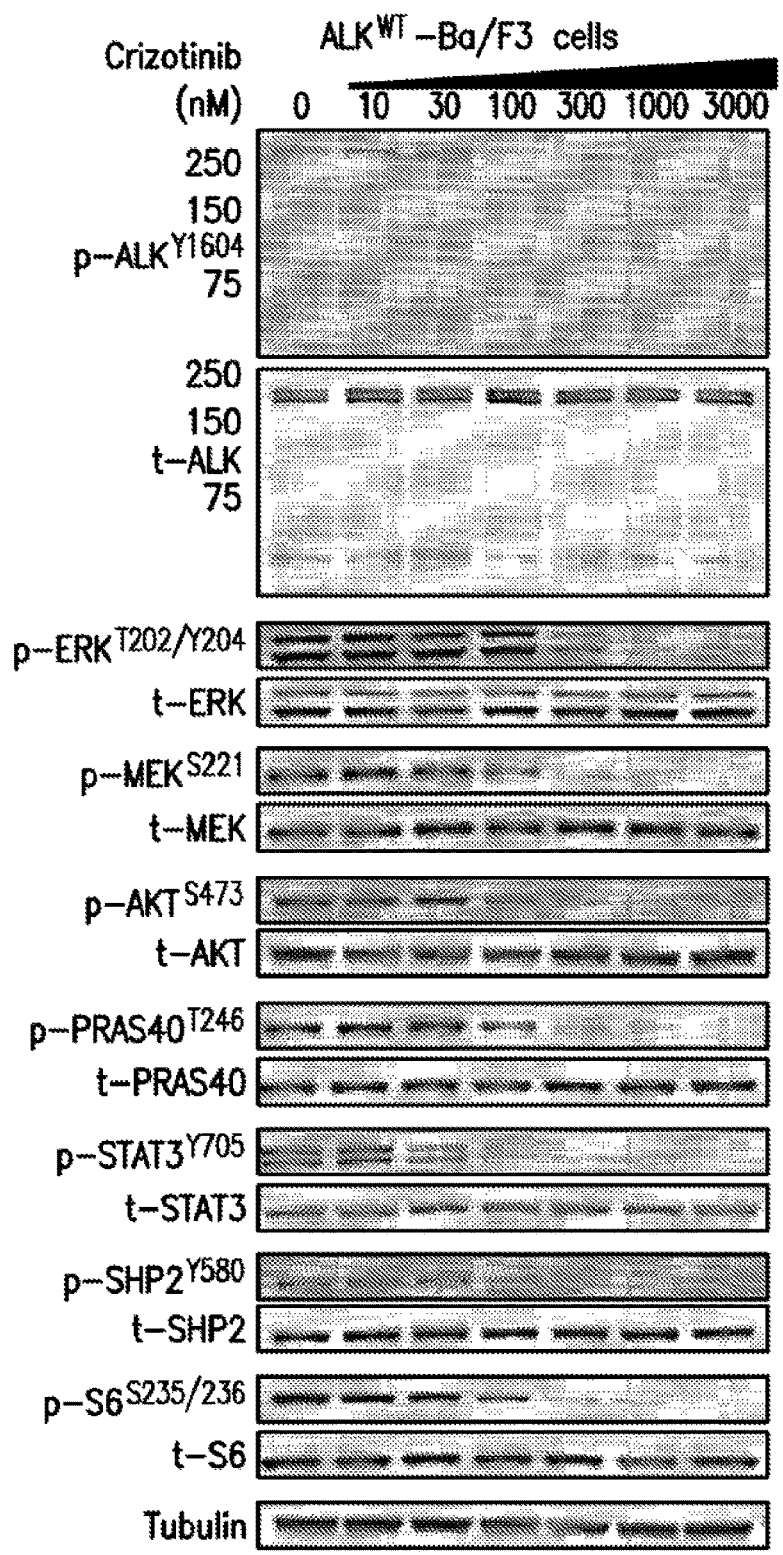
Figure 13D:
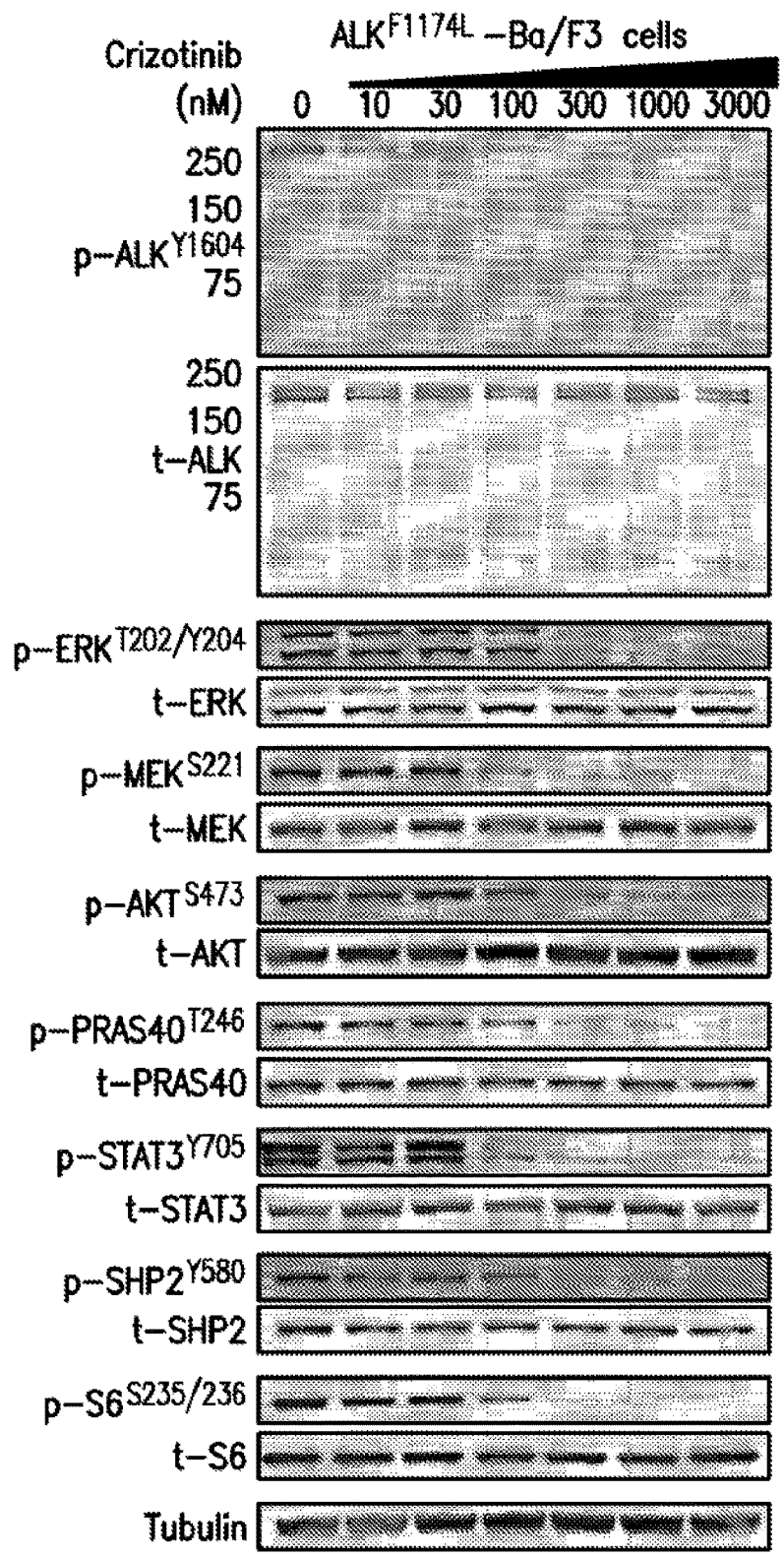
Figure 13E:
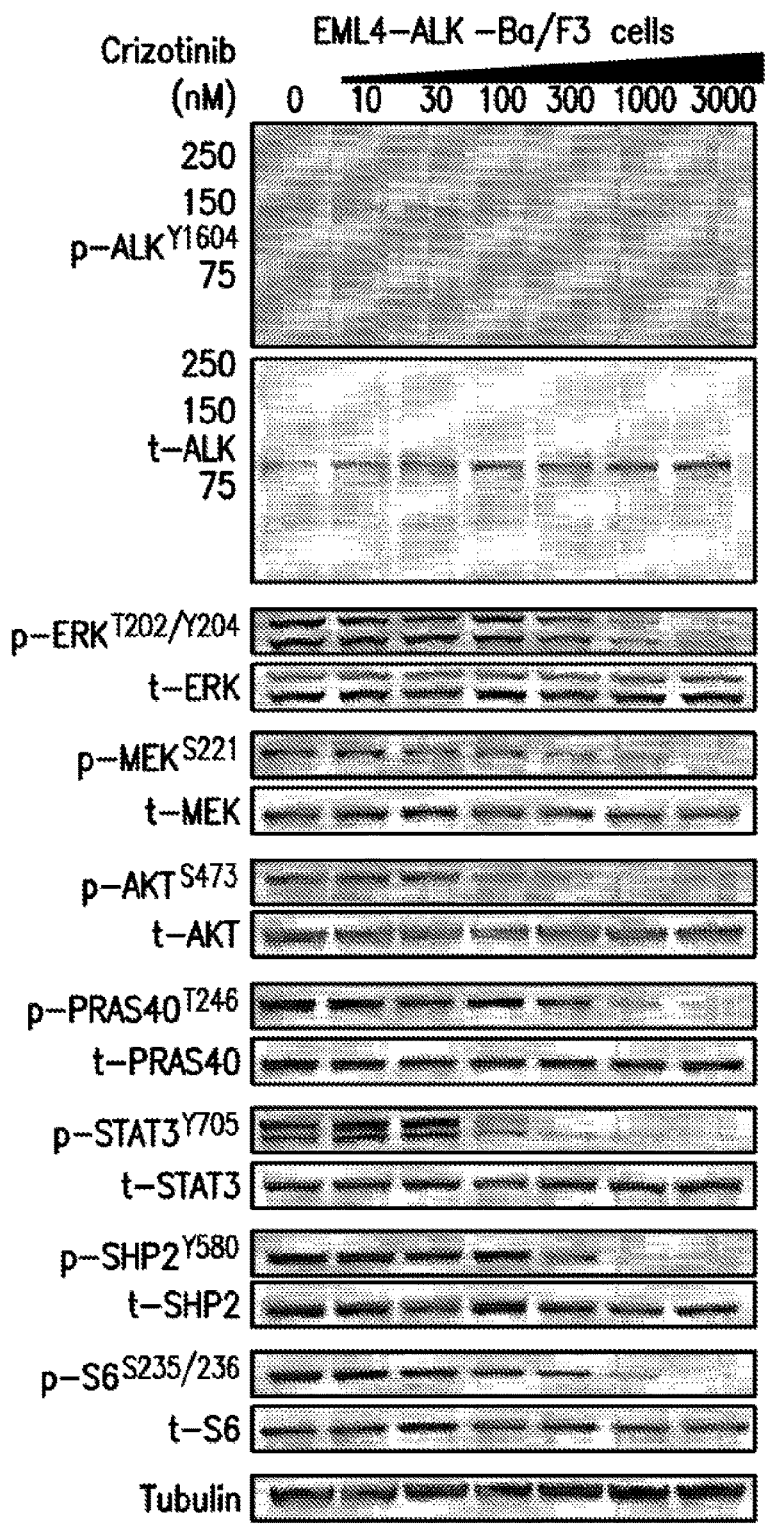
Figure 14A:
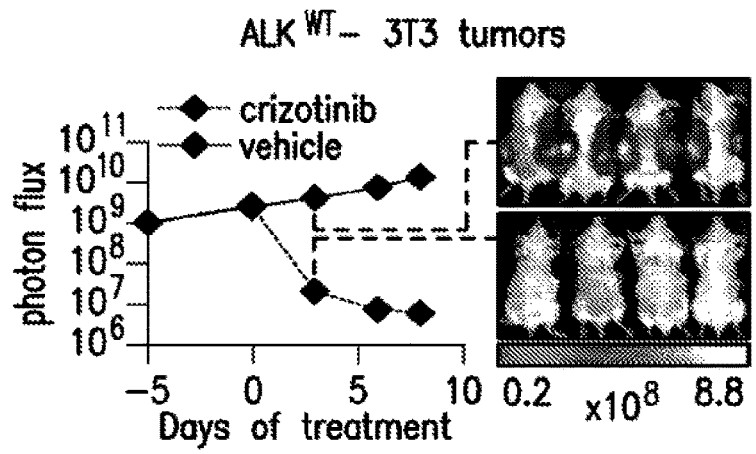
Figure 14B:
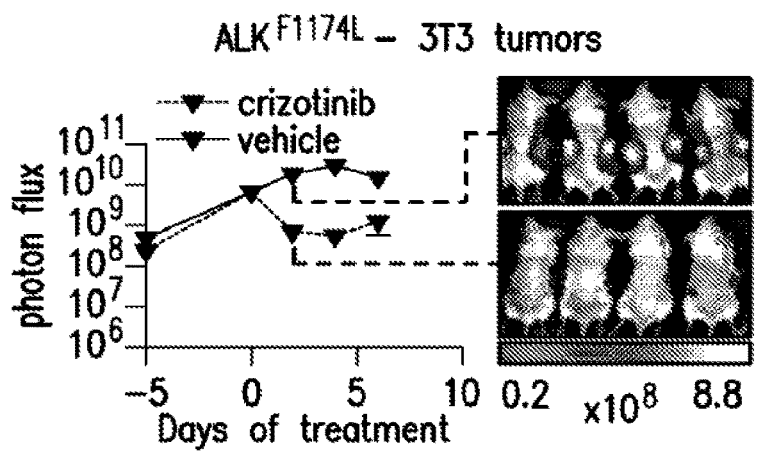
Figure 14C:
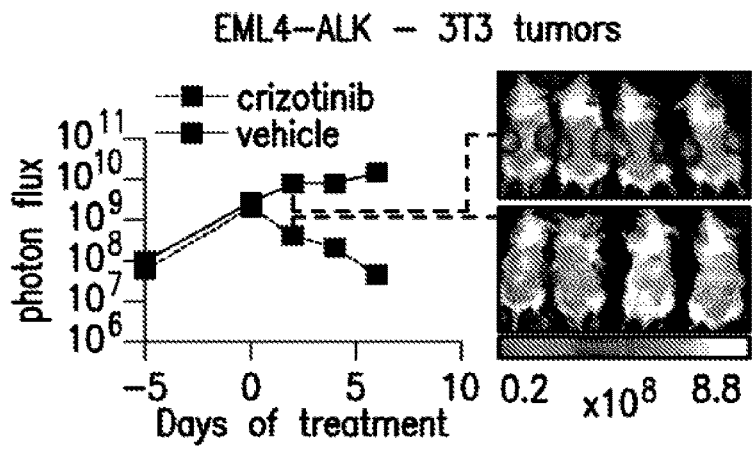
Figure 14D:
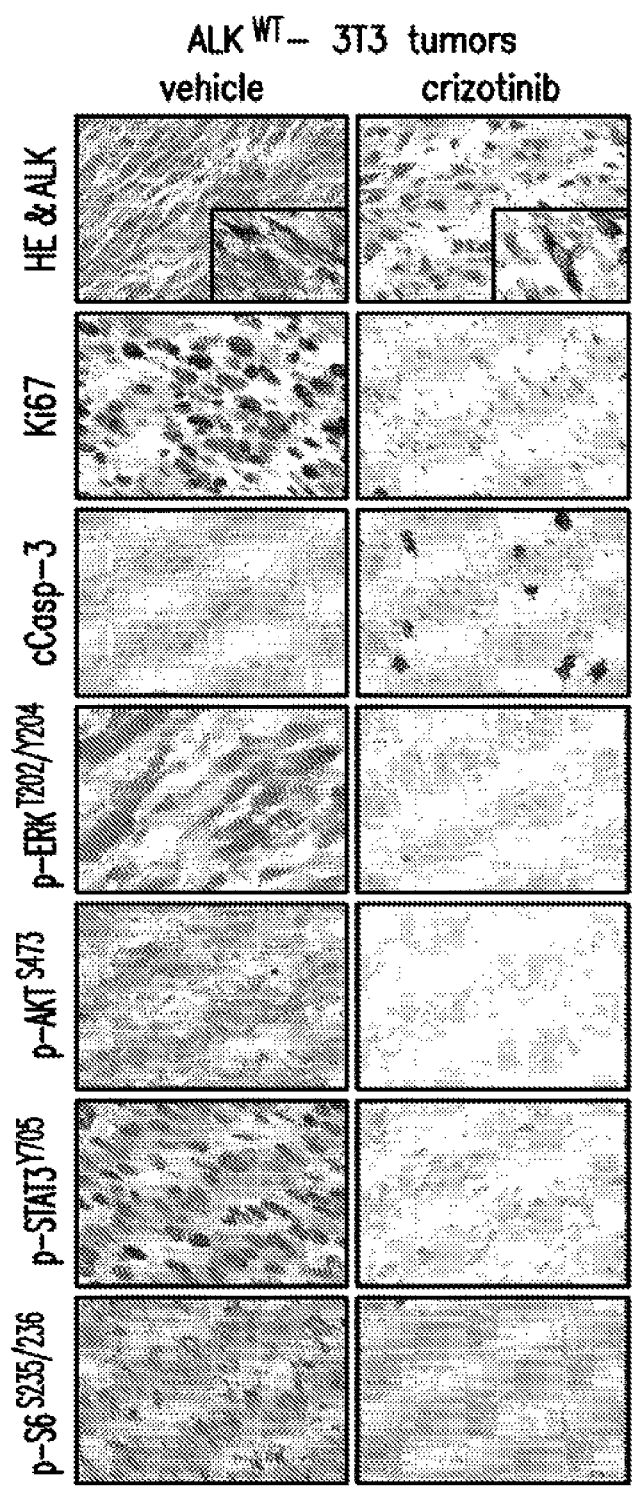
Figure 14E:
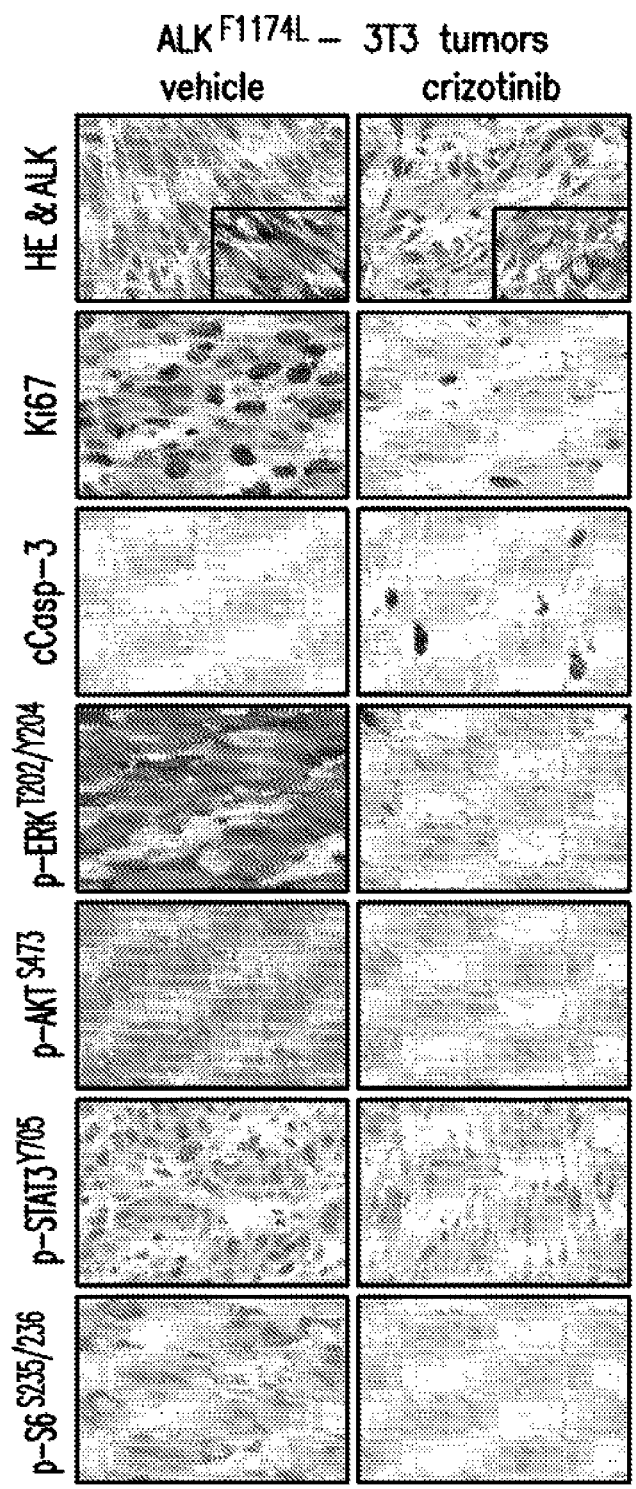
Figure 14F:
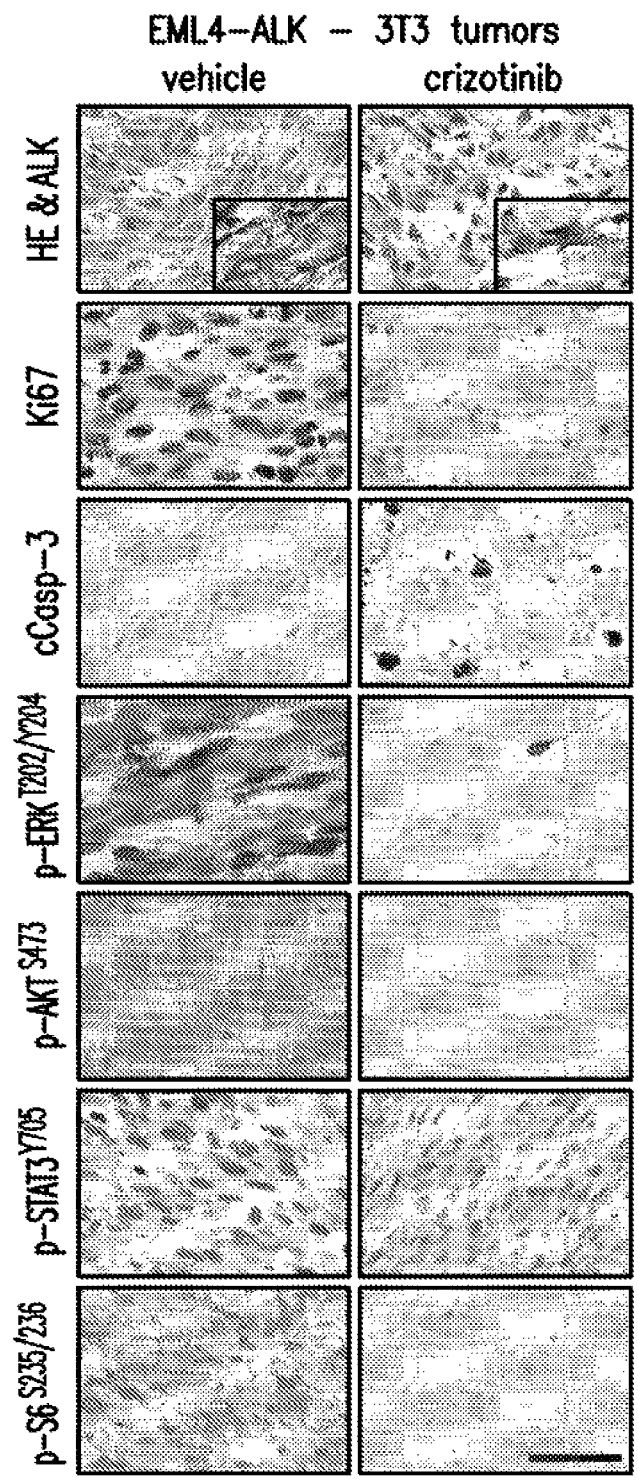

To examine the therapeutic responses to pharmacologic ALK inhibition, Ba/F3 cells stably expressing various ALK isoforms were treated with three different ALK inhibitors (crizotinib, ceritinib, TAE-684). All ALK inhibitors effectively inhibited IL-3-independent growth of ALK-transformed Ba/F3 cells, whereas they had no effect on growth in the presence of IL-3 (FIGS. 4A and 13A-13B). Crizotinib inhibited ALK$^{ATI}$ phosphorylation and downstream signaling in a concentration-dependent manner, further corroborating that ALK$^{ATI}$ is activated through auto-phosphorylation (FIGS. 4B and 13E-13E). Crizotinib treatment induced also regression of ALKATI driven NIH-3T3-tumors in vivo, and immunohistochemistry of explanted tumors confirmed reduced cell proliferation, increased apoptosis, and inhibition of several oncogenic signaling pathways (FIGS. 4C-4E and 14A-14F).

Based on this encouraging pre-clinical data, a patient with metastatic melanoma with ALK$^{ATI}$ expression was identified (FIGS. 4F and 4G). The patient had previously progressed on the combination of ipilimumab and nivolumab immunotherapy in a clinical trial, followed by palliative radiation and then dacarbazine chemotherapy. The compassionate use of crizotinib resulted in marked symptomatic improvement and tumor shrinkage within 6 weeks of therapy (FIG. 4H). This patient case provides additional evidence that ALK$^{ATI}$ confers gain-of-function in patients and is amenable to pharmacologic targeting, warranting further clinical investigation.

Taken together, a novel ALK transcript, ALK$^{ATI}$, which arises independently of genomic aberrations at the ALK locus through alternative transcriptional initiation, was identified. ALK$^{ATI}$ encodes shortened ALK proteins that are capable of driving oncogenesis in vitro and in vivo. ALK$^{ATI}$-driven tumors are sensitive to ALK inhibitors, suggesting that patients harboring such tumors could potentially benefit from ALK inhibitor therapy, but may not be identified using current clinical genomic assays, particularly those based on DNA sequencing. Importantly, alternative transcriptional initiation was discovered as a novel mechanism for oncogene activation, in addition to well-established genetic mechanisms such as mutations, translocations or amplifications. Other oncogenes may be activated via similar mechanisms in other human malignancies and their identification may provide new insights into oncogenesis and opportunities for therapeutic intervention.

REFERENCES

1. Consortium, G. T. The Genotype-Tissue Expression (GTEx) project. Nat Genet 45, 580-5 (2013).
2. Lawrence, M. S. et al. Mutational heterogeneity in cancer and the search for new cancer-associated genes. Nature 499, 214-8 (2013).
3. Lawrence, M. S. et al. Discovery and saturation analysis of cancer genes across 21 tumor types. Nature 505, 495-501(2014).
4. Comprehensive molecular characterization of human colon and rectal cancer. Nature 487, 330-7 (2012).
5. Comprehensive genomic characterization of squamous cell lung cancers. Nature 489, 519-25 (2012).
6. Vogelstein, B. et al. Cancer genome landscapes. Science 339, 1546-58 (2013).
7. Imielinski, M. et al. Mapping the hallmarks of lung adenocarcinoma with massively parallel sequencing. Cell 150, 1107-20 (2012).
8. Weinstein, J. N. et al. The Cancer Genome Atlas Pan-Cancer analysis project. Nat Genet 45, 1113-20 (2013).
9. Anders, S., Reyes, A. & Huber, W. Detecting differential usage of exons from RNA-seq data. Genome Res 22, 2008-17 (2012).
10. Mosse, Y. P. et al. Identification of ALK as a major familial neuroblastoma predisposition gene. Nature 455, 930-5 (2008).
11. Chen, Y. et al. Oncogenic mutations of ALK kinase in neuroblastoma. Nature 455, 971-4 (2008).
12. Janoueix-Lerosey, I. et al. Somatic and germline activating mutations of the ALK kinase receptor in neuroblastoma. Nature 455, 967-70 (2008).
13. George, R. E. et al. Activating mutations in ALK provide a therapeutic target in neuroblastoma. Nature 455, 975-8 (2008).
14. Morris, S. W. et al. Fusion of a kinase gene, ALK, to a nucleolar protein gene, NPM, in non-Hodgkin's lymphoma. Science 263, 1281-4 (1994).
15. Soda, M. et al. Identification of the transforming EML4-ALK fusion gene in non-small-cell lung cancer. Nature 448, 561-6 (2007).
16. Lipson, D. et al. Identification of new ALK and RET gene fusions from colorectal and lung cancer biopsies. Nat Med 18, 382-4 (2012).
17. Kouzarides, T. Chromatin modifications and their function. Cell 128, 693-705 (2007).
18. Ram, O. et al. Combinatorial patterning of chromatin regulators uncovered by genome-wide location analysis in human cells. Cell 147, 1628-39 (2011).
19. Wang, Z. et al. Combinatorial patterns of histone acetylations and methylations in the human genome. Nat Genet 40, 897-903 (2008).
20. Mitelman, F., Johansson, B. & Mertens, F. The impact of translocations and gene fusions on cancer causation. Nature reviews. Cancer 7, 233-45 (2007).
21. Cazes, A. et al. Characterization of rearrangements involving the ALK gene reveals a novel truncated form associated with tumor aggressiveness in neuroblastoma. Cancer Res 73, 195-204 (2013).
22. Okubo, J. et al. Aberrant activation of ALK kinase by a novel truncated form ALK protein in neuroblastoma. Oncogene 31, 4667-76 (2012).
23. Horn, S. et al. TERT promoter mutations in familial and sporadic melanoma. Science 339, 959-61 (2013).
24. Huang, F. W. et al. Highly recurrent TERT promoter mutations in human melanoma. Science 339, 957-9 (2013).
25. Lappalainen, T. et al. Transcriptome and genome sequencing uncovers functional variation in humans. Nature 501, 506-11(2013).
26. Li, H. et al. The Sequence Alignment/Map format and SAMtools. Bioinformatics 25, 2078-9 (2009).

27. Trapnell, C., Pachter, L. & Salzberg, S. L. TopHat: discovering splice junctions with RNA-Seq. Bioinformatics 25, 1105-11(2009).
28. Sboner, A. et al. FusionSeq: a modular framework for finding gene fusions by analyzing paired-end RNA-sequencing data. Genome Biol 11, R104 (2010).
29. McKenna, A. et al. The Genome Analysis Toolkit: a MapReduce framework for analyzing next-generation DNA sequencing data. Genome Res 20, 1297-303 (2010).
30. Robinson, J. T. et al. Integrative genomics viewer. Nat Biotechnol 29, 24-6 (2011).
31. Carbon, S. et al. AmiGO: online access to ontology and annotation data. Bioinformatics 25, 288-9 (2009).
32. Chi, P. et al. ETV1 is a lineage survival factor that cooperates with KIT in gastrointestinal stromal tumors. Nature 467, 849-53 (2010).
33. Zhang, Y. et al. Model-based analysis of ChIP-Seq (MACS). Genome Biol 9, R137 (2008).
34. Won, H. H., Scott, S N., Brannon, A. R., Shah, R. H. & Berger, M. F. Detecting somatic genetic alterations in tumor specimens by exon capture and massively parallel sequencing. J Vis Exp, e50710 (2013).
35. Li, H. & Durbin, R. Fast and accurate short read alignment with Burrows-Wheeler transform. Bioinformatics 25, 1754-60 (2009).
36. DePristo, M. A. et al. A framework for variation discovery and genotyping using next-generation DNA sequencing data. Nat Genet 43, 491-8 (2011).
37. Cibulskis, K. et al. Sensitive detection of somatic point mutations in impure and heterogeneous cancer samples. Nat Biotechnol 31, 213-9 (2013).
38. Rausch, T. et al. DELLY: structural variant discovery by integrated paired-end and split-read analysis. Bioinformatics 28, i333-i339 (2012).
39. Geiss, G. K. et al. Direct multiplexed measurement of gene expression with color-coded probe pairs. Nat Biotechnol 26, 317-25 (2008).
40. Bennett, D. C., Cooper, P. J. & Hart, I. R. A line of non-tumorigenic mouse melanocytes, syngeneic with the B16 melanoma and requiring a tumor promoter for growth. Int J Cancer 39, 414-8 (1987).
41. Refaeli, Y., Van Parijs, L., Alexander, S. I. & Abbas, A. K. Interferon gamma is required for activation-induced death of T lymphocytes. J Exp Med 196, 999-1005 (2002).
42. Ponomarev, V. et al. A novel triple-modality reporter gene for whole-body fluorescent, bioluminescent, and nuclear noninvasive imaging. Eur J Nucl Med Mol Imaging 31, 740-51 (2004).
43. Northcott, P. A. et al. Enhancer hijacking activates GFI1 family oncogenes in medulloblastoma. Nature 511, 428-434 (2014).
44. Karolchik, D. et al. The UCSC Table Browser data retrieval tool. Nucleic Acids Res 32, D493-496 (2004).
45. Xie, M. et al. DNA hypomethylation within specific transposable element families associates with tissue-specific enhancer landscape. Nat Genet 45, 836-841 (2013).
46. Consortium, E. P. An integrated encyclopedia of DNA elements in the human genome. Nature 489, 57-74 (2012).
47. Cab, E. & Wysocka, J. Modification of enhancer chromatin: what, how, and why? Mol Cell 49, 825-837 (2013).
48. Grant, C. E., Bailey, T. L. & Noble, W. S. FIMO: scanning for occurrences of a given motif Bioinformatics 27, 1017-1018 (2011).
49. Moog-Lutz, C. et al. Activation and inhibition of anaplastic lymphoma kinase receptor tyrosine kinase by monoclonal antibodies and absence of agonist activity of pleiotrophin. J Biol Chem 280, 26039-26048 (2005).
50. Lemmon, M. A. & Schlessinger, J. Cell signaling by receptor tyrosine kinases. Cell 141, 1117-1134 (2010).
51. Reis, P. P. et al. mRNA transcript quantification in archival samples using multiplexed, color-coded probes. BMC Biotechnol 11, 46 (2011).
52. Mathelier, A. et al. JASPAR 2014: an extensively expanded and updated open-access database of transcription factor binding profiles. Nucleic Acids Res 42, D142-147 (2014).
53. Krueger, F. & Andrews, S. R. Bismark: a flexible aligner and methylation caller for Bisulfite-Seq applications. *Bioinformatics* 27, 1571-1572 (2011).
54. Boeva, V. et al. Control-free calling of copy number alterations in deep-sequencing data using GC-content normalization. *Bioinformatics* 27, 268-269 (2011).
55. Wang, J. et al. CREST maps somatic structural variation in cancer genomes with base-pair resolution. *Nat Methods* 8, 652-654 (2011).
56. McLaren, W. et al. Deriving the consequences of genomic variants with the Ensembl API and SNP Effect Predictor. *Bioinformatics* 26, 2069-2070 (2010).
57. Krzywinski, M. et al. Circos: an information aesthetic for comparative genomics. *Genome Res* 19, 1639-1645 (2009).
58. Schulte, J. H. et al. High ALK receptor tyrosine kinase expression supersedes ALK mutation as a determining factor of an unfavorable phenotype in primary neuroblastoma. *Clin Cancer Res* 17, 5082-5092 (2011).
59. Passoni, L. et al. Mutation-independent anaplastic lymphoma kinase overexpression in poor prognosis neuroblastoma patients. Cancer Res 69, 7338-7346 (2009).
60. Bresler, S. C. et al. Differential inhibitor sensitivity of anaplastic lymphoma kinase variants found in neuroblastoma. Sci Transl Med 3, 108-114 (2011).
61. Montavon, G. et al. Wild-type ALK and activating ALK-R1275Q and ALKF1174L mutations upregulate Myc and initiate tumor formation in murine neural crest progenitor cells. Oncotarget 5, 4452-4466 (2014).
62. Wiesner, T. et al. Kinase fusions are frequent in Spitz tumors and spitzoid melanomas. Nat Commun 5, 3116 (2014)

Various publications are cited herein, the contents of which are hereby incorporated by reference in their entireties.

What is claimed is:

1. An isolated complementary DNA (cDNA) molecule comprising the nucleic acid sequence of exons 20-29 and a portion of intron 19 of an Anaplastic Lymphoma Kinase (ALK) gene, wherein the cDNA molecule does not comprise the nucleic acid sequence of exons 1-19 of the ALK gene, either individually or in any combination and wherein the portion of intron 19 of the ALK gene is about 400 bp in length located upstream of exon 20 of the ALK gene.

2. The isolated cDNA molecule of claim 1, wherein the ALK gene is a human ALK gene.

3. The isolated cDNA molecule of claim 1, comprising:
   (a) nucleic acids 405-2063 of the nucleotide sequence set forth in SEQ ID NO: 11;
   (b) nucleic acids 411-2063 of the nucleotide sequence set forth in SEQ ID NO: 11; or
   (c) nucleic acids 465-2063 of the nucleotide sequence set forth in SEQ ID NO: 11.

4. The isolated cDNA acid molecule of claim 1, wherein the cDNA molecule consists essentially of SEQ ID NO: 11.

5. A vector comprising the isolated nucleic acid molecule of claim 1.

6. A vector comprising the isolated cDNA molecule of claim 4.

7. A host cell comprising the vector of claim 5 or 6.

* * * * *

SEQUENCE LISTING

```
<160> NUMBER OF SEQ ID NOS: 196

<210> SEQ ID NO 1
<211> LENGTH: 1560
<212> TYPE: PRT
<213> ORGANISM: Homo sapiens
```

<400> SEQUENCE: 1

```
Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
```

```
            405                 410                 415
Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
            435                 440                 445

Leu Gln Leu Gly Gln Ala Cys Asp Phe His Gln Asp Cys Ala Gln Gly
            450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
            515                 520                 525

Ser Glu Ser Ala Thr Val Thr Ser Ala Thr Phe Pro Ala Pro Ile Lys
            530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
            610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
            690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
            770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Ala Thr Tyr Val Phe Lys Met Lys Asp
            820                 825                 830
```

```
Gly Val Pro Val Pro Leu Ile Ile Ala Ala Gly Gly Gly Arg Ala
        835                 840                 845

Tyr Gly Ala Lys Thr Asp Thr Phe His Pro Glu Arg Leu Glu Asn Asn
        850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
                900                 905                 910

Trp Gly Trp Glu Thr Arg Gly Gly Phe Gly Gly Gly Gly Gly Cys
        915                 920                 925

Ser Ser Gly Gly Gly Gly Gly Tyr Ile Gly Gly Asn Ala Ala Ser
        930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
                965                 970                 975

Gly Glu Val Asn Ile Lys His Tyr Leu Asn Cys Ser His Cys Glu Val
        980                 985                 990

Asp Glu Cys His Met Asp Pro Glu Ser His Lys Val Ile Cys Phe Cys
        995                 1000                1005

Asp His Gly Thr Val Leu Ala Glu Asp Gly Val Ser Cys Ile Val
        1010                1015                1020

Ser Pro Thr Pro Glu Pro His Leu Pro Leu Ser Leu Ile Leu Ser
        1025                1030                1035

Val Val Thr Ser Ala Leu Val Ala Ala Leu Val Leu Ala Phe Ser
        1040                1045                1050

Gly Ile Met Ile Val Tyr Arg Arg Lys His Gln Glu Leu Gln Ala
        1055                1060                1065

Met Gln Met Glu Leu Gln Ser Pro Glu Tyr Lys Leu Ser Lys Leu
        1070                1075                1080

Arg Thr Ser Thr Ile Met Thr Asp Tyr Asn Pro Asn Tyr Cys Phe
        1085                1090                1095

Ala Gly Lys Thr Ser Ser Ile Ser Asp Leu Lys Glu Val Pro Arg
        1100                1105                1110

Lys Asn Ile Thr Leu Ile Arg Gly Leu Gly His Gly Ala Phe Gly
        1115                1120                1125

Glu Val Tyr Glu Gly Gln Val Ser Gly Met Pro Asn Asp Pro Ser
        1130                1135                1140

Pro Leu Gln Val Ala Val Lys Thr Leu Pro Glu Val Cys Ser Glu
        1145                1150                1155

Gln Asp Glu Leu Asp Phe Leu Met Glu Ala Leu Ile Ile Ser Lys
        1160                1165                1170

Phe Asn His Gln Asn Ile Val Arg Cys Ile Gly Val Ser Leu Gln
        1175                1180                1185

Ser Leu Pro Arg Phe Ile Leu Leu Glu Leu Met Ala Gly Gly Asp
        1190                1195                1200

Leu Lys Ser Phe Leu Arg Glu Thr Arg Pro Arg Pro Ser Gln Pro
        1205                1210                1215

Ser Ser Leu Ala Met Leu Asp Leu Leu His Val Ala Arg Asp Ile
        1220                1225                1230
```

| | | | | | | | | | |
|---|---|---|---|---|---|---|---|---|---|
|Ala|Cys|Gly|Cys|Gln|Tyr|Leu|Glu|Glu|Asn|His|Phe|Ile|His|Arg|
|1235| | | | |1240| | | | |1245| | | | |

Ala Cys Gly Cys Gln Tyr Leu Glu Glu Asn His Phe Ile His Arg
1235                1240                1245

Asp Ile Ala Ala Arg Asn Cys Leu Leu Thr Cys Pro Gly Pro Gly
1250                1255                1260

Arg Val Ala Lys Ile Gly Asp Phe Gly Met Ala Arg Asp Ile Tyr
1265                1270                1275

Arg Ala Ser Tyr Tyr Arg Lys Gly Gly Cys Ala Met Leu Pro Val
1280                1285                1290

Lys Trp Met Pro Pro Glu Ala Phe Met Glu Gly Ile Phe Thr Ser
1295                1300                1305

Lys Thr Asp Thr Trp Ser Phe Gly Val Leu Leu Trp Glu Ile Phe
1310                1315                1320

Ser Leu Gly Tyr Met Pro Tyr Pro Ser Lys Ser Asn Gln Glu Val
1325                1330                1335

Leu Glu Phe Val Thr Ser Gly Gly Arg Met Asp Pro Pro Lys Asn
1340                1345                1350

Cys Pro Gly Pro Val Tyr Arg Ile Met Thr Gln Cys Trp Gln His
1355                1360                1365

Gln Pro Glu Asp Arg Pro Asn Phe Ala Ile Ile Leu Glu Arg Ile
1370                1375                1380

Glu Tyr Cys Thr Gln Asp Pro Asp Val Ile Asn Thr Ala Leu Pro
1385                1390                1395

Ile Glu Tyr Gly Pro Leu Val Glu Glu Glu Lys Val Pro Val
1400                1405                1410

Arg Pro Lys Asp Pro Glu Gly Val Pro Pro Leu Leu Val Ser Gln
1415                1420                1425

Gln Ala Lys Arg Glu Glu Glu Arg Ser Pro Ala Ala Pro Pro Pro
1430                1435                1440

Leu Pro Thr Thr Ser Ser Gly Lys Ala Ala Lys Lys Pro Thr Ala
1445                1450                1455

Ala Glu Ile Ser Val Arg Val Pro Arg Gly Pro Ala Val Glu Gly
1460                1465                1470

Gly His Val Asn Met Ala Phe Ser Gln Ser Asn Pro Pro Ser Glu
1475                1480                1485

Leu His Lys Val His Gly Ser Arg Asn Lys Pro Thr Ser Leu Trp
1490                1495                1500

Asn Pro Thr Tyr Gly Ser Trp Phe Thr Glu Lys Pro Thr Lys Lys
1505                1510                1515

Asn Asn Pro Ile Ala Lys Lys Glu Pro His Asp Arg Gly Asn Leu
1520                1525                1530

Gly Leu Glu Gly Ser Cys Thr Val Pro Pro Asn Val Ala Thr Gly
1535                1540                1545

Arg Leu Pro Gly Ala Ser Leu Leu Leu Glu Pro Ser
1550                1555                1560

<210> SEQ ID NO 2
<211> LENGTH: 6267
<212> TYPE: DNA
<213> ORGANISM: Homo sapiens

<400> SEQUENCE: 2
agctgcaagt ggcgggcgcc caggcagatg cgatccagcg gctctggggg cggcagcggt      60
ggtagcagct ggtacctccc gccgcctctg ttcggagggt cgcggggcac cgaggtgctt     120
tccggccgcc ctctggtcgg ccacccaaag ccgcgggcgc tgatgatggg tgaggagggg     180

```
gcggcaagat tcgggcgcc cctgccctga acgccctcag ctgctgccgc cggggccgct      240
ccagtgcctg cgaactctga ggagccgagg cgccggtgag agcaaggacg ctgcaaactt      300
gcgcagcgcg ggggctggga ttcacgccca gaagttcagc aggcagacag tccgaagcct      360
tcccgcagcg gagagatagc ttgagggtgc gcaagacggc agcctccgcc ctcggttccc      420
gcccagaccg ggcagaagag cttggaggag ccaaaaggaa cgcaaaaggc ggccaggaca      480
gcgtgcagca gctgggagcc gccgttctca gccttaaaag ttgcagagat tggaggctgc      540
cccgagaggg gacagacccc agctccgact gcgggggggca ggagaggacg gtacccaact      600
gccacctccc ttcaaccata gtagttcctc tgtaccgagc gcagcgagct acagacgggg      660
gcgcggcact cggcgcggag agcgggaggc tcaaggtccc agccagtgag cccagtgtgc      720
ttgagtgtct ctggactcgc ccctgagctt ccaggtctgt ttcatttaga ctcctgctcg      780
cctccgtgca gttgggggaa agcaagagac ttgcgcgcac gcacagtcct ctggagatca      840
ggtggaagga gccgctgggt accaaggact gttcagagcc tcttcccatc tcggggagag      900
cgaagggtga ggctgggccc ggagagcagt gtaaacgcc tcctccggcg ggatgggagc       960
catcgggctc ctgtggctcc tgccgctgct gctttccacg gcagctgtgg gctccgggat     1020
ggggaccggc cagcgcgcgg gctccccagc tgcggggccg ccgctgcagc cccggagcc      1080
actcagctac tcgcgcctgc agaggaagag tctggcagtt gacttcgtgg tgccctcgct     1140
cttccgtgtc tacgcccggg acctactgct gccaccatcc tcctcggagc tgaaggctgg     1200
caggcccgag gccgcggct cgctagtct ggactgcgcc ccgctgctca ggttgctggg      1260
gccggcgccg ggggtctcct ggaccgccgg ttcaccagcc ccggcagagg cccggacgct     1320
gtccaggtg ctgaagggcg gctccgtgcg caagctccgg cgtgccaagc agttggtgct      1380
ggagctgggc gaggaggcga tcttggaggg ttgcgtcggg ccccccgggg aggcggctgt     1440
ggggctgctc cagttcaatc tcagcgagct gttcagttgg tggattcgcc aaggcgaagg     1500
gcgactgagg atccgcctga tgcccgagaa gaaggcgtcg gaagtgggca gagagggaag     1560
gctgtccgcg gcaattcgcg cctcccagcc ccgccttctc ttccagatct tcggggactgg    1620
tcatagctcc ttggaatcac caacaaacat gccttctcct tctcctgatt attttacatg     1680
gaatctcacc tggataatga aagactcctt ccctttcctg tctcatcgca gccgatatgg     1740
tctggagtgc agctttgact tccctgtgac gctggagtat tcccctccac tgcatgacct     1800
caggaaccag agctggtcct ggcgccgcat cccctccgag gaggcctccc agatggactt     1860
gctggatggg cctggggcag agcgttctaa ggagatgccc agaggctcct ttctccttct     1920
caacacctca gctgactcca agcacaccat cctgagtccg tggatgagga gcagcagtga     1980
gcactgcaca ctggccgtct cggtgcacag gcacctgcag ccctctggaa ggtacattgc     2040
ccagctgctg ccccacaacg aggctgcaag agagatcctc ctgatgccca ctccagggaa     2100
gcatggttgg acagtgctcc agggaagaat cgggcgtcca gacaacccat ttcgagtggc     2160
cctggaatac atctccagtg gaaaccgcag cttgtctgca gtggacttct ttgccctgaa     2220
gaactgcagt gaaggaacat ccccaggctc caagatggcc ctgcagagct ccttcacttg     2280
ttggaatggg acagtcctcc agcttgggca ggcctgtgac ttccaccagg actgtgccca     2340
gggagaagat gagagccaga tgtgccggaa actgcctgtg gttttttact gcaactttga     2400
agatggcttc tgtggctgga cccaaggcac actgtcaccc cacactcctc aatggcaggt     2460
caggacccta aaggatgccc ggttccagga ccaccaagac catgctctat tgctcagtac     2520
```

```
cactgatgtc cccgcttctg aaagtgctac agtgaccagt gctacgtttc ctgcaccgat    2580
caagagctct ccatgtgagc tccgaatgtc ctggctcatt cgtggagtct tgagggaaa     2640 cgtgtccttg gtgctagtgg agaacaaaac cgggaaggag caaggcagga tggtctggca    2700
tgtcgccgcc tatgaaggct tgagcctgtg gcagtggatg gtgttgcctc tcctcgatgt    2760
gtctgacagg ttctggctgc agatggtcgc atggtgggga caaggatcca gagccatcgt    2820
ggcttttgac aatatctcca tcagcctgga ctgctacctc accattagcg gagaggacaa    2880
gatcctgcag aatacagcac ccaaatcaag aaacctgttt gagagaaacc caaacaagga    2940
gctgaaaccc ggggaaaatt caccaagaca gaccccatc tttgacccta cagttcattg     3000
gctgttcacc acatgtgggg ccagcgggcc ccatggcccc acccaggcac agtgcaacaa    3060
cgcctaccag aactccaacc tgagcgtgga ggtggggagc gagggccccc tgaaaggcat    3120
ccagatctgg aaggtgccag ccaccgacac ctacagcatc tcgggctacg agctgctgg    3180 cgggaaaggc gggaagaaca ccatgatgcg gtcccacggc gtgtctgtgc tgggcatctt    3240
caacctggag aaggatgaca tgctgtacat cctggttggg cagcagggag aggacgcctg    3300
ccccagtaca aaccagttaa tccagaaagt ctgcattgga gagaacaatg tgatagaaga    3360
agaaatccgt gtgaacagaa gcgtgcatga gtgggcagga ggcggaggag gaggggtgg     3420 agccacctac gtatttaaga tgaaggatgg agtgccggtg cccctgatca ttgcagccgg    3480
aggtggtggc agggcctacg gggccaagac agacacgttc cacccagaga gactggagaa    3540
taactcctcg gttctagggc taaacggcaa ttccggagcc gcaggtggtg gaggtggctg    3600
gaatgataac acttccttgc tctgggccgg aaaatctttg caggagggtg ccaccggagg    3660
acattcctgc ccccaggcca tgaagaagtg ggggtgggag acaagagggg gtttcggagg    3720
gggtggaggg gggtgctcct caggtggagg aggcggagga tataggcg gcaatgcagc      3780 ctcaaacaat gaccccgaaa tggatgggga agatggggtt tccttcatca gtccactggg    3840
catcctgtac accccagctt taaaagtgat ggaaggccac ggggaagtga atattaagca    3900
ttatctaaac tgcagtcact gtgaggtaga cgaatgtcac atggaccctg aaagccacaa    3960
ggtcatctgc ttctgtgacc acgggacggt gctggctgag gatggcgtct cctgcattgt    4020
gtcacccacc ccggagccac acctgccact ctcgctgatc ctctctgtgg tgacctctgc    4080
cctcgtggcc gccctggtcc tggctttctc cggcatcatg attgtgtacc gccgaagca    4140 ccaggagctg caagccatgc agatggagct gcagagccct gagtacaagc tgagcaagct    4200
ccgcacctcg accatcatga ccgactacaa ccccaactac tgctttgctg caagacctc     4260 ctccatcagt gacctgaagg aggtgccgcg gaaaaacatc accctcattc ggggtctggg    4320
ccatggcgcc tttggggagg tgtatgaagg ccaggtgtcc ggaatgccca acgacccaag    4380
ccccctgcaa gtggctgtga gacgctgcc tgaagtgtgc tctgaacagg acgaactgga    4440
tttcctcatg gaagccctga tcatcagcaa attcaaccac cagaacattg ttcgctgcat    4500 tgggtgtgagc ctgcaatccc tgccccggtt catcctgctg gagctcatgg cggggggaga   4560
cctcaagtcc ttcctccgag agacccgccc tcgcccgagc cagccctcct ccctggccat    4620
gctggacctt ctgcacgtgg ctcgggacat tgctgtggc tgtcagtatt ggaggaaaa      4680 ccacttcatc caccgagaca ttgctgccag aaactgcctc ttgacctgtc caggccctgg    4740
aagagtggcc aagattggag acttcgggat ggcccgagac atctacaggg cgagctacta    4800
tagaaaggga ggctgtgcca tgctgccagt taagtgatg ccccccagagg ccttcatgga    4860 aggaatattc acttctaaaa cagacacatg gtcctttgga gtgctgctat gggaaatctt    4920
```

```
ttctccttgga tatatgccat accccagcaa aagcaaccag gaagttctgg agtttgtcac    4980
cagtggaggc cggatggacc cacccaagaa ctgccctggg cctgtatacc ggataatgac    5040
tcagtgctgg caacatcagc ctgaagacag gcccaacttt gccatcattt tggagaggat    5100
tgaatactgc acccaggacc cggatgtaat caacaccgct tgccgatag aatatggtcc     5160
acttgtggaa gaggaagaga aagtgcctgt gaggcccaag gaccctgagg gggttcctcc    5220
tctcctggtc tctcaacagg caaaacggga ggaggagcgc agcccagctg ccccaccacc    5280
tctgcctacc acctcctctg gcaaggctgc aaagaaaccc acagctgcag agatctctgt    5340
tcgagtccct agagggccgg ccgtggaagg gggacacgtg aatatggcat tctctcagtc    5400
caaccctcct tcggagttgc acaaggtcca cggatccaga aacaagccca ccagcttgtg    5460
gaacccaacg tacggctcct ggtttacaga gaaacccacc aaaagaata atcctatagc     5520
aaagaaggag ccacacgaca ggggtaacct ggggctggag ggaagctgta ctgtcccacc    5580
taacgttgca actgggagac ttccgggggc ctcactgctc ctagagccct cttcgctgac    5640
tgccaatatg aaggaggtac ctctgttcag gctacgtcac ttcccttgtg ggaatgtcaa    5700
ttacggctac cagcaacagg gcttgcccct agaagccgct actgcccctg agctggtca   5760
ttacgaggat accattctga aaagcaagaa tagcatgaac cagcctgggc cctgagctcg    5820
gtcgcacact cacttctctt ccttgggatc cctaagaccg tggaggagag agaggcaatg    5880
gctccttcac aaaccagaga ccaaatgtca cgttttgttt tgtgccaacc tattttgaag    5940
taccaccaaa aaagctgtat tttgaaaatg ctttagaaag gttttgagca tgggttcatc    6000
ctattctttc gaaagaagaa aatatcataa aaatgagtga taaatacaag gcccagatgt    6060
ggttgcataa ggtttttatg catgtttgtt gtatacttcc ttatgcttct ttcaaattgt    6120
gtgtgctctg cttcaatgta gtcagaatta gctgcttcta tgtttcatag ttggggtcat    6180
agatgttttcc ttgccttgtt gatgtggaca tgagccattt gaggggagag ggaacggaaa    6240
taaaggagtt atttgtaatg actaaaaa                                        6267
```

<210> SEQ ID NO 3
<211> LENGTH: 1068
<212> TYPE: PRT
<213> ORGANISM: Homo sapiens

<400> SEQUENCE: 3

```
Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125
```

-continued

```
Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
```

-continued

```
            545                 550                 555                 560
Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
                580                 585                 590

Trp Gln Trp Met Val Leu Pro Leu Asp Val Ser Asp Arg Phe Trp
                595                 600                 605

Leu Gln Met Val Ala Trp Trp Gly Gln Gly Ser Arg Ala Ile Val Ala
610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
                675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
                755                 760                 765

Asp Met Leu Tyr Ile Leu Val Gly Gln Gln Gly Glu Asp Ala Cys Pro
                770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Gly Ala Thr Tyr Val Phe Lys Met Lys Asp
                820                 825                 830

Gly Val Pro Val Pro Leu Ile Ile Ala Ala Gly Gly Gly Gly Arg Ala
                835                 840                 845

Tyr Gly Ala Lys Thr Asp Thr Phe His Pro Glu Arg Leu Glu Asn Asn
                850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
                900                 905                 910

Trp Gly Trp Glu Thr Arg Gly Gly Phe Gly Gly Gly Gly Gly Gly Cys
                915                 920                 925

Ser Ser Gly Gly Gly Gly Gly Tyr Ile Gly Gly Asn Ala Ala Ser
                930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
                965                 970                 975
```

```
Gly Glu Val Asn Ile Lys His Tyr Leu Asn Cys Ser His Cys Glu Val
            980                 985                 990

Asp Glu Cys His Met Asp Pro Glu Ser His Lys Val Ile Cys Phe Cys
            995                 1000                1005

Asp His Gly Thr Val Leu Ala Glu Asp Gly Val Ser Cys Ile Val
        1010                1015                1020

Ser Pro Thr Pro Glu Pro His Leu Pro Leu Ser Leu Ile Leu Ser
        1025                1030                1035

Val Val Thr Ser Ala Leu Val Ala Ala Leu Val Leu Ala Phe Ser
        1040                1045                1050

Gly Ile Met Ile Val Tyr Arg Arg Lys His Gln Glu Leu Gln Ala
        1055                1060                1065

<210> SEQ ID NO 4
<211> LENGTH: 1043
<212> TYPE: PRT
<213> ORGANISM: Homo sapiens

<400> SEQUENCE: 4

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
50                  55                  60

Arg Val Tyr Ala Arg Asp Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
```

```
                    275                 280                 285
Ser Trp Arg Arg Ile Pro Ser Glu Glu Ala Ser Gln Met Asp Leu Leu
290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
                340                 345                 350

Arg His Leu Gln Pro Ser Gly Arg Tyr Ile Ala Gln Leu Leu Pro His
                355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
                435                 440                 445

Leu Gln Leu Gly Gln Ala Cys Asp Phe His Gln Asp Cys Ala Gln Gly
450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
                500                 505                 510

Asp His Gln Asp His Ala Leu Leu Leu Ser Thr Thr Asp Val Pro Ala
                515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
                580                 585                 590

Trp Gln Trp Met Val Leu Pro Leu Leu Asp Val Ser Asp Arg Phe Trp
                595                 600                 605

Leu Gln Met Val Ala Trp Trp Gly Gln Gly Ser Arg Ala Ile Val Ala
                610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
                675                 680                 685

Gly Ala Ser Gly Pro His Gly Pro Thr Gln Ala Gln Cys Asn Asn Ala
690                 695                 700
```

-continued

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
            725                 730                 735

Ser Gly Tyr Gly Ala Ala Gly Gly Lys Gly Gly Lys Asn Thr Met Met
        740                 745                 750

Arg Ser His Gly Val Ser Val Leu Gly Ile Phe Asn Leu Glu Lys Asp
    755                 760                 765

Asp Met Leu Tyr Ile Leu Val Gly Gln Gln Gly Glu Asp Ala Cys Pro
770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Gly Ala Thr Tyr Val Phe Lys Met Lys Asp
                820                 825                 830

Gly Val Pro Val Pro Leu Ile Ile Ala Ala Gly Gly Gly Gly Arg Ala
            835                 840                 845

Tyr Gly Ala Lys Thr Asp Thr Phe His Pro Glu Arg Leu Glu Asn Asn
850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
        915                 920                 925

Ser Ser Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
        980                 985                 990

Asp Glu Cys His Met Asp Pro Glu Ser His Lys Val Ile Cys Phe Cys
    995                 1000                1005

Asp His Gly Thr Val Leu Ala Glu Asp Gly Val Ser Cys Ile Val
    1010                1015                1020

Ser Pro Thr Pro Glu Pro His Leu Pro Leu Ser Leu Ile Leu Ser
    1025                1030                1035

Val Val Thr Ser Ala
    1040

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcatacacat acgatttagg tgacactata gagcggccgc ctgcaggaaa           50

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggtcactg atggaggagg tcttgccagc aaagca                         36

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaatacgac tcactatagg gc                                        22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acacctggcc ttcatacacc tcc                                       23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccatccca tctccagtct gcttc                                     25

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agagaagtga gtgtgcgacc                                           20

<210> SEQ ID NO 11
<211> LENGTH: 2513
<212> TYPE: DNA
<213> ORGANISM: Homo sapiens

<400> SEQUENCE: 11
cagccttccc tggctccctc cccatttcct ctcatgggca tttcttctaa taaaatctgc    60
agaccatatt gggtctaatc ccatctccag tctgcttctt ggaggaacca gactaacatg   120
actctgccct atataataca aataattatt ttccatatat ctgattttta gctttgcatt   180

```
tactttaaat catgcttcaa ttaaagacac accttcttta atcattttat tagtatttct      240
aagtatgatg gaaaggttca gagctcaggg gaggatatgg agatccaggg aggcttcctg      300
taggaagtgg cctgtgtagt gcttcaaggg ccaggctgcc aggccatgtt gcagctgacc      360
acccacctgc agtgtaccgc cggaagcacc aggagctgca agccatgcag atggagctgc      420
agagccctga gtacaagctg agcaagctcc gcacctcgac catcatgacc gactacaacc      480
ccaactactg ctttgctggc aagacctcct ccatcagtga cctgaaggag gtgccgcgga      540
aaaacatcac cctcattcgg ggtctgggcc atggcgcctt tggggaggtg tatgaaggcc      600
aggtgtccga aatgcccaac gacccaagcc cctgcaagt ggctgtgaag acgctgcctg       660
aagtgtgctc tgaacaggac gaactggatt cctcatgga gccctgatc atcagcaaat        720 tcaaccacca gaacattgtt cgctgcattg gggtgagcct gcaatccctg ccccggttca      780
tcctgctgga gctcatggcg gggggagacc tcaagtcctt cctccgagag acccgccctc      840
gcccgagcca gccctcctcc ctggccatgc tggaccttct gcacgtggct cgggacattg      900
cctgtggctg tcagtatttg gaggaaaacc acttcatcca ccgagacatt gctgccagaa      960
actgcctctt gacctgtcca ggccctggaa gagtggccaa gattgagac ttcgggatgg      1020 cccgagacat ctacagggcg agctactata gaaagggagg ctgtgccatg ctgccagtta    1080
agtggatgcc cccagaggcc ttcatggaag gaatattcac ttctaaaaca gacacatggt    1140
cctttggagt gctgctatgg gaaatctttt ctcttggata tgccatac cccagcaaaa       1200 gcaaccagga agttctggag tttgtcacca gtggaggccg gatggaccca cccaagaact    1260
gccctgggcc tgtataccgg ataatgactc agtgctggca acatcagcct gaagacaggc    1320
ccaactttgc catcattttg gagaggattg aatactgcac ccaggacccg gatgtaatca    1380
acaccgcttt gccgatagaa tatggtccac ttgtggaaga ggaagagaaa gtgcctgtga    1440
ggcccaagga ccctgagggg gttcctcctc tcctggtctc tcaacaggca aaacgggagg    1500
aggagcgcag cccagctgcc ccaccacctc tgcctaccac ctcctctggc aaggctgcaa    1560
agaaacccac agctgcagag atctctgttc gagtccctag agggccggcc gtggaagggg    1620
gacacgtgaa tatggcattc tctcagtcca accctccttc ggagttgcac aaggtccacg    1680
gatccagaaa caagcccacc agcttgtgga acccaacgta cggctcctgg tttacagaga    1740
aacccaccaa aaagaataat cctatagcaa agaaggagcc acgacagg ggtaacctgg      1800 ggctggaggg aagctgtact gtcccaccta acgttgcaac tgggagactt ccgggggcct    1860
cactgctcct agagccctct tcgctgactg ccaatatgaa ggaggtacct ctgttcaggc    1920
tacgtcactt cccttgtggg aatgtcaatt acggctacca gcaacagggc ttgcccttag    1980
aagccgctac tgcccctgga gctggtcatt acgaggatac cattctgaaa agcaagaata    2040
gcatgaacca gcctgggccc tgagctcggt cgcacactca cttctcttcc ttgggatccc    2100
taagaccgtg gaggagagag aggcaatggc tccttcacaa accagagacc aaatgtcacg    2160
ttttgttttg tgccaaccta ttttgaagta ccaccaaaaa agctgtattt tgaaaatgct    2220
ttagaaaggt tttgagcatg ggttcatcct attctttcga aagaagaaaa tatcataaaa    2280
atgagtgata aatacaaggc ccagatgtgg ttgcataagg ttttttatgca tgtttgttgt    2340 atacttcctt atgcttcttt caaattgtgt gtgctctgct tcaatgtagt cagaattagc    2400
tgcttctatg tttcatagtt ggggtcatag atgtttcctt gccttgttga tgtggacatg    2460
agccatttga ggggagaggg aacggaaata aaggagttat ttgtaatgac taa            2513
```

<210> SEQ ID NO 12
<211> LENGTH: 552
<212> TYPE: PRT
<213> ORGANISM: Homo sapiens

<400> SEQUENCE: 12

Met Gln Met Glu Leu Gln Ser Pro Glu Tyr Lys Leu Ser Lys Leu Arg
1               5                   10                  15

Thr Ser Thr Ile Met Thr Asp Tyr Asn Pro Asn Tyr Cys Phe Ala Gly
            20                  25                  30

Lys Thr Ser Ser Ile Ser Asp Leu Lys Glu Val Pro Arg Lys Asn Ile
        35                  40                  45

Thr Leu Ile Arg Gly Leu Gly His Gly Ala Phe Gly Glu Val Tyr Glu
    50                  55                  60

Gly Gln Val Ser Gly Met Pro Asn Asp Pro Ser Pro Leu Gln Val Ala
65                  70                  75                  80

Val Lys Thr Leu Pro Glu Val Cys Ser Glu Gln Asp Glu Leu Asp Phe
                85                  90                  95

Leu Met Glu Ala Leu Ile Ile Ser Lys Phe Asn His Gln Asn Ile Val
            100                 105                 110

Arg Cys Ile Gly Val Ser Leu Gln Ser Leu Pro Arg Phe Ile Leu Leu
        115                 120                 125

Glu Leu Met Ala Gly Gly Asp Leu Lys Ser Phe Leu Arg Glu Thr Arg
    130                 135                 140

Pro Arg Pro Ser Gln Pro Ser Ser Leu Ala Met Leu Asp Leu Leu His
145                 150                 155                 160

Val Ala Arg Asp Ile Ala Cys Gly Cys Gln Tyr Leu Glu Glu Asn His
                165                 170                 175

Phe Ile His Arg Asp Ile Ala Ala Arg Asn Cys Leu Leu Thr Cys Pro
            180                 185                 190

Gly Pro Gly Arg Val Ala Lys Ile Gly Asp Phe Gly Met Ala Arg Asp
        195                 200                 205

Ile Tyr Arg Ala Ser Tyr Tyr Arg Lys Gly Gly Cys Ala Met Leu Pro
    210                 215                 220

Val Lys Trp Met Pro Pro Glu Ala Phe Met Glu Gly Ile Phe Thr Ser
225                 230                 235                 240

Lys Thr Asp Thr Trp Ser Phe Gly Val Leu Leu Trp Glu Ile Phe Ser
                245                 250                 255

Leu Gly Tyr Met Pro Tyr Pro Ser Lys Ser Asn Gln Glu Val Leu Glu
            260                 265                 270

Phe Val Thr Ser Gly Gly Arg Met Asp Pro Pro Lys Asn Cys Pro Gly
        275                 280                 285

Pro Val Tyr Arg Ile Met Thr Gln Cys Trp Gln His Gln Pro Glu Asp
    290                 295                 300

Arg Pro Asn Phe Ala Ile Ile Leu Glu Arg Ile Glu Tyr Cys Thr Gln
305                 310                 315                 320

Asp Pro Asp Val Ile Asn Thr Ala Leu Pro Ile Glu Tyr Gly Pro Leu
                325                 330                 335

Val Glu Glu Glu Glu Lys Val Pro Val Arg Pro Lys Asp Pro Glu Gly
            340                 345                 350

Val Pro Pro Leu Leu Val Ser Gln Gln Ala Lys Arg Glu Glu Glu Arg
        355                 360                 365

Ser Pro Ala Ala Pro Pro Pro Leu Pro Thr Thr Ser Ser Gly Lys Ala
    370                 375                 380

```
Ala Lys Lys Pro Thr Ala Ala Glu Ile Ser Val Arg Val Pro Arg Gly
385                 390                 395                 400

Pro Ala Val Glu Gly Gly His Val Asn Met Ala Phe Ser Gln Ser Asn
            405                 410                 415

Pro Pro Ser Glu Leu His Lys Val His Gly Ser Arg Asn Lys Pro Thr
            420                 425                 430

Ser Leu Trp Asn Pro Thr Tyr Gly Ser Trp Phe Thr Glu Lys Pro Thr
        435                 440                 445

Lys Lys Asn Asn Pro Ile Ala Lys Lys Glu Pro His Asp Arg Gly Asn
    450                 455                 460

Leu Gly Leu Glu Gly Ser Cys Thr Val Pro Pro Asn Val Ala Thr Gly
465                 470                 475                 480

Arg Leu Pro Gly Ala Ser Leu Leu Leu Glu Pro Ser Ser Leu Thr Ala
                485                 490                 495

Asn Met Lys Glu Val Pro Leu Phe Arg Leu Arg His Phe Pro Cys Gly
            500                 505                 510

Asn Val Asn Tyr Gly Tyr Gln Gln Gln Gly Leu Pro Leu Glu Ala Ala
        515                 520                 525

Thr Ala Pro Gly Ala Gly His Tyr Glu Asp Thr Ile Leu Lys Ser Lys
    530                 535                 540

Asn Ser Met Asn Gln Pro Gly Pro
545                 550

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcctcatgg ctcagcttgt                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcactacac aggccacttc                                                   20

<210> SEQ ID NO 15
<211> LENGTH: 100
<212> TYPE: DNA
<213> ORGANISM: Homo sapiens

<400> SEQUENCE: 15
gcctggactg ctacctcacc attagcggag aggacaagat cctgcagaat acagcaccca      60
aatcaagaaa cctgtttgag agaaacccaa acaaggagct                           100

<210> SEQ ID NO 16
<211> LENGTH: 100
<212> TYPE: DNA
<213> ORGANISM: Homo sapiens

<400> SEQUENCE: 16
```

```
taactcctcg gttctagggc taaacggcaa ttccggagcc gcaggtggtg gaggtggctg    60
gaatgataac acttccttgc tctgggccgg aaaatctttg                         100

<210> SEQ ID NO 17
<211> LENGTH: 100
<212> TYPE: DNA
<213> ORGANISM: Homo sapiens

<400> SEQUENCE: 17
tttattagta tttctaagta tgatggaaag gttcagagct caggggagga tatggagatc    60
cagggaggct tcctgtagga agtggcctgt gtagtgcttc                         100

<210> SEQ ID NO 18
<211> LENGTH: 100
<212> TYPE: DNA
<213> ORGANISM: Homo sapiens

<400> SEQUENCE: 18
cttcaagggc caggctgcca ggccatgttg cagctgacca cccacctgca gtgtaccgcc    60
ggaagcacca ggagctgcaa gccatgcaga tggagctgca                         100

<210> SEQ ID NO 19
<211> LENGTH: 100
<212> TYPE: DNA
<213> ORGANISM: Homo sapiens

<400> SEQUENCE: 19
agaggccttc atggaaggaa tattcacttc taaaacagac acatggtcct ttggagtgct    60
gctatgggaa atcttttctc ttggatatat gccataccccc                        100

<210> SEQ ID NO 20
<211> LENGTH: 100
<212> TYPE: DNA
<213> ORGANISM: Homo sapiens

<400> SEQUENCE: 20
cacactcact tctcttcctt gggatcccta agaccgtgga ggagagagag gcaatggctc    60
cttcacaaac cagagaccaa atgtcacgtt ttgttttgtg                         100

<210> SEQ ID NO 21
<211> LENGTH: 100
<212> TYPE: DNA
<213> ORGANISM: Homo sapiens

<400> SEQUENCE: 21
tgcagaagga gatcactgcc ctggcaccca gcacaatgaa gatcaagatc attgctcctc    60
ctgagcgcaa gtactccgtg tggatcggcg gctccatcct                         100

<210> SEQ ID NO 22
<211> LENGTH: 100
<212> TYPE: DNA
<213> ORGANISM: Homo sapiens

<400> SEQUENCE: 22
gggccgggtg gttgctgccg aaatgggcaa gttcatgaaa cctgggaagg tggtgcttgt    60
cctggctgga cgctactccg gacgcaaagc tgtcatcgtg                         100

<210> SEQ ID NO 23
```

<211> LENGTH: 100
<212> TYPE: DNA
<213> ORGANISM: Homo sapiens

<400> SEQUENCE: 23
gcatcttgag aggaacagaa aggataagga tgctaaattc cgtctgattc taatagagag    60
ccggattcac cgtttggctc gatattataa gaccaagcga                         100

<210> SEQ ID NO 24
<211> LENGTH: 100
<212> TYPE: DNA
<213> ORGANISM: Homo sapiens

<400> SEQUENCE: 24
tcgaatcacc ctaacaagcc gcaacgtaaa atccttggaa aaggtgtgtg ctgacttgat    60
aagaggcgca aagaaaaga atctcaaagt gaaaggacca                          100

<210> SEQ ID NO 25
<211> LENGTH: 71
<212> TYPE: DNA
<213> ORGANISM: Homo sapiens

<400> SEQUENCE: 25
acgtctaaaa taatcttctt tacgggtact ctcctttacc cctccctcgg tcccttccga    60
cccacttggt c                                                        71

<210> SEQ ID NO 26
<211> LENGTH: 604
<212> TYPE: DNA
<213> ORGANISM: Homo sapiens

<400> SEQUENCE: 26
agccttccct ggctccctcc ccatttcctc tcatgggcat ttctcctaat aaaatctgca    60
gaccatattg ggtctaatcc catctccagt ctgcttcttg gaggaaccag actaacatga   120
ctctgcccta tataatacaa taattatttt ccatatatct gattttagc tttgcattta   180 cttaaaatca tgcttcaatt aaagacacac cttctttaat catttttatta gtatttctaa   240 gtatgatgga aaggttcaga gctcaggga ggatatggag atccagggag cttcctgta    300 ggaagtggcc tgtgtagtgc ttcaagggcc aggctgccag gccatgttgc agctgaccac   360
ccacctgcag tgtaccgccg gaagcaccag gagctgcaag ccatgcagat ggagctgcag   420
agccctgagt acaagctgag caagctccgc acctcgacca tcatgaccga ctacaacccc   480
aactactgct ttgctggcaa gacctcctcc atcagtgacc tgaaggaggt gccgcggaaa   540
aacatcaccc tcattcgggg tctgggccat ggcgcctttg ggaggtgta tgaaggccag   600 gtgt                                                               604

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acaagctgag ccatgaggac                                               20

<210> SEQ ID NO 28

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aggagttacc atccctgcct                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaggggagcc aggtagactt                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgagaggag aaccagggct                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
attcagcccc tacactgcac                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgcggaaaaa catcaccctc                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaggcggggg taacatacac                                                    20

<210> SEQ ID NO 34
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgaagaact ggaagcccga                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcatgctcct tggggagaga                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctagagcaa ctgcgccttc                                                    20

<210> SEQ ID NO 37
<211> LENGTH: 15
<212> TYPE: DNA
<213> ORGANISM: Homo sapiens

<400> SEQUENCE: 37
gagtacaagc tgagc                                                         15

<210> SEQ ID NO 38
<211> LENGTH: 15
<212> TYPE: DNA
<213> ORGANISM: Homo sapiens

<400> SEQUENCE: 38
aacatgactc tgccc                                                         15

<210> SEQ ID NO 39
<211> LENGTH: 15
<212> TYPE: DNA
<213> ORGANISM: Homo sapiens

<400> SEQUENCE: 39
ataatgaggc agctg                                                         15

<210> SEQ ID NO 40
<211> LENGTH: 11
<212> TYPE: DNA
<213> ORGANISM: Homo sapiens

<400> SEQUENCE: 40
cccacgtgaa c                                                             11

<210> SEQ ID NO 41
<211> LENGTH: 19
```

```
<212> TYPE: DNA
<213> ORGANISM: Homo sapiens

<400> SEQUENCE: 41
tgacctgaag gaggtgccg                                                   19

<210> SEQ ID NO 42
<211> LENGTH: 19
<212> TYPE: DNA
<213> ORGANISM: Homo sapiens

<400> SEQUENCE: 42
tctccagtag gagactccc                                                   19

<210> SEQ ID NO 43
<211> LENGTH: 12
<212> TYPE: DNA
<213> ORGANISM: Homo sapiens

<400> SEQUENCE: 43
cagtgcaatc ac                                                          12

<210> SEQ ID NO 44
<211> LENGTH: 12
<212> TYPE: DNA
<213> ORGANISM: Homo sapiens

<400> SEQUENCE: 44
ctatgcaatc tc                                                          12

<210> SEQ ID NO 45
<211> LENGTH: 15
<212> TYPE: DNA
<213> ORGANISM: Homo sapiens

<400> SEQUENCE: 45
ttccctccct ccctc                                                       15

<210> SEQ ID NO 46
<211> LENGTH: 15
<212> TYPE: DNA
<213> ORGANISM: Homo sapiens

<400> SEQUENCE: 46
ctccctccct cgttc                                                       15

<210> SEQ ID NO 47
<211> LENGTH: 15
<212> TYPE: DNA
<213> ORGANISM: Homo sapiens

<400> SEQUENCE: 47
ttccctccag gggag                                                       15

<210> SEQ ID NO 48
<211> LENGTH: 15
<212> TYPE: DNA
<213> ORGANISM: Homo sapiens

<400> SEQUENCE: 48
ctccctcgtt cacgt                                                       15

<210> SEQ ID NO 49
```

```
<211> LENGTH: 15
<212> TYPE: DNA
<213> ORGANISM: Homo sapiens

<400> SEQUENCE: 49
ctccctcccc atttc                                                           15

<210> SEQ ID NO 50
<211> LENGTH: 11
<212> TYPE: DNA
<213> ORGANISM: Homo sapiens

<400> SEQUENCE: 50
gggagggaag g                                                               11

<210> SEQ ID NO 51
<211> LENGTH: 11
<212> TYPE: DNA
<213> ORGANISM: Homo sapiens

<400> SEQUENCE: 51
gggagggagg g                                                               11

<210> SEQ ID NO 52
<211> LENGTH: 11
<212> TYPE: DNA
<213> ORGANISM: Homo sapiens

<400> SEQUENCE: 52
tggagggaag g                                                               11

<210> SEQ ID NO 53
<211> LENGTH: 11
<212> TYPE: DNA
<213> ORGANISM: Homo sapiens

<400> SEQUENCE: 53
gggagggagc c                                                               11

<210> SEQ ID NO 54
<211> LENGTH: 11
<212> TYPE: DNA
<213> ORGANISM: Homo sapiens

<400> SEQUENCE: 54
acgagggagg g                                                               11

<210> SEQ ID NO 55
<211> LENGTH: 11
<212> TYPE: DNA
<213> ORGANISM: Homo sapiens

<400> SEQUENCE: 55
ccctccaggg g                                                               11

<210> SEQ ID NO 56
<211> LENGTH: 11
<212> TYPE: DNA
<213> ORGANISM: Homo sapiens

<400> SEQUENCE: 56
ctcccctgag c                                                               11
```

```
<210> SEQ ID NO 57
<211> LENGTH: 11
<212> TYPE: DNA
<213> ORGANISM: Homo sapiens

<400> SEQUENCE: 57
ctccccaagg a                                                          11

<210> SEQ ID NO 58
<211> LENGTH: 11
<212> TYPE: DNA
<213> ORGANISM: Homo sapiens

<400> SEQUENCE: 58
ctctcatggg c                                                          11

<210> SEQ ID NO 59
<211> LENGTH: 14
<212> TYPE: DNA
<213> ORGANISM: Homo sapiens

<400> SEQUENCE: 59
cctcctcctc ctcc                                                       14

<210> SEQ ID NO 60
<211> LENGTH: 14
<212> TYPE: DNA
<213> ORGANISM: Homo sapiens

<400> SEQUENCE: 60
cagcctcctc ctcc                                                       14

<210> SEQ ID NO 61
<211> LENGTH: 14
<212> TYPE: DNA
<213> ORGANISM: Homo sapiens

<400> SEQUENCE: 61
gaacctcccc cggg                                                       14

<210> SEQ ID NO 62
<211> LENGTH: 14
<212> TYPE: DNA
<213> ORGANISM: Homo sapiens

<400> SEQUENCE: 62
caccctcccc ttct                                                       14

<210> SEQ ID NO 63
<211> LENGTH: 14
<212> TYPE: DNA
<213> ORGANISM: Homo sapiens

<400> SEQUENCE: 63
cccaagcccc ctgc                                                       14

<210> SEQ ID NO 64
<211> LENGTH: 15
<212> TYPE: DNA
<213> ORGANISM: Homo sapiens

<400> SEQUENCE: 64
cctcctcctc ctccc                                                      15
```

```
<210> SEQ ID NO 65
<211> LENGTH: 10
<212> TYPE: DNA
<213> ORGANISM: Homo sapiens

<400> SEQUENCE: 65
ccgccggaag                                                          10

<210> SEQ ID NO 66
<211> LENGTH: 11
<212> TYPE: DNA
<213> ORGANISM: Homo sapiens

<400> SEQUENCE: 66
gtgcttccgg c                                                        11

<210> SEQ ID NO 67
<211> LENGTH: 11
<212> TYPE: DNA
<213> ORGANISM: Homo sapiens

<400> SEQUENCE: 67
agaggaaatg g                                                        11

<210> SEQ ID NO 68
<211> LENGTH: 11
<212> TYPE: DNA
<213> ORGANISM: Homo sapiens

<400> SEQUENCE: 68
agaggaaggc g                                                        11

<210> SEQ ID NO 69
<211> LENGTH: 11
<212> TYPE: DNA
<213> ORGANISM: Homo sapiens

<400> SEQUENCE: 69
acaggaagcc t                                                        11

<210> SEQ ID NO 70
<211> LENGTH: 20
<212> TYPE: DNA
<213> ORGANISM: Homo sapiens

<400> SEQUENCE: 70
atggcctggc agcctggccc                                               20

<210> SEQ ID NO 71
<211> LENGTH: 20
<212> TYPE: DNA
<213> ORGANISM: Homo sapiens

<400> SEQUENCE: 71
ccccaaaggc gccatggccc                                               20

<210> SEQ ID NO 72
<211> LENGTH: 20
<212> TYPE: DNA
<213> ORGANISM: Homo sapiens

<400> SEQUENCE: 72
ctgctggttc acccagcctt                                               20
```

<210> SEQ ID NO 73
<211> LENGTH: 15
<212> TYPE: DNA
<213> ORGANISM: Homo sapiens

<400> SEQUENCE: 73
gggtgagggt gtctc                                                       15

<210> SEQ ID NO 74
<211> LENGTH: 11
<212> TYPE: DNA
<213> ORGANISM: Homo sapiens

<400> SEQUENCE: 74
ccaagggcag g                                                           11

<210> SEQ ID NO 75
<211> LENGTH: 12
<212> TYPE: DNA
<213> ORGANISM: Homo sapiens

<400> SEQUENCE: 75
aagccaaggg ca                                                          12

<210> SEQ ID NO 76
<211> LENGTH: 15
<212> TYPE: DNA
<213> ORGANISM: Homo sapiens

<400> SEQUENCE: 76
cccatttcct ctcat                                                       15

<210> SEQ ID NO 77
<211> LENGTH: 15
<212> TYPE: DNA
<213> ORGANISM: Homo sapiens

<400> SEQUENCE: 77
gcgccttcct ctgtc                                                       15

<210> SEQ ID NO 78
<211> LENGTH: 15
<212> TYPE: DNA
<213> ORGANISM: Homo sapiens

<400> SEQUENCE: 78
tccatatcct cccct                                                       15

<210> SEQ ID NO 79
<211> LENGTH: 11
<212> TYPE: DNA
<213> ORGANISM: Homo sapiens

<400> SEQUENCE: 79
gccggaagca c                                                           11

<210> SEQ ID NO 80
<211> LENGTH: 12
<212> TYPE: DNA
<213> ORGANISM: Homo sapiens

<400> SEQUENCE: 80

```
aaatgttat tc                                                              12

<210> SEQ ID NO 81
<211> LENGTH: 12
<212> TYPE: DNA
<213> ORGANISM: Homo sapiens

<400> SEQUENCE: 81
gtatgttggc tt                                                             12

<210> SEQ ID NO 82
<211> LENGTH: 11
<212> TYPE: DNA
<213> ORGANISM: Homo sapiens

<400> SEQUENCE: 82
tcaaatccac t                                                              11

<210> SEQ ID NO 83
<211> LENGTH: 11
<212> TYPE: DNA
<213> ORGANISM: Homo sapiens

<400> SEQUENCE: 83
aaatgtttat t                                                              11

<210> SEQ ID NO 84
<211> LENGTH: 11
<212> TYPE: DNA
<213> ORGANISM: Homo sapiens

<400> SEQUENCE: 84 catagttat g                                                               11

<210> SEQ ID NO 85
<211> LENGTH: 11
<212> TYPE: DNA
<213> ORGANISM: Homo sapiens

<400> SEQUENCE: 85
ccggaagcac c                                                              11

<210> SEQ ID NO 86
<211> LENGTH: 14
<212> TYPE: DNA
<213> ORGANISM: Homo sapiens

<400> SEQUENCE: 86
tgaatgttat caca                                                           14

<210> SEQ ID NO 87
<211> LENGTH: 10
<212> TYPE: DNA
<213> ORGANISM: Homo sapiens

<400> SEQUENCE: 87
gcaatcacag                                                                10

<210> SEQ ID NO 88
<211> LENGTH: 15
<212> TYPE: DNA
<213> ORGANISM: Homo sapiens

<400> SEQUENCE: 88
```

```
gggggagcaaa gggcc                                                15

<210> SEQ ID NO 89
<211> LENGTH: 15
<212> TYPE: DNA
<213> ORGANISM: Homo sapiens

<400> SEQUENCE: 89
aaggttcaga gctca                                                 15

<210> SEQ ID NO 90
<211> LENGTH: 15
<212> TYPE: DNA
<213> ORGANISM: Homo sapiens

<400> SEQUENCE: 90
attctagaca cttct                                                 15

<210> SEQ ID NO 91
<211> LENGTH: 12
<212> TYPE: DNA
<213> ORGANISM: Homo sapiens

<400> SEQUENCE: 91
ttgcaggggg ct                                                    12

<210> SEQ ID NO 92
<211> LENGTH: 10
<212> TYPE: DNA
<213> ORGANISM: Homo sapiens

<400> SEQUENCE: 92
agggtgggga                                                       10

<210> SEQ ID NO 93
<211> LENGTH: 10
<212> TYPE: DNA
<213> ORGANISM: Homo sapiens

<400> SEQUENCE: 93
tccccaccct                                                       10

<210> SEQ ID NO 94
<211> LENGTH: 10
<212> TYPE: DNA
<213> ORGANISM: Homo sapiens

<400> SEQUENCE: 94
ctccctcccc                                                       10

<210> SEQ ID NO 95
<211> LENGTH: 10
<212> TYPE: DNA
<213> ORGANISM: Homo sapiens

<400> SEQUENCE: 95
cctcctcccc                                                       10

<210> SEQ ID NO 96
<211> LENGTH: 10
<212> TYPE: DNA
<213> ORGANISM: Homo sapiens
```

```
<400> SEQUENCE: 96
gcccctcctc                                                            10

<210> SEQ ID NO 97
<211> LENGTH: 10
<212> TYPE: DNA
<213> ORGANISM: Homo sapiens

<400> SEQUENCE: 97
ccctcacccc                                                            10

<210> SEQ ID NO 98
<211> LENGTH: 10
<212> TYPE: DNA
<213> ORGANISM: Homo sapiens

<400> SEQUENCE: 98
ctccctccct                                                            10

<210> SEQ ID NO 99
<211> LENGTH: 10
<212> TYPE: DNA
<213> ORGANISM: Homo sapiens

<400> SEQUENCE: 99
ttccctccct                                                            10

<210> SEQ ID NO 100
<211> LENGTH: 15
<212> TYPE: DNA
<213> ORGANISM: Homo sapiens

<400> SEQUENCE: 100
ctctgtcact cactg                                                      15

<210> SEQ ID NO 101
<211> LENGTH: 15
<212> TYPE: DNA
<213> ORGANISM: Homo sapiens

<400> SEQUENCE: 101
atctgtctct cccca                                                      15

<210> SEQ ID NO 102
<211> LENGTH: 10
<212> TYPE: DNA
<213> ORGANISM: Homo sapiens

<400> SEQUENCE: 102
ccagctgcct                                                            10

<210> SEQ ID NO 103
<211> LENGTH: 15
<212> TYPE: DNA
<213> ORGANISM: Homo sapiens

<400> SEQUENCE: 103
atgactctgc cctat                                                      15

<210> SEQ ID NO 104
<211> LENGTH: 15
<212> TYPE: DNA
<213> ORGANISM: Homo sapiens
```

<400> SEQUENCE: 104
taacatgact ctgcc                                                    15

<210> SEQ ID NO 105
<211> LENGTH: 15
<212> TYPE: DNA
<213> ORGANISM: Homo sapiens

<400> SEQUENCE: 105
ctgggtgaac cagca                                                    15

<210> SEQ ID NO 106
<211> LENGTH: 11
<212> TYPE: DNA
<213> ORGANISM: Homo sapiens

<400> SEQUENCE: 106
tggcttttcc c                                                        11

<210> SEQ ID NO 107
<211> LENGTH: 12
<212> TYPE: DNA
<213> ORGANISM: Homo sapiens

<400> SEQUENCE: 107
aggcagctgg gg                                                       12

<210> SEQ ID NO 108
<211> LENGTH: 12
<212> TYPE: DNA
<213> ORGANISM: Homo sapiens

<400> SEQUENCE: 108
gagcaactgc gc                                                       12

<210> SEQ ID NO 109
<211> LENGTH: 12
<212> TYPE: DNA
<213> ORGANISM: Homo sapiens

<400> SEQUENCE: 109
tcccagctgc ac                                                       12

<210> SEQ ID NO 110
<211> LENGTH: 11
<212> TYPE: DNA
<213> ORGANISM: Homo sapiens

<400> SEQUENCE: 110
aacctctcca g                                                        11

<210> SEQ ID NO 111
<211> LENGTH: 17
<212> TYPE: DNA
<213> ORGANISM: Homo sapiens

<400> SEQUENCE: 111
aaggttcaga gctcagg                                                  17

<210> SEQ ID NO 112
<211> LENGTH: 15
<212> TYPE: DNA

<213> ORGANISM: Homo sapiens

<400> SEQUENCE: 112
tgggggcaga gggga                                                    15

<210> SEQ ID NO 113
<211> LENGTH: 14
<212> TYPE: DNA
<213> ORGANISM: Homo sapiens

<400> SEQUENCE: 113
tgagctctga acct                                                     14

<210> SEQ ID NO 114
<211> LENGTH: 15
<212> TYPE: DNA
<213> ORGANISM: Homo sapiens

<400> SEQUENCE: 114
caagccaagg gcagg                                                    15

<210> SEQ ID NO 115
<211> LENGTH: 15
<212> TYPE: DNA
<213> ORGANISM: Homo sapiens

<400> SEQUENCE: 115
aatgtcaagg cttgt                                                    15

<210> SEQ ID NO 116
<211> LENGTH: 14
<212> TYPE: DNA
<213> ORGANISM: Homo sapiens

<400> SEQUENCE: 116
atcatgcttc aatt                                                     14

<210> SEQ ID NO 117
<211> LENGTH: 14
<212> TYPE: DNA
<213> ORGANISM: Homo sapiens

<400> SEQUENCE: 117
ttgaagcatg attt                                                     14

<210> SEQ ID NO 118
<211> LENGTH: 14
<212> TYPE: DNA
<213> ORGANISM: Homo sapiens

<400> SEQUENCE: 118
gagggctagg ggtg                                                     14

<210> SEQ ID NO 119
<211> LENGTH: 14
<212> TYPE: DNA
<213> ORGANISM: Homo sapiens

<400> SEQUENCE: 119
gggggcagag ggga                                                     14

<210> SEQ ID NO 120
<211> LENGTH: 14

```
<212> TYPE: DNA
<213> ORGANISM: Homo sapiens

<400> SEQUENCE: 120
aaggccctaa gggg                                                    14

<210> SEQ ID NO 121
<211> LENGTH: 14
<212> TYPE: DNA
<213> ORGANISM: Homo sapiens

<400> SEQUENCE: 121
tgggggcaga gggg                                                    14

<210> SEQ ID NO 122
<211> LENGTH: 15
<212> TYPE: DNA
<213> ORGANISM: Homo sapiens

<400> SEQUENCE: 122
ctggagaaaa gggga                                                   15

<210> SEQ ID NO 123
<211> LENGTH: 10
<212> TYPE: DNA
<213> ORGANISM: Homo sapiens

<400> SEQUENCE: 123
tgggcattcc                                                         10

<210> SEQ ID NO 124
<211> LENGTH: 10
<212> TYPE: DNA
<213> ORGANISM: Homo sapiens

<400> SEQUENCE: 124
ctggatttcc                                                         10

<210> SEQ ID NO 125
<211> LENGTH: 15
<212> TYPE: DNA
<213> ORGANISM: Homo sapiens

<400> SEQUENCE: 125
ctccatggca cccag                                                   15

<210> SEQ ID NO 126
<211> LENGTH: 20
<212> TYPE: DNA
<213> ORGANISM: Homo sapiens

<400> SEQUENCE: 126
cctcacccca actcccctct                                              20

<210> SEQ ID NO 127
<211> LENGTH: 20
<212> TYPE: DNA
<213> ORGANISM: Homo sapiens

<400> SEQUENCE: 127
caccctcacc ccaactcccc                                              20

<210> SEQ ID NO 128
```

<211> LENGTH: 11
<212> TYPE: DNA
<213> ORGANISM: Homo sapiens

<400> SEQUENCE: 128
ctctgtggct t                                                                11

<210> SEQ ID NO 129
<211> LENGTH: 11
<212> TYPE: DNA
<213> ORGANISM: Homo sapiens

<400> SEQUENCE: 129
ttttgtggct a                                                                11

<210> SEQ ID NO 130
<211> LENGTH: 15
<212> TYPE: DNA
<213> ORGANISM: Homo sapiens

<400> SEQUENCE: 130
tctctctgtg gcttt                                                            15

<210> SEQ ID NO 131
<211> LENGTH: 15
<212> TYPE: DNA
<213> ORGANISM: Homo sapiens

<400> SEQUENCE: 131
caactctgtg gcttg                                                            15

<210> SEQ ID NO 132
<211> LENGTH: 15
<212> TYPE: DNA
<213> ORGANISM: Homo sapiens

<400> SEQUENCE: 132
gcctttgtgt gctag                                                            15

<210> SEQ ID NO 133
<211> LENGTH: 11
<212> TYPE: DNA
<213> ORGANISM: Homo sapiens

<400> SEQUENCE: 133
caagggccag g                                                                11

<210> SEQ ID NO 134
<211> LENGTH: 15
<212> TYPE: DNA
<213> ORGANISM: Homo sapiens

<400> SEQUENCE: 134
agtttatgga gttta                                                            15

<210> SEQ ID NO 135
<211> LENGTH: 13
<212> TYPE: DNA
<213> ORGANISM: Homo sapiens

<400> SEQUENCE: 135
ctgtctctcc cca                                                              13

```
<210> SEQ ID NO 136
<211> LENGTH: 13
<212> TYPE: DNA
<213> ORGANISM: Homo sapiens

<400> SEQUENCE: 136
ctggctccct ccc                                                              13

<210> SEQ ID NO 137
<211> LENGTH: 15
<212> TYPE: DNA
<213> ORGANISM: Homo sapiens

<400> SEQUENCE: 137
cccccgcctc tcgtg                                                            15

<210> SEQ ID NO 138
<211> LENGTH: 15
<212> TYPE: DNA
<213> ORGANISM: Homo sapiens

<400> SEQUENCE: 138
gcccctcctc tgagc                                                            15

<210> SEQ ID NO 139
<211> LENGTH: 15
<212> TYPE: DNA
<213> ORGANISM: Homo sapiens

<400> SEQUENCE: 139
tccccaccct cccct                                                            15

<210> SEQ ID NO 140
<211> LENGTH: 15
<212> TYPE: DNA
<213> ORGANISM: Homo sapiens

<400> SEQUENCE: 140
cctcctcctc cccac                                                            15

<210> SEQ ID NO 141
<211> LENGTH: 15
<212> TYPE: DNA
<213> ORGANISM: Homo sapiens

<400> SEQUENCE: 141
cctcctcccc accct                                                            15

<210> SEQ ID NO 142
<211> LENGTH: 15
<212> TYPE: DNA
<213> ORGANISM: Homo sapiens

<400> SEQUENCE: 142
caccctcccc ttctc                                                            15

<210> SEQ ID NO 143
<211> LENGTH: 15
<212> TYPE: DNA
<213> ORGANISM: Homo sapiens

<400> SEQUENCE: 143
catgagagga aatgg                                                            15
```

```
<210> SEQ ID NO 144
<211> LENGTH: 15
<212> TYPE: DNA
<213> ORGANISM: Homo sapiens

<400> SEQUENCE: 144
tgacagagga aggcg                                                    15

<210> SEQ ID NO 145
<211> LENGTH: 10
<212> TYPE: DNA
<213> ORGANISM: Homo sapiens

<400> SEQUENCE: 145
ctcagctcac                                                          10

<210> SEQ ID NO 146
<211> LENGTH: 18
<212> TYPE: DNA
<213> ORGANISM: Homo sapiens

<400> SEQUENCE: 146
ttagacccaa tatggtct                                                 18

<210> SEQ ID NO 147
<211> LENGTH: 11
<212> TYPE: DNA
<213> ORGANISM: Homo sapiens

<400> SEQUENCE: 147
actcccagga a                                                        11

<210> SEQ ID NO 148
<211> LENGTH: 11
<212> TYPE: DNA
<213> ORGANISM: Homo sapiens

<400> SEQUENCE: 148
atttctaagt a                                                        11

<210> SEQ ID NO 149
<211> LENGTH: 18
<212> TYPE: DNA
<213> ORGANISM: Homo sapiens

<400> SEQUENCE: 149
gttatcacag caccgcag                                                 18

<210> SEQ ID NO 150
<211> LENGTH: 18
<212> TYPE: DNA
<213> ORGANISM: Homo sapiens

<400> SEQUENCE: 150
gcaatctcgg gcttccag                                                 18

<210> SEQ ID NO 151
<211> LENGTH: 11
<212> TYPE: DNA
<213> ORGANISM: Homo sapiens

<400> SEQUENCE: 151
ggcagctggg g                                                        11
```

<210> SEQ ID NO 152
<211> LENGTH: 11
<212> TYPE: DNA
<213> ORGANISM: Homo sapiens

<400> SEQUENCE: 152
cccagctgca c                                                          11

<210> SEQ ID NO 153
<211> LENGTH: 11
<212> TYPE: DNA
<213> ORGANISM: Homo sapiens

<400> SEQUENCE: 153
cccagctgcc t                                                          11

<210> SEQ ID NO 154
<211> LENGTH: 11
<212> TYPE: DNA
<213> ORGANISM: Homo sapiens

<400> SEQUENCE: 154
cccacctgca g                                                          11

<210> SEQ ID NO 155
<211> LENGTH: 11
<212> TYPE: DNA
<213> ORGANISM: Homo sapiens

<400> SEQUENCE: 155
gacacctggc c                                                          11

<210> SEQ ID NO 156
<211> LENGTH: 11
<212> TYPE: DNA
<213> ORGANISM: Homo sapiens

<400> SEQUENCE: 156
gtcagctgca a                                                          11

<210> SEQ ID NO 157
<211> LENGTH: 12
<212> TYPE: DNA
<213> ORGANISM: Homo sapiens

<400> SEQUENCE: 157
cgccttcctc tg                                                         12

<210> SEQ ID NO 158
<211> LENGTH: 15
<212> TYPE: DNA
<213> ORGANISM: Homo sapiens

<400> SEQUENCE: 158
acctcccccg gggaa                                                      15

<210> SEQ ID NO 159
<211> LENGTH: 15
<212> TYPE: DNA
<213> ORGANISM: Homo sapiens

<400> SEQUENCE: 159
ccctccctat gggca 15

<210> SEQ ID NO 160
<211> LENGTH: 15
<212> TYPE: DNA
<213> ORGANISM: Homo sapiens

<400> SEQUENCE: 160
cttccctcca gggga 15

<210> SEQ ID NO 161
<211> LENGTH: 14
<212> TYPE: DNA
<213> ORGANISM: Homo sapiens

<400> SEQUENCE: 161
tggcagttct ccaa 14

<210> SEQ ID NO 162
<211> LENGTH: 14
<212> TYPE: DNA
<213> ORGANISM: Homo sapiens

<400> SEQUENCE: 162
tggctcttct ccaa 14

<210> SEQ ID NO 163
<211> LENGTH: 15
<212> TYPE: DNA
<213> ORGANISM: Homo sapiens

<400> SEQUENCE: 163
acaagccttg acatt 15

<210> SEQ ID NO 164
<211> LENGTH: 11
<212> TYPE: DNA
<213> ORGANISM: Homo sapiens

<400> SEQUENCE: 164
gccaggtgtc c 11

<210> SEQ ID NO 165
<211> LENGTH: 12
<212> TYPE: DNA
<213> ORGANISM: Homo sapiens

<400> SEQUENCE: 165
caacatggct tt 12

<210> SEQ ID NO 166
<211> LENGTH: 12
<212> TYPE: DNA
<213> ORGANISM: Homo sapiens

<400> SEQUENCE: 166
caacatggcc tg 12

<210> SEQ ID NO 167
<211> LENGTH: 20
<212> TYPE: DNA
<213> ORGANISM: Homo sapiens

<400> SEQUENCE: 167

-continued gttcacccag ccttccctgg    20

<210> SEQ ID NO 168
<211> LENGTH: 20
<212> TYPE: DNA
<213> ORGANISM: Homo sapiens

<400> SEQUENCE: 168
tcctccccac cctccccttc    20

<210> SEQ ID NO 169
<211> LENGTH: 20
<212> TYPE: DNA
<213> ORGANISM: Homo sapiens

<400> SEQUENCE: 169
tggcacccag ggtgcttcca    20

<210> SEQ ID NO 170
<211> LENGTH: 20
<212> TYPE: DNA
<213> ORGANISM: Homo sapiens

<400> SEQUENCE: 170
ttgctcccct gctccctgg    20

<210> SEQ ID NO 171
<211> LENGTH: 20
<212> TYPE: DNA
<213> ORGANISM: Homo sapiens

<400> SEQUENCE: 171
gccttccctg gctccctccc    20

<210> SEQ ID NO 172
<211> LENGTH: 21
<212> TYPE: DNA
<213> ORGANISM: Homo sapiens

<400> SEQUENCE: 172
aggggagggt ggggaggagg a    21

<210> SEQ ID NO 173
<211> LENGTH: 21
<212> TYPE: DNA
<213> ORGANISM: Homo sapiens

<400> SEQUENCE: 173
ggaggaggag gaggctgtga g    21

<210> SEQ ID NO 174
<211> LENGTH: 21
<212> TYPE: DNA
<213> ORGANISM: Homo sapiens

<400> SEQUENCE: 174
ggagggtggg gaggaggagg a    21

<210> SEQ ID NO 175
<211> LENGTH: 21
<212> TYPE: DNA
<213> ORGANISM: Homo sapiens

```
<400> SEQUENCE: 175
agagaagggg agggtgggga g                                              21

<210> SEQ ID NO 176
<211> LENGTH: 21
<212> TYPE: DNA
<213> ORGANISM: Homo sapiens

<400> SEQUENCE: 176
gagggaggga gggaaggttg g                                              21

<210> SEQ ID NO 177
<211> LENGTH: 21
<212> TYPE: DNA
<213> ORGANISM: Homo sapiens

<400> SEQUENCE: 177
gagggtgggg aggaggagga g                                              21

<210> SEQ ID NO 178
<211> LENGTH: 21
<212> TYPE: DNA
<213> ORGANISM: Homo sapiens

<400> SEQUENCE: 178
tggggaggga gccagggaag g                                              21

<210> SEQ ID NO 179
<211> LENGTH: 21
<212> TYPE: DNA
<213> ORGANISM: Homo sapiens

<400> SEQUENCE: 179
gggtggggag gaggaggagg c                                              21

<210> SEQ ID NO 180
<211> LENGTH: 21
<212> TYPE: DNA
<213> ORGANISM: Homo sapiens

<400> SEQUENCE: 180
gagggaggga aggttgggtg g                                              21

<210> SEQ ID NO 181
<211> LENGTH: 21
<212> TYPE: DNA
<213> ORGANISM: Homo sapiens

<400> SEQUENCE: 181
ggggcagagg ggagttgggg t                                              21

<210> SEQ ID NO 182
<211> LENGTH: 21
<212> TYPE: DNA
<213> ORGANISM: Homo sapiens

<400> SEQUENCE: 182
ggaggagagg ggtgcagtgt a                                              21

<210> SEQ ID NO 183
<211> LENGTH: 21
<212> TYPE: DNA
<213> ORGANISM: Homo sapiens
```

```
<400> SEQUENCE: 183
gagggaaggt tgggtggaag c                                      21

<210> SEQ ID NO 184
<211> LENGTH: 21
<212> TYPE: DNA
<213> ORGANISM: Homo sapiens

<400> SEQUENCE: 184
gggggcagag gggagttggg g                                      21

<210> SEQ ID NO 185
<211> LENGTH: 21
<212> TYPE: DNA
<213> ORGANISM: Homo sapiens

<400> SEQUENCE: 185
ggagcagggg agcaaagggc c                                      21

<210> SEQ ID NO 186
<211> LENGTH: 21
<212> TYPE: DNA
<213> ORGANISM: Homo sapiens

<400> SEQUENCE: 186
agaaggggag ggtggggagg a                                      21

<210> SEQ ID NO 187
<211> LENGTH: 21
<212> TYPE: DNA
<213> ORGANISM: Homo sapiens

<400> SEQUENCE: 187
aaaggagaag acaagaggag a                                      21

<210> SEQ ID NO 188
<211> LENGTH: 21
<212> TYPE: DNA
<213> ORGANISM: Homo sapiens

<400> SEQUENCE: 188
gagggaaggg gagccaggta g                                      21

<210> SEQ ID NO 189
<211> LENGTH: 21
<212> TYPE: DNA
<213> ORGANISM: Homo sapiens

<400> SEQUENCE: 189
gaaggaggtg ccgcggaaaa a                                      21

<210> SEQ ID NO 190
<211> LENGTH: 21
<212> TYPE: DNA
<213> ORGANISM: Homo sapiens

<400> SEQUENCE: 190
cgtgaacgag ggagggaggg a                                      21

<210> SEQ ID NO 191
<211> LENGTH: 21
<212> TYPE: DNA
```

```
<213> ORGANISM: Homo sapiens

<400> SEQUENCE: 191
tgggcagaga aggggagggt g                                            21

<210> SEQ ID NO 192
<211> LENGTH: 21
<212> TYPE: DNA
<213> ORGANISM: Homo sapiens

<400> SEQUENCE: 192
gaaggggagg gtggggagga g                                            21

<210> SEQ ID NO 193
<211> LENGTH: 21
<212> TYPE: DNA
<213> ORGANISM: Homo sapiens

<400> SEQUENCE: 193
cagagaaggg gagggtgggg a                                            21

<210> SEQ ID NO 194
<211> LENGTH: 21
<212> TYPE: DNA
<213> ORGANISM: Homo sapiens

<400> SEQUENCE: 194
ggaggaggag gctgtgagct g                                            21

<210> SEQ ID NO 195
<211> LENGTH: 21
<212> TYPE: DNA
<213> ORGANISM: Homo sapiens

<400> SEQUENCE: 195
agggaagggg agccaggtag a                                            21

<210> SEQ ID NO 196
<211> LENGTH: 21
<212> TYPE: DNA
<213> ORGANISM: Homo sapiens

<400> SEQUENCE: 196
agaggaaatg gggagggagc c                                            21
```